United States Patent [19]

Carson et al.

[11] Patent Number: 5,275,042
[45] Date of Patent: Jan. 4, 1994

[54] VARIABLE GATE FLOW ANALYZING METHOD AND APPARATUS

[75] Inventors: Douglas T. Carson; Larry L. Fritz; Lowell R. Nickolaus, all of Lincoln; Louis F. Lederer, Seward, all of Nebr.

[73] Assignee: Isco, Inc., Lincoln, Nebr.

[21] Appl. No.: 592,960

[22] Filed: Oct. 4, 1990

[51] Int. Cl.⁵ ............................................. G01F 1/52
[52] U.S. Cl. .................................................... 73/216
[58] Field of Search ............... 73/215, 216, 861.42, 73/861.53, 861.62

[56] References Cited

U.S. PATENT DOCUMENTS

| | | | |
|---|---|---|---|
| 1,081,246 | 12/1913 | McCall | 73/216 |
| 1,258,867 | 3/1918 | Burnham | 73/216 |
| 1,813,100 | 7/1931 | Swindle | 73/861.62 X |
| 2,544,948 | 3/1951 | Caldwell | 73/216 X |
| 2,606,445 | 8/1952 | Eckman | 73/861.53 |
| 3,412,612 | 11/1968 | Carr | 73/215 |
| 4,375,169 | 3/1983 | Torresin | 73/861.53 |
| 4,476,707 | 10/1984 | Burns et al. | 73/861.52 X |
| 4,896,542 | 1/1990 | Hunter | 73/215 X |

FOREIGN PATENT DOCUMENTS 0035219 2/1985 Japan ..................................... 73/215
213060 3/1924 United Kingdom ................. 73/216

OTHER PUBLICATIONS

Ideas/Applications in Engineering and Design vol. 1g No. 12 p. 241 Dec. 1975 copy.

Primary Examiner—Herbert Goldstein
Attorney, Agent, or Firm—Vincent L. Carney

[57] ABSTRACT

To measure flow rates, the cross-sectional shape of the flow path is changed by inserting a multiple position gate into the flow path and altering the position of the gate to maintain the head of liquid constant with a reduced flow cross section. To maintain the head at a desirable range, the depth is measured and controls the position of the gate as a feedback signal. The position of the multiple position gate is correlated with the depth to provide an indication of flow rate. For this purpose, a flow path housing is clamped to a pipe and a multiple position gate is moved by pneumatic pressure into the flow stream to change the flow cross section. The depth of the head upstream of the gate is measured and the position of the gate is measured. Flow rate is determined from these two measurements. Sampling may be performed at an increased depth caused by the gate.

7 Claims, 21 Drawing Sheets

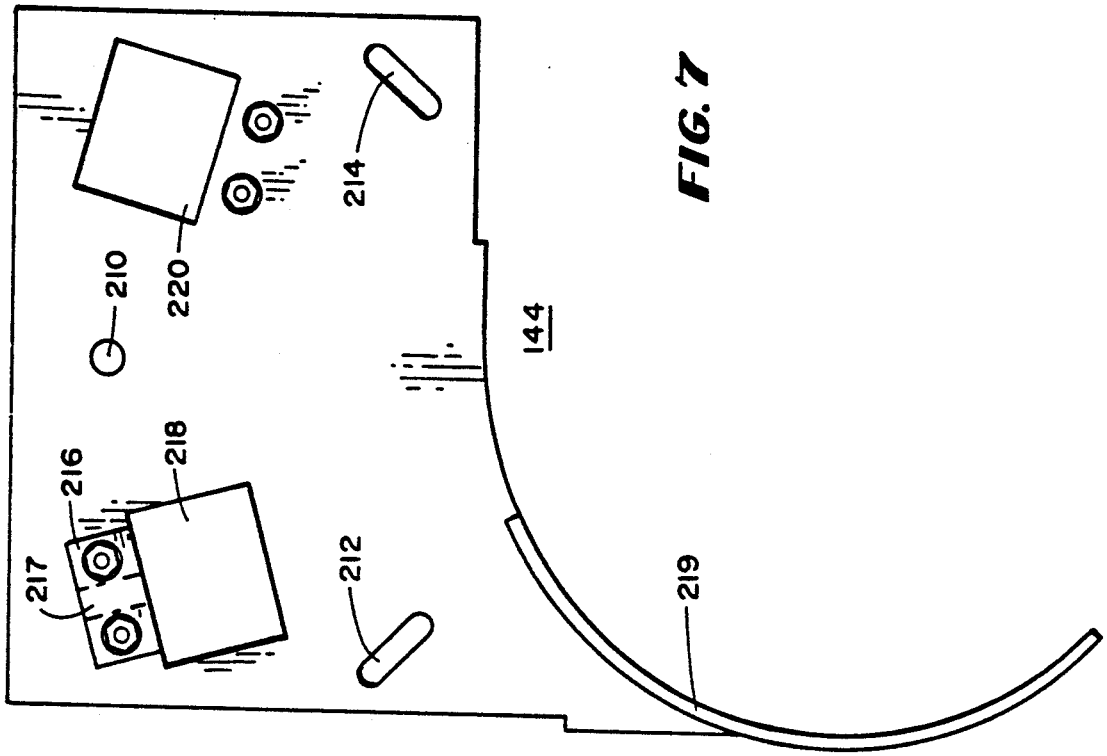
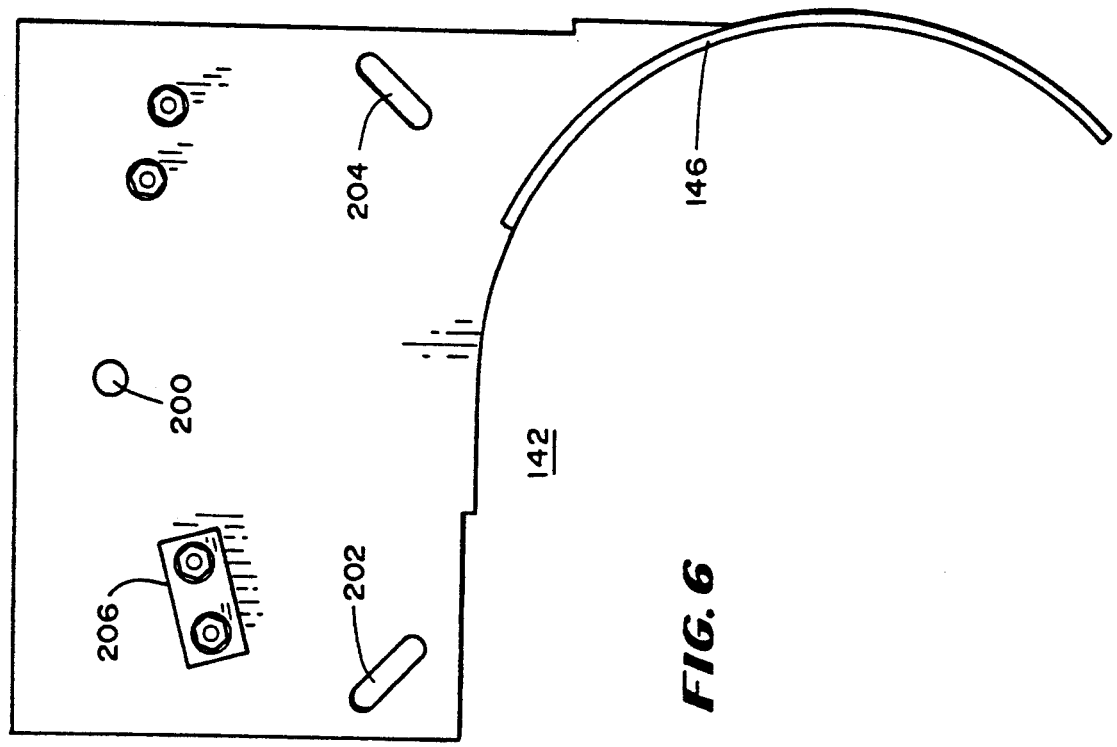

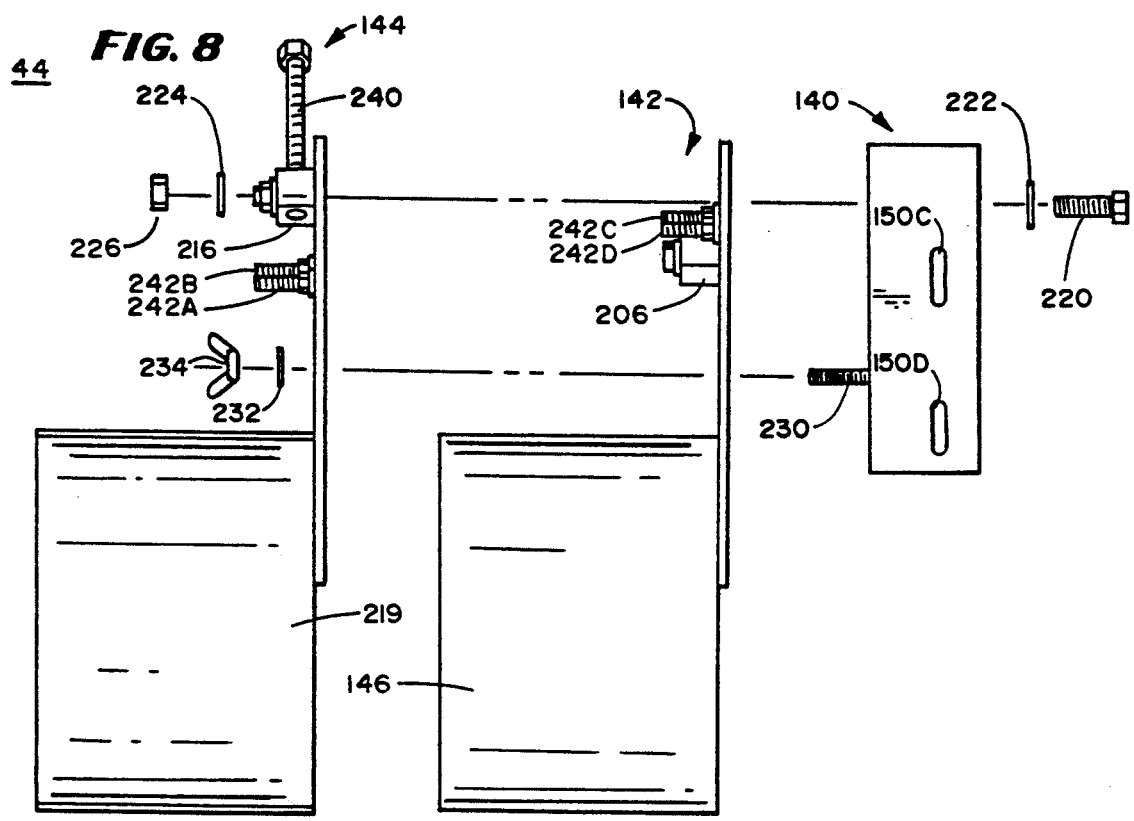
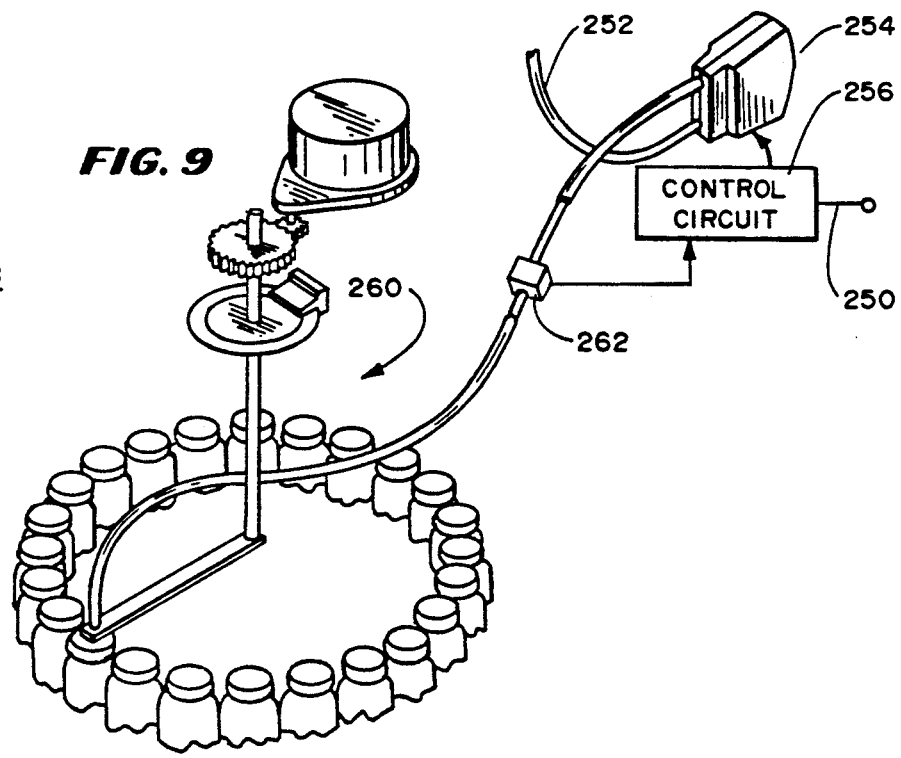

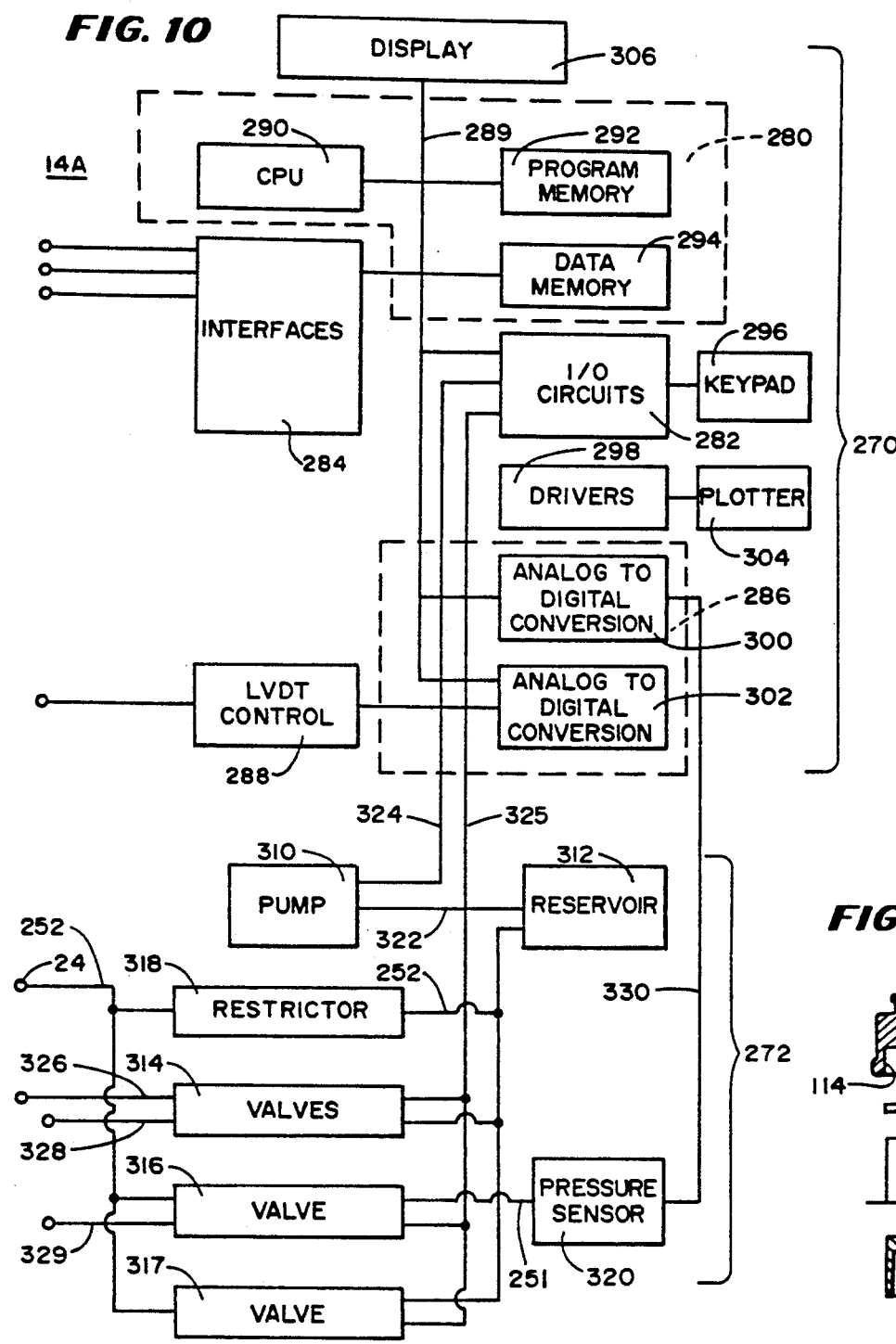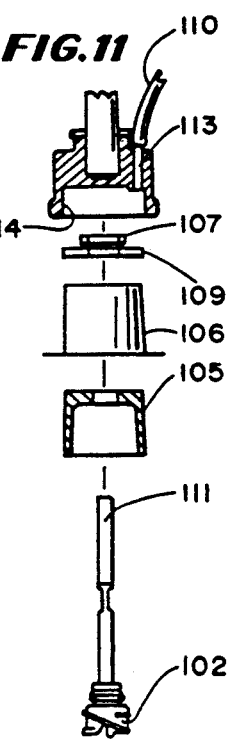
FIG. 10
FIG. 11

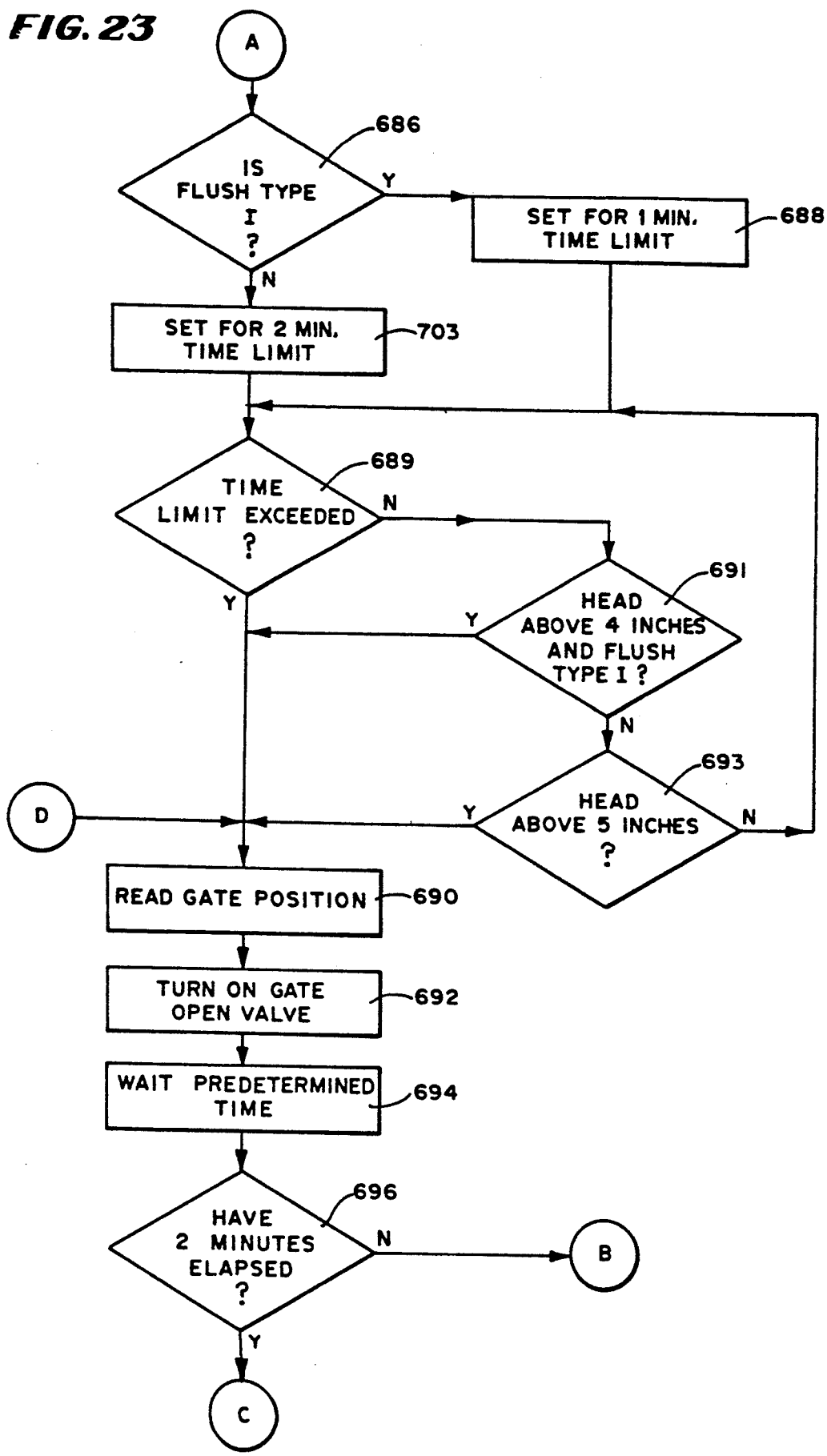

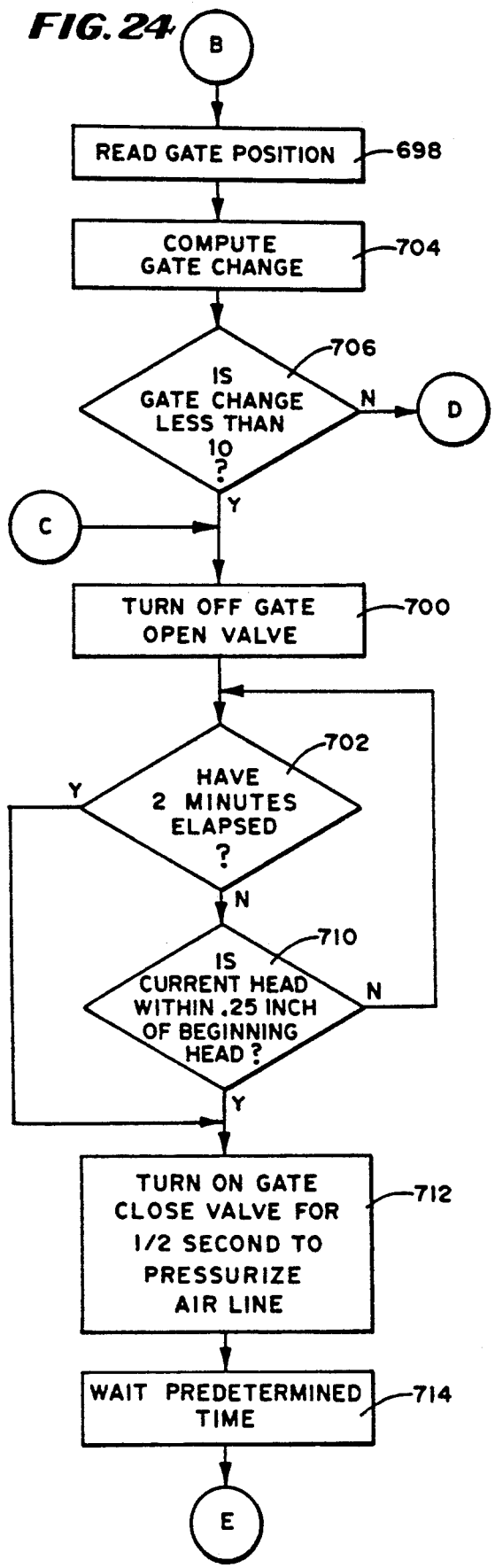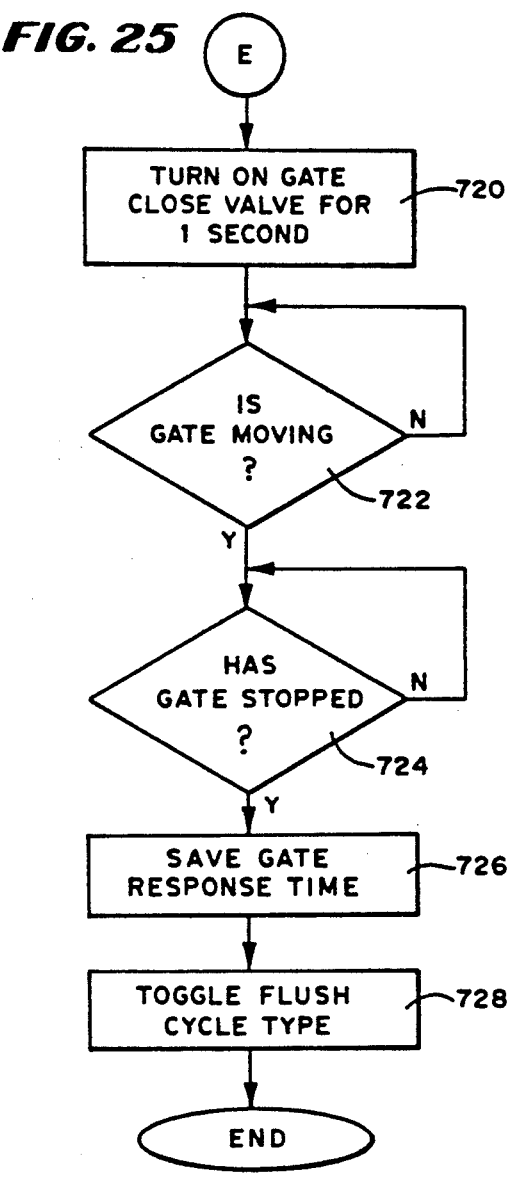

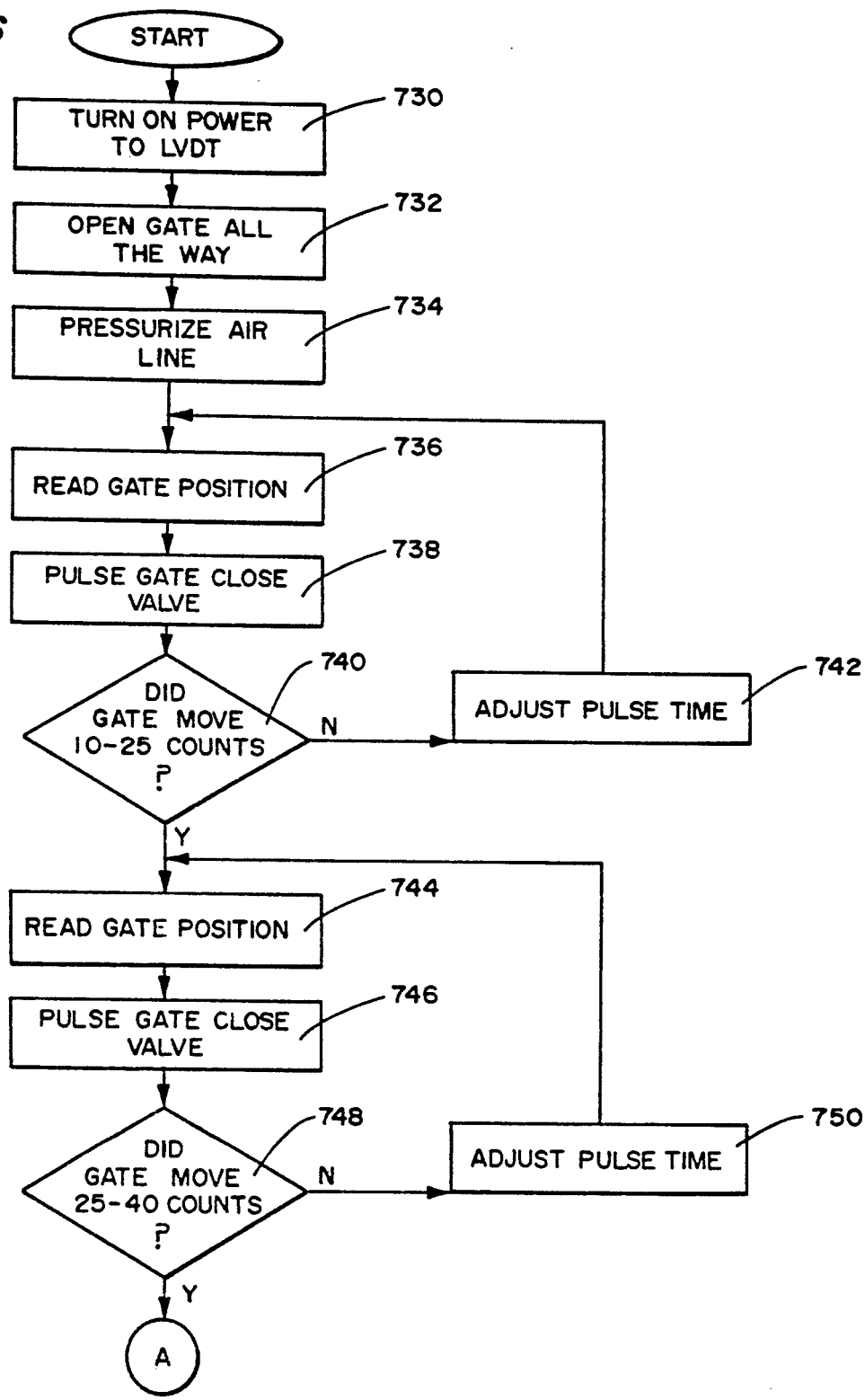

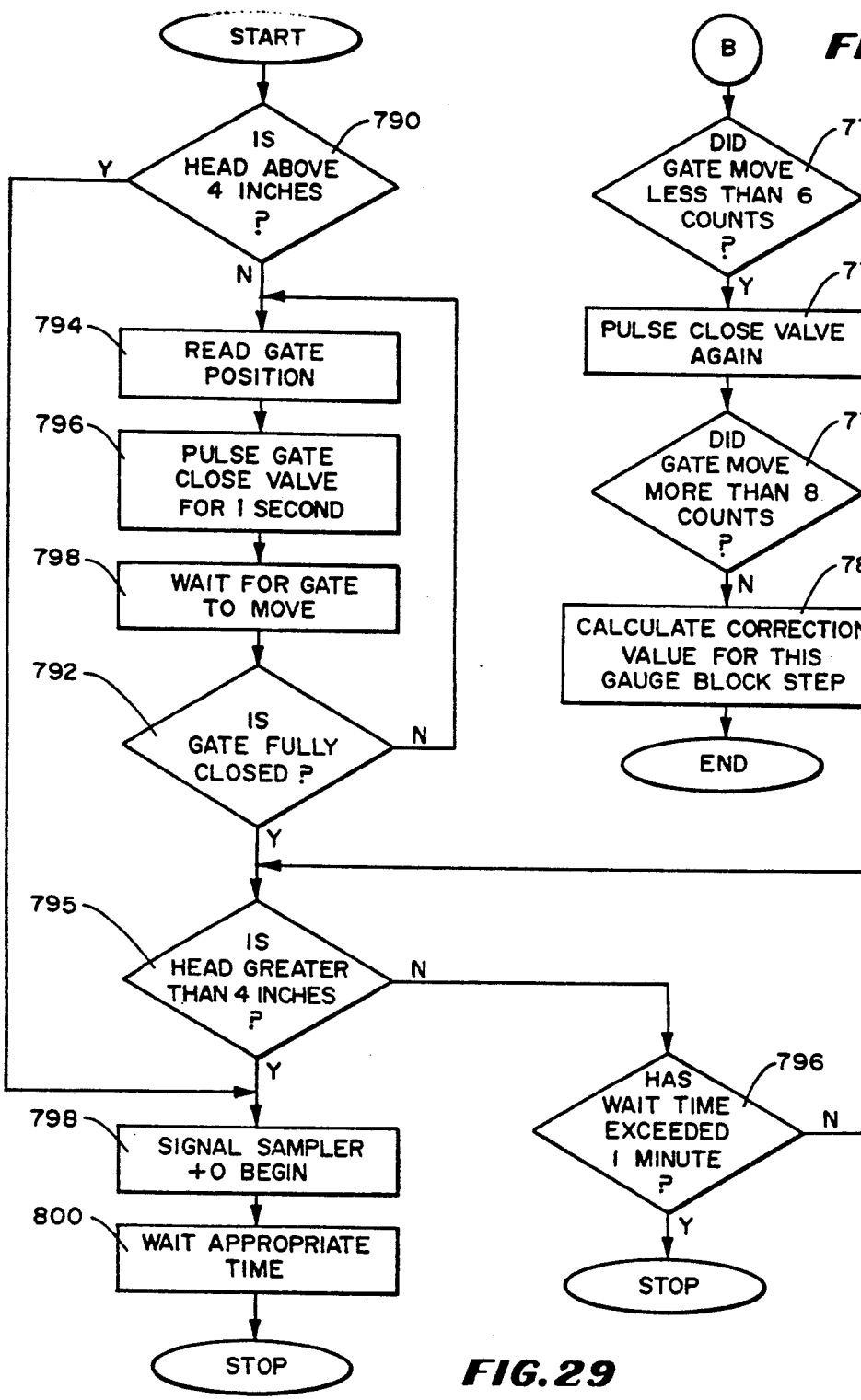

VARIABLE GATE FLOW ANALYZING METHOD AND APPARATUS

BACKGROUND OF THE INVENTION

This invention relates to liquid flow rate measuring and liquid sampling methods and apparatuses and more particularly to methods and apparatus which are adjustable to provide for measurement and/or sampling of liquid streams including streams that are flowing at a low rate or are shallow.

One class of flow meter utilizes a movable gate or obstruction in a flow stream to alter the flow so as to enable easier measurement of flow rate and one type of sampler uses an obstruction and fixed flow bed to provide a location of relatively still and deep water from which to draw a representative sample.

One prior art flow measuring device for altering the flow stream to be measured utilizes a buoyant weir plate in the stream of a liquid. The tip of the buoyant weir includes a graduated depth gauge so that as the buoyant weir is lifted by its buoyancy and the rate of flow, the depth can be read on its graduated scale and a calculation of flow rate made therefrom. This type of device is disclosed in U.S. Pat. No. 3,087,335.

This type of flow measuring device has several disadvantages such as: (1) it is not as precise in its measurements as desired; and (2) it requires a visual on-sight reading and manual entry of depth data to obtain flow rates.

Another prior art flow device is disclosed in U.S. Pat. No. 4,200,120. This device controls gas flow with two movable valves in series in a gas stream, such as may be used to mix air with fuel in an internal combustion engine. The first valve is located upstream from the second valve and is varied in orientation in the stream such that the pressure difference between the pressure upstream of the first valve and the pressure between the two valves is kept constant. This is accomplished by extracating the pressure of the two chambers and sending them to a device which measures and amplifies any difference.

The result of this difference is sent to a feedback control mechanism and then to a valve opening mechanism which changes the position of the first valve to maintain the pressure differential between the two chambers. The position of the first valve is used to calculate the velocity of the gas.

This type of apparatus has a disadvantage in that it is complicated and not easily adaptable to a wide range of liquid flow rates because of the fixed position of the second valve and the location of the conduits connecting the chambers.

SUMMARY OF THE INVENTION

Accordingly, it is an object of the invention to provide a novel method and apparatus for measuring the flow rate of liquids and for sampling.

It is a further object of the invention to provide a novel method and apparatus for measuring flow rates of flowing fluids.

It is a still further object of the invention to provide a novel method and apparatus for drawing samples from liquids to be analyzed.

It is a still further object of the invention to provide a novel method and apparatus for altering the flow path of flowing liquids.

It is a still further object of the invention to provide a novel apparatus and method for calibrating flow meters and depth measuring devices for liquids.

It is a still further object of the invention to provide a novel apparatus and method for determining the rate of flow of fluid in a stream by maintaining the altered flow at a constant value with an obstruction and measuring the position of the obstruction.

It is a still further object of the invention to provide a novel method and apparatus for measuring characteristics of slowly moving or shallow moving bodies of water.

It is a still further object of the invention to provide a novel method and apparatus for increasing the depth of moving liquids to permit easier measurement of the liquids.

It is a still further object of the invention to provide a novel method and apparatus for measuring characteristics of streams which are sufficiently versatile to make such measurements at either low flow rates or high flow rates.

In accordance with the above and further objects of the invention, flow rates in a flow path are measured by changing the shape of the flow path with a barrier; determining the position of the barrier; determining a characteristic of the flow path; and determining the flow rate. In this method, the head of liquid pressure is measured which together with the position of the barrier is used to determine the flow rate.

In one mode of operation, the barrier is maintained in a position such that the height of the fluid on the upstream side of the barrier remains constant at a height higher than in the unobstructed flow path, wherein the measurement is made at a higher head of pressure and variations in barrier position relate to flow rate.

In another mode of operation, the barrier is substantially removed from the flow path when the height of the fluid on the upstream side of the barrier reaches a predetermined height. Advantageously, liquid is sampled upstream from the barrier, whereby samples may be taken from fluid having a substantial depth.

For calibration of a bubbler used to measure upstream depth, a zero measurement from the probe is periodically obtained by opening a conduit to the atmosphere connected to the housing wherein the sensor is exposed to atmospheric pressure. Moreover, the flow path is kept clean by opening the gate to flush accumulated solids downstream. The flushing may also be done automatically upon sensing excessive solids near the gate such as by the reflection of ultrasonic waves from the solids.

In making such measurements, a flow housing having a tube with a flow path therethrough, an inlet and an exit is mounted to the flow path with means for changing the flow path incorporated therein. Depth is measured with a pressure sensor mounted in the housing upstream of the barrier.

The barrier comprises a gate mounted in said flow path, means for moving said gate such that said gate can be positioned open, closed and in a plurality of positions between said open and closed position relative to said flow path and means for determining the position of said barrier.

The housing includes means for adjusting said flow path housing with respect to walls of said flow path. This apparatus includes an adjustable clamp and bubble level. This measuring apparatus and method is especially suitable for open channel measurements.

From the above summary, it can be understood that the novel method and apparatus of this invention has several advantages, such as for example: (1) it is relatively simple, inexpensive and easy to use; (2) it is capable of convenient and easy adjustment in a flow path; (3) it is versatile and can be used both to measure flow rates and take samples in a wide variety of streams and at a wide variety of different depths of flow and flow rates; (4) it is capable of great precision under difficult measuring conditions; and (5) the apparatus can be used to perform a number of different measuring methods.

SUMMARY OF THE DRAWINGS

The above-noted and other features of the invention will be better understood from the following detailed description when considered in connection with the accompanying drawings in which:

FIG. 6 is a front elevational view of another portion of the adjustable mounting means;

FIG. 7 is a front elevational view of still another portion of the mounting means;

FIG. 8 is an exploded side elevational view of a portion of the mounting means;

FIG. 9 is a schematic view of a portion of a sampling means used with the embodiment of FIG. 1;

FIG. 10 is a block diagram of a portion of the embodiment of FIG. 1 for controlling the apparatus of FIG. 3;

FIG. 11 is an exploded, fragmentary, sectional view of a pneumatic gate control mechanism;

FIGS. 22-25 are flow diagrams of a gate flush program sequence usable in the embodiment of FIG. 10;

FIGS. 26-28 are flow diagrams of a calibration with gauge block program sequence usable in the embodiment of FIG. 10; and FIG. 29 is a sampling program sequence usable in the embodiment of FIG. 10.

DETAILED DESCRIPTION

Figure 1:
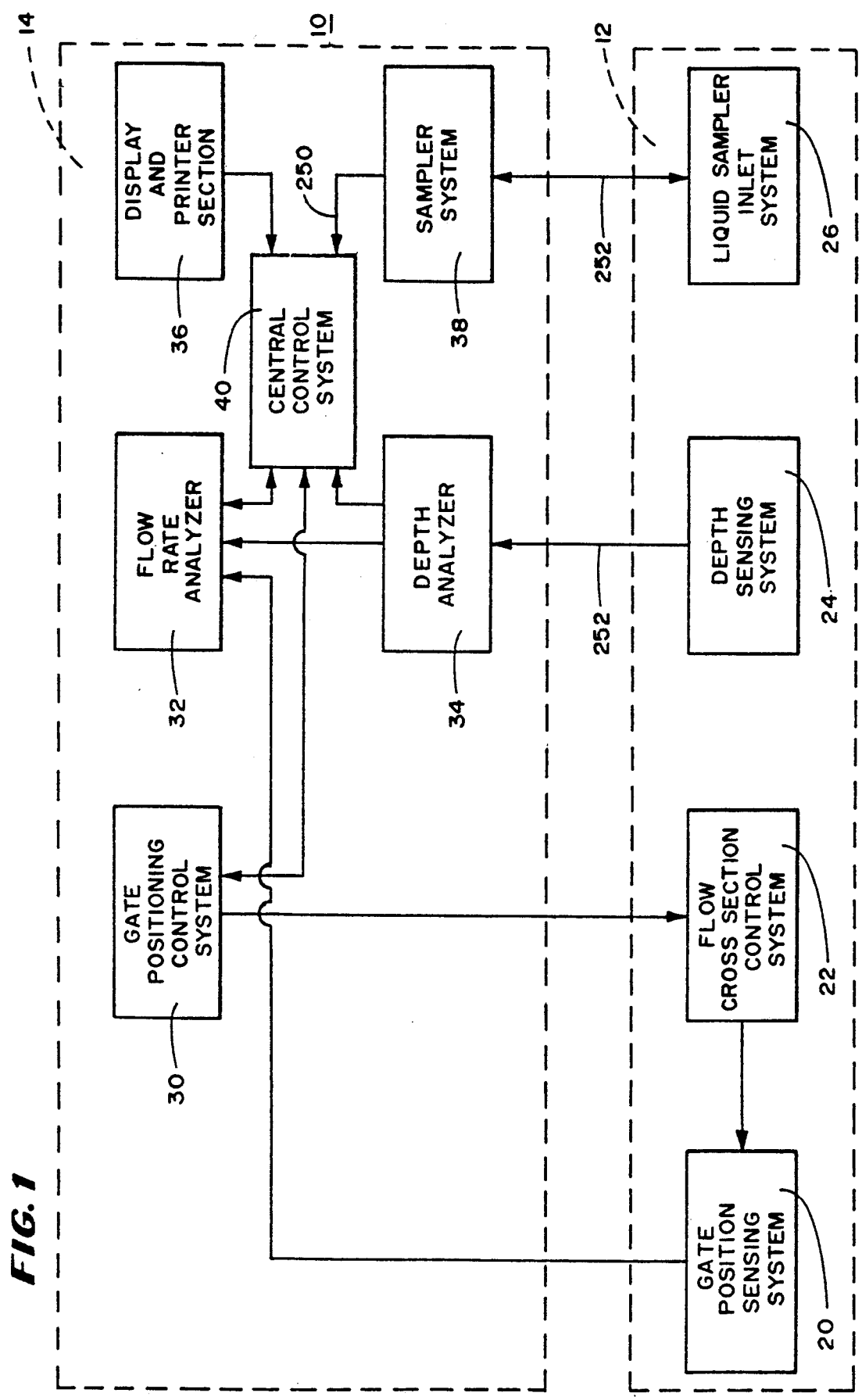
FIG. 1 is a block diagram of an embodiment of the invention.

In FIG. 1, there is shown one embodiment of a water flow rate measuring and liquid sensing apparatus 10 having a flow-stream local station 12, and a remote station 14 connected together with the flow-stream local station 12 being partly within the flow stream and generally connected together. It communicates with the remote station 14 through electrical conductors and pneumatic lines.

The flow-stream local station 12 and remote station 14 are arranged so as to alter the shape of a barrier to the flow stream and: (1) measure characteristics of the stream such as depth which permits a calculation of flow rate or other data; and (2) in some embodiments, draw samples of fluid for later analysis. The barrier may be erected in cases of low flow and removed from the flow stream in high flow conditions so as to permit easier measurement under low flow conditions in the manner of a weir. It can be raised to a level to increase depth so as to increase the dynamic range of a pressure sensor used to calculate flow rates or it may be controlled so as to block the flow over an area related to the flow rate and thus maintain the depth constant, in which case the shape of the barrier such as the profile or projection into the direction of the flow streams indicates the rate of flow.

The flow-stream local station 12 includes a gate position sensing system 20, a flow cross section control system 22, a depth sensing system 24 and a liquid sampler inlet system 26. The flow cross section control system 22 and the gate position sensing system 20 are interconnected and communicate with the remote station 14 so that the gate position sensing system 20 indicates a gate position to the remote station 14 which in turn sends signals to control the flow cross section control system 22 and alters the barrier. In the preferred embodiment, the barrier is a gate-like structure so as to provide a greater or lower cross sectional area of flow projected into the direction of the flowing stream.

The depth sensing system 24 and the flow cross-section control system 22 also communicate with the remote station 14 to send back signals indicating depth, such as by indicating the head of pressure at a location in the bottom of the flow path and to draw samples from an appropriate location. The signals are interpreted in the light of the position of the barrier and the barrier can aid in creating a still location for appropriate samples to be drawn.

The remote station 14 includes a gate positioning control system 30, a flow rate analyzer 32, a depth analyzer 34, a display and printer section 36, a sampler system 38 and a central control system 40. The depth analyzer 34 is electrically connected to the flow rate analyzer 32 and the gate positioning control system 30 to provide signals thereto indicating the depth of the flow stream.

The flow rate analyzer 32 receives signals from the gate position sensing system 20 and from the depth analyzer 34 and transmits signals to the central control system 40. The central control system 40, in response, transmits signals to the gate positioning control system. The gate position sensing system 20 transmits information to the flow rate analyzer 32 and the flow rate analyzer 32 utilizes this information together with the information received from the depth anaylzer 34 to calculate flow rate.

The sampler system 38 communicates with the liquid sampler inlet system 26 to periodically draw samples at times which are appropriate for later analysis. In the preferred embodiment, the liquid sampler inlet system 26 is mounted one inch upwardly on the gate (not shown in FIG. 1) of the flow cross section control system 22 and should be mounted at or close to the gate, away from settling material but sufficiently low to be covered with liquid during sampling. The sampler system 38 may be of any suitable type and not every configuration of water flow rate measuring and liquid sensing apparatus 10 includes such a sampling system. However, when combined in conjunction with the controllable barrier, the sampler system 38 and liquid sampler inlet system 26 permit drawing of samples under good conditions even though the flow rate may be low and the water shallow in the flow bed from which samples are to be drawn since the barrier may increase the depth for the drawing of a sample.

The central control system 40 receives signals from the depth analyzer 34, the gate positioning control system 30, the flow rate analyzer 32, the display and printer section 36 and the sampler system 38. It utilizes those signals to control each of the above units and prepare data for display and printing by the display and printer section 36. Thus the central control system 40 can make necessary calculations and store information such as look up tables related to coordination of depth and flow rate or can calculate values utilizing the Manning equations and display and print data as desired. It can also time and record the time of the drawing of samples by the sampler system 38.

The flow rate measuring and liquid sensing apparatus 10 shown in FIG. 1 may be implemented by a variety of different known components. For example, the central control system 40 may be a computer and many of the functions such as those performed by the flow rate analyzer 32 may be software implemented by that computer. Moreover, the sampler system 38 may be a unit which has an independent computer in it which performs some of the functions indicated as being performed by the central control system 40 or the central control system 40 may control the operations of the sampler system 38.

Figure 2:
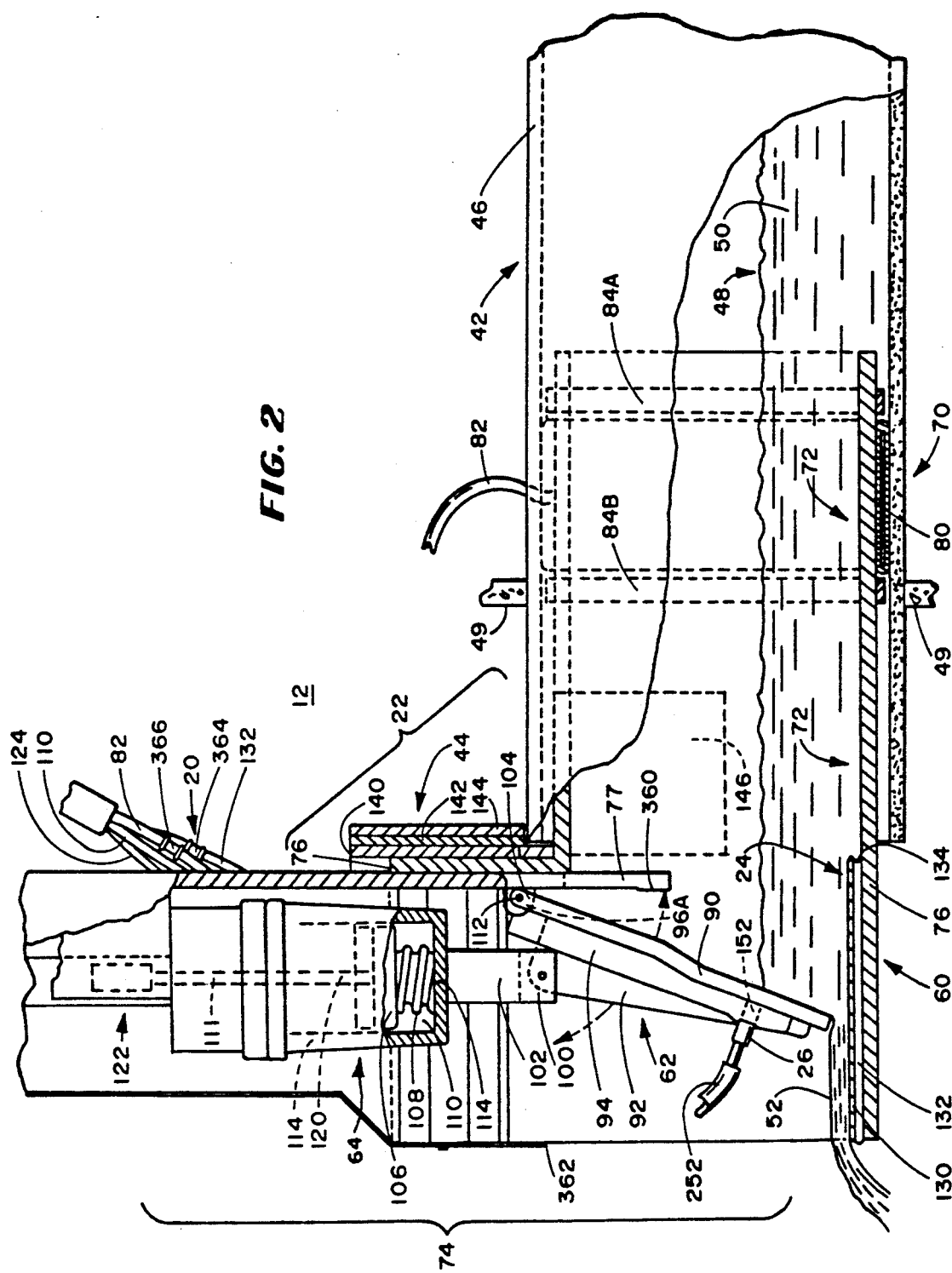
FIG. 2 is a simplified broken away partly schematic drawing of a portion of the embodiment of FIG. 1.

In FIG. 2, there is shown a broken away elevational view sectioned to show the flow-stream local station 12 mounted within a flow stream 42 and including the liquid sampler inlet system shown generally at 26, the depth sensing system shown generally at 24 within the flow stream 42. The flow cross section control system 22 is mounted in place in close cooperation with the gate position sensing system 20. A clamping unit 44 positions the flow path bed and the housing for level flow as explained hereinafter.

The flow stream 42 may be any flow bed for a liquid together with the liquid itself. In FIG. 2, there is shown as part of the flow stream 42, a pipe 46 with a bed of water 48 which may contain debris or sewage or the like such as would be carried by sewage lines in a city. In FIG. 2, the pipe 46 extends into a manhole indicated by the walls of 49 generally so that the flow cross section control system 22 extends partly into the pipe 46 and partly beyond it into the manhole.

The bed of water 48 for convenience is considered as having an upstream portion 50 which enters the flow cross section control system 22 and a downstream portion 52 which exits it beyond a barrier to be described hereinafter. The dividing line between the upstream portion 50 and downstream portion 52 of the flowbed is the barrier controlled by the flow cross section control system 22.

The flow cross section control system 22 includes a flow housing 60, a gate assembly 62 and a gate control assembly 64. The gate assembly 62 and gate control assembly 64 are mounted together so that the gate control assembly 64 controls the gate assembly 62 in forming a barrier to the upstream portion 50, which barrier changes its shape insofar as it projects a different profile upstream of the flow. The gate assembly 62 and gate control assembly 64 are mounted to the flow housing 60 by the clamping unit 44, which in turn, is mounted to the flow stream 42 to receive the flow of liquid 48.

To mount the flow housing 60 in position where it receives the flow of liquid 48 at the gate assembly 62 and gate control assembly 64 properly, the flow housing 60 includes a sealing section 70, a flowbed section 72, a gate housing section 74 and the clamping section 44. The gate control housing 74 includes within it the mechanism for positioning the gate assembly 64 and the gate position sensing system 20. The flowbed section 72 includes internal walls 76 which receive the water 48 or water combined with sewage or debris or the like from upstream and supports its flow downstream. It is sealed by the sealing section 70 to the flow bed or flow stream 42 so that all of the water or other liquid to be measured flows into the flowbed section 72. The gate housing section 74 is joined to the flowbed section 72 and clamping section 44 clamps the entire assembly in position to the flow stream 42.

In the preferred embodiment, the flow stream 42 is a cylindrical pipe and the internal walls 76 of the flowbed section 72 is a conformingly shaped cylinder slightly lower in outer diameter than the inner diameter of the walls of the pipe 46, forming a portion of the flow stream 42. However, the flow stream 42 may assume other shapes and the internal walls 76 will also take other shapes in such a case.

To mount the gate assembly 62, the gate control assembly 64 and gate position sensing system 20, the gate housing section 74 of the flow housing 60 includes internal walls which are rigidly mounted to or integrally formed with the internal walls 76 of the flowbed section 72 that extend upwardly so as to be usually, or in most installations above, the upstream portion 50. To this gate housing section 74 are mounted the gate position sensing system 20, the gate control assembly 64 and the gate assembly 62 which extends downwardly into the liquid 48 to divide the upstream portion 50 from the downstream portion 52. In FIG. 2, the gate housing section 74 is fragmentary and shown broken at its uppermost portion.

To seal the internal walls 76 against the walls of the pipe 46, the sealing section 70, in the preferred embodiment, includes a bladder 80, a pneumatic bladder tube 82 and retaining members 84A and 84B in one embodiment for sealing the bladder 80 to the internal walls 76. With this configuration, after the flow cross section control system 22 and gate position sensing system 20 are in place within the pipe 46, air may be applied to the bladder 80 through the pneumatic bladder tube 82 to inflate it and form a sealing connection between the internal walls 76 and the walls of the pipe 46. Of course, while an air bladder is shown as one mechanism, other sealing mechanisms can be used, such as for example, in a permanant installation, cement or the like may be utilized to seal the walls 46 to the walls 76 or putty or the like or a bladder filled with solid material and a tight fit may be used even in temporary installations.

To form a barrier to the flow of the liquid 48, the gate assembly 62 includes a plastic plate portion 90 and a plurality of integrally formed ridges extending from its surface, such as 92 and 94 in the preferred embodiment. One of those ridges centrally located cooperates with the gate control assembly 64 that pivots the gate upwardly away from the liquid stream 48 or downwardly into its surface and at greater depths to create a barrier in the liquid which will cause the upstream .pa portion 50 to be higher than the downstream portion 52.

The plastic plate portion 90 includes two yokes, 96A unit and 96B, (96A only being shown in FIG. 2) cut into its end and pivotably mounted to one wall 77 of the gate control housing. Of course the barrier may assume other shapes and may be an expandable bladder or sliding gate for example, or the plastic plate, instead of having ridges that fasten to the gate assembly, may include a yoke that fastens to the gate control assembly 64.

Figure 4:
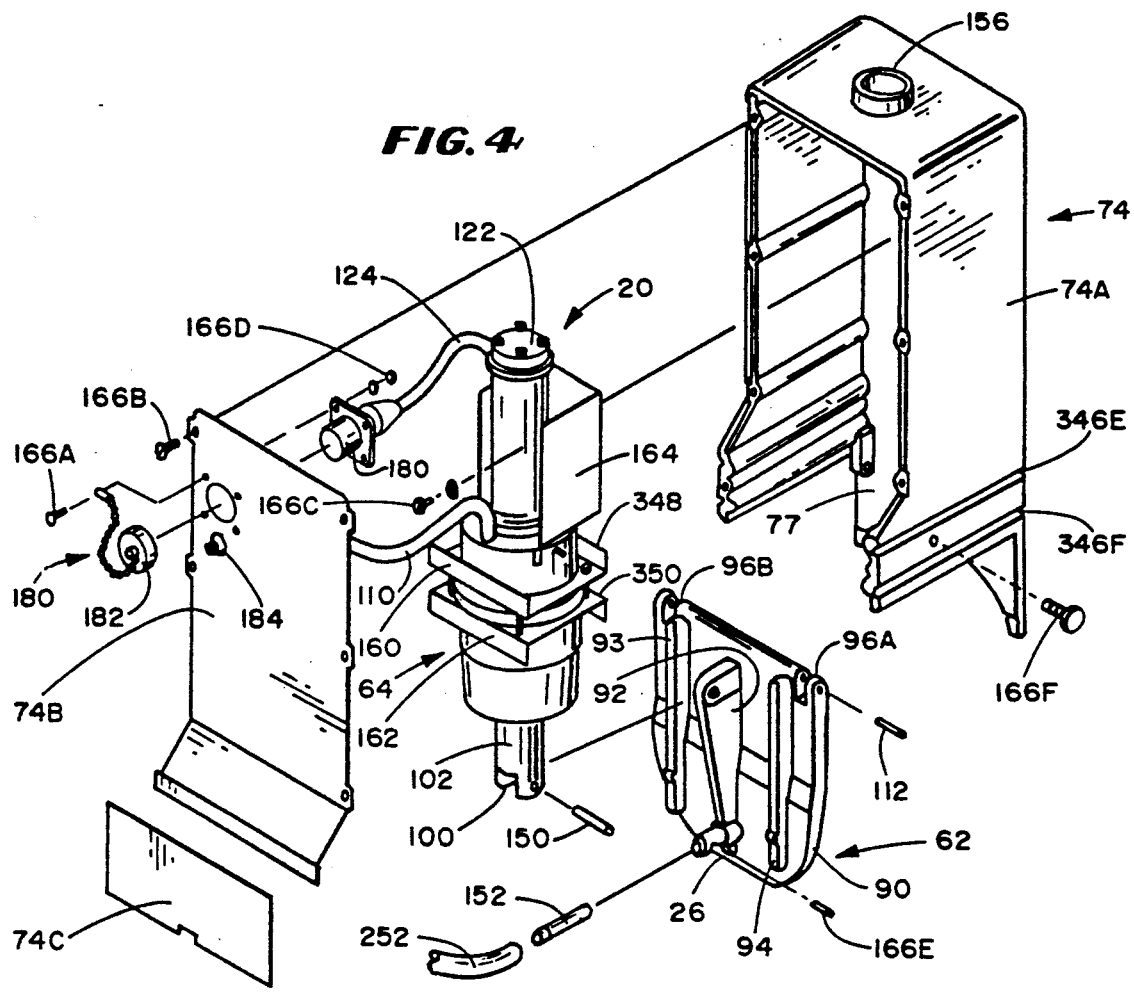
FIG. 4 is an exploded perspective view of a portion of the embodiment of FIGS. 1-3 from a viewpoint different from that of FIG. 3.

The gate control assembly 64 includes a yoke 100, a piston shaft 102, an ear 104, a piston diaphram 106, a helical compression spring 108, a pneumatic tube 110 and a piston 105 (not shown in FIG. 2). The piston shaft 102 is connected to the piston 105 under the diaphram 106 at one end and at the other end has the yoke 100. The ear 104 is integrally formed with or fastened to the internal wall 77 of the gate housing 74 spaced from the movable piston shaft 102 and cooperates with a yoke 96A by receiving a pin 112. A similar ear cooperates with a yoke 76B (FIG. 4).

The yoke 100 similarly receives a pin and is pivotably mounted to the ridge 92 so that as it moves up and down, it causes movement of the plastic plate portion 90 with respect to the ear 104, which pivots about the pin 112 through the yoke 96. The helical compression spring 108 is mounted between the piston 106 and a wall 114 of a piston chamber within which the piston bladder 106 moves. Below the piston bladder 106, the helical compression spring 108 communicates with the cylinder so that air pressure applied by the tube 110 to the upper part of the piston chamber moves the piston and piston bladder 106 downwardly against the force of the compression spring 108. When the pressure is released, the spring 108 moves the piston 106 upwardly to move the shaft 102 upwardly, which in turn pivots the gate assembly 62 about the pin 112 upwardly and away from the bottom of the liquid 48. Similarly, pressure applied to the chamber wall 114 above the piston diaghram 106 through the tube 110 (see FIGS. 3 and 11 for location) moves the gate assembly 62 downwardly into increasing depths of the liquid 48, where it may be held by maintaining the gas pressure in the chamber.

The gate position sensing system 20 includes a shaft 120 and a position sensor 122. The shaft 120 is connected at one side to the piston 105 (under bladder 106) and at its other side to a core of the sensor 122 so that as the piston 105 moves upwardly and downwardly, the shaft 120 moves and causes the sensor 122 to generate a signal indicating the position of the piston 105 and therefore the gate assembly 62.

The position sensor 122, in the preferred embodiment, is a LVDT (linear variable-differential transformer) which generates a signal that varies linearly with shaft 120 movement. It is energized by two of the conductors 124 and applies a signal on two other conductors, all of which are in the cable 124.

The liquid sampler inlet system 26 includes a conduit which communicates in a typical manner through a fitting or the like, preferably in the gate assembly 62, for drawing under the control of a sampler system 38 (FIG. 1) periodic samples of fluid for analysis. It is generally located on the gate assembly 62 at a location which has sufficient depths, is sufficiently nonturbulent to draw representative samples and sufficiently turbulent to reduce clogging. Prior to drawing a sample, the gate assembly 62 may be opened so as to remove solids and then closed until the depth is sufficient for taking a sample. The inlet to the sampler should be between 0 to 10 feet from the gate to provide a reasonable height of liquid and a normal flow rate. Generally it will be between one-eighth of an inch above the bottom to a height no greater than one-half the inner diameter of the pipe 46.

To determine the depth of the fluid, any type of depth measuring device may be used including pressure sensors or mechanical depth measuring devices. However, in the preferred embodiment, a bubbler tube 132 is mounted adjacent to the bottom wall 76 of the flow path and under a protective cover and flat calibrating surface 130. The pressure measuring point or entrance to the housing of the bubble tube is at location 134 approximately 0 inches from the location of the gate to 2 feet when fully closed. It should be at a known elevation from the end of the gate assembly or the same elevation. The distance is selected to be sufficiently far from the end of the wall 76 and of the gate so that neither the gate nor the flow of water off of the end of the wall 76 into a manhole affect the measurement by velocity or by having an unusual rise or lowering of the liquid level at that point but sufficiently close so as to obtain scrubbing from the velocity of the liquid flowing over it.

The internal walls 76 of the flow bed housing 60 are normally in a diameter range of between 3 inches and 2 feet and usually cylindrical although other sizes are usable and the measuring device may be mounted in an existing flow bed without the flow bed housing to specifically shape the flow bed. The gate mount may be mounted separately to an existing pipe extending into a manhole or through a cut out top of a pipe extending through a manhole without the flow housing so that it utilizes the flow bed itself instead of the flow housing 60. The dynamic range of measurement of the system and the sensor is normally adjusted within a range of 1/10 of a gallon per minute to 500 gallons per minute in a six inch pipe and scaled upwardly for larger pipes to as high as 1 gallon per minute to 16,000 gallons and ranges of 5,000 to 1 for a six inch pipe and 16,000 to 1 in a two foot pipe in the preferred embodiments. Generally, all of the components are preferably capable of dealing with this range.

To mount the flow cross section control system 22 to the flow stream 42 (pipe 46), an adjustable clamping unit 44 includes a bracket 140, a first adjustable clamp 142 and a second adjustable clamp 144. The first and second adjustable clamps 142-144 each include an adjustable plate with a curved clamp portion mounted thereto to grip the walls of the pipe 46, one curved clamp member being shown at 146 formed integrally with the outer plate of the second or outer adjustable clamp 144. The clamping plates 142 and 144 are pivotable about the bracket 140 and adjustable with respect to each other so that the flow cross section control system 22 may be positioned at different heights and angles with respect to the clamping means. With this arrangement, the wall 76 may be supported at an adjustable angle, generally level or horizontal with the gate assembly 62 positioned to rise and drop vertically and on center and the depth sensor positioned at the lowermost location. This arrangement permits easy insertion and adjustment of the flow-stream local station by an operator from outside of the flow-stream for convenience.

Figure 3:
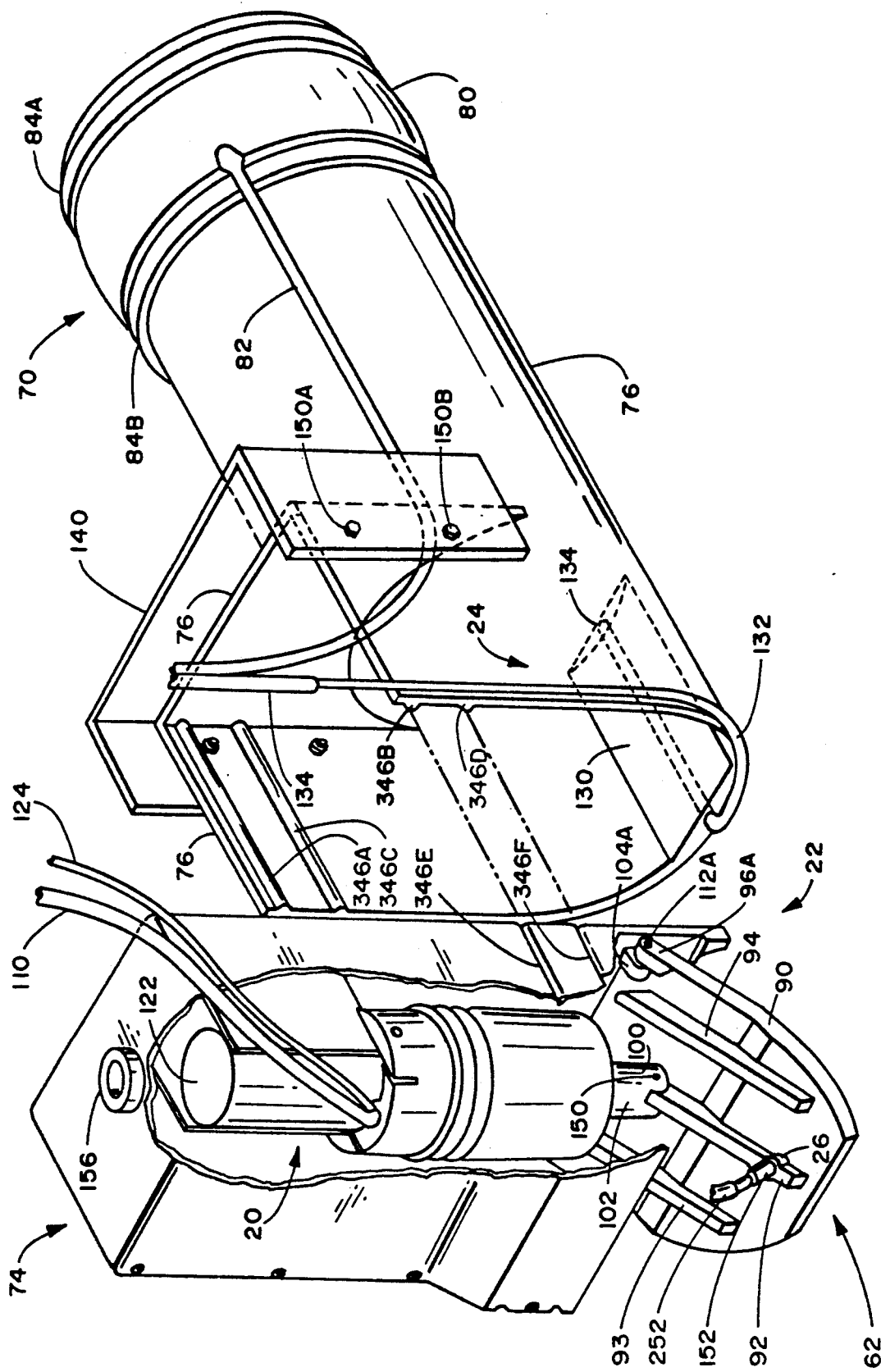
FIG. 3 is an exploded, fragmentary, broken away, perspective view of a flow path, variable position gate and measuring apparatus in accordance with the embodiment of FIG. 1.

In FIG. 3, there is shown an exploded perspective view partly broken away of the flow cross section control system 22, gate position sensing system 20 and depth sensing system 24 mounted together and showing only the bracket 140 of the clamping means.

As best shown in this view, the gate assembly 62 includes three reinforcing ribs 93, 92 and 94 with the rib 92 fitting within the yoke 100 of the shaft 102 and being pinned therein by a pin 150 for pivotable movement about the pins 112A and 112B (112B not shown in FIG. 3) through the ear 104A and 104B (ear 104B not shown in FIG. 3) and the yokes formed of the cutout portion 96A and 96B (96A only shown in FIG. 3) of the gate assembly 62 so that as the shaft 102 moves upwardly and downwardly, the gate is raised and lowered as the LVDT senses its position and transmits it through a cable 124 to the remote station 14 (FIG. 1).

A gate insert or opening 152 extends through the rib 92 and a plate 90 to face upstream, thus serving as a sample inlet 26. The samples are drawn to the surface through a tube 252. Sampling at this location provides representative samples. They are drawn within 15 minutes after closing the gate and as soon as the liquid is sufficiently high such as 3 or 4 minutes.

A bubble level 156 is mounted on top of the housing 74 and may be used in conjunction with the adjustable clamping unit 44 (FIG. 2) to cause the wall 76 to be horizontal for accurate measurement by an operator looking down so as to be free from the flow into the manhole.

The bracket 140 is generally shaped in cross section as a U facing on its side so as to provide a front surface and side wings which may be fastened by bolts to the wall 76, such as by the bolts 150A and 150B or by any other convenient fasteners and thus support a pivot point and locking screws (not shown in FIGS. 2 and 3) as well as the adjustable clamps 142 and 144 (FIG. 2).

In FIG. 4, there is shown another exploded perspective view of the gate position sensing system 20, the gate control assembly 64, and the gate assembly 62 as they are mounted together. As shown in this figure, the gate housing 74 includes a plurality of disassemblable sections 74A, 74B, and 74C to permit ready access to the gate assembly 62, gate position sensing system 20 and gate control assembly 64.

To support the gate assembly 62, the gate position sensing system 20, and the gate control assembly 64, the gate assembly 62 is mounted to the housing 74 by yokes 96A and 96B and the gate position sensing system 20 is mounted to the gate control assembly 64 by brackets 160 and 162 and to the housing 74 by bracket 164. The brackets and portions of the housing are held together by conventional screws, bolts, nuts and pins such as those shown at 166A-166F.

To seal a conductor 124 when not electrically connected and to provide a socket for connecting electrical wires, a connector 180 fits within the housing member 74B so that it may be sealed when not connected to a cable by cap 182. Similarly, the pneumatic conduit 110 for energizing the piston and thus the shaft 102 communicates with a connector 184 for connection to an external pneumatic tube. In the preferred embodiment, one connector is used for both pneumatic and electrical connectors.

Figure 5:
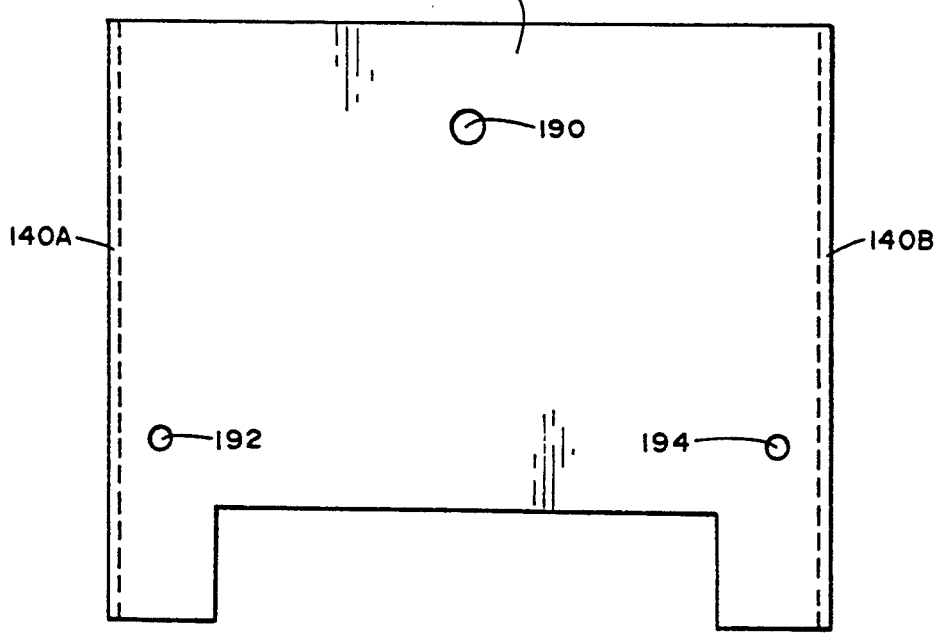
FIG. 5 is a front elevational view of a portion of an adjustable mounting means for clamping the apparatus of FIG. 3 to a flow path.

In FIG. 5, there is shown a plan view of the bracket 140 of the adjustable mounting clamping unit 44 (FIG. 2) having a front surface 140C side portions 140A and 140B, a central pivot hole 190 in the front surface 140C about which the first and second adjustment clamps pivot and holes 192 and 194 adapted to receive wing nuts for tightening the first and second adjustable clamps 142 and 144 (FIG. 2) in place to hold the flow path housing level. The side portions 140A and 140B are used for mounting to the housing walls 76 (not shown in FIG. 5).

In FIG. 6, there is shown the front elevational view of the rear adjustment plate 142 (left expandable clamp) having a pivot hole 200, right and left wing nut slots 202 and 204, a detent at 206 and a curved clamping plate 146. The pivot hole 200 is positioned to be aligned with the bracket pivot hole 190 (FIG. 5) in the bracket plate 140 (FIG. 5), the wing nut slots 202 and 204 are adapted to be slideably aligned with the wing nut holes 192 and 194 (FIG. 5) in the bracket plate 140 (FIG. 5) for pivotable adjustment about the pivot hole 200 and the detent at 206 is adapted to extend through the front bracket plate 144 (FIG. 2) for adjustment of the two plates with respect to each other. The curved clamp portion 146 has a radius of curvature similar to the pipe 46 and is adapted to adjustably clamp it so that the flow bed housing is mounted thereto as adjustable by the right and left adjustment clamps.

In FIG. 7, there is shown a front elevational view of the front adjustment clamp 144 (right expansion clamp) having a pivot hole 210, first and second wing nut slots 212 and 214, detent 216 and detent openings 218 and 220. The pivot hole 210 is adapted to be aligned with the pivot holes 190 (FIG. 5) in the bracket 140 (FIG. 5) and pivot hole 200 (FIG. 6) in the rear adjustment clamp 142 for pivoting of the adjustment clamps to an expanded position to release the pipe 46 or contract its position against each other to grip the pipe 46. The wing nut slots 212 and 214 are adapted to correspond with the wing nuts 202 (FIG. 6) and 204 (FIG. 6) in the rear adjustment clamp 142 and the wing nut holes 192 (FIG. 5) and 194 (FIG. 5) in the bracket 140 to permit adjustment and eventually tightening of the wing nuts so that the two plates may move with respect to each other and the bracket and then be tightened in place by wing nuts.

The detent 216 includes a tapped hole 217 adapted to receive a threaded stud for threading downwardly over the square opening 218 through which the detent 206 (FIG. 6) of the left clamp 142 passes so that the threaded stud may push the detent 206 to move it with respect to the detent 216 and thus pivot the clamping members from each other. The detent opening 220 is a blank hole but may be used to mount another detent combination if desired. It is formed during the die cutting operation. On the left hand side of the front plate 144 is a curved clamping bracket 219 complimentarily formed with a curved clamping plate 146 (FIG. 6) to hold the pipe 46 therein between.

In FIG. 8, there is shown an exploded side view of the clamping unit 44 having the front adjustable clamping plate 144, the rear adjustable clamping plate 142 and the bracket 140 shown in position with a pivot bolt first washer, second washer and nuts 220, 222, 224 and 226 respectively shown positioned to engage the pivot holes 190 (FIG. 5), 200 (FIG. 6) and 210 (FIG. 7) respectively to permit pivoting of the clamping plates 144 and 142 with respect to each other. This motion of the clamping plates 144 and 142 positions the curved bracket plates 146 (FIG. 6) and 219 (FIG. 7) on opposite sides of the pipe 46 (FIG. 2).

One of the two wing nut assemblies, each of which includes a combination such as a threaded shaft or bolt 230, washer 232 and wing nut 234 as shown with the threaded shaft or bolt 230 engaging the bracket 140 and extending through the plates 142 and 144. By tightening the wing nut 234 to press the washer 232 tightly sandwiching the plates 142 and 144 and the bracket 140 therebetween, the pivotable plates are held in place. Upper detent 206 on the rear plate 142 is positioned to extend through an opening in plate 144 to position it below the detent 216 where the adjustment screw 240 threaded through the detent 216 pressed against it to pivot the plates apart. With this arrangement, convenient adjustments may be made from above by the adjustment screw 240.

In FIG. 9, there is shown a simplified perspective view of the sampler 38 (FIG. 1) having a cable 250, a conduit 252, a pump 254, a control circuit 256, and a sample collecting system 260. The cable 250 connects the sampler 38 (FIG. 1) to the central control system 40 (FIG. 1). The conduit 252 communicates with the liquid sampler inlet system 26 (FIGS. 1–4) through the peristaltic pump 254 which pumps samples to the sample collecting system 260 under the control of the control circuit 256 and a liquid interface detector 262.

This sampler is substantially the same as the sampler disclosed in U.S. Pat. No. 4,415,011 granted Nov. 15, 1983 to Douglas M. Grant, the disclosure of which is incorporated herein by reference. Samples may be initiated by a signal from a central control system or may operate under the control of a separate timer. While a specific embodiment of a pump is disclosed, the nature of the pump itself is not part of the invention but only its combination with the gate assembly that permits effective drawing of samples.

In FIG. 10, there is shown a block diagram of another embodiment of remote station 14A similar to the embodiment 14 of FIG. 1 having an electronic portion 270 and an air portion 272. The embodiment 14A performs the same functions as the embodiment 14 of FIG. 1 but utilizes a standard microprocessor and a standard LVDT. The program used in it is attached hereto as Attachment A and flow diagrams in accordance therewith comprise FIGS. 12–26 to be described hereinafter.

The electronic portion 270 includes as its principal parts, a microprocessor 280, an input output section 282, certain interfaces 284, an analog to digital conversion section 286 and a LVDT control section 288. All of these sections communicate with the microprocessor 280 through a central bus 289 so that the microprocessor 280 can; (1) provide signals to the interface section 284; and (2) receive programming and data from and provide signals to the input-output circuits 282. Similarly, the analog to digital conversion section 286 serves as an interface for the microprocessor 280 and other units, being connected to the air portion 272 to receive analog pressure signals representing depth and to the LVDT control system 288 to receive buffered analog signals indicating gate position.

To provide as a centralized source of calculations and control operations, the microprocessor 280 includes a CPU (central processing unit) 290, a program memory 292 and a data memory 294. These units function together to make calculations and perform control operations. The program memory 292 includes inter alia a look-up table capable of providing flow rates in response to depth information and gate position information under the control of the central processing unit 290. The input-output circuits 282 receive information from a keypad 296, supply signals to certain drivers 298 for driving a plotter 304 in a manner known in the art, and receive and transmit signals from and to the microprocessor 280.

The interfaces 284 include buffering interfaces to provide signals received by it from the computer unit 280 to the sampler, the remote plotter and any other units that it may be desirable to communicate with but which require buffering different than that provided by the input-output circuits 282. The analog to digital conversion section 286 includes two analog to digital converters 300 and 302, one of which is connected to receive analog signals from the LVDT control 288 which receives analog signals from the gate position sensing system 20 and buffers them for application to the analog to digital converter 302 and the other of which receives signals from the air portion 272 indicating pressure upon the depth sensing system 24 (FIG. 1). These units communicate with a display 306 to display data, with the computer system 280 for calculations and with the input-output circuits 282 for operating the driver 298 and plotter 304.

The central processing unit 290, in the preferred embodiment, is a Hitachi America, Ltd, Number HD64180RCP-6X available from the Hitachi America Ltd., Semi-Conductor and IC Division, 2210 O'Toole Ave., San Jose, Calif. 95131. This is an 8-bit microprocessor referred to as a HD64180 8-bit Microprocessor. The LVDT is an AC-AC Displacement Transducer Series 280 sold by TRANSTEK, Inc., P.O. Box 338, Route 83, Ellington, Conn. 06029 and is sold under Catalog Number 0283-0007.

The air portion 272 includes an air pump 310, an air reservoir 312, gate control valves 314, bubbler control valve 316, purge valve 317, an air restrictor 318 and a pressure sensor 320. The air pump 310 supplies air under pressure to reservoir 312 through a conduit 322 in response to signals received over an electrical conductor 324 from the input-output circuits 282. Pressure is supplied by the reservoir 312: (1) directly to the control valves 314 for the gate positioning control system 30 for positioning the gate assembly 62; and (2) through a restrictor 318 for operating a bubbler that includes a port 24 (FIGS. 1, 2 and 4). Valve 316 connects the pressure sensor 320 to atmosphere through conduit 329 for calibration or in another position to the bubbler port and restrictor to sense pressure. Valve 317 when opened connects the reservoir to the bubbler port for a speed up super bubble. This valve may also be used for purging by holding it open for a longer time.

To position the gate assembly 62, the gate assembly is moved and held: (1) down by applying pressurized air from the reservoir 312 to the compartment above piston 106 (FIG. 2) through a first conduit 326 by pulsing one of the valves 314 with a signal on conductor 324; and (2) upward by venting air to atmosphere through the other valve 314 to a conduit 328, in which case, the spring 108 (FIG. 2) moves the gate assembly 62 (FIG. 2) upwardly to the new position established by pressure in the reservoir above the piston 106. This motion causes the LVDT to provide a new signal to the control unit 288 as feedback for controlling the position of the gate assembly 62.

To calibrate the pressure sensor 320, the valve 316 is mounted near the pressure sensor 320. To free the system from losses that vary with tube length, the restrictor is connected near the bubbler port 24 in the housing of the gate assembly. The valve 316: (1) is activated to vent the tube 252 to atmosphere through a conduit 329 in one position for calibration; and (2) to connect line 252 from the outlet of the restrictor 318 and outlet port 24 to conduit 251 to apply pressure representative to sensor 320 which in turn supplies an electrical signal on conductor 330 to the analog to digital converter 300.

The restrictor 318 in the preferred embodiment is mounted in the housing of the local station so that it is near the bubbler outlet port 24 and the pressure applied to the pressure sensor 320 is not affected by the length of bubbler tube extending to a location near or in the remote station. This bubbler tube may be long and may thus introduce pressure errors from resistance in the bubbler tube is between the pressure controlling restrictor and the port 24.

While in the preferred embodiment, the restrictor is mounted in the housing, it could be mounted at some other short distance from the port 24 if this is convenient. For example, it could be mounted within 10 or 15 feet of the port. By mounting this restrictor close to the port, a smaller diameter air tube can be used for the bubbler and this permits the air tube to fit within a small connector along with the air tube for controlling the gate control mechanism and the electrical conductors because the pressure drop in the tube can be compensated.

In FIG. 11, there is shown a simplified, exploded sectional view of a portion of the flow cross section control system 22 showing the diaphram 106, the piston 105, the upper part of the piston chamber 114, and the air conduit 110 as its principal parts. As shown in this view, the rolling diaphram 106 fits over the piston 105 with the shaft 102 fitting within the piston 105 and being tightened there against by the nut 107 which holds the washer 109 against the top of the diaphram 106 and presses the top of the diaphram 106 sealingly against the piston to prevent leakage. The shaft 102 has mounted to it a core member 111 that cooperates with the LVDT to indicate the amount of motion of the piston shaft or rod 102 as it moves with the piston 105.

The air conduit 110 communicates with the upper part of the chamber wall 114 through an air conduit 113 that opens into this chamber so that, when air is applied under pressure, it moves the diaphram 106 downwardly, moving the piston 105 and the piston rod 102 down so as to change the position of the gate assembly 62. Similarly, when air pressure is reduced through the conduit 110 the spring 102 moves the piston upwardly to a new position. The diaphragm 106 is a rolling diaphragm which may be purchased from any of a number of commercial sources for this purpose such as Bellofram, at 30 Blanchard Rd., Burlington, Mass. U.S.A.

In operation, the remote station 14 and the flow-stream local station 12 are brought to a site, such as a manhole or the like. The air and electrical conduits are connected and the bladder 80 (FIG. 2) is deflated and the flow housing 60 (FIG. 2) is inserted into the pipe 46 (FIG. 2). The bladder is then inflated to grip the inside of the pipe 46 (FIG. 2) and the adjustable mounting unit 44 (FIG. 2 and FIGS. 5-8) is then adjusted or leveled.

To level the local station along its right to left axis, the clamping plates 140 and 142 are pivoted so that they hold the gate housing 74 horizontally with the end of the pipe housing abutting the outer plates or being adjacent thereto but leaving sufficient room for their adjustment. Leveling is accomplished by turning the bolt 240 (FIG. 8) or its counterpart on the opposite side while holding the unit so that the bubble is aligned along its right to left centerline. The wing nuts 234 are then tightened.

To level the local station along its front to back axis, screws 150A-150D (FIG. 3) are loosened and the housing lifted until the bubbler level 156 (FIG. 3) indicates that the flow path is level. The screws 150A-150D are then tightened. The bladder 80 may be further inflated by pumping air through the tube 82 (FIG. 2) to seal against the flow and the leveling process repeated. It is desirable to check the bubbler level 156 and readjust the flow bed if it is now off-center.

The housing is generally assembled prior to installation but, under some circumstances, the flow bed may not be used and the gate assembly 62, the gate control assembly 64 and the gate position sensing system 20 are mounted directly to the pipe 46 without its own flow bed. To enable easy disassembly and assembly, a plurality of guides, such as those shown at 346 (FIGS. 3 and 4), cooperate for easy alignment. Brackets 348 and 350 provide support for convenient mounting of the gate control and gate sensing assemblies 20 and 64. Of course, such guides are not necessary and other aides to assemble may be used. The bracket 164 is mounted to the housing 74 and to the gate position sensing unit in such a way as to permit pivoting as the gate assembly moves.

The equipment is built so that it may be easily assembled and disassembled by such guides and by fasteners. This is done so that the flow meter may be used in different manners, such as for example: (1) an arrangement in which the flow housing and gate housing are permanently attached either with a controller that is dedicated to the combination or with a single controller being moved from site to site; (2) an arrangement in which the flow housing and gate housing are permanently attached to each other but are moved from site to site; and (3) the flow and gate housings are used independently of each other with one of them being installed and the other moved.

After the local station is mounted in place to the pipe 46 (FIG. 2) and leveled using the adjustable mounting means 44 and bubble level 156 (FIG. 3), it is calibrated. For convenience in calibration and as a safety measure, the gate assembly 62 is restricted in its movement so that at the limits of its movement it can be easily calibrated and it does not extend beyond those limits in a manner that could cause damage. A lower stop is provided at which point gate assembly 62 is at its lowest position to create the maximum head. At this point, the gate assembly 62 impinges upon a stop 360 (FIG. 2) mounted to a downwardly extending portion of the wall of the housing. An upper stop is provided at the uppermost retracted position of the gate assembly 62 where there is no obstruction of the flow path. At this point, the gate impinges upon an upper stop 362 (FIG. 2).

While downwardly extending walls are used to mount stops to the gate in the preferred embodiment, stops may be mounted elsewhere such as on the piston shaft 102 (FIG. 2) or piston 106 (FIG. 2) or elsewhere where there are moving parts. Thus, when the gate is against the stop and cannot move further, the electrical apparatus can be zeroed, either at the appropriate minimum or maximum limit for calibration purposes.

For one method of calibration, the electronic portion of the remote station is calibrated to zero when the gate is at one of its two stops and at full scale when it is at its other. However, in the preferred embodiment, the gate 62 is closed by the gate cross section control against a gauge block placed on a flat surface 130 (FIG. 3) prior to use of the flow meter. The gate position sensing system 20 then stores the gate position for that gauge block. A series of gauge blocks may be used to provide a profile.

Even though a stop 360 (FIG. 2) is used to restrict movement of the gate assembly 62, it is possible to place the stop elsewhere and to raise the wall thus removing the stop so that the gate may be used to measure flow in either direction. Some minor modifications in the gate assembly 62 would be needed for convenient movement, but since there are many different level and expansion arrangements, it is well within the skill of a person of ordinary skill in the art to make such changes.

The bubbler may be periodically corrected for drift by incorporating an electrically-controlled valve in the line to: (1) close the line to water; (2) open the portion of the line communicating with the high pressure side of the pressure-to-electrical transducer to atmosphere while the low pressure side is at atmospheric pressure to develop a zero signal for calibration; and (3) to connect the high pressure side of the transducer to atmosphere through the valve 316. A check valve may be used to prevent the air from flowing from the bladder 80 back to the reservoir (FIG. 10) and prevent the inflow of water as it depressurizes.

To use the variable gate apparatus 10 (FIG. 1), some preliminary data or information related to the calculations are needed. It is possible to correlate mathematically the flow cross section through an unobstructed conduit with the cross section as changed by the gate and the head of pressure upstream of the gate and downstream of the gate together with angle of the flow path and roughness coefficient of the flow path with a flow rate and these may be obtained from a knowledge of the equipment being used and its manner of installment. A computer can make such calculations based on instantaneous measurements and a recording of the roughness coefficient and angle of the flow path. The well-known Manning equation is useful but there are also well-known equations for weirs and the like which can be used since this apparatus may in some ways be likened to a weir with an adjustable gate.

However, in the preferred embodiment, a look-up table has been constructed which correlates gate position and depth upstream of the gate (head of pressure) with the flow rate. This table has been constructed by adjusting the gate and making measurements using a weigh tank and timer to arrive

TABLE 1

GATE = 0.0

| HEAD Inches | FLOW Gallons Per Minute |
|---|---|
| 1.225 | 0.4942 |
| 1.735 | 0.9558 |
| 2.650 | 1.9186 |
| 3.755 | 3.0196 |
| 5.145 | 4.5570 |
| 6.805 | 6.1836 |
| 20.460 | 19.5831 |
| 20.465 | 19.5831 |
| 20.470 | 19.5831 |
| 20.475 | 19.5831 |

TABLE 2

GATE = 0.053

| HEAD Inches | FLOW Gallons Per Minute |
|---|---|
| 0.940 | 0.4942 |
| 1.220 | 0.9558 |
| 1.935 | 1.9186 |
| 2.810 | 3.0196 |
| 4.125 | 4.5570 |
| 4.830 | 6.1836 |
| 6.240 | 7.8852 |
| 20.465 | 25.0707 |
| 20.470 | 25.0707 |
| 20.475 | 25.0707 |

TABLE 3

GATE = 0.073

| HEAD Inches | FLOW Gallons Per Minute |
|---|---|
| 0.865 | 0.4942 |
| 1.095 | 0.9558 |
| 1.625 | 1.9186 |
| 3.415 | 4.5570 |
| 4.630 | 6.1836 |
| 5.620 | 7.8852 |
| 20.460 | 33.4271 |
| 20.465 | 33.4271 |
| 20.470 | 33.4271 |
| 20.475 | 33.4271 |

TABLE 4

GATE = 0.099

| HEAD Inches | FLOW Gallons Per Minute |
|---|---|
| 0.795 | 0.4942 |
| 0.970 | 0.9558 |
| 1.425 | 1.9186 |
| 1.960 | 3.0196 |
| 2.995 | 4.5570 |
| 4.000 | 6.1836 |
| 4.955 | 7.8852 |
| 6.255 | 11.5798 |
| 20.470 | 52.0071 |
| 20.475 | 52.0071 |

TABLE 5

GATE = 0.133

| HEAD Inches | FLOW Gallons Per Minute |
|---|---|
| 0.755 | 0.4942 |
| 0.890 | 0.9558 |
| 1.245 | 1.9186 |
| 1.645 | 3.0196 |
| 3.170 | 6.1836 |
| 4.100 | 7.8852 |
| 5.180 | 9.6494 |
| 6.210 | 13.2091 |
| 20.470 | 62.5268 |
| 20.475 | 62.5268 |

TABLE 6

GATE = 0.172

| HEAD Inches | FLOW Gallons Per Minute |
|---|---|
| 0.845 | 0.9558 |
| 1.140 | 1.9186 |

TABLE 6-continued

GATE = 0.172

| HEAD Inches | FLOW Gallons Per Minute |
|---|---|
| 1.435 | 3.0196 |
| 1.995 | 4.5570 |
| 2.600 | 6.1836 |
| 3.365 | 7.8852 |
| 4.280 | 9.6494 |
| 5.470 | 11.8968 |
| 6.655 | 15.3332 |
| 20.475 | 55.4242 |

TABLE 7

GATE = 0.230

| HEAD Inches | FLOW Gallons Per Minute |
|---|---|
| 1.280 | 3.0196 |
| 2.145 | 6.1836 |
| 2.770 | 7.8852 |
| 3.525 | 9.6940 |
| 5.060 | 13.2932 |
| 6.275 | 16.8211 |
| 20.460 | 58.0676 |
| 20.465 | 58.0676 |
| 20.470 | 58.0676 |
| 20.475 | 58.0676 |

TABLE 8

GATE = 0.297

| HEAD Inches | FLOW Gallons Per Minute |
|---|---|
| 1.455 | 4.5570 |
| 1.810 | 6.1836 |
| 2.175 | 7.8852 |
| 2.770 | 9.6494 |
| 3.555 | 11.8968 |
| 4.070 | 13.2932 |
| 5.120 | 16.3444 |
| 6.640 | 21.2070 |
| 6.825 | 21.4622 |
| 20.475 | 62.4498 |

TABLE 9

GATE = 0.372

| HEAD Inches | FLOW Gallons Per Minute |
|---|---|
| 1.595 | 6.1836 |
| 1.915 | 7.8852 |
| 2.320 | 9.6494 |
| 2.900 | 11.8968 |
| 3.325 | 13.2932 |
| 4.230 | 16.3444 |
| 5.455 | 21.1145 |
| 6.780 | 24.8283 |
| 7.525 | 27.2140 |
| 20.475 | 68.6996 |

TABLE 10

GATE = 0.473

| HEAD Inches | FLOW Gallons Per Minute |
|---|---|
| 1.440 | 6.1836 |
| 1.650 | 7.8852 |
| 1.865 | 9.6494 |
| 2.245 | 11.8968 |

TABLE 10-continued

GATE = 0.473

| HEAD Inches | FLOW Gallons Per Minute |
|---|---|
| 2.525 | 13.2932 |
| 3.335 | 16.3444 |
| 4.345 | 21.1145 |
| 5.890 | 27.3200 |
| 7.400 | 32.5750 |
| 20.475 | 78.0951 |

TABLE 11

GATE = 0.586

| HEAD Inches | FLOW Gallons Per Minute |
|---|---|
| 1.555 | 7.8852 |
| 1.710 | 9.6494 |
| 1.960 | 11.8968 |
| 2.235 | 13.2932 |
| 2.820 | 16.3444 |
| 3.520 | 21.1145 |
| 5.860 | 27.6350 |
| 7.095 | 32.6340 |
| 7.645 | 37.0070 |
| 20.475 | 39.2580 |

TABLE 12

GATE = 0.709

| HEAD Inches | FLOW Gallons Per Minute |
|---|---|
| 1.550 | 9.6494 |
| 1.795 | 11.8968 |
| 1.945 | 13.2932 |
| 2.300 | 16.3444 |
| 2.895 | 21.3230 |
| 3.870 | 27.6440 |
| 4.795 | 32.7420 |
| 6.010 | 39.0020 |
| 7.785 | 46.8940 |
| 20.475 | 103.3384 |

TABLE 13

GATE = 0.843

| HEAD Inches | FLOW Gallons Per Minute |
|---|---|
| 1.690 | 11.8012 |
| 2.120 | 16.5317 |
| 2.585 | 21.2380 |
| 3.270 | 27.6440 |
| 4.015 | 32.8620 |
| 5.015 | 39.1560 |
| 6.330 | 47.2190 |
| 8.205 | 56.0820 |
| 20.470 | 114.1051 |
| 20.475 | 114.1051 |

TABLE 14

GATE = 0.988

| HEAD Inches | FLOW Gallons Per Minute |
|---|---|
| 1.975 | 16.3444 |
| 2.365 | 21.2100 |
| 2.935 | 27.5460 |
| 3.445 | 32.8660 |
| 4.245 | 39.2420 |
| 5.300 | 47.4380 |

TABLE 14-continued

GATE = 0.988

| HEAD Inches | FLOW Gallons Per Minute |
|---|---|
| 6.725 | 56.6910 |
| 8.620 | 67.4060 |
| 10.520 | 76.6020 |
| 20.475 | 124.8084 |

TABLE 15

GATE = 1.143

| HEAD Inches | FLOW Gallons Per Minute |
|---|---|
| 2.195 | 21.1145 |
| 2.675 | 27.3650 |
| 3.110 | 32.8330 |
| 3.690 | 39.1690 |
| 4.660 | 48.1870 |
| 5.690 | 56.6770 |
| 7.140 | 67.9510 |
| 8.480 | 76.4380 |
| 10.675 | 88.2300 |
| 20.475 | 140.9045 |

TABLE 16

GATE = 1.308

| HEAD Inches | FLOW Gallons Per Minute |
|---|---|
| 2.365 | 27.8920 |
| 3.345 | 39.2160 |
| 4.060 | 48.1410 |
| 4.965 | 56.8600 |
| 6.085 | 67.9570 |
| 7.250 | 77.3600 |
| 7.985 | 83.5800 |
| 8.780 | 89.2310 |
| 10.635 | 104.5320 |
| 20.475 | 172.3966 |

TABLE 17

GATE = 1.483

| HEAD Inches | FLOW Gallons Per Minute |
|---|---|
| 3.095 | 39.1150 |
| 3.680 | 47.7920 |
| 4.400 | 56.8550 |
| 5.345 | 68.6140 |
| 6.235 | 77.7480 |
| 6.835 | 83.6510 |
| 7.470 | 90.1600 |
| 8.945 | 106.7150 |
| 10.990 | 120.7420 |
| 20.475 | 185.8355 |

TABLE 18

GATE = 1.669

| HEAD Inches | FLOW Gallons Per Minute |
|---|---|
| 3.395 | 48.0450 |
| 4.035 | 56.9560 |
| 4.775 | 68.4810 |
| 5.495 | 77.5830 |
| 6.020 | 84.1080 |
| 6.465 | 89.7600 |
| 7.695 | 105.8150 |
| 9.305 | 121.6120 |

TABLE 18-continued

GATE = 1.669

| HEAD Inches | FLOW Gallons Per Minute |
|---|---|
| 11.520 | 139.8620 |
| 20.475 | 213.6859 |

TABLE 19

GATE = 1.866

| HEAD Inches | FLOW Gallons Per Minute |
|---|---|
| 3.015 | 47.7520 |
| 3.720 | 56.8390 |
| 4.340 | 68.4540 |
| 4.950 | 77.6930 |
| 5.415 | 83.7110 |
| 6.080 | 96.5500 |
| 6.710 | 106.4120 |
| 9.795 | 140.4580 |
| 12.070 | 160.6100 |
| 20.475 | 235.1059 |

TABLE 20

GATE = 2.074

| HEAD Inches | FLOW Gallons Per Minute |
|---|---|
| 4.010 | 68.5500 |
| 4.525 | 77.7790 |
| 4.890 | 83.8590 |
| 5.210 | 89.2790 |
| 5.520 | 97.2102 |
| 5.990 | 105.9830 |
| 7.015 | 122.7260 |
| 10.300 | 163.2900 |
| 12.435 | 183.6870 |
| 20.475 | 259.1155 |

TABLE 21

GATE = 2.293

| HEAD Inches | FLOW Gallons Per Minute |
|---|---|
| 4.100 | 77.7720 |
| 4.465 | 84.0090 |
| 4.755 | 89.3210 |
| 5.015 | 97.6988 |
| 5.435 | 105.4170 |
| 6.270 | 122.4618 |
| 8.875 | 166.7375 |
| 10.565 | 188.9430 |
| 12.405 | 206.8650 |
| 20.475 | 285.5172 |

TABLE 22

GATE = 2.486

| HEAD Inches | FLOW Gallons Per Minute |
|---|---|
| 4.620 | 98.3247 |
| 5.040 | 104.3350 |
| 5.780 | 121.4438 |
| 6.675 | 143.5430 |
| 7.875 | 166.6070 |
| 9.360 | 189.6480 |
| 10.875 | 209.6490 |
| 13.145 | 239.5890 |
| 13.410 | 250.3600 |

TABLE 22-continued

GATE = 2.486

| HEAD Inches | FLOW Gallons Per Minute |
|---|---|
| 20.475 | 537.7221 |

TABLE 23

GATE = 2.687

| HEAD Inches | FLOW Gallons Per Minute |
|---|---|
| 5.365 | 121.0845 |
| 6.115 | 143.3739 |
| 7.015 | 166.7570 |
| 9.555 | 210.2960 |
| 11.495 | 239.3090 |
| 11.715 | 242.7200 |
| 20.460 | 378.6173 |
| 20.465 | 378.6173 |
| 20.470 | 378.6173 |
| 20.475 | 378.6173 |

TABLE 24

GATE = 2.898

| HEAD Inches | FLOW Gallons Per Minute |
|---|---|
| 5.650 | 143.1130 |
| 6.400 | 166.4600 |
| 8.485 | 213.1688 |
| 10.060 | 241.7350 |
| 10.295 | 245.0530 |
| 12.575 | 295.1650 |
| 20.460 | 469.2704 |
| 20.465 | 469.2704 |
| 20.470 | 469.2704 |
| 20.475 | 469.2704 |

TABLE 25

GATE = 3.074

| HEAD Inches | FLOW Gallons Per Minute |
|---|---|
| 5.940 | 165.6120 |
| 6.655 | 187.5380 |
| 7.720 | 215.6280 |
| 11.220 | 284.5830 |
| 13.720 | 340.8720 |
| 20.455 | 493.0774 |
| 20.460 | 493.0774 |
| 20.465 | 493.0774 |
| 20.470 | 493.0774 |
| 20.475 | 493.0774 |

TABLE 26

GATE = 3.258

| HEAD Inches | FLOW Gallons Per Minute |
|---|---|
| 6.075 | 188.1180 |
| 7.085 | 215.2590 |
| 8.425 | 247.3200 |
| 10.145 | 287.1820 |
| 12.265 | 348.5370 |
| 14.165 | 384.5890 |
| 20.460 | 504.4144 |
| 20.465 | 504.4144 |
| 20.470 | 504.4144 |
| 20.475 | 504.4144 |

TABLE 27

GATE = 3.450

| HEAD Inches | FLOW Gallons Per Minute |
|---|---|
| 7.675 | 249.3770 |
| 9.025 | 286.0820 |
| 10.945 | 344.5130 |
| 12.590 | 389.6930 |
| 15.045 | 447.1190 |
| 20.455 | 574.2448 |
| 20.460 | 574.2447 |
| 20.465 | 574.2447 |
| 24.970 | 574.2447 |
| 20.475 | 574.2447 |

TABLE 28

GATE = 3.650

| HEAD Inches | FLOW Gallons Per Minute |
|---|---|
| 6.865 | 249.5500 |
| 8.380 | 290.6870 |
| 9.900 | 338.2120 |
| 11.295 | 392.9270 |
| 13.425 | 445.0250 |
| 15.870 | 494.3395 |
| 19.205 | 569.9960 |
| 20.465 | 598.9201 |
| 20.470 | 598.9201 |
| 20.475 | 598.9201 |

TABLE 29

GATE = 3.860

| HEAD Inches | FLOW Gallons Per Minute |
|---|---|
| 8.865 | 340.2440 |
| 10.015 | 393.1670 |
| 11.695 | 450.7050 |
| 13.755 | 501.7390 |
| 16.810 | 577.2370 |
| 20.455 | 667.9334 |
| 20.460 | 667.9334 |
| 20.465 | 667.9334 |
| 20.470 | 667.9334 |
| 20.475 | 667.9334 |

TABLE 30

GATE = 4.082

| HEAD Inches | FLOW Gallons Per Minute |
|---|---|
| 9.965 | 392.4900 |
| 11.630 | 454.6340 |
| 13.650 | 508.5350 |
| 16.520 | 568.6760 |
| 20.450 | 651.6580 |
| 20.455 | 651.6580 |
| 20.460 | 651.6580 |
| 20.465 | 651.6580 |
| 20.470 | 651.6580 |
| 20.475 | 651.6580 | at values corresponding to different positions of the gate and different depths of head. This look-up table is shown in Tables 1–30 herein, and is used by the controller to provide data concerning the flow rate in response to received signals from the gate sensing system 20 and depth sensing system 24. These coordinates are used in a well known manner to access data in the look-up table and provide a flow rate. Other look-up tables with greater accuracy or less accuracy or for modifications of the equipment can be constructed in a similar manner.

Once the look-up table is in place, the equipment can be operated in a number of modes to obtain flow measurement and to provide a simulated stilling well for drawing samples. In its operation, some benefits are obtained by maintaining a clean, flushed flow path and this can be conveniently automatically accomplished, if desired. For this purpose, the gate assembly 62 is periodically closed, a head of liquid created and then opened. The onrush of fluid clears the flow bed for the benefit of a bubbler port 24 (FIGS. 1-4) or for the sample port at 26.

The flow meter may operate in any of several modes, for example, the gate may be moved to maintain a predetermined constant head and the look-up table may utilize gate position at the predetermined head to determine flow rate. To accommodate many different flow rates, several such positions can be selected, each of which has a look-up table.

In an alternative mode of measurement, the gate may select incremental positions such as fully open in which equations for fully opened conduits can be used, or it can assume incremental positions appropriate for the flow rate to maintain a head well within the dynamic range of the measuring instruments and a look-up table can be used for that position and different depths, or for example, the gate may be changed in position and the rate of change of head and increase in head may be correlated with flow rate.

Another method of flushing and then measuring flows using a look up table is to fully close the gate to reduce flow to near zero. The upstream conduit will begin to fill, thus increasing the head. At a predetermined first head, the gate opens and flushes the line at velocities that can support a large amount of solids. As the conduit is flushed, the head drops. At a second predetermined head, the gate again closes to reduce flow to zero and refill the conduit. Such a method consumes more power in positioning the gate, but is more effective in especially low flow conduits that have excessive solids.

In this method of flow monitoring, the gate may be fully closed or almost closed while filling the conduit. When flushing and lowering the head, the ideal gate position is slightly into the flow stream although it may be also lifted out of the flow stream. The measurements of gate position and depth are at sufficiently frequent intervals and the look up table sufficiently detailed so that the readings during the closed gate and open gate positions can be plotted and measurements of flow rate that are not distorted by such fluctuation used or the time period of averaging can be selected to be large enough to average out the zero flow to high flow fluctuations.

Adaptive programs may be used to determine the number of increments that is most efficient in changing the positions of the gate. Moreover, additional corrections may be obtained by a downstream bubbler which is calibrated to provide correction for backing up of fluid downstream. In such use, a look-up table may compare both upstream and downstream water depth with gate position and correlate this with flow rate prior to use of the instrument. This provision at the cost of more equipment will provide more precise results.

The different modes of operation are each possible because, closing the gate assembly 62 relative to the flow path, causes the flow to "back-up" and the level of the liquid behind the multiple position gate assembly 62 to increase at a rate related to rate of flow of the fluid. Similarly, the raising of the gate opens the flow path and reduces its cross sectional blocking area, increasing the cross section of flow, causing the level of fluid to decrease at a flow rate related to the rate of flow of liquid in the pipe. Similarly, if the gate is moved to a fixed position and maintained in that position, the head will stabilize at a level related to the flow of fluid in the pipe 46. All of these factors may be utilized in determining the flow rate.

To move the multiple position gate assembly 62 in a direction which reduces the flow cross section, air is pumped into the chamber above the piston 106 causing it to move downwardly and stabilize at a location where the spring 108 and forces of upstream liquid counteract the pressure. Similarly, when the gate assembly 62 is to be opened, air is removed causing the spring 108 to move the piston 106 upwardly and thus moves the rod 102 upwardly. Any movement is sensed by the LVDT and the movement and new location are transmitted to the remote unit which may be used for correction of the location of the gate in some modes and/or directly calculate flow rate in other modes.

Moreover, there are several modes available for cooperation between the sampler and the electronics and air portions of the controller at the remote station. For example, sampling may be performed periodically in units of time. As the units pass, the gate assembly 62 may be closed to back up the liquid so that the depth at which sampling occurs is increased sufficiently for a sample which is above the inlet port for the entire time of sampling and the sample is thus more representative. A flush cycle may be performed before sampling, if desirable.

In another mode related to flow, flow rate may be determined and timed and when a predetermined amount of volume of liquid has passed, the gate may close to raise the volume to a sufficient height for an accurate sample. A flush mode may be performed before the closing of the gate if desirable. All of these modes may be easily programmed in the manner disclosed hereinafter.

In the event of failure, a positive force positioning the gate assembly 62 downwardly coupled with a helical spring biasing it upwardly provides a fail safe approach since the gate, in the event of failure is moved upwardly. As an alternative, the monitor can check battery values or periodically correlate the gate with the head or test motion at the gate and in the event of a fault, retract the gate.

Moreover, if power fails, a check valve will bleed air from above piston 106 back into the pressure line from air reservoir 312. As air flows from air reservoir 312 out bubbler tube 134, the pressure drops towards zero, thus dropping air pressure above piston 106 to zero. During normal operation, the pressure in reservoir 312 is greater than above piston 106 and thus no air flows through the check valve during normal operation.

Figure 12:
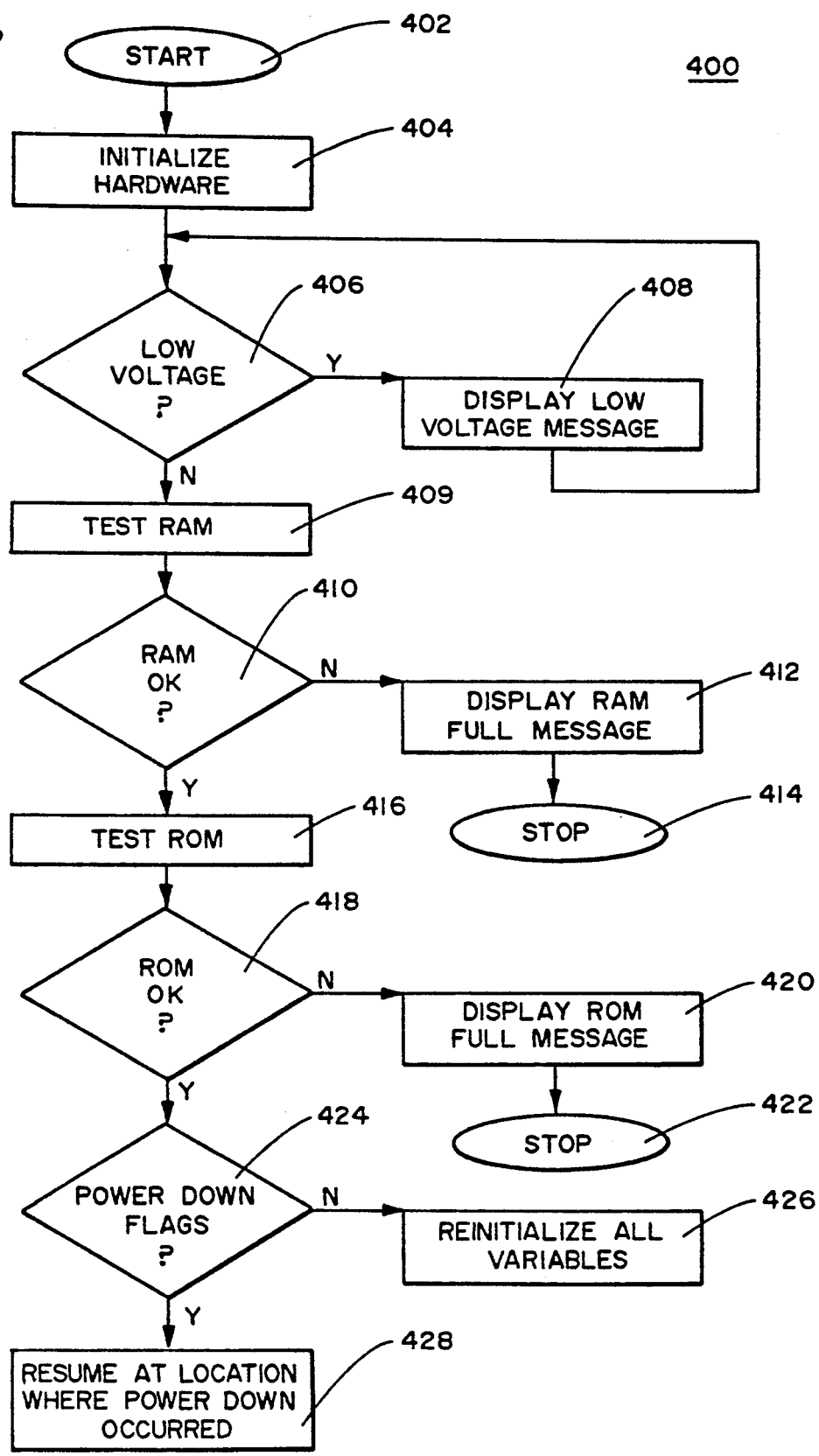
FIG. 12 is a flow diagram of a power up program sequence usable in the embodiment of FIG. 10.

FIG. 12 shows a flow diagram 400 of a power up sequence usable in the preferred embodiment of the invention in accordance with FIG. 10 and attachment A. In the flow diagram 400, the start step 402 is followed by an initializing step 404 initializing the hardware, followed by decision step 406 to determine if the voltage is low or high. Upon determination of a low voltage, the low voltage is displayed as indicated by the step 408 so that the battery may be changed or the like.

If the voltage is not low, the random access memory is tested as shown in step 409 and if the ram is faulty as indicated by the decision step 410, the fail message for the ram is displayed as indicated by the step 412 and the program stopped as indicated at 414. If the decision is that the ram is satisfactory, then the read only memory is tested as shown at 416 and the decision made as to whether it is faulty or not as shown by the step 418. If faulty, a fail message is displayed as indicated at step 420 and the program stopped as shown at 422. If it is satisfactory, a decision is made as to whether there are power down flags or not as shown at 424 and if not, the variables are all reinitiated as shown at 426. If there is a power down flag, then the power up sequence is restarted at the point at which the program was when the power failure occurred.

Figure 13:
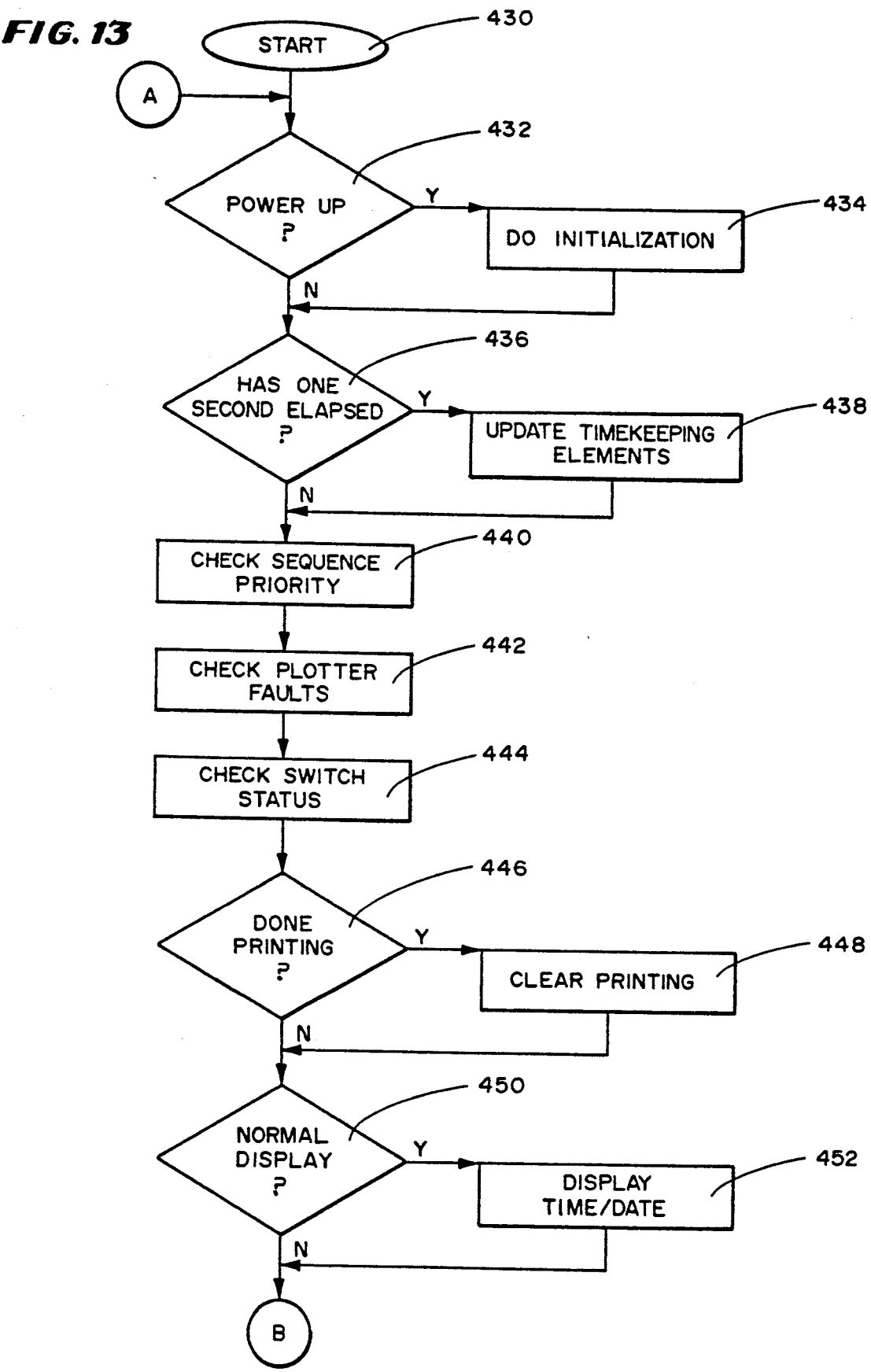
FIGS. 13-16 are flow diagrams of program sequences for a main loop program usable in the embodiment of FIG. 10.
Figure 14:
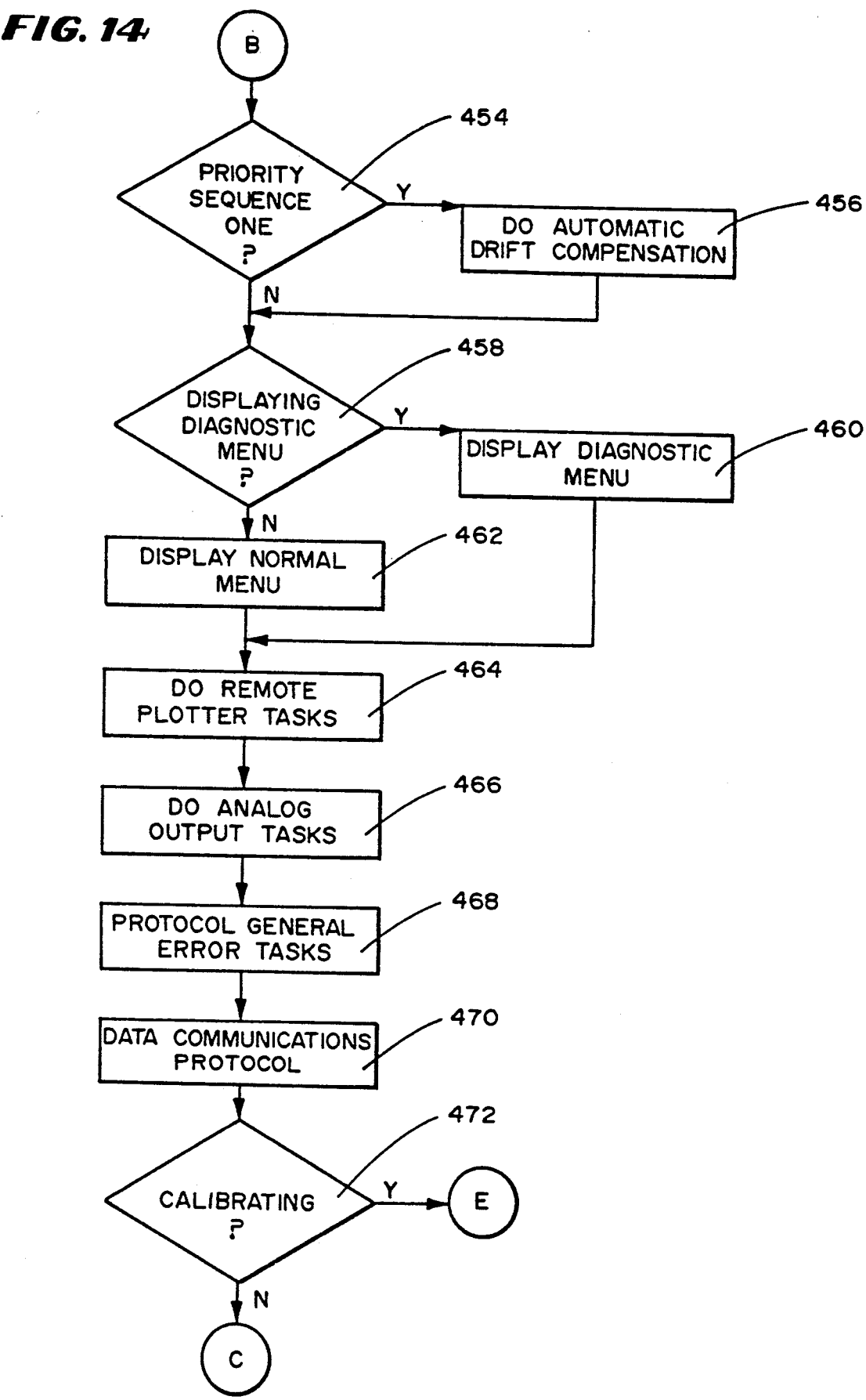
Figure 15:
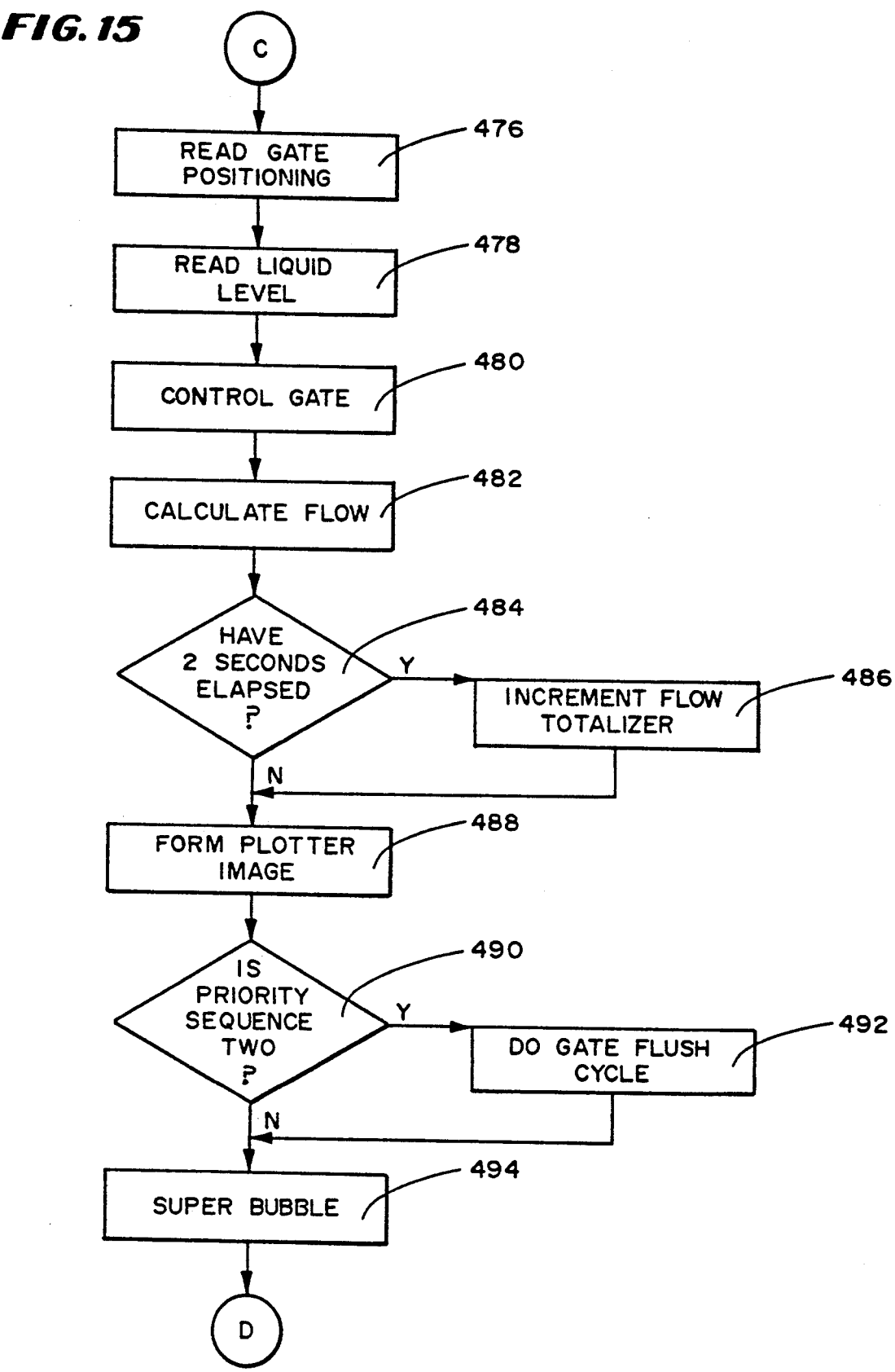

In FIGS. 13–16, there is shown a flow diagram of the main loop program including in FIG. 13, the start step 430, followed by the decision step for power up 432, which if it is yes is followed by the step of 434 for initialization and if no, goes to the step 436 to determine if one second has elapsed.

If one second has elapsed, then the time keeping elements are updated in the step 438, and if not, the sequence priority is checked at step 440. After the sequence priority is checked, the plotter is checked for faults at step 442, and after this, the switch status is checked at step 444. After the checks for plotter faults and for switch status condition, a printing decision is made at decision step 446.

If printing is completed, then the printer is cleared at step 448, and if not, a decision is made concerning a normal display at step 450. If the display is to be normal, the time and date are displayed at shown at step 452, if not, the program proceeds to step 454 shown in FIG. 14. Step 454 is a decision step to decide if the program sequence is a one. If it is, the program proceeds to step 456 for an automatic drift comprension, if not, a decision is made at step 458 about displaying the diagnostic menu. If it is to be displayed, the display is made at step 460, if it not to be displayed, as indicated by programming or at the keyboard, then the normal menu is displayed as shown at step 462.

After the displaying of the normal menu, any remote plotter tasks are performed as shown at step 464 followed by analog output tasks at step 466 followed by protocol general error tasks at 468 followed by data communications protocol at step 470 which is followed by a calibration decision at step 472. If a calibration step is in progress, the program proceeds to the calibration print request at step 474 in FIG. 16 and if not, it proceeds to step 476 in FIG. 15. Step 476 reads the gate position and is followed by a read liquid level step 478 which is followed by a control gate step 480 and a calculate flow step 482.

The calculate flow step 482 is followed by a decision 484 to determine if two seconds have elapsed. If they have, the step to increment the flow totalizer is performed at 486; otherwise, the step of forming the plotter image is performed at 488. After forming the plotter image, a decision is made as to the priority sequence two at decision step 490. If priority sequence two is to be followed, then a gate flush is performed at step 492. If it is not, then a clearing step is performed at the super bubble step 494 by increasing the pressure through the bubbler.

Figure 16:
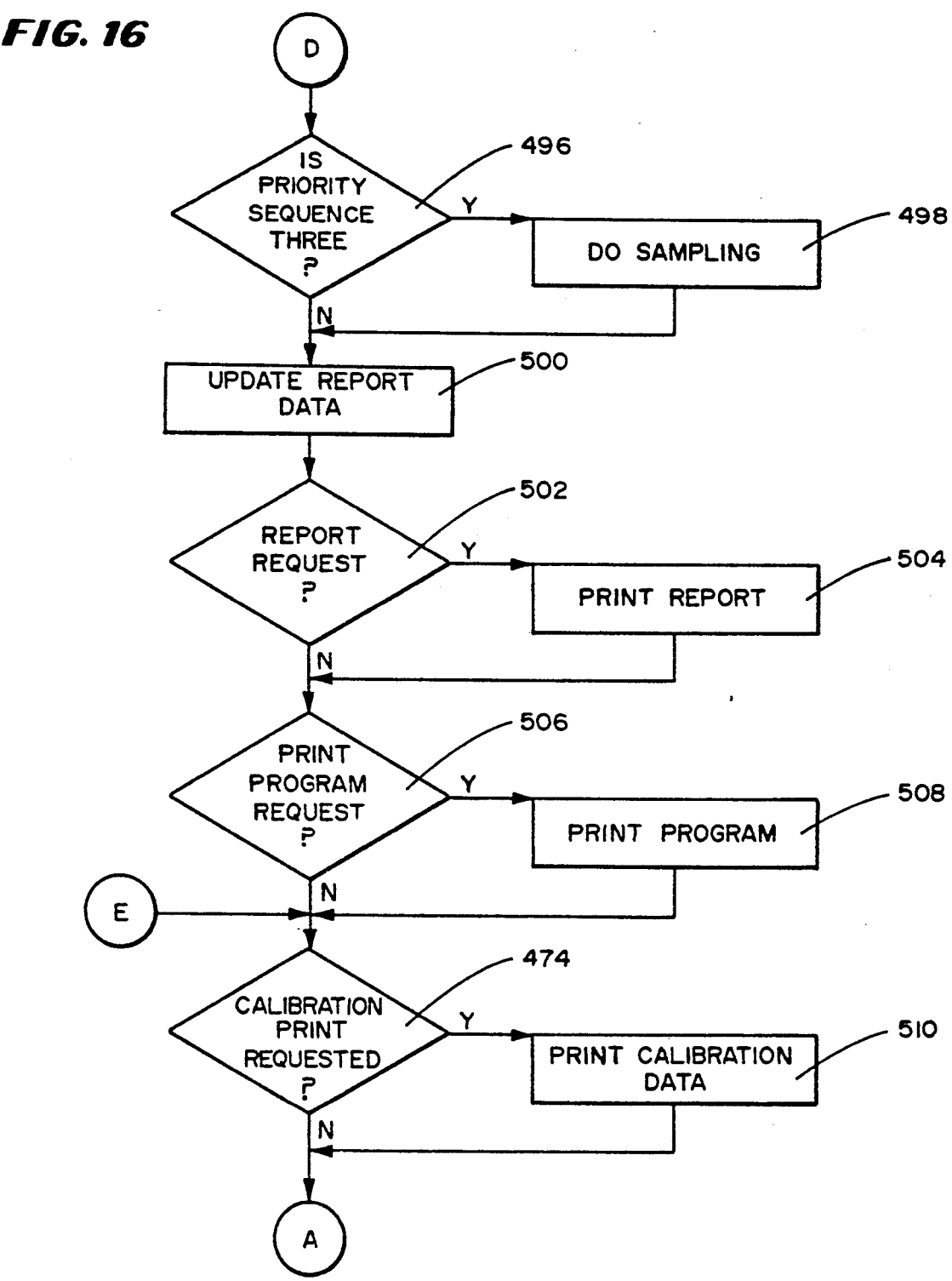

After clearing the bubbler, the program proceeds to step 496, which is a decision step shown in FIG. 16 to determine if the priority sequence is three. If it is, sampling is performed as shown at step 498. If not, the report data is updated at step 500.

After the update report step 500 is performed, a decision step 502 is made to determine if a report request has been entered into the keyboard or the time has arrived for an automatic report as programmed through the menus. If a report has been requested, then it is printed at step 504; otherwise, a decision step at 506 is performed to determine if the user entered program is to be printed. If it is, then the program proceeds to step 508 to print the program, otherwise it proceeds to decision step 474 to determine if there is a request for printing the calibration data. If step 474 is yes then the print calibration data is printed as shown at step 510, if not, or after the printing of the calibration data, the program returns to step 432 in FIG. 13.

Figure 17:
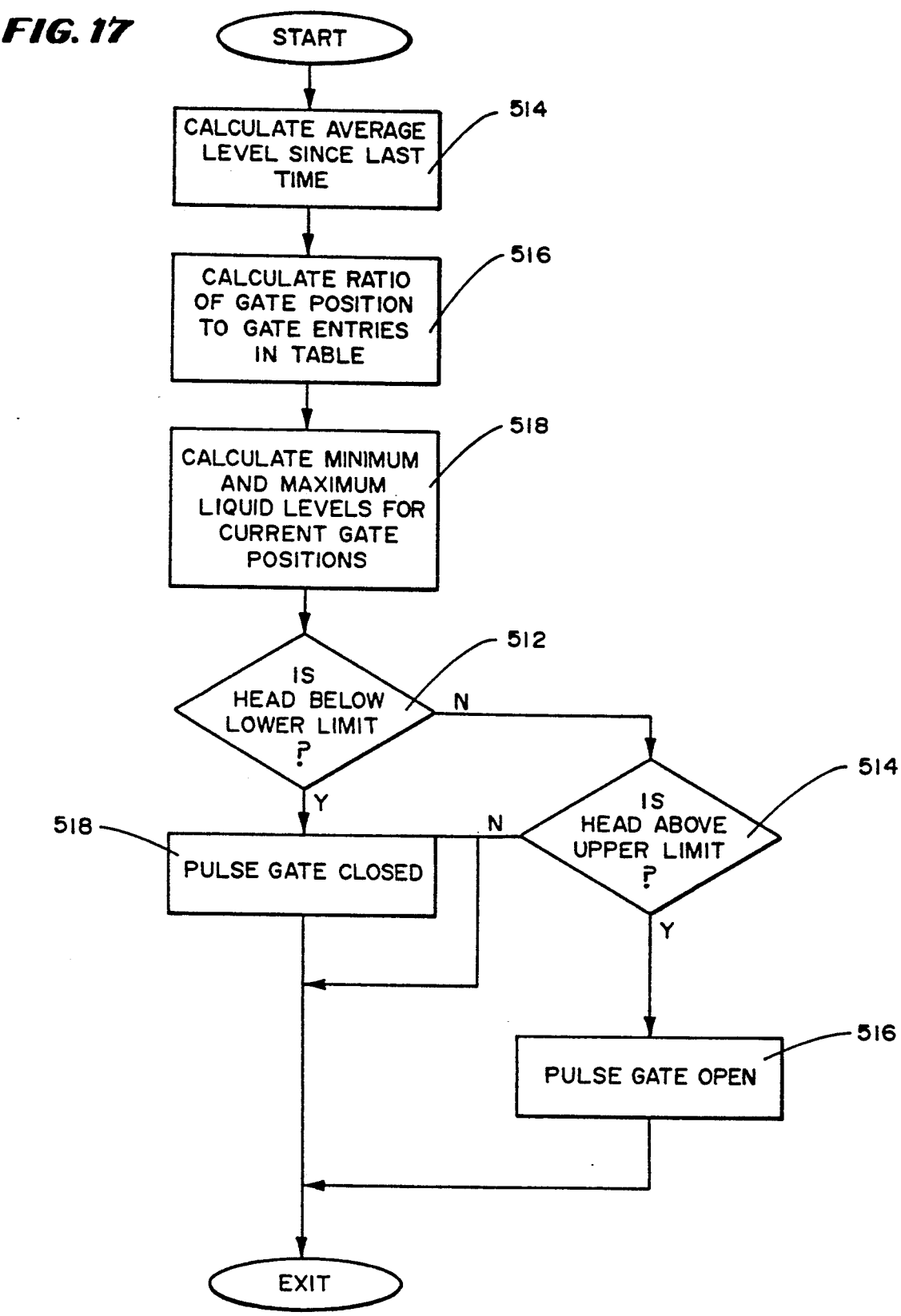
FIG. 17 is a flow diagram of a gate control sequence program usable in the embodiment of FIG. 10.

In FIG. 17, a flow chart is shown of the program segment 512 for positioning the gate. In this program, after start, the first step 514 is to calculate the average level since the last time, followed by the step 516 of calculating the ratio of gate position to gate entries in the look-up table followed by the step of calculating minimum and maximum liquid levels for current gate position shown at 519 followed by the decision step 512 to determine if the head is below the lower limit on the housing for movement of the gate in accordance with the look up table.

If head of pressure is not below the lower limit, the program proceeds to the decision step 514 to determine if the head is above the upper limit. If it is, the program proceeds to pulse the gate open shown at step 516 and then to exit. If the decision is that the head is below the lower limit, the gate is pulsed closed at step 518. If at decision 514, the head is above the upper limit, the program exits.

Figures 18, 19:
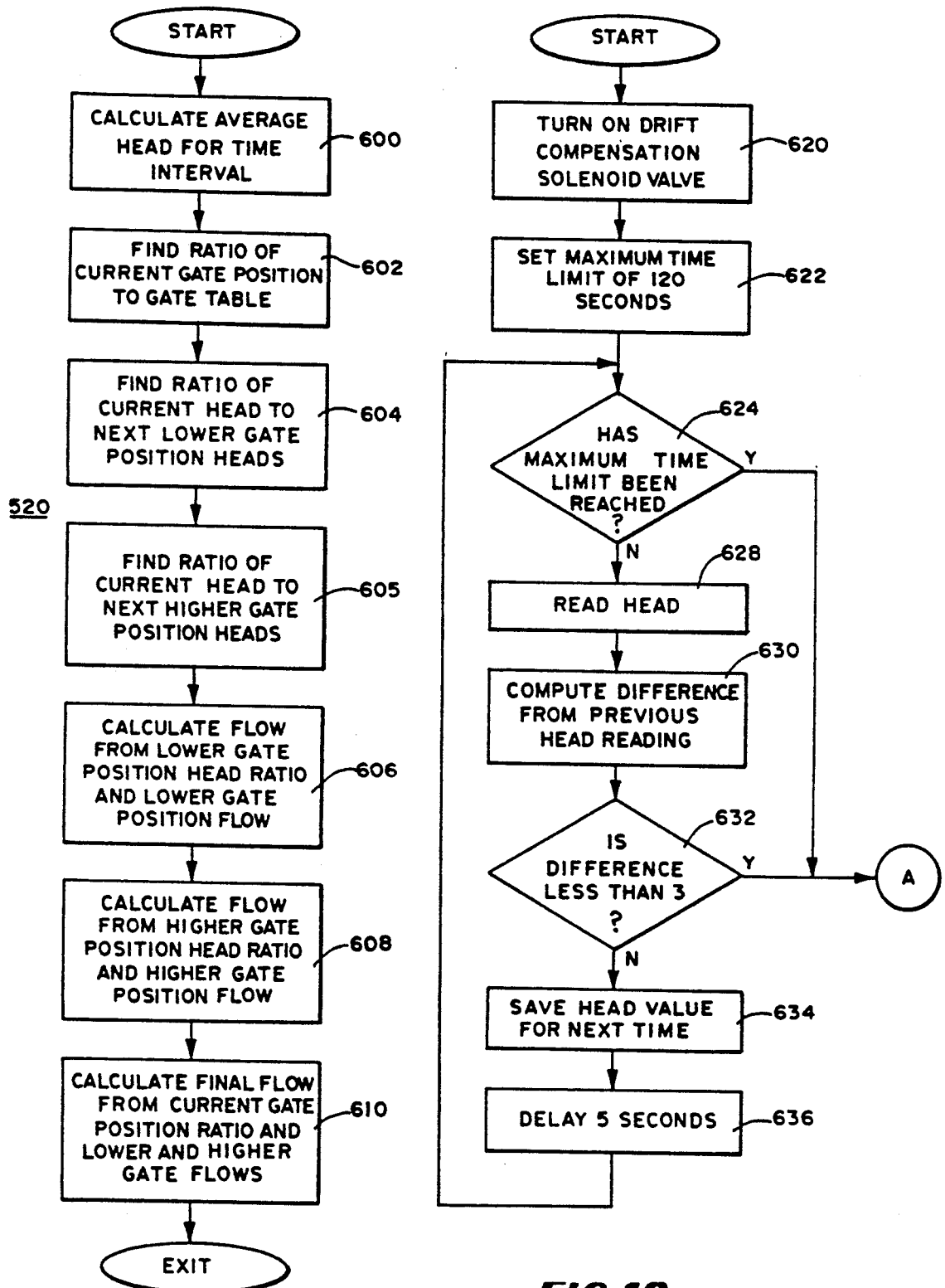
FIG. 18 is a flow diagram of a calculation of a flow sequence program usable in the embodiment of FIG. 10.
FIGS. 19-21 are flow diagrams of a program sequence for automatic drift compensation usable in the embodiment FIG. 10.

In FIG. 18, there is shown a flow diagram 520 for a program to calculate the flow by interpolating the look-up table, including the step 600 of calculating the average head for the time interval, followed by the step 602 of finding the ratio of current gate position to gate table value, followed by the step 604 of finding the ratio of current head to next lower gate position heads, followed by the step 605 of finding the ratio of current head to next higher gate position heads, followed by the step 606 of calculating the flow from lower gate position head ratio and lower gate position flow, followed by the step 608 of calculating the flow from higher gate position head ratio and higher gate position flow, followed by the step 610 of calculating final flow from the correct gate position ratio and lower and higher gate flows.

Figure 20:
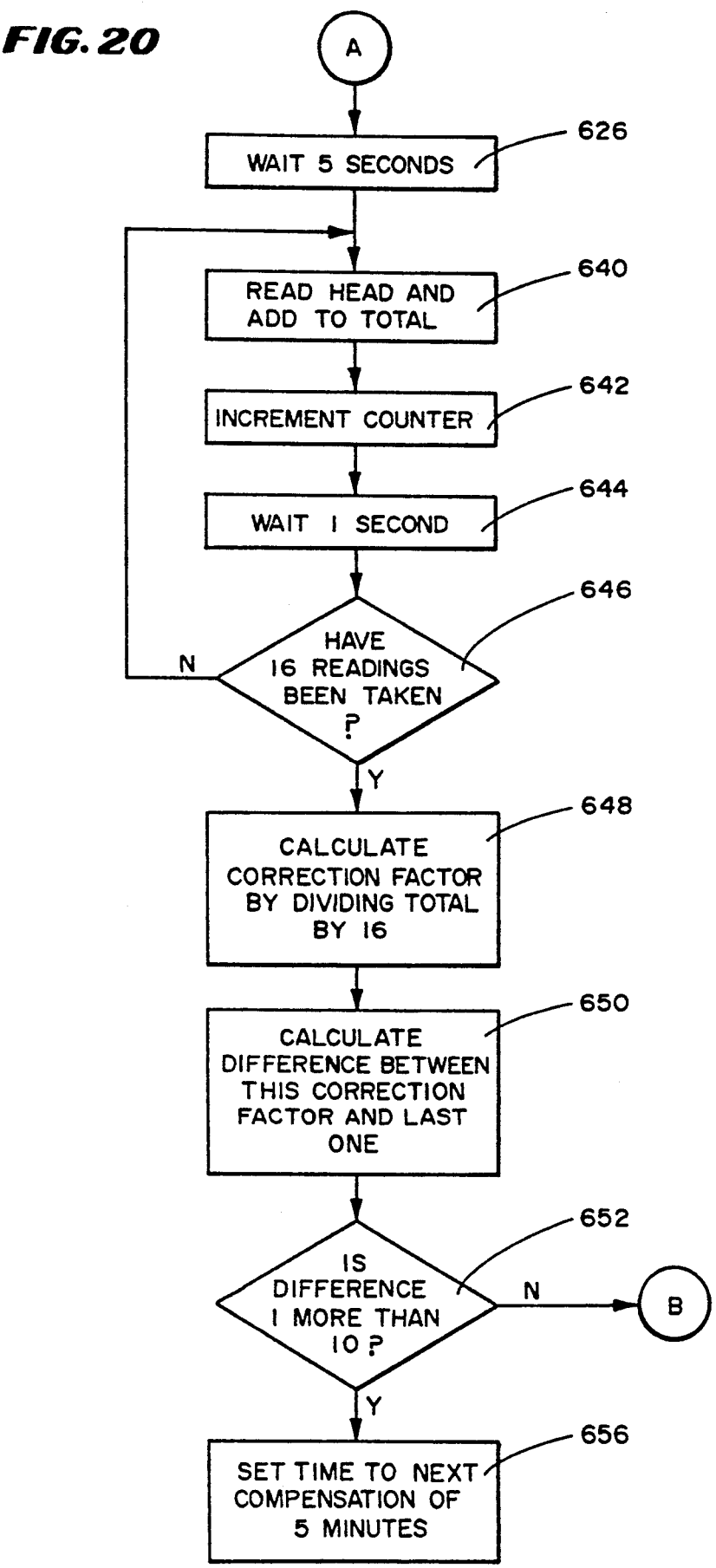
Figure 21:
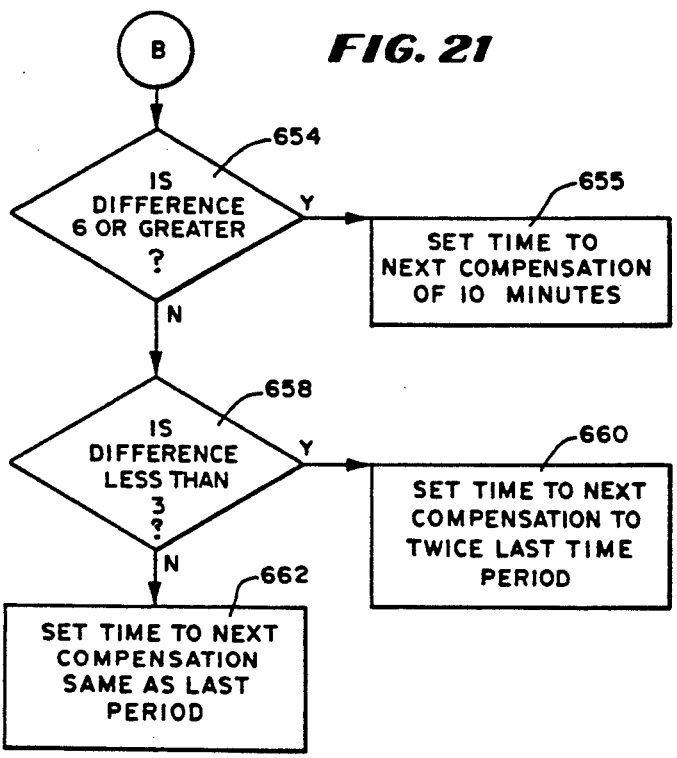
Figure 22:
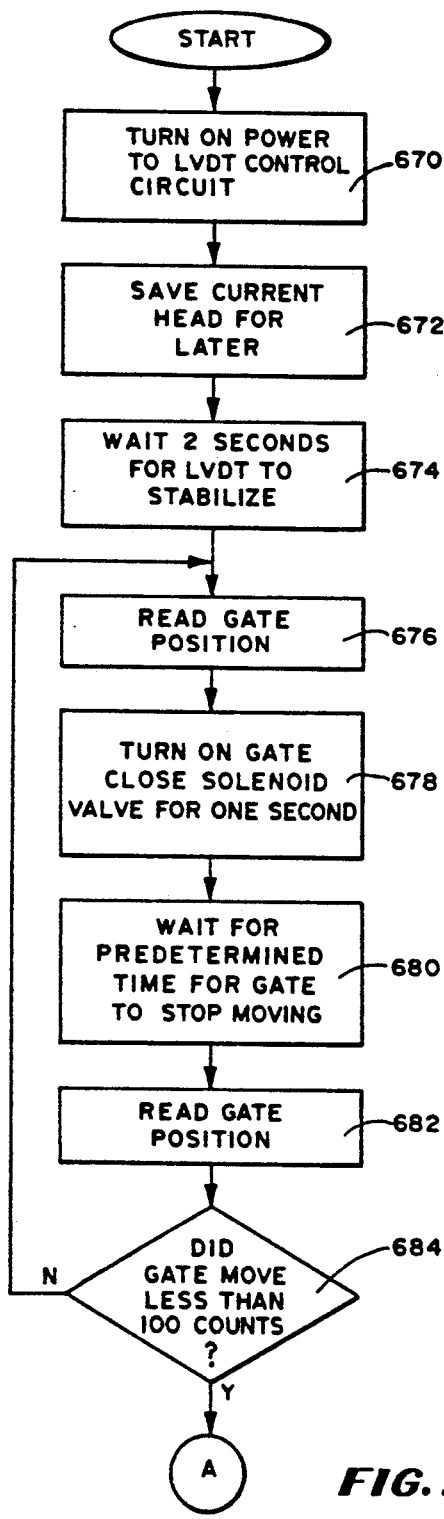

In FIG. 19–21, there is a shown a flow diagram for automatic drift compensation, including the step 620 of turning on the drift compensation solonoid valve, followed by the step 622 of setting the maximum time limit of 120 seconds, followed by the decision step 624 of determining if the maximum time limit has been reached.

If the maximum time limit has been reached, then the program exits to step 626 on FIG. 20 of waiting five seconds. If the maximum time limit has not been reached, then the program proceeds to step 628 of reading the head followed by the step 630 of computing the difference from the previous head reading followed by the step 632 of determining if the difference is less than three. If the difference is less than three, then the program proceeds to step 636 of waiting five seconds. If the difference is not less than 3, then the program proceeds to step 634 of saving the head value for next time followed by the step 636 of delaying 5 seconds followed by a return along the stabilization loop to the step 628 of reading the head. This sequence continues until it exits at step 626 in FIG. 20.

After the step 626, the head is read and added to the total at step 640, followed by the step 642 of incrementing the counter, followed by the step 644 of waiting one second, followed by the decision 646 of determining if 16 readings have been taken. If 16 readings have not been taken, then the program returns to the step 640 of reading the head and adding to the total. If 16 readings have been taken, then the program proceeds to step 648 of calculating the correction factor by dividing the total by 16 followed by the step 650 of calculating the difference between this correction factor and the last one followed by the decision 652 of determining if the difference is more or less than 10. If it is not, the program exits to step 654 in FIG. 21 of determining if the difference is six or greater.

If the difference is more than 10, then it proceeds to the step 656 of setting the time to the next compensation at five minutes. This procedure averages the readings over 16 readings for calibration purposes. If the decision 654 decides that the difference is six or greater, then the program proceeds to step 655 of setting the time to the next compensation of 10 minutes. If it is not, then it proceeds to the decision step 658 of determining if the difference is less than three. If the difference is less than three, then the program proceeds to step 660 to set the time to the next compensation at twice the last time limit. If the difference is more than three, then the program proceeds to the step 662 to set the time to the next compensation the same as the last.

In FIG. 22-25, there is shown a program for flushing the system using the gate assembly 62 including the step 670 of turning on the power to the LVDT control circuit, followed by the step 672 of saving the current head for later, followed by the step 674 of waiting two seconds for the LVDT to stabilize, followed by the step 676 of reading the gate position; followed by the step 678 of turning on the gate close solonoid valve for one second, followed by the step 680 of waiting for a predetermined time for the gate to stop moving, followed by the step 682 of reading the gate position, followed by the decision step 684 of determining if the gate has moved more or less than 100 counts during the flushing operation. If less than 100 counts, the program goes to the decision step 686 in FIG. 23 of determining if it is a flush type 1. If more than 100 counts, the program returns to step 676 of reading the gate position and continues until the closing of the gate takes less than 100 counts so that the gate is closed as far as it can go.

When gate moves less than 100 counts and the gate is fully closed, the program goes to the decision step 686 to determine if it is flush type 1. If it is, then the program goes to step 688 to set for one minute time limit, followed by the decision step 689 to determine if the time limit is exceeded. If it is not, then the program goes to step 691 to determine if the head is above 4 inches and if its flush type 1. If that's not so, then the head goes to step 693 to determine if the head is above five inches. If it is not, the program returns to decision step 689.

When the time limit is exceeded, then the decision step 689 causes the program to proceed to step 690 to read the gate position, followed by the step 692 to turn on the gate open valve, followed by the step 694 to wait a predetermined time, followed by the decision step 696 to determine if two minutes have lapsed. If two minutes have not lapsed, then the program goes to step 698 in FIG. 24 to read the gate position. If two minutes have elapsed, then the program goes to step 700 in FIG. 24 to turn off the gate open valve. If the head is above four inches and flush type 1 is met in decision step 691, then step 691 goes immediately to step 690 and to the decision step 696. If in step 691, the decision is not flush type 1 or not above four inches, then the program proceeds to step 693 to determine if the head is above five inches. If it is, the program proceeds to steps 690, 692, 694 and 696 as described above. If the time limit is exceeded in step 689, the program proceeds through steps 690, 692 and 694 to decision step 696 as described above. If in step 686, the decision is no for flush type 1, the program proceeds to step 703 to set for two minute time limit, followed by step 689 to see if the time limit is exceeded and from there follows through the sequence as above described.

After the step 698 in FIG. 24, the program proceeds to the step 704 of computing the gate change and from there to the decision step 706 of determining if the gate change is less than 10. If it is not, the program returns to step 690 in FIG. 23 to read the gate position and then follows through again. If the gate change is less than 10, then the program proceeds to the step 700 to turn off the valve that opens the gate and from there to decision step 702 to determine if two minutes have lapsed. If two minutes have not lapsed, then the program goes to the step 710 of determining if the current head is within ¼ of an inch of the beginning head. If it is not, the program returns to step 702 and cycles again. If it is, then the program goes to step 712 to turn on the gate close valve for ½ second to pressurize the air line.

If the decision step 702 of determining if two minutes have lapsed determines that two minutes have indeed lapsed, then the program immediately goes to step 712, skipping the step 710 of determining if the current head is within ¼ of an inch of the beginning head. The purpose of this sequence is to wait until the head falls to evaluate if it was at the start of the flush cycle.

The step 712 of turning on the gate close valve for ½ second to pressurize the air line is followed by the step 714 of waiting a predetermined time. If step 710 determines that current head is not within ¼ inch of beginning head, the program returns to step 702 to check if the two minute time has elapsed.

After step 712 of turning on the gate close valve for ½ second to pressurize the air line, the program proceeds to step 714 of waiting a predetermined time followed by 720 in FIG. 25 of turning on the gate close valve for one second followed by the decision step 722 of determining if the gate is moving. If the gate is not moving, then the program returns again to the step 722 and when the gate does start moving the program moves to decision step 724 to determine if the gate has stopped. If the gate is not stopped, the program returns again to step 724 and if it has stopped, it proceeds to step 726 of saving the gate response time followed by step 728 of going through a toggling of the flush cycle type from type 1 to type 2 or type 2 to type 1 and then exiting the program.

Figure 27:
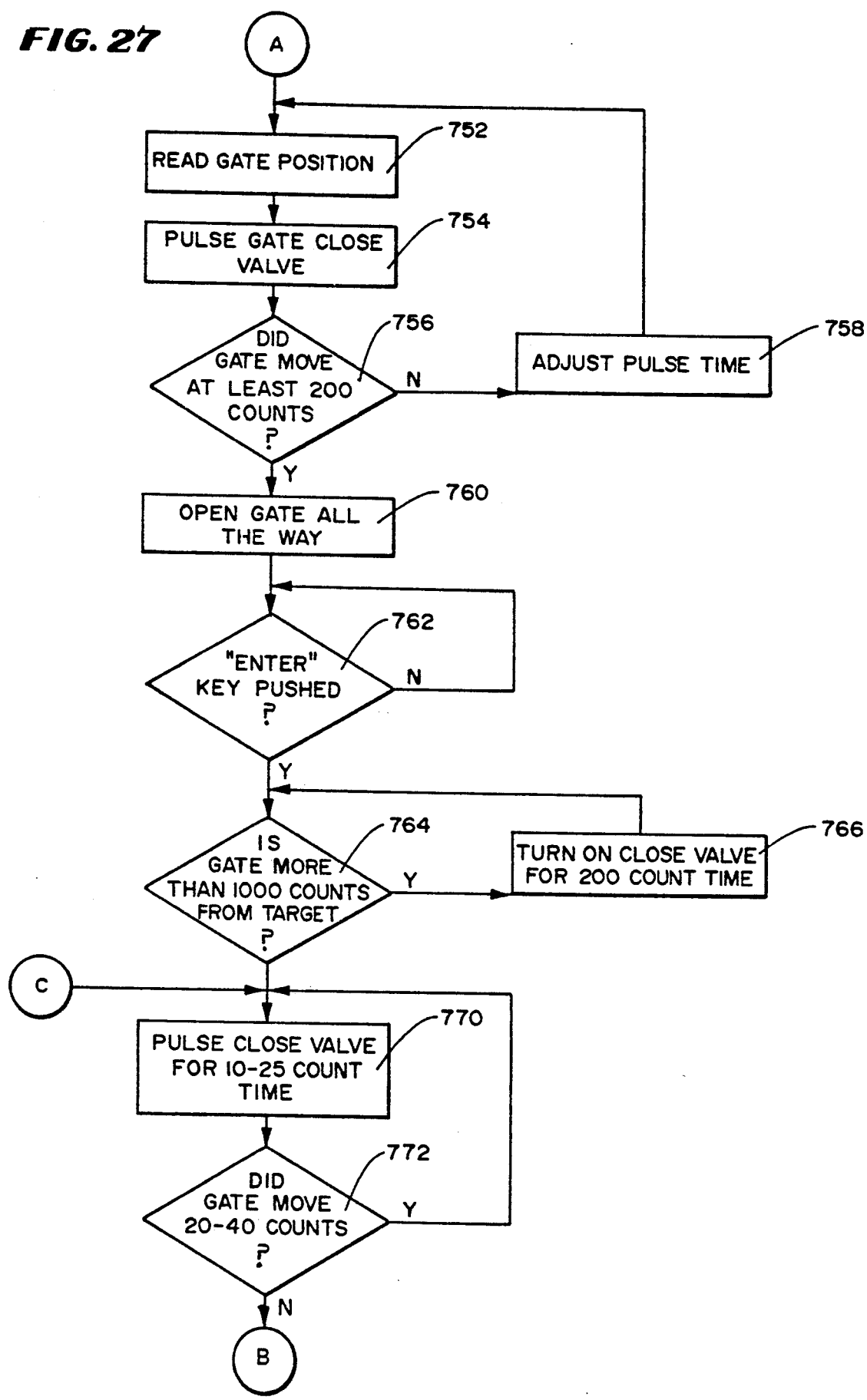

In FIG. 26-28, there is shown a flow diagram of a program for calibration with a gauge block including the steps 730 of turning on the power to the LVDT, followed by the step 732 of opening the gate all the way, followed by the step 734 of pressurizing the air line, followed by the step 736 of reading the gate position followed by the step 738 of pulsing the gate close valve, followed by the decision step 740 of determining if the gate moved 10 to 25 counts.

If the gate has not moved 10 to 25 counts, then the program proceeds to step 742 of adjusting the pulse time and returns to step 736 from there to read the gate position. If the gate has moved 10 to 25 counts, then the program proceeds to step 744 of reading the gate position, followed by the step 746 of pulsing the gate close valve, followed by the decision step 748 of determining if the gate moved 25 to 40 counts.

If the gate did not move 25 to 40 counts, then the program proceeds to step 750 of adjusting the pulse time and then returns to step 744 of reading the gate position. If it has, then the program proceeds to step 752 in FIG. 27 of reading the gate position followed by the step 754 of pulsing the gate close valve followed by the decision step 756 of determining if the gate moved at least 200 counts.

If the gate has not moved at least 200 counts, then the program moves to the step 758 of adjusting the pulse time and then returns to step 752 of reading the gate position. If the decision step 756 determines that the gate has moved 200 counts, then the program proceeds to step 760 of opening the gate all the way, followed by the decision step 762 of determining if the enter key has been pushed. If it has not, then the program returns to step 762. When it has been pushed, then the program moves on to decision step 764 to determine if the gate is more than 1,000 counts from the target. If it is, then the program proceeds to step 766 of turning on the close valve for a 200 count time and from there back to step 764 of determining if the gate is more than 1,000 counts from its target. If the gate is not more than 1,000 counts from its target, then the program proceeds to step 770 of pulsing the close valve for 10 to 25 count times followed by the decision step 772 of determining if the gate moved 20 to 40 counts If it has, the program returns to step 770 of pulsing the close valve for 10 to 25 count times. If it has not, then the program goes to decision step 774 in FIG. 28 to determine if the gate has moved less than six counts. If it has not, then the program returns to step 770 in FIG. 27 and proceeds through that sequence again. If it has, then the program proceeds to step 776 of pulsing the close valve again, followed by the decision step 778 of determining if the gate moved more than eight counts. If the program has moved more than eight counts, then the program returns to step 770 in FIG. 27 and proceeds through that sequence again. If the gate has not moved more than eight counts, then it proceeds to step 780 to calculate the correction value for the gauge block stop and then exits.

In FIG. 29, there is shown a flow diagram for a sampling sequence including the decision step 790 of determining if the head is above four inches. If it is above four inches, then the program proceeds to step 798 to begin sampling. If it is not above four inches, then the program moves to step 794 which is to read the gate position.

After reading the gate position at step 794, the program moves to step 796 of pulsing the gate close valve for one second followed by the step 798 of waiting for the gate to move, followed by the decision step 792 of determining if the gate is fully closed. If the gate is fully closed, then the program moves to decision step 795 of determining if the head is greater than four inches. If the gate is determined to be less than four inches, then the program moves to decision step 796 of determining if the wait time exceeded one minute. If the wait time has not exceeded one minute, then the program returns to the decision step 795. If it has, then it exits the program. If the head is determined to be greater than four inches in steps 795, then the program moves to step 798 which is to signal the sampler to begin, followed by the step 800 which is to wait an appropriate time and then exits.

From the above description, it can be understood that the novel method and apparatus of this invention has several advantages, such as for example: (1) it is relatively simple, inexpensive and easy to use; (2) it is capable of convenient and easy adjustment in a flow path; (3) it is versatile and can be used both to measure flow rates and take samples in a wide variety of streams and at a wide variety of different depths of flow and flow rates; (4) it is capable of great precision under difficult measuring conditions; and (5) the apparatus can be used to perform a number of different measuring methods.

Although a preferred embodiment has been described with some particularily, many modifications in variations are possible in the preferred embodiment without deviating from the invention. Therefore, it is to be understood that, within the scope of the appended claims, the invention may be practiced other than as specifically described.

```
/*    AUGUST 02, 1990    LF7.C    VAU17 */ include "type3240.h"
typedef char *STRING;

extern char             cable_len;
extern char             calib_mode;
extern int              calib_temp[8];
extern char             change_flag1;
extern char             change_flag3;
extern char             change_flag4;
extern char             clear_flag;
extern char             digit_count;
extern char             digit_key_enable;
extern char             digit_value;
extern char             fault_msg_time;
extern char             fl_rt_unts_col;
extern char             fl_rt_unts_row;

extern const float      flow_conversion[3][4];
extern const char       flow_plot_dec[3][4];
extern const char       flow_plot_digits[3][4];
extern const float      flow_plot_max[3][4];
extern const float      flow_plot_min[3][4];
extern float            flow_total;
extern int              gage_block_act[32];
extern const int        head_lim[3][32];
extern char             int_str_day;
extern char             int_str_hr;
extern char             int_str_min;
extern char             int_str_mnth;
extern int              int_str_yr;
extern const STRING     line_one[74];
extern const struct menus line_two;
extern char             lock_flag;
extern char             lock_timer;
char                    lvdt_disp=1;
extern struct tm_date   max_fst;
extern struct tm_date   max_lst;
extern unsigned char    menu_number;
extern int              menu_time;
extern struct tm_date   min_fst;
extern struct tm_date   min_lst;
extern const char       month_name[36];
extern char             paper_adv_flag;
extern char             paper_out_flag;
extern int              plotter_full_scale;
extern char             plotter_jammed_flag;
extern char             plotter_mode;
extern char             plotter_speed;
extern char             prog_unlock_flag;
extern char             power_up_flag;
char                    pp_step;
extern int              purge_time1;
extern unsigned char    reentry_menu_number;
extern unsigned char    reentry_menu_number2;
```

```c
extern char          report_gen;
extern int           report_interval;
extern char          report_interval_units;
extern struct report_data rg_data1;
float                rg_flow_total;
extern struct tm_date rg_int_end;
extern struct tm_date rg_int_start;
extern int           rg_max_count;
extern float         rg_max_flow;
extern int           rg_min_count;
extern float         rg_min_flow;
extern char          rg_print_step;
extern char          rg_step;
char                 rg_vol_print_flag;
unsigned char        rg_vol_print_time;
extern char          s[41];
extern struct SamplerEnable SamplerEnab;
extern char          sampler_init;
extern const char    samp_enable_digits[3][4];
extern const char    samp_enable_dec[3][4];
extern const float   samp_enable_max[3][4];
extern const float   samp_enable_min[3][4];
extern float         samp_vol_limit;
extern char          sb_freq;
extern char          se_latch_flag;
char                 se_reset=1;
extern int           SiteID;
char                 spc_msg_time;
extern struct tm_date sys_tm_dt;
extern char          sx[252];
extern char          sy[252];
extern char          temp[8];
extern int           tempc;
extern int           tempd;
extern float         tempy;
extern char          text_print_flag;
extern int           time_per_pulse;
extern const float   volume_conversion[6];
extern char          volume_units;
extern char          Vp_power_flag;
int                  xmit_full_scale=50;
int sprintf(char *,const char *,...);

void step_setup3(char,char);

void menu_select(char,char,char);

/***********************************************************/ void display_menu3()
{
int  calc_calib_check_digit();
void check_lock();
void check_min_max();
void check_report_gen();
void clear_display();
```

```c
void cursor_control();
void digit_wait2();
void display_calib_const();
void display_units();
void menu_select();
void screen_fill();
void screen_fill2();
void sdisplay();
void step_setup2();
void step_setup3();
void step_setup4();

switch(menu_number)
{ case 162: /*   STEP 2.3   */
    if(SamplerEnab.LockPanel || SamplerEnab.OpMode > 2)
        {
        sdisplay(0,line_one[44]);
        sdisplay(40,line_one[9]);
        menu_number=166;
        }
    else step_setup3(SamplerEnab.OpMode+1,1);
    break;

case 163:
    step_setup2(45,14);
    break;

case 164:
    menu_select(14,1,4);
    break;

case 165:
    if(temp[1]==3)
        {
        menu_number=168;
        change_flag3=change_flag4;
        }
    else
        {
        SamplerEnab.OpMode = temp[1] - 1;
        menu_number=54;
        }
    break;

case 166:
    break;

case 167:
    menu_number=54;
    break;

case 168:          /*   STEP 2.31   */
    step_setup4(SamplerEnab.Flow_or_Level/100,
```

```
            samp_enable_min[fl_rt_unts_row][fl_rt_unts_col-1],
            samp_enable_max[fl_rt_unts_row][fl_rt_unts_col-1],65);
    break;

case 169:
    screen_fill2(46,samp_enable_dec[fl_rt_unts_row]
        [fl_rt_unts_col-1],65);
    break;

case 170:   /*  WAIT FOR DIGITS  */
    digit_wait2(samp_enable_dec[fl_rt_unts_row]
        [fl_rt_unts_col-1],65,samp_enable_digits
        [fl_rt_unts_row][fl_rt_unts_col-1]);
    break;

case 171:         /*  CHECK VALUE AGAINST MIN AND MAX  */
    check_min_max(samp_enable_min[fl_rt_unts_row]
        [fl_rt_unts_col-1],samp_enable_max
        [fl_rt_unts_row][fl_rt_unts_col-1]);
    break;

case 172:  /*   STEP 2.32  */
    step_setup3(SamplerEnab.ModeFlags & 0x4 ? 1 : 2,2);
    break;

case 173:
    step_setup2(47,16);
    sprintf(s,"%-1.*f",samp_enable_dec[fl_rt_unts_row]
        [fl_rt_unts_col-1],tempy/flow_conversion
        [fl_rt_unts_row][fl_rt_unts_col-1]);
    sdisplay(70,s);
    display_units(fl_rt_unts_row,fl_rt_unts_col);
    break;

case 174:
    menu_select(16,2,3);
    break;

case 175: /*   STEP 2.33  */
    if(temp[2]==1 && se_latch_flag==on)
        step_setup3(se_reset,3);
    else
        {
        temp[3]=se_reset;
        menu_number=178;
        }
    break;

case 176:
    step_setup2(48,17);
    sdisplay(40,line_one[49]);
    break;

case 177:
    menu_select(17,3,3);
    break;
```

```
case 178:  /*   STEP 2.34  */
    step_setup3(SamplerEnab.PlotterControl==1 ? 1 : 2,4);
    break;

case 179:
    step_setup2(50,7);
    break;

case 180:
    menu_select(7,4,3);
    break;

case 181:
    SamplerEnab.Flow_or_Level = tempy * 100.0;
    SamplerEnab.OpMode = temp[1] - 1;
    SamplerEnab.ModeFlags = temp[2]==1 ? 0x5 : 0x1;
    se_reset=temp[3];
    SamplerEnab.PlotterControl = temp[4]==1 ? 1 : 0;
    if(temp[2]==2 || se_reset==1) se_latch_flag=off;
    menu_number=54;
    break;

case 182:
    spc_msg_time=10;
    clear_display();
    sdisplay(0,line_one[51]);
    sdisplay(40,line_one[52]);
    menu_number=183;
    break;

case 183:
    if(spc_msg_time<1) menu_number=0;
    break;

case 187:
    fault_msg_time=6;
    clear_display();
    sdisplay(0,line_one[54]);
    menu_number=210;
    break;

case 188:
    break;

case 189:         /*  STEP 11  */
    step_setup2(41,7);
    break;

case 190:         /*  WAIT FOR SELECTION  */
    menu_select(7,0,3);
    break;

case 191:         /*  END OF STEP 11  */
    digit_key_enable=off;
    if(lock_flag==2 && temp[0]==1)
        {
```

```
            lock_timer=30;
            prog_unlock_flag=on;
            }
        lock_flag=temp[0];
        menu_number=0;
        break;

case 192: /*    STEP 10.4 */
        reentry_menu_number=194;
        tempc=0;
        tempd=calib_temp[0];
        menu_number=193;
        break;
    case 193:
        reentry_menu_number2=193;
        calib_temp[tempc]=tempd;
        digit_count=0;
        menu_number=194;
        break;

case 194:
        clear_display();
        sdisplay(0,line_one[40]);
        display_calib_const(on);
        digit_key_enable=on;
        menu_number=195;
        break;

case 195:
        if(digit_value<10)
            {
            if(change_flag1==off)
                {
                calib_temp[tempc]=0;
                sprintf(s,"    ");
                sdisplay(40+tempc*4,s);
                }
            calib_temp[tempc]=calib_temp[tempc]*10 + digit_value;
        change_flag1=on;
            digit_value=99;
            if(++digit_count>=3) digit_key_enable=off;
            if(lock_flag==on && prog_unlock_flag==off)
                menu_number=35;
            check_report_gen();
            }
        if(digit_count==0 && tempc<7)
            sprintf(s,"%03d",calib_temp[tempc]);
        else sprintf(s,"%0*d",digit_count,calib_temp[tempc]);
sdisplay(40+tempc*4,s);
        cursor_control(40+tempc*4+digit_count,on);
        if(clear_flag==on)
            {
            clear_flag=off;
            change_flag1=off;
            digit_count=0;
            calib_temp[tempc]=tempd;
```

```
                digit_key_enable=on;
                }
            change_flag4=change_flag1 | change_flag3;
            break;
    case 196:
            if(tempc<7) sprintf(s,"%03d",calib_temp[tempc]);
            else sprintf(s,"%ld",calib_temp[7]);
            sdisplay(40+tempc*4,s);
            change_flag3=change_flag4;
            change_flag1=off;
            digit_count=0;
            digit_key_enable=on;
            if(++tempc>=8) menu_number=197;
            else menu_number=195;
            tempd=calib_temp[tempc];
            break;

case 197:
            digit_key_enable=off;
            if(calc_calib_check_digit()==calib_temp[7])
                menu_number=160;
            else menu_number=192;
            break;

case 198:  /* STEP 10.1 */
            step_setup3(cable_len,0);

case 199:
            step_setup2(58,19);
            break;

case 200:
            menu_select(19,0,6);
            break;

case 201:
            digit_key_enable=off;
            step_setup3(calib_mode,1);
            menu_number=138;
            break;

case 202:           /*  STEP 10.0 */
            step_setup4((long)xmit_full_scale,
                flow_plot_min[fl_rt_unts_row][fl_rt_unts_col-1],
                flow_plot_max[fl_rt_unts_row][fl_rt_unts_col-1],52);
            break;

case 203:
            screen_fill(59,flow_plot_dec[fl_rt_unts_row]
                [fl_rt_unts_col-1],flow_plot_min[fl_rt_unts_row]
        [fl_rt_unts_col-1],flow_plot_max[fl_rt_unts_row]
    [fl_rt_unts_col-1],17,52);
            break;
    case 204:  /*  WAIT FOR DIGITS */
            digit_wait2(flow_plot_dec[fl_rt_unts_row]
                [fl_rt_unts_col-1],52,flow_plot_digits
```

```
            [fl_rt_unts_row][fl_rt_unts_col-1]);
        break;

case 205:          /*   CHECK VALUE AGAINST MIN AND MAX   */
        check_min_max(flow_plot_min[fl_rt_unts_row]
            [fl_rt_unts_col-1],flow_plot_max
            [fl_rt_unts_row][fl_rt_unts_col-1]);
        break;

case 206:
        menu_number=198;
        break;

case 207:
        fault_msg_time=6;
        clear_display();
        sdisplay(0,line_one[60]);
        menu_number=210;
        break;

case 208:
        fault_msg_time=6;
        clear_display();
        sdisplay(0,line_one[61]);
        menu_number=210;
        break;

case 209:
        fault_msg_time=6;
        clear_display();
        sdisplay(0,line_one[62]);
        menu_number=210;
        break;

case 210:
        if(fault_msg_time<5) menu_number=0;
        break;

case 211:
        menu_number=0;
        break;

default:
        menu_number=0;
        break;
        }
}

/*****************************************************/ void prn_prgm()
{
int cc;
void clear_s();
```

```
void display_calib_const();
char inbit();
void print_formt_flow();
void print_formt_vol();
void print_menu_selection();
void splot();

if(text_print_flag==off && menu_number==20 &&
    !paper_out_flag && !Vp_power_flag)
    {
    if(plotter_jammed_flag && pp_step > 1)
        pp_step=0;
    clear_s();
    switch(pp_step)
        {
case 0:
    break;

case 1:
    splot(s);
    pp_step=2;
    break;

case 2:
    sprintf(s,"----------------------------------------");
splot(s);
    pp_step=3;
    break;

case 3:
    sprintf(s,"FLOW RATE UNITS:   ");
    print_menu_selection(18,fl_rt_unts_row,fl_rt_unts_col);
splot(s);
    pp_step=4;
    break;

case 4:
    sprintf(s,"TOTALIZED VOLUME UNITS:   ");
    print_menu_selection(25,3,volume_units);
    splot(s);
    pp_step=5;
    break;

case 5:
    sprintf(s,"SAMPLER PACING:   ");
    print_menu_selection(17,4,sampler_init);
    splot(s);
    if(sampler_init==2) pp_step=6;
    else if(sampler_init==3) pp_step=7;
    else pp_step=8;
    break;

case 6:
    sprintf(s,"  SAMPLER INTERVAL:   ");
    print_formt_vol(21,samp_vol_limit,on);
```

```
        splot(s);
        pp_step=8;
        break;

case 7:
        sprintf(s,"  SAMPLER INTERVAL:  %02d HOUR %02d MIN",
            time_per_pulse/60,time_per_pulse%60);
        splot(s);
        pp_step=8;
        break;

case 8:
        sprintf(s,"SAMPLER CONTROL:   ");
        print_menu_selection(18,14,SamplerEnab.OpMode + 1);
        splot(s);
        if(SamplerEnab.OpMode==2) pp_step=9;
        else pp_step=13;
        break;

case 9:
        sprintf(s,"  SAMPLER ENABLE FLOW:   ");
        print_formt_flow(24,(float)SamplerEnab.Flow_or_Level /
            100.0,on,off);
        splot(s);
        pp_step=10;
        break;

case 10:
        sprintf(s,"  SAMPLER WILL:   ");
        print_menu_selection(17,16,SamplerEnab.ModeFlags & 0x4
            ? 1 : 2);
        s[30]=0x20;
        if(!(SamplerEnab.ModeFlags & 0x4))
            print_formt_flow(31,(float)SamplerEnab.Flow_or_Level /
                100.0,on,off);
        splot(s);
        pp_step=12;
        break;

case 11:
        pp_step=12;
        break;

case 12:
        sprintf(s,"  PLOTTER ON/OFF WITH SAMP ENAB:   ");
        print_menu_selection(34,17,
            SamplerEnab.PlotterControl==1 ? 1 : 2);
        splot(s);
        pp_step=13;
        break;

case 13:
        sprintf(s,"PLOTTER MODE OF OPERATION:   ");
        print_menu_selection(28,5,plotter_mode);
        splot(s);
        if(plotter_mode==2) pp_step=14;
```

```
      else pp_step=16;
      break;

case 14:
      sprintf(s," FULL SCALE:  ");
      print_formt_flow(15,(float)plotter_full_scale,on,off);
      splot(s);
      pp_step=15;
      break;

case 15:
      sprintf(s," PLOTTER CHART SPEED:  ");
      print_menu_selection(24,6,plotter_speed);
      splot(s);
      pp_step=16;
      break;

case 16:
      sprintf(s,"SITE ID:  %-3d",SiteID);
      splot(s);
      pp_step=17;
      break;

case 17:
      sprintf(s,"REPORT GENERATION:  ");
      print_menu_selection(20,8,report_gen);
      splot(s);
      if(report_gen==1) pp_step=18;
      else pp_step=20;
      break;

case 18:
      cc=sprintf(s," REPORT INTERVAL:   %ld",report_interval);
   s[cc]=0x20;
      print_menu_selection(++cc,9,report_interval_units);
      splot(s);
      pp_step=19;
      break;

case 19:
      sprintf(s," START TIME:  %02d:%02d %02d-   -%02d",
          int_str_hr,int_str_min,int_str_day,int_str_yr);
      cc=(int_str_mnth-1)*3;
      s[24]=month_name[cc];
      s[25]=month_name[cc+1];
      s[26]=month_name[cc+2];
      splot(s);
      pp_step=21;
      break;

case 20:

case 21:
      sprintf(s,"GATE FLUSH TIME:   %2d HOURS   %2d MIN",
      purge_time1/60,purge_time1%60);
      splot(s);
```

```
        pp_step=23;
        break;

case 22:

case 23:
        sprintf(s,"AUTO-PURGE:   ");
        print_menu_selection(13,18,sb_freq);
        splot(s);
        pp_step=24;
        break;

case 24:
        sprintf(s,"2312/ANALOG FULL SCALE:   ");
        print_format_flow(25,(float)xmit_full_scale,on,off);
        splot(s);
        pp_step=25;
        break;

case 25:
        sprintf(s,"CABLE LENGTH:   ");
        print_menu_selection(15,19,cable_len);
        splot(s);
        pp_step=26;
        break;

case 26:
        sprintf(s,"CHARACTERIZATION NUMBER:   ");
        splot(s);
        pp_step=27;
        break;

case 27:
        display_calib_const(off);
        splot(s);
        pp_step=28;
        break;

case 28:
        sprintf(s,"----------------------------------------");
splot(s);
        pp_step=29;
        break;

case 29:
        splot(s);
        pp_step=30;
        break;

default:
        pp_step=0;
        break;
            }
        }
}
```

```
/****************************************************/ void rg_print()
{
float avg_f;

void clear_s();
void splot();
void tm_dt_to_text();
if(text_print_flag==off)
    {
    if(plotter_jammed_flag && rg_print_step > 1)
        rg_print_step=0;
    switch(rg_print_step)
        {
    case 0:
        break;

case 1:
        clear_s();
        sprintf(s,"-------------------------------------------");
        splot(s);
        rg_print_step=2;
        break;

case 2:
        clear_s();
        sprintf(s,"   SITE %3d - INTERVAL FROM",SiteID);
        splot(s);
        rg_print_step=3;
        break;

case 3:
        clear_s();
        tm_dt_to_text(2,&rg_int_start,0);
        s[18]=0x54;
        s[19]=0x4f;
        tm_dt_to_text(23,&rg_int_end,0);
        s[36]=0;
        splot(s);
        rg_print_step=4;
        break;

case 4:
        clear_s();
        splot(s);
        rg_print_step=5;
        break;

case 5:
        clear_s();
        sprintf(s,"MAXIMUM FLOW RATE:   ");
        print_formt_flow(20,rg_max_flow,on,off);
        splot(s);
        if(rg_max_count==1) rg_print_step=6;
```

```
        else rg_print_step=7;
        break;

case 6:
    clear_s();
    sprintf(&s[5],"ON ");
    tm_dt_to_text(8,&max_fst,1);
    splot(s);
    rg_print_step=10;
    break;

case 7:
    clear_s();
    sprintf(&s[5],"OCCURRED %4d TIMES",rg_max_count);
splot(s);
    rg_print_step=8;
    break;

case 8:
    clear_s();
    sprintf(&s[5],"FIRST ON ");
    tm_dt_to_text(14,&max_fst,1);
    splot(s);
    rg_print_step=9;
    break;

case 9:
    clear_s();
  . sprintf(&s[5],"LAST ON ");
    tm_dt_to_text(13,&max_lst,1);
    splot(s);
    rg_print_step=10;
    break;

case 10:
    clear_s();
    sprintf(s,"MINIMUM FLOW RATE:   ");
    print_formt_flow(20,rg_min_flow,on,off);
    splot(s);
    if(rg_min_count==1) rg_print_step=11;
    else rg_print_step=12;
    break;

case 11:
    clear_s();
    sprintf(&s[5],"ON ");
    tm_dt_to_text(8,&min_fst,1);
    splot(s);
    rg_print_step=15;
    break;

case 12:
    clear_s();
  . sprintf(&s[5],"OCCURRED %4d TIMES",rg_min_count);
splot(s);
    rg_print_step=13;
    break;
```

```
case 13:
    clear_s();
    sprintf(&s[5],"FIRST ON ");
    tm_dt_to_text(14,&min_fst,1);
    splot(s);
    rg_print_step=14;
    break;

case 14:
    clear_s();
    sprintf(&s[5],"LAST ON ");
    tm_dt_to_text(13,&min_lst,1);
    splot(s);
    rg_print_step=15;
    break;

case 15:
    clear_s();
    sprintf(s,"AVERAGE FLOW RATE:   ");
    if(rg_data1.month_count)
            avg_f=rg_data1.month_sum / rg_data1.month_count;
        else if(rg_data1.day_count)
            avg_f=rg_data1.day_sum / rg_data1.day_count;
    else if(rg_data1.hour_count)
            avg_f=rg_data1.hour_sum / rg_data1.hour_count;
      else if(rg_data1.min_count)
            avg_f=rg_data1.min_sum / rg_data1.min_count;
    else avg_f=0.0;
    print_format_flow(20,avg_f,on,off);
    splot(s);
    rg_print_step=16;
    break;

case 16:
    clear_s();
    sprintf(s,"INTERVAL FLOW VOLUME:  ");
    rg_flow_total=flow_total;
    rg_vol_print_flag=on;
    rg_vol_print_time=0;
    print_formt_vol(23,
        rg_flow_total - rg_data1.old_flow_vol,on);
    splot(s);
    rg_print_step=17;
    break;

case 17:
    clear_s();
    sprintf(s,"TOTAL FLOW VOLUME:  ");
    print_formt_vol(20,rg_flow_total,on);
    splot(s);
    rg_print_step=18;
    break;

case 18:
    clear_s();
    sprintf(s,"NUMBER OF SAMPLES:  %2d",
```

```
                rg_data1.sample_count);
            splot(s);
            rg_print_step=19;
            break;

case 19:
            clear_s();
            sprintf(s,"------------------------------------------");
            splot(s);
            rg_print_step=20;
            break;

case 20:
            if(text_print_flag==0) rg_print_step=21;
            break;

default:
            if(rg_step==3) rg_step=4;
            rg_print_step=0;
            break;
            }
        }
}

/*    JULY 27, 1990    LF8.C      VAU13 */ define             off 0
define             on 1
#define             port2a 0x20     /* .01 second */
#define             port2b 0x21     /* hour    */
#define             port2c 0x22     /* minute  */
#define             port2d 0x23     /* second  */
#define             port2e 0x24     /* month   */
#define             port2f 0x25     /* day     */
#define             port2g 0x26     /* year    */
#define             port5b 0x51
#define             port5c 0x52
#define             port6a 0x60
define             port6c 0x62 struct              menus{
    int position[20][6];
    char text[20][44];};

struct              tm_date{
    char cent;
    char year;
    char month;
    char day;
    char hour;
    char min;
    char sec;};

struct              report_data{
    float month_sum;
    int month_count;
```

```
    float day_sum;
    int day_count;
    float hour_sum;
    int hour_count;
    float min_sum;
    int min_count;
    float flow_vol;
    int sample_count;};

extern char            auto_zero_control;
extern unsigned int    auto_zero_time;
extern char            az_delay;
extern char            bottle_count;
char                   bottle_count2;
extern char            cable_len;
char                   event_mark3;
char                   event_mark4;
extern char            fl_rt_unts_col;
extern char            fl_rt_unts_row;
extern float           flow;
extern const float     flow_conversion[3][4];
extern float           flow_total;
extern int             head;
extern int             head_count;
extern int             head_count2;
extern long            head_total;
extern long            head_total2;
extern const struct menus line_two;
extern char            man_purge;
extern char            menu_active;
extern unsigned char   menu_number;
extern char            mode_letter;
char                   paper_out_flag;
extern char            pevent_mark;
extern char            plotter_mode;
extern char            plotter_speed;
extern char            prior_req;
extern char            purge_flag;
extern char            report_gen;
char                   report_gen_lock_out;
extern char            s[41];
char                   sample_num;
extern char            samp_req;
extern char            sb_control;
extern char            sb_freq;
int                    sb_head;
char                   sb_head_count;
unsigned char          sb_pulse_time;
extern unsigned int    sb_time;
extern char            SiteDescrip[18];
extern int             SiteID;
char                   str2312[111];
char                   *str2312_ptr;
extern struct tm_date  sys_tm_dt;
char                   tx1_enable_f;
char                   typeD_old_time;
```

```
char                     typeD_time;
extern const float       volume_conversion[6];
const float              volume_conversion2[6]=
   {1.33671969,1.0,3.785011355,3.068689547,3.785011355,1.0};
   /* * flow in gpm to convert */
extern const char        vol_dec_places[6];
extern char              volume_units;
char                     Vp_power_flag;
char                     x2312_tx_time;
extern int               xmit_full_scale;

int sprintf(char *,const char *,...);

void step_setup3(char,char);

void menu_select(char,char,char);

/***********************************************************/
int calc_av_head()

{
int av_head;
void sdisplay();
int sprintf();

av_head=head_total / head_count;
/*sprintf(s,"%4d",av_head);
sdisplay(20,s);*/
head_total=0;
head_count=0;
return(av_head);
}

/***********************************************************/ int calc_av_head2()

{
int av_head2;
void sdisplay();
int sprintf();

av_head2=head_total2 / head_count2;
head_total2=0;
head_count2=0;
/*sprintf(s,"%4d",av_head2);
sdisplay(14,s);*/
return(av_head2);
}

/***********************************************************/
```

```c
void check_report_gen()

{
void clear_display();
void sdisplay();

if(report_gen==1 && report_gen_lock_out==on)
      {
      menu_number=161;
      }
}

/***************************************************/ void do_2312()
{
int index;
int t3;
float tfl;
char inbyte();
char *strcpy();

if(event_mark3==1)
      {
      event_mark3=2;
      event_mark4=on;
      }
if(x2312_tx_time>12)
      {
      str2312_ptr=str2312;
      tx1_enable_f=on;
      x2312_tx_time=0;
      for(index=0;index<110;index++)
            str2312[index]=0x20;
      sprintf(str2312,"+00.000F ");
      sprintf(&str2312[9],"%06.2f%% ",flow /
            xmit_full_scale * 100.0);
      if(str2312[9]==0x20) str2312[9]=0x30;
      if(str2312[10]==0x20) str2312[10]=0x30;
      sprintf(&str2312[17],"%5.3e ",(float)xmit_full_scale /
            flow_conversion[fl_rt_unts_row][fl_rt_unts_col-1]);
      str2312[22]=str2312[23];

str2312[23]=str2312[25];
      str2312[24]=0x20;
      index=line_two.position[fl_rt_unts_row][fl_rt_unts_col-1] -
            line_two.position[fl_rt_unts_row][0] + 3;
      str2312[25]=line_two.text[fl_rt_unts_row][index++];
      str2312[26]=line_two.text[fl_rt_unts_row][index++];
      str2312[27]=line_two.text[fl_rt_unts_row][index];

tfl=flow_total * volume_conversion2[volume_units-1];
      t3=-vol_dec_places[volume_units-1];
      while(tfl>10000000.0)
            {
            tfl/=10.0;
```

```c
            t3++;
            }
    sprintf(&str2312[32],"%7.0f",tf1);
    index=32;
    while(str2312[index]==0x20)
        str2312[index++]=0x30;
    sprintf(&str2312[39],"%+ld ",t3);
    index=line_two.position[3][volume_units-1] -
        line_two.position[3][0] + 3;
    t3=42;
    while(line_two.text[3][index]!=0x20)
        str2312[t3++]=line_two.text[3][index++];
    if(event_mark3==0 && event_mark4==on)
        {
        event_mark4=off;
        bottle_count2=bottle_count;
        pevent_mark=on;
        if(++sample_num>=100) sample_num=0;
        }
    sprintf(&str2312[49],"%02d %02d ",
        sample_num,bottle_count2);
    strcpy(&str2312[55],SiteDescrip);
    str2312[72]=0x20;
    sprintf(&str2312[84],"%03d ",SiteID);
    if(plotter_mode==1) index=0;
    else index=plotter_speed;
    sprintf(&str2312[88],"%ld ",index);
    sprintf(&str2312[90],"%02d %02d %02d %02d %02d ",
        sys_tm_dt.year,sys_tm_dt.month,sys_tm_dt.day,
        sys_tm_dt.hour,sys_tm_dt.min);
    inbyte(port2a);
    sprintf(&str2312[105],"%02d ",inbyte(port2d));
    str2312[108]=0x0D;
    str2312[109]=0x0A;
    str2312[110]=0;
        }
}

/****************************************************/ void do_typeD()
{
float tf2;
int ti1;
void load_timer();

if(typeD_time>typeD_old_time)
    {
    if(typeD_time>100)
        {
        typeD_time=0;
        typeD_old_time=0;
        }
    else typeD_old_time=typeD_time;
```

```
    tf2=flow/(float)xmit_full_scale * 1000.0 + 0.5;
    til=(int)tf2 + 1;
    tf2=til;
    if(tf2>1001.0) tf2=1001.0;
    tf2=(tf2 * 256.0 + 74.0) / 20.0 + 0.5;

load_timer((int)tf2);
    }
}

/**************************************************/ void plotter_check()
{
char inbit();

if(inbit(port6c,0)) paper_out_flag=on;
else paper_out_flag=off;

if(inbit(port6a,7)) Vp_power_flag=off;
else Vp_power_flag=on;
}

/**************************************************/ void prior_check()
{ if(prior_req==0)
    {
    if(auto_zero_time==0 && auto_zero_control != 1) prior_req=1;
    else if(menu_active==off && purge_flag)
        prior_req=2;
        else if(samp_req) prior_req=3;
    }
}

/**************************************************/ void super_bubble()
{
int sb_freq_sec;

if(sb_time<4) mode_letter=0x50;
if(sb_freq==2) sb_freq_sec=300;
else if(sb_freq==3) sb_freq_sec=600;
else if(sb_freq==4) sb_freq_sec=900;
else if(sb_freq==5) sb_freq_sec=1800;
else sb_freq_sec=3600;

if((sb_freq!=1 && sb_time > sb_freq_sec && sb_control != 1)
    || man_purge)
    {
    if(sb_control != 1) sb_time=0;
```

```c
    sb_pulse_time=cable_len * 20;
    man_purge=off;
    }
else if(head>sb_head && az_delay==0 && sb_control != 1)
    {
    if(++sb_head_count>10)
        {
        sb_pulse_time=2 * cable_len;
        sb_head_count=0;
        sb_time=0;
        }
    }
    else sb_head_count=0;
sb_head=head;
}
/*   AUGUST 02, 1990   LF9.C   VAU17 */ typedef char *STRING;

const struct table{
    int gate_pos[32];
    int head_ht[32][10];
    float flow_val[32][11];
    } flow_table={
    {  0, 315, 819, 993,1174,1388,1582,1820,
    2072,2318,2614,2911,3203,3490,3781,4072,
    4364,4655,4951,5243,5534,5826,6074,6318,
    6563,6761,6958,7155,7348,7546,7739,8192}, {{ 245, 347, 530, 751,1029,1361,4096,4096,4096,4096},/*<CL*/
     { 245, 347, 530, 751,1029,1361,4096,4096,4096,4096},/* CL*/
     { 188, 244, 387, 562, 825, 966,1248,4096,4096,4096},/* D6*/
     { 173, 219, 325, 683, 926,1124,4096,4096,4096,4096},/* D5*/
     { 159, 194, 285, 392, 599, 800, 991,1251,4096,4096},/* D4*/
     { 151, 178, 249, 329, 634, 820,1036,1242,4096,4096},/* D3*/
     { 169, 228, 287, 399, 520, 673, 856,1094,1331,4096},/* D2*/
     { 256, 429, 554, 705,1012,1255,4096,4096,4096,4096},/* D1*/

{ 291, 362, 435, 554, 711, 814,1024,1328,1365,4096},/* C5*/
     { 319, 383, 464, 580, 665, 846,1091,1356,1505,4096},/* C4*/
     { 288, 330, 373, 449, 505, 667, 869,1178,1480,4096},/* C3*/
     { 311, 342, 392, 447, 564, 704,1172,1419,1529,4096},/* C2*/
     { 310, 359, 389, 460, 579, 774, 959,1202,1557,4096},/* C1*/

{ 338, 424, 517, 654, 803,1003,1266,1641,4096,4096},/* B6*/
     { 395, 473, 587, 689, 849,1060,1345,1724,2104,4096},/* B5*/
     { 439, 535, 622, 738, 932,1138,1428,1696,2135,4096},/* B4*/
     { 473, 669, 812, 993,1217,1450,1597,1756,2127,4096},/* B3*/
     { 619, 736, 880,1069,1247,1367,1494,1789,2198,4096},/* B2*/
     { 679, 807, 955,1099,1204,1293,1539,1861,2304,4096},/* B1*/

{ 603, 744, 868, 990,1083,1216,1342,1959,2414,4096},/*A12*/
     { 802, 905, 978,1042,1104,1198,1403,2060,2487,4096},/*A11*/
     { 820, 893, 951,1003,1087,1254,1775,2113,2481,4096},/*A10*/
     { 924,1008,1156,1335,1575,1872,2175,2629,2682,4096},/* A9*/
```

```
 {1073,1223,1403,1911,2299,2343,4096,4096,4096,4096},/* A8*/
 {1130,1280,1697,2012,2059,2515,4096,4096,4096,4096},/* A7*/
 {1188,1331,1544,2244,2744,4096,4096,4096,4096,4096},/* A6*/
 {1215,1417,1685,2029,2453,2833,4096,4096,4096,4096},/* A5*/
 {1535,1805,2189,2518,3009,4096,4096,4096,4096,4096},/* A4*/
 {1373,1676,1980,2259,2685,3174,3841,4096,4096,4096},/* A3*/
 {1773,2003,2339,2751,3362,4096,4096,4096,4096,4096},/* A2*/
 {1993,2326,2730,3304,4096,4096,4096,4096,4096,4096}},/*A1*/
{{   .4942,    .9558,   1.9186,   3.0196,   4.5570,   6.1836,
    19.5831,  19.5831,  19.5831,  19.5831,  19.5831},/*<CLOSED*/
 {   .4942,    .9558,   1.9186,   3.0196,   4.5570,   6.1836,
    19.5831,  19.5831,  19.5831,  19.5831,  19.5831},/* CLOSED*/
 {   .4942,    .9558,   1.9186,   3.0196,   4.5570,   6.1836,
     7.8852,  25.0707,  25.0707,  25.0707,  25.0707}, /* D6*/
 {   .4942,    .9558,   1.9186,   4.5570,   6.1836,   7.8852,
    33.4271,  33.4271,  33.4271,  33.4271,  33.4271}, /* D5*/
 {   .4942,    .9558,   1.9186,   3.0196,   4.5570,   6.1836,
     7.8852,  11.5798,  52.0071,  52.0071,  52.0071}, /* D4*/
 {   .4942,    .9558,   1.9186,   3.0196,   6.1836,   7.8852,
     9.6494,  13.2091,  62.5268,  62.5268,  62.5268}, /* D3*/
 {   .9558,   1.9186,   3.0196,   4.5570,   6.1836,   7.8852,
     9.6494,  11.8968,  15.3332,  55.4242,  55.4242}, /* D2*/
 {  3.0196,   6.1836,   7.8852,   9.6494,  13.2932,  16.8211,
    58.0676,  58.0676,  58.0676,  58.0676,  58.0676}, /* D1*/

{  4.5570,   6.1836,   7.8852,   9.6494,  11.8968,  13.2932,
    16.3444,  21.2070,  21.4622,  62.4498,  62.4498}, /* C5*/
 {  6.1836,   7.8852,   9.6494,  11.8968,  13.2932,  16.3444,
    21.1145,  24.8283,  27.2140,  68.6996,  68.6996}, /* C4*/
 {  6.1836,   7.8852,   9.6494,  11.8968,  13.2932,  16.3444,
    21.1145,  27.3200,  32.5750,  78.0951,  78.0951}, /* C3*/
 {  7.8852,   9.6494,  11.8968,  13.2932,  16.3444,  21.1145,
    27.6350,  32.6340,  37.0070,  39.2580,  91.7882}, /* C2*/
 {  9.6494,  11.8968,  13.2932,  16.3444,  21.3230, 27.6440,
    32.7420,  39.0020,  46.8940,103.3384,103.3384}, /* C1*/

{ 11.8012,  16.5317,  21.2380,  27.6440,  32.8620,  39.1560,
    47.2190,  56.0820,114.1051,114.1051,114.1051},/* B6*/
 { 16.3444,  21.2100,  27.5460,  32.8660,  39.2420,  47.4380,
    56.6910,  67.4060,  76.6020,124.8084,124.8084},/* B5*/
 { 21.1145,  27.3650,  32.8330,  39.1690,  48.1870,  56.6770,
    67.9510,  76.4380,  88.2300,140.9045,140.9045},/* B4*/
 { 27.8920,  39.2160,  48.1410,  56.8600,  67.9570,  77.3600,
    83.5800,  89.2310,104.5320,172.3966,172.3966},/* B3*/
 { 39.1150,  47.7920,  56.8550,  68.6140,  77.7480,  83.6510,
    90.1600,106.7150,120.7420,185.8355,185.8355},/* B2*/
 { 48.0450,  56.9560,  68.4810,  77.5830,  84.1080,  89.7600,
   105.8150,121.6120,139.8620,213.6859,213.6859},/* B1*/

{ 47.7520,  56.8390,  68.4540,  77.6930,  83.8110,  96.5500,
   106.4120,140.4580,160.6100,235.1059,235.1059},/*A12*/
 { 68.5500,  77.7790,  83.8590,  89.2790,  97.2102,105.9830,
   122.7260,163.2900,183.3870,259.1155,259.1155},/*A11*/
 { 77.7720,  84.0090,  89.3210,  97.6988,105.4170,122.4618,
   166.7375,188.9430,206.8650,285.5172,285.5172},/*A10*/
 { 98.3247,104.3350,121.4438,143.5430,166.6070,189.6480,
```

```
             209.6490,239.5890,250.3600,537.7221,537.7221},/* A9*/
            {121.0845,143.3739,166.7570,210.2960,239.3090,242.7200,
             378.6173,378.6173,378.6173,378.6173,378.6173},/* A8*/
            {143.1130,166.4600,213.1688,241.7350,245.0530,295.1650,
             469.2704,469.2704,469.2704,469.2704,469.2704},/* A7*/
            {165.6120,187.5380,215.6280,284.5830,340.8720,493.0774,
             493.0774,493.0774,493.0774,493.0774,493.0774},/* A6*/
            {188.1180,215.2590,247.3200,287.1820,348.5370,384.5890,
             504.4144,504.4144,504.4144,504.4144,504.4144},/* A5*/
            {249.3770,286.0820,344.5130,389.6930,447.1190,574.2448,
             574.2447,574.2447,574.2447,574.2447,574.2447},/* A4*/
            {249.5500,290.6870,338.2120,392.9270,445.0250,494.3395,
             569.9960,598.9201,598.9201,598.9201,598.9201},/* A3*/
            {340.2440,393.1670,450.7050,501.7390,577.2370,667.9334,
             667.9334,667.9334,667.9334,667.9334,667.9334},/* A2*/
            {392.4900,454.6340,508.5350,568.6760,651.6580,651.6580,
             651.6580,651.6580,651.6580,651.6580,651.6580}}/* A1*/
    };

const char char_pattern0[97]={
    /*SPACE   */ 0x20,0x00,0x00,0x00,0x00,0x00,
    /*QUOTE   */ 0x22,0x00,0x70,0x00,0x70,0x00,
    /*PERCENT */ 0x25,0x62,0x64,0x08,0x13,0x23,
    /*AND     */ 0x26,0x36,0x49,0x55,0x22,0x05,
    /*MULT    */ 0x6D,0x22,0x14,0x08,0x14,0x22,
    /*PLUSMI  */ 0x70,0x11,0x11,0x3D,0x11,0x11,
    /*DIVIDE  */ 0x64,0x08,0x08,0x2A,0x08,0x08,
    /*CUBE    */ 0x01,0x54,0x54,0x54,0x28,0x00,
                 0x02,0x20,0x20,0x20,0x20,0x20,
                 0x03,0x10,0x10,0x10,0x10,0x10,
                 0x04,0x08,0x08,0x08,0x08,0x08,
                 0x05,0x04,0x04,0x04,0x04,0x04,
                 0x06,0x02,0x02,0x02,0x02,0x02,
                 0x07,0x01,0x01,0x01,0x01,0x01,
    /*SQUOTE  */ 0x27,0x00,0x00,0x70,0x70,0x00,
    /*BLANK   */ 0xA0,0x00,0x00,0x00,0x00,0x00,
                 0x00};

const char char_pattern1[280]={
    /*LPAR    */ 0x00,0x1C,0x22,0x41,0x00,
    /*RPAR    */ 0x00,0x41,0x22,0x1C,0x00,
    /*STAR    */ 0x14,0x08,0x3E,0x08,0x14,
    /*PLUSc   */ 0x08,0x08,0x3E,0x08,0x08,
    /*COMMA   */ 0x00,0x05,0x06,0x00,0x00,
    /*MINUSc  */ 0x08,0x08,0x08,0x08,0x08,
    /*DPOINT  */ 0x00,0x03,0x03,0x00,0x00,
    /*SLAS,   */ 0x02,0x04,0x08,0x10,0x20,
    /*ZERO    */ 0x3E,0x45,0x49,0x51,0x3E,
    /*ONE     */ 0x00,0x21,0x7F,0x01,0x00,
    /*TWO     */ 0x21,0x43,0x45,0x49,0x31,
    /*T,REE   */ 0x42,0x41,0x51,0x69,0x46,
    /*FOUR    */ 0x0C,0x14,0x24,0x7F,0x04,
    /*FIVE    */ 0x72,0x51,0x51,0x51,0x4E,
    /*SIX     */ 0x1E,0x29,0x49,0x49,0x06,
    /*SEVEN   */ 0x40,0x47,0x48,0x50,0x60,
```

```
/*EIGHT   */ 0x36,0x49,0x49,0x49,0x36,
/*NINE    */ 0x30,0x49,0x49,0x4A,0x3C,
/*COLON   */ 0x00,0x36,0x36,0x00,0x00,
/*APOST   */ 0x00,0x35,0x36,0x00,0x00,
/*LESS    */ 0x00,0x41,0x22,0x14,0x08,
/*LARROW     0x08,0x1C,0x2A,0x08,0x08,*/
/*EQUAL   */ 0x14,0x14,0x14,0x14,0x14,
/*GREAT   */ 0x08,0x14,0x22,0x41,0x00,
/*RARROW     0x08,0x08,0x2A,0x1C,0x08,*/
/*QUEST   */ 0x20,0x40,0x45,0x48,0x30,
/*AMP     */ 0x26,0x49,0x4F,0x41,0x3E,
/*A       */ 0x3F,0x44,0x44,0x44,0x3F,
/*B       */ 0x7F,0x49,0x49,0x49,0x36,
/*C       */ 0x3E,0x41,0x41,0x41,0x22,
/*D       */ 0x7F,0x41,0x41,0x22,0x1C,
/*E       */ 0x7F,0x49,0x49,0x49,0x41,
/*F       */ 0x7F,0x48,0x48,0x48,0x40,
/*G       */ 0x3E,0x41,0x49,0x49,0x2F,
/*H       */ 0x7F,0x08,0x08,0x08,0x7F,
/*I       */ 0x00,0x41,0x7F,0x41,0x00,
/*J       */ 0x02,0x01,0x41,0x7E,0x40,
/*K       */ 0x7F,0x08,0x14,0x22,0x41,
/*L       */ 0x7F,0x01,0x01,0x01,0x01,
/*M       */ 0x7F,0x20,0x18,0x20,0x7F,
/*N       */ 0x7F,0x10,0x08,0x04,0x7F,
/*O       */ 0x3E,0x41,0x41,0x41,0x3E,
/*P       */ 0x7F,0x48,0x48,0x48,0x30,
/*Q       */ 0x3E,0x41,0x45,0x42,0x3D,
/*R       */ 0x7F,0x48,0x4C,0x4A,0x31,
/*S       */ 0x31,0x49,0x49,0x49,0x46,
/*T       */ 0x40,0x40,0x7F,0x40,0x40,
/*U       */ 0x7E,0x01,0x01,0x01,0x7E,
/*V       */ 0x7C,0x02,0x01,0x02,0x7C,
/*W       */ 0x7E,0x01,0x0E,0x01,0x7E,
/*X       */ 0x63,0x14,0x08,0x14,0x63,
/*Y       */ 0x70,0x08,0x07,0x08,0x70,
/*Z       */ 0x43,0x45,0x49,0x51,0x61,
/*LBRAK   */ 0x00,0x7F,0x41,0x41,0x00,
/*BSLASH  */ 0x20,0x10,0x08,0x04,0x02,
/*RBRAK   */ 0x00,0x41,0x41,0x7F,0x00,
/*UARROW  */ 0x08,0x10,0x3E,0x10,0x08,
/*UNDER   */ 0x01,0x01,0x01,0x01,0x01};
const STRING line_one[74]={
" TOTAL          FLOW RATE",
"ENTER PROGRAM STEP NUMBER 1-11:",
"SELECT FLOW RATE UNITS:",
"SELECT TOTALIZED VOLUME UNITS:",
"EXIT WILL DISCARD CHANGES",
"PRESS '0' TO EXIT, '1' TO CONTINUE",
"ENTER PASSNUMBER",
"INVALID PASSNUMBER",
"CAUTION: SAMPLER INITIATION TURNED OFF",
"PRESS 'ENTER' KEY TO CONTINUE",
"ENTER SAMPLER PACING:",/* [10] */
"SAMPLER INTERVAL:   (",
"INTERVAL PER PULSE = ",
```

```
"ENTER SAMPLER INTERVAL:",
"TIME INTERVAL PER PULSE =    HOUR    MIN",
"SELECT PLOTTER MODE OF OPERATION:",
"PLOTTER FULL-SCALE: (",
"100% FLOW =          ",
"SELECT PLOTTER CHART SPEED:",
"SET: YEAR   MONTH   DAY  HOUR  MINUTE",
"CAUTION: PLOTTER TURNED OFF",/* [20] */
"SET SITE IDENTIFICATION NUMBER:",
"SITE NUMBER =",
"RESET FLOW TOTALIZER:",
"REPORT GENERATION:",
"CLEAR REPORT DATA AFTER PRINT:",
"REPORT INTERVAL TO BE IN:",
"ENTER INTERVAL IN HOURS:",
"ENTER INTERVAL IN DAYS:",
"ENTER INTERVAL IN MONTHS:",
"ENTER THE INTERVAL START TIME:",/* [30] */
"YR:     MONTH:    DAY:    HR:    MIN:",
"SELECT GATE FLUSH MODE:",
"SELECT TIME BETWEEN FLUSHES:",
"   HOURS      MINUTES",
"VOLUME BETWEEN FLUSHES: (",
"VOLUME BETWEEN FLUSHES =",
"SELECT AUTO-PURGE FREQUENCY:",
"SELECT CALIBRATION MODE:",
"PLACE STEP X UNDER GATE, PRESS ENTER.",
"ENTER CHARACTERIZATION NUMBER:",/* [40] */
"ENABLE PROGRAM LOCK?",
"REPORT GENERATION IS IN PROGRESS",
"MUST TURN REPORT GENERATOR OFF TO CHANGE",
"SAMPLER ENABLE OVERRRIDDEN",
"SELECT SAMPLER CONTROL:",
"ENTER FLOW AT WHICH TO ENABLE SAMPLER:",
"ONCE ENABLED, SAMPLER WILL:",
"SAMPLER CURRENTLY ENABLED, RESET TO",
"DISABLED STATE",
"SELECT PLOTTER ON/OFF WITH SAMP ENABLE:",/* [50] */
"MODEL 3240 VERSION AU17",
"(c) COPYRIGHT 1990 ISCO INC.",
"D2.  SELECT LVDT/HEAD DISPLAY:",
"PLOTTER IS OUT OF PAPER",
"CALIBRATION IN PROGRESS.  PLEASE WAIT.",
"CALIBRATION CONSTANT:",
"CALIBRATING STEP",
"SELECT CABLE LENGTH:",
"TRANSMIT FULL SCALE: (",
"NO 12 VOLT POWER - CHECK FUSE",            /* [60] */
"PLOTTER JAMMED",
"UNIT NOT CALIBRATED",
"D3.  SUPER BUBBLE:",
"D4.  HEAD AVERAGING:",
"D5.  AUTO ZERO:",
"D6.  ZERO PRESSURE TRANSDUCER:",
"D1.  CLOCK ADJUST:",
"D7.  HEAD OFFSET:",
```

```
"D8. PUMP TIME:",
"D9. DIAGNOSTICS:     1. ALL   2. Rom/Ram",/* [70] */
"3. PLOTTER 4. UART 5. SAMPLER 6. DISPLAY",
"D10. GAUGE BLOCK TEST",
"USE ARROWS AND 'O' KEY TO MOVE GATE"};

const struct menus {
    int position[20][6];
    char text[20][44];}
    line_two={
{{43,51,59,67,75,80},
 {43,51,59,67,75,80},
 {43,51,59,67,75,80},
 {36,43,51,58,65,71},
 {43,52,64,80,80,80},
 {43,51,80,80,80,80},
 {43,54,64,74,80,80},
 {43,51,80,80,80,80},
 {43,50,58,80,80,80},
 {43,53,62,80,80,80},
 {43,52,61,80,80,80},
 {43,51,80,80,80,80},
 {43,59,80,80,80,80},
 {43,50,80,80,80,80},
 {43,54,66,80,80,80},
 {43,54,80,80,80,80},
 {43,56,80,80,80,80},
 {60,68,80,80,80,80},
 {43,51,57,64,71,78},
 {43,50,57,65,73,80}},
{{"1. GPM  2. GPS  3. MGD  4. CFS  5. Other"},
 {"1. CMS  2. CMH  3. CMD  4. LPS  5. Other"},
 {"1. CFD  2. GPH  3. AFD  4. CFH  5. Other"},
 {"1. CF  2. GAL  3. CM  4. AF  5. L  6. MGAL "},
 {"1. NONE 2.  BY\240FLOW  3. BY\240TIME           "},
 {"1. OFF  2. FLOW                              "},
 {"1. .5\042/HR  2. 1\042/HR  3. 2\042/HR  4. 4\042/HR "},
 {"1. YES  2. NO                                "},
 {"1. ON  2. OFF  3. PRINT                      "},
 {"1. HOURS  2. DAYS  3. MONTHS                 "},
 {"1. TIME  2. FLOW  3. TIME\240OR\240FLOW            "},
 {"1. OFF  2. ON                                "},
 {"1. GAUGE\240BLOCK  2. CHARACTERIZATION\240#    "},
 {"1. ON  2. OFF                                "},
 {"1. ENABLE  2. DISABLE  3. ENABLE\240BY\240FLOW"},
 {"1.                                           "},
 {"1. STAY\240ENAB 2. DISABLE\240BELOW "},
 {"1. YES  2. NO "},
 {"1. OFF  2. 5  3. 10  4. 15  5. 30  6. 60"},
 {"1. 25  2. 50  3. 100  4. 175  5. 250     "}}
};

const float flow_plot_min[3][4]=
{{50,1,.07,.1},
 {.03,10,250,3},
 {10000,3000,.2,400}};
```

```c
const float flow_plot_max[3][4]=
{{500,10,.7,1},
 {.3,100,2500,30},
 {100000,30000,2,4000}};
const char flow_plot_digits[3][4]=
{{3,2,2,2},
 {2,3,4,2},
 {6,5,2,4}};
const char flow_plot_dec[3][4]=
{{0,0,2,1},
 {2,0,0,0,},
 {0,0,1,0}};

const float samp_enable_min[3][4]=
{{1,.02,.001,.002},
 {.0001,.2,5,.06},
 {200,60,.004,8}};
const float samp_enable_max[3][4]=
{{300,5,.43,.7},
 {.02,70,1634,19},
 {58000,18000,1.33,2400}};
const char samp_enable_digits[3][4]=
{{3,3,3,3},
 {4,3,4,4},
 {5,5,4,4,}};
const char samp_enable_dec[3][4]=
{{0,2,3,3},
 {4,1,0,2},
 {0,0,3,0}};

/*    JUNE 21, 1990    LF10.C    VAR02  */ include "type3240.h"
include "cmndset0.h"
#include "c_packet.h"
#include "d_packet.h"
#include "protocol.h"

char                          Abort_Flg;
int                           blocktimer;
short                         c_command;
struct commandEntry           commandtbl[12];
char                          conversation;
char                          commandrdy;
long                          curtime;
struct data_pac               LastPacket;
unsigned char                 *logging_alloc=
    (unsigned char *)0x8B00;
struct cmnd_pac               MyCPacket;
struct data_pac               MyDPacket;
char                          NewMin;
char                          Num_Partitions;
long                          offset1;
long                          OldPTime;
char                          OldTimeCondition;
struct Partition              Partit[3];
```

```
char                     pevent_mark;
char                     pfailflg;
char                     plotterhalt;
char                     PORT_MAP=0x03;
struct Port              Ports[2];
long                     PTime;
long                     Ptime_Offset;
unsigned long            RestartNumReadings;
struct Partition         *RestartPartPtr;
struct cmnd_pac          rx_data1;
TimeRec                  SampETimes[SupportedTRecords];
char                     SampFlg;
char                     SampHist[3];/* Guess */
struct SamplerEnable     SamplerEnab={0,0,0,0,5000,0x1,0};
unsigned int             sampler_init1;
int                      scaleexp;
unsigned int             SEDuration;
char                     se_latch_flag;
char                     se_pl_en_flag;
unsigned long            SEStartTime;
char                     SiteDescrip[18]="   3240 FLOW METER";
char                     SlaveLocked;
int                      Slavepassword;
long                     StartOfDay;
long                     StartOfWeek;
char                     TCheckCondition;
struct Partition         *TempPart;
long                     Time_SL;
long                     Time_TA;
long                     tlong1;
long                     tlong2;
long                     TmpFlow;
unsigned int             TPRaincounts;
short                    tshort1;
struct timestruct        ttime;
int                      Xmit_Delay;   /* number of
       milliseconds to wait between blocks */

/*      JULY 09, 1990    LF11.C    VAS07 */ include "type3240.h"
include "cmndset0.h"
#include "c_packet.h"
#include "d_packet.h"
#include "protocol.h"

extern short             c_command;
extern struct cmnd_pac   MyCPacket;
extern char              conversation,commandrdy;
extern struct data_pac   MyDPacket;
extern char              SlaveLocked;
extern char              TCheckCondition;
extern unsigned char     tx_count;
char                     xxxx;
extern char              s[41];

extern int (*CommandTbl[39])();
```

```
/***************************************************************/
/*int sprintf(char *,const char *,...);

void stop_f(xval)
char xval;
{
void sdisplay();

sprintf(s,"%ld",xxxx);
sdisplay(8,s);
while(xxxx==xval);
}
*/

/***************************************************************/ void check_proto()
{ void CheckSampE();
void clear_commandtbl();
int do_tx_gen_error();
void EndConv();
void get_command();
void InitDP();
long SendDP();
void Update_Parts();
void Update_lf_Ports();
Update_lf_Ports();

Update_Parts();      /* Set PTime if new minute */ if (TCheckCondition)
    {
    CheckSampE();
    TCheckCondition = 0;
    } if(conversation && !do_tx_gen_error())
    {
    if (conversation || commandrdy)
        {
        conversation = 1;
        /* if a command is ready, we must have a conversation
*/
        if (commandrdy)
            {
            get_command(&MyCPacket);
            InitDP(&MyCPacket,&MyDPacket);
            /* copy the command ID, put in table, etc */
            if ((MyCPacket.command <= UNLATCH_SE) &&
                (CommandTbl[MyCPacket.command]))
                {
                SendDP(&MyDPacket,
```

```
                    (*CommandTbl[MyCPacket.command])
                    (&MyCPacket,&MyDPacket),1);
                if (c_command == END_CONV)
                    {
/* wait for last packet to be transmitted before ending
conversation */
                    while(tx_count!=0);
                    EndConv();
/* if connected to modem, signal to hang up after carrier dropped
*/
                    clear_commandtbl();
                    if (!commandrdy) conversation = 0;
                    }
                }
            else
                {
                MyDPacket.response = UNKNOWN_COMMAND;
                SendDP(&MyDPacket,0,0);
/* secondary response of 0, no store in command table */
                }
            }
        }
    else SlaveLocked = 1;
    }
}

/*      JUNE 26, 1990    LF12.C    VAR02 */ include "type3240.h"
include "protocol.h"
#include "c_packet.h"
#include "d_packet.h"

define logging_start     (unsigned char *)0x8B00 extern int              blocktimer;
extern char             bottle_count2;
extern short            c_command;
extern char             commandrdy;
extern struct commandEntry commandtbl[12];
extern long             curtime;
extern float            flow_total;
extern unsigned char    *logging_alloc;
extern char             NewMin;
extern char             Num_Partitions;
extern long             offset1;
extern long             OldPTime;
extern struct Partition Partit[3];
extern char             pevent_mark;
extern char             PORT_MAP;
extern struct Port      Ports[2];
extern long             Ptime_Offset;
extern struct cmnd_pac  rx_data1;
extern int              scaleexp;
```

```c
extern long            tlong1;
extern long            tlong2;
extern struct Partition *TempPart;
extern long            Time_TA;
extern long            Time_SL;
extern long            TmpFlow;
extern unsigned int    TPRaincounts;
extern long            PTime;
extern struct timestruct ttime;
extern char            Volunits[6];
extern const float     volume_conversion2[6];
extern char            volume_units;
extern const char      vol_dec_places[6];
extern int             Xmit_Delay;   /* number of milliseconds
      to wait between blocks */
int                    sprintf(char *,const char *,...);

extern int             CheckHaltedSlate();
extern void            fillmem();
extern void            get_time();
extern long            IscoTime();
extern void            set_time();
extern void            UpdateHaltFlag();

/****************************************************/ void   clear_commandtbl()

{
unsigned char   count;

for(count=0;count<12;count++)
    {
    commandtbl[count].command = 0;
    commandtbl[count].commandID = 0;
    commandtbl[count].retcode = 0;
    }
}

/****************************************************/ long Blks_Avail()

{
    return((MEM_END - logging_alloc) >> 7);
}

/****************************************************/ long Blks_Total()
```

```
{
    return((MEM_END - logging_start) >> 7);
}

/*****************************************************
 * This routine checks for the existence of the port and if ckflg
 * is non-zero, it will also compare the type and sub_type for a
match
 *****************************************************/ char CheckPort(pnum,ckflg,ptype,psub_type)

register char pnum,ckflg,ptype,psub_type;
{
    if (!(PORT_MAP & (1<<pnum))) return(0);

if (ckflg) {
        if (Ports[pnum].type != ptype) return(0);
        if (ckflg > 1) {
            if (Ports[pnum].sub_type != psub_type) return(0);
        }
    }
    return(1);
}

/*****************************************************/ void CInit_Part(Partptr,partnum,size,Addr)

register struct Partition *Partptr;
unsigned char partnum;
register short size;
unsigned char *Addr;
{
  fillmem(Partptr,sizeof(struct Partition),0);    /* clear the
partition structure */
  Partptr->partition_num = partnum;
  Partptr->logging_type = UNINITIALIZED;
  fillmem((Partptr->PartAddr) = Addr,(Partptr->Num_Blocks = size)
<< 7,0);   /* clear the partition memory */
}

/*****************************************************/ void Decptr(Pptr)

register struct Partition *Pptr;
/* This routine decrements the Block_Offset and Current_Block
fields as necessary */
{
    if (Pptr->data_width <= (unsigned int)Pptr->Block_Offset) {

Pptr->Block_Offset -= (unsigned char)Pptr->data_width;
    }
```

```
    else {
        if ((Pptr->Current_Block) == 0)
            Pptr->Current_Block = Pptr->Num_Blocks;
        (Pptr->Current_Block)--;
        if (Pptr->Rollover) (Pptr->Rollover)--;
        Pptr->Block_Offset = 128 - Pptr->data_width;
    }
}
```

/******************************************************/

/* struct command_pac localbuf; */

```
void get_command(cpacket)

struct cmnd_pac *cpacket;
{
*cpacket=rx_data1;
commandrdy=0;
}
```

/******************************************************/

```
void Incptr(Pptr)

register struct Partition *Pptr;
/* This routine increments the Block_Offset and Current_Block
fields as necessary */
{
    if ((Pptr->Block_Offset += Pptr->data_width) > 127) {
        Pptr->Block_Offset -= 128;
        if (++(Pptr->Current_Block) >= Pptr->Num_Blocks) {
            Pptr->Current_Block = 0;
            if (Pptr->Rollover < 255) Pptr->Rollover++;
        }
    }
}
```

/******************************************************/

```
void InitDP(CPacket,DPacket)
struct cmnd_pac *CPacket;
struct data_pac *DPacket;
{
fillmem(DPacket,sizeof(struct data_pac),0);
DPacket->commandid=CPacket->commandid;
c_command=CPacket->command;
}
```

/******************************************************/

```
long LTotalFlow()
```

```
{
scaleexp = -vol_dec_places[volume_units-1];
return((long)(flow_total * volume_conversion2[volume_units-1]));
}
```

/**********************************************************/

```
unsigned char *PAddr(Pptr)

register struct Partition *Pptr;
{
   return(Pptr->PartAddr + (Pptr->Current_Block << 7) +
Pptr->Block_Offset);
}
```

/**********************************************************/

```
void PartTimeChange(mode)     /* Do a time change on the active
partitions */
char mode;
{
     register char Partcntr;
     register struct Partition *Partptr;
     void Tchange_EPart();
     void Tchange_SPart();
     void Tchange_TPart();

Partptr = Partit;

for (Partcntr = 0; Partcntr < Num_Partitions; Partcntr++) {
         if (Partptr->Time_Last_Storage)      /* Only update if
records are written */
                 if (Partptr->logging_type == TIME_DRIVEN)
                     Tchange_TPart(Partptr,mode);
                 else if ((Partptr->logging_type == EVENT_DRIVEN))
                     Tchange_EPart(Partptr,mode);
                 else if ((Partptr->logging_type == SCRATCH_PAD))
                     Tchange_SPart(Partptr,mode);
         Partptr++;
     }

}
```

/**********************************************************/

```
long ProtocolTime()    /* The protocol time in seconds */

{
       get_time(&ttime);    /* initialize the time structure from
the hardware clock */
```

```c
        return(Ptime_Offset + (IscoTime(&ttime)* 60) + ttime.sec);
}

/**********************************************************/ long ProtocolTimeMin()   /* The protocol time in minutes */

{
     return(ProtocolTime() / 60);
}

/**********************************************************/ void Putit(l,c)

long l;
int *c;
{
*c=l;
}

/**********************************************************/ void Reset_Part(Partptr)

register struct Partition *Partptr;
{
   fillmem(Partptr->PartAddr,Partptr->Num_Blocks << 7,0);  /*
clear the partition memory */
   Partptr->Time_Last_Storage = 0;
   Partptr->Block_Offset = 0;
   Partptr->Current_Block = 0;
   Partptr->Rollover = 0;

Partptr->EventCounts = 0;
   Partptr->SlateModeBits &= 0xFE;   /* clear the halt flag */
   Partptr->ConditionStartTime = 0;
/* Should really zero these fields also to be clean about things
     unsigned short End_Block;
     unsigned char EndBlock_Offset;
But, for the sake of rom space, we leave them alone */

}

/**********************************************************/ void RInit_part(Partptr,cptr)
```

```c
register struct Partition *Partptr;
register struct scb000C *cptr;
{
char *movmem();

CInit_Part(Partptr,Partptr->partition_num,
      (short)Partptr->Num_Blocks,Partptr->PartAddr);   /* clear the
partition */
  Partptr->data_width = cptr->d_width;
  Partptr->logging_type = cptr->type;
  Partptr->in_port = cptr->port_no;
  Partptr->time_interval = cptr->d_interval;
  Partptr->partition_type = cptr->partition_type;
  Partptr->Recording_Mode = cptr->Recording_Mode;
  Partptr->SlateModeBits = cptr->SlateModeBits;
  movmem(&cptr->Triggerinfo,&Partptr->Triggerinfo,
      sizeof(cptr->Triggerinfo));
  Partptr->Rainbuf.RainTripPoint =
cptr->Triggerinfo.RainSlate.TotaledRain;
  Partptr->Rainbuf.RainInterval =
cptr->Triggerinfo.RainSlate.ReadingInterval;
}

/****************************************************/ long SendDP(dpacket,retcode,tabstore)

register struct data_pac *dpacket;
register char retcode, tabstore;
{
long SSendDP();

while (blocktimer);
    SSendDP(dpacket,retcode,tabstore);
    blocktimer = Xmit_Delay / 10 + 1;  /* block timer has
resolution of 1/100 of a second */
}

/****************************************************/ void Set_Time(dt)   /* Handles setting the realtime clock and keeping the PTime_Offset updated so protocol time does not change
*/
struct timestruct *dt;
{
    get_time(&ttime);
    set_time(dt);
    Ptime_Offset += (IscoTime(&ttime)*60 + ttime.sec) -
IscoTime(dt)*60;
}
```

```c
long SSendDP(dpacket,retcode,tabstore)

struct data_pac *dpacket;
char retcode, tabstore;
{ unsigned char counter;
    void StartTransmit();
    unsigned long CalcCheckSum();
    if (retcode) {
        dpacket->response = 1;   /* Indicate that a secondary
response is present */
        fillmem(dpacket->db.body,128,0);  /* clear out the body
*/
        dpacket->db.body[0] = retcode;
        dpacket->address = 0;
    } dpacket->preamble[0] = 0;
    dpacket->preamble[1] = 0;
    dpacket->flag[0] = 0xAA;
    dpacket->flag[1] = 0x55;

dpacket->crc = CalcCheckSum(dpacket);   /* set the checksum
*/ if (tabstore) {   /* Check to see if we store this in command
table */
        if (c_command != 0x18) {   /* Do not store if command is
NO_OP */
            for (counter = 11; counter; counter--) {  /* move
all entries to the next one */
                commandtbl[counter] = commandtbl[counter-1];
            }
            commandtbl[0].command = c_command;
            commandtbl[0].commandID = dpacket->commandid;
            commandtbl[0].retcode = retcode;
        }
    }

StartTransmit(dpacket);
}

/****************************************************************/ void StoreEvent(Pptr)   /* Store an event ports' counts in a Timed partition */
register struct Partition *Pptr;
{
```

```c
        register char *charptr;
        register unsigned int tcounts;
        register unsigned char stochar;

charptr = (char *)PAddr(Pptr);
        tcounts = Pptr->EventCounts;

Pptr->EventCounts = 0;

if (tcounts > 1200) {
              stochar = 0xFA;    /* Error code for out of range */
        }
        if (tcounts > 120) {
              stochar = (tcounts / 10) | 0x80;
        }
        else
              stochar = tcounts;

*charptr = stochar;
}

/****************************************************************/ void StoreFlow(Pptr)

struct Partition *Pptr;
{
        int *intptr;
        unsigned int Cflow;

intptr = (int *)PAddr(Pptr);
        TmpFlow = Ports[0].typeopts.cur_flow;
        if (Ports[Pptr->in_port].err_flag)
           Cflow = INPUT_ERROR;
        else if (TmpFlow > Max_Level)
           Cflow = Max_Level;
        else if (TmpFlow < 0)
           Cflow = 0;
        else
           Cflow = TmpFlow;
        *intptr = Cflow;
}

/****************************************************************/ void Tchange_EPart(Pptr,mode)

register struct Partition *Pptr;
char mode;
{
        register unsigned char *cptr;
        register unsigned char *fptr;
```

```
        if (mode == TIME_FIXED)
            if (offset1 < 0) {    /* do nothing if time is advanced
(offset > 0) because Update_EPart() will catch-up next time a
sample occurs */
                /* remember the starting pointer so if we wrap
around on ourselves we can Reset_Part() */
                fptr = Pptr->Rollover ? PAddr(Pptr) :
Pptr->PartAddr;
                while (Pptr->Time_Last_Storage > (curtime +
offset1)) {
                    /* We need to calculate cptr each time
through loop in case partition has rolled over */
                    Decptr(Pptr);

cptr = PAddr(Pptr);

if ((fptr != cptr) && Pptr->Time_Last_Storage
> *cptr)
                        Pptr->Time_Last_Storage -= *cptr;
                    else {
                        Reset_Part(Pptr);
                        break;
                    }
                    *cptr = 0xFF;
                    *(cptr+1) = 0x00;

}    /* end of while */
            }  /* end of if (offset1 < 0) */
        else   /* TIME-RELATIVE */
            Pptr->Time_Last_Storage += offset1;

}

/****************************************************************/ void Tchange_SPart(Pptr,mode)

register struct Partition *Pptr;
char mode;
{
    Pptr->Time_Last_Storage += offset1;
}

/****************************************************************/

/* #define curtime tlong1 */
/* #define offset tlong2 */ void Tchange_TPart(Pptr,mode)

register struct Partition *Pptr;
char mode;
{
    register int Records, CurRecords;
    register int *intptr;
```

```
        if (mode == TIME_FIXED) {

Time_SL = (curtime - Pptr->Time_Last_Storage);
                if (offset1 > 0) {
                        Records = (offset1 + Time_SL) /
(long)Pptr->time_interval;
                }
                else {
                        Records = offset1 / (long)Pptr->time_interval;
                        if (((-offset1) % (long)Pptr->time_interval) >
Time_SL) Records--;
                }
                /* Calculate the number of possible records in the
partition */
                CurRecords = (Pptr->Num_Blocks << 7) /
Pptr->data_width;

if (Records == 0) return;
                if (Records > 0) {        /* Need to add/create records
*/
                        if (Records >= CurRecords) {
                            Reset_Part(Pptr);
                            return;
                        }
                        while (Records > 1) {
                            Pptr->Time_Last_Storage +=
Pptr->time_interval;
                            intptr = (int *)PAddr(Pptr);
                            *intptr = CLOCK_CHANGE;
                            Incptr(Pptr);
                            Records--;
                        }
                        Pptr->Time_Last_Storage += Pptr->time_interval;
                        StoreFlow(Pptr);
                        Incptr(Pptr);
                }
                else {   /* Need to delete records */
                        if (!Pptr->Rollover)  /* If no rollover, get
number of actual records */
                            CurRecords = ((Pptr->Current_Block << 7) +
Pptr->Block_Offset) / Pptr->data_width;
                        Records = -Records;
                        if (Records >= CurRecords) {
                            Reset_Part(Pptr);
                            return;
                        }
                        while (Records) {
                            Pptr->Time_Last_Storage -=
Pptr->time_interval;
                            Decptr(Pptr);
                            intptr = (int *)PAddr(Pptr);
                            *intptr = (int)RECORD_DELETED;
                            Records--;
```

```
            }

}
    }
    else { /* TIME-RELATIVE */
        Time_TA = (long)Pptr->time_interval * ((offsetl +
(long)(Pptr->time_interval >> 1)) / (long)Pptr->time_interval);
        Pptr->Time_Last_Storage += Time_TA;
        Time_SL = curtime + offsetl - Pptr->Time_Last_Storage;
        if (Time_SL < 0) {   /* delete a record */
            Decptr(Pptr);
            intptr = (int *)PAddr(Pptr);
            *intptr = (int)RECORD_DELETED;
            Pptr->Time_Last_Storage -= Pptr->time_interval;
            /* if deleted the only record, reset the partition
*/
            if (!(Pptr->Rollover || Pptr->Current_Block ||
Pptr->Block_Offset)) {
                Reset_Part(Pptr);
                return;
            }
        }
        else if (Time_SL >= (long)Pptr->Time_Last_Storage) {
/* create a record */
            StoreFlow(Pptr);
            Pptr->Time_Last_Storage += Pptr->time_interval;
            Incptr(Pptr);
        }
    }
}

/***********************************************************/ define Timediff tlongl void Update_EPart(Pptr)
register struct Partition *Pptr;
{
    register unsigned char Bottl;
    register unsigned char *cptr;
    register unsigned char port;

port = Pptr->in_port;

/* Return immediately if slate mode and the partition is
halted */
    if ((Pptr->Recording_Mode > 0) && (Pptr->SlateModeBits & 1))
return;

if (port = CheckPort(port,2,1,0)) {   /* check for event mark
input port */
```

```c
        if (bottle_count2 &&
            (Pptr->Old_Bottle != bottle_count2)) {
               Bottl = Pptr->Old_Bottle = bottle_count2;
        }
        else
           Bottl = 0;
     } if (!(Pptr->Time_Last_Storage))    /* check if first storage
*/
        Timediff = 0;
     else
        Timediff = PTime - Pptr->Time_Last_Storage;

while (Timediff >= 0) {
        /* We need to calculate cptr each time through loop in
case partition has rolled over */
        cptr = PAddr(Pptr);
           if (Timediff > 254) {
              *cptr = 0xFF;
              if (port) /* event mark input */
                 *cptr = 0;  /*zero for bottle number */

}
           else {
              *cptr = (unsigned char)Timediff; /*store the time
difference */
              cptr++;
              if (port) /* event mark input */
                 *cptr = Bottl;   /*store the bottle number */
           }
           Incptr(Pptr);
           Timediff -= 255;
     }

Pptr->Time_Last_Storage = PTime;
     Pptr->EventCounts = 0;
}

/***********************************************************/ void Update_Parts() /* Update the active partitions */

/* Warning: This MUST be called at least every minute for time
driven partitions so partitions remain updated */
/* Warning: This MUST be called at least once for each event mark
for event driven partitions */
{
     register char Partcntr;
     register struct Partition *Partptr;
```

```
    register char Event;
char Update_EPorts();
void Update_TPart();

Event = Update_EPorts();      /* update the event ports,
return true if event occurred */

PTime = ProtocolTimeMin();

if (OldPTime && (PTime > (OldPTime + 1))) {  /* check if
more than 1 minute has elapsed */
        offset1 = PTime - OldPTime;
        curtime = OldPTime;
        PartTimeChange(TIME_FIXED);   /* Do a time change on
the active partitions */
    } if (OldPTime && (OldPTime != PTime)) {
        NewMin = 1;  /* Flag that a new PTime is here */
    }

OldPTime = PTime;

Partptr = Partit;

for (Partcntr = 0; Partcntr < Num_Partitions; Partcntr++) {
        if (Partptr->logging_type == TIME_DRIVEN) {
            Update_TPart(Partptr);
        }
        else if ((Partptr->logging_type == EVENT_DRIVEN) &&
Event) {
            Update_EPart(Partptr);
        }
        Partptr++;
    }

}

/***********************************************************/ void Update_TPart(Pptr)

struct Partition *Pptr;
{
    char PortType;

TempPart = Pptr;  /* since ovcall11 does not pass parameters,
use global*/ if (CheckHaltedSlate()) return;
```

```
        if ((PTime > Pptr->Time_Last_Storage) && ((PTime %
Pptr->time_interval) == 0)) {
            Pptr->Time_Last_Storage = PTime;

PortType = Ports[Pptr->in_port].type;

switch (PortType) {
                case 0:   /* Level Port */
                    break;
                case 1:   /* Event Port */
                    StoreEvent(Pptr);
                    break;
                case 2:   /* Flow port */
                    StoreFlow(Pptr);
                    break;
            }

Incptr(Pptr);

UpdateHaltFlag();

}
}

/***********************************************************/ char Update_EPorts()

{
    register char Partcntr;
    register struct Partition *Partptr;
    register char Evmark;
    register char retcode;

if (Evmark = pevent_mark)      /* get the value now so if it
changes */
        pevent_mark = 0;           /* in the middle of a updating the
  */
                            /* partitions, we get consistency     */
                            /* between partitions */ retcode = 0;

if (Evmark || TPRaincounts) {
        Partptr = Partit;

for (Partcntr = 0; Partcntr < Num_Partitions;
Partcntr++) {
            if (Partptr->logging_type != UNINITIALIZED) {
                if (Evmark &&
CheckPort(Partptr->in_port,2,1,0)) { /* Check for the event mark
port */
```

```
                    Partptr->EventCounts++;
                    retcode = 1;
                }
                else if (TPRaincounts &&
CheckPort(Partptr->in_port,2,1,1)) { /* Check for the Rainport */
                    Partptr->EventCounts += TPRaincounts;
                    retcode = 1;
                }
            }
            Partptr++;
        }
        TPRaincounts = 0;
    } return(retcode);
}

/*    JUNE 21, 1990    LF13.C    VAR02 */ include "type3240.h"
include "protocol.h"
#include "c_packet.h"
#include "d_packet.h"

extern char                 Abort_Flg;
extern struct commandEntry  commandtbl[12]; /*12???*/
extern long                 curtime;
extern struct data_pac      LastPacket;
extern unsigned char        *logging_alloc;
extern char                 NewMin;
extern char                 Num_Partitions;
extern long                 offset1;
extern long                 OldPTime;
extern struct Partition     Partit[3];
extern char                 pfailflg;
extern char                 PORT_MAP;
extern struct Port          Ports[2];
extern long                 PTime;
extern long                 Ptime_Offset;
extern struct Partition     *RestartPartPtr;
extern TimeRec              SampETimes[SupportedTRecords];
extern char                 SampFlg;
extern struct SamplerEnable SamplerEnab;
extern unsigned int         sampler_init1;
extern int                  scaleexp;
extern char                 SiteDescrip[18];
extern int                  SiteID;
extern char                 SlaveLocked;
extern int                  Slavepassword;
extern char                 str2312[111];    /* 2312 output
string */
extern long                 tlong1, tlong2;
extern short                tshort1;
extern struct timestruct    ttime;
extern int                  Xmit_Delay;   /* number of
milliseconds to wait between blocks */
```

```c
define CMNDSET 4 extern          char Volunits[6];

int sprintf(char *,const char *,...);

extern long            Blks_Avail();
extern long            Blks_Total();
extern char            CheckPort();
extern void            CInit_Part();
extern void            DisableSampler();
extern void            EnableSampler();
extern void            fillmem();
extern void            get_command();
extern void            get_time();
extern void            InitDP();
extern long            IscoTime();
extern long            LTotalFlow();
extern unsigned char   *PAddr();
extern void            PartTimeChange();
extern long            ProtocolTimeMin();
extern void            ResetLatch(); /* Reset the sampler enable latch */
extern char            RestartPart();/* REQUIRES RestartPartPtr be initialized before calling */
extern void            Reset_Part();
extern void            RInit_part();
extern char            SEnableState();
extern long            SendDP();
extern char            *strcpy();
extern char            *strncpy();
extern void            Update_Parts();

/**********************************************************/ int Abort_Cmd(packet)
register struct cmmd_pac *packet;
{
    return(0);
}

/**********************************************************/ int Send_Stat(cpacket,dpacket)
register struct cmmd_pac *cpacket;
register struct data_pac *dpacket;
{
void copy_vol_units();
long ProtocolTime();

register struct sdb0001 *StatPack;
```

```
    StatPack = &(dpacket->db.db0001);

strcpy(StatPack->model,"3240 ");

StatPack->revision = REVNUM;
    StatPack->datetime = (PTime = ProtocolTime()) / 60;
    StatPack->seconds = PTime % 60;
    StatPack->misc_options = 0;
    StatPack->site_id = SiteID;
    strcpy(StatPack->description,SiteDescrip);
    StatPack->partition_cnt = Num_Partitions;
    StatPack->port_map = PORT_MAP;
    StatPack->mem_avail = Blks_Avail();
    StatPack->mem_total = Blks_Total();
    StatPack->xmt_delay = Xmit_Delay;
    StatPack->cmnd_sets[0] = CMNDSET;
    StatPack->flow_total = LTotalFlow();
    copy_vol_units();
    strncpy(StatPack->flow_units,Volunits,6);
    StatPack->flow_exp = scaleexp > 0 ? scaleexp : (0x80 |
(unsigned char)(-scaleexp));
    StatPack->partition_max = MAX_PARTITIONS;
    StatPack->power_fail = 0;
    StatPack->lock_flag = !SlaveLocked;
    strncpy(StatPack->pcnt_flow,str2312+9,6);
    strncpy(StatPack->max_flow,str2312+17,7);
    strncpy(StatPack->units_of_flow,str2312+25,6);

/*XXXXXXX*/ return(0);         /* send the data block */
}

/**********************************************************/ int Ret_Cmnds(cpacket,dpacket)
register struct cmnd_pac *cpacket;
register struct data_pac *dpacket;
{
char *movmem();

movmem(commandtbl,&(dpacket->db.db0002.cmnds[0]),48);
    return(0);
}

/**********************************************************/ int End_Conv()
{
    return(0);         /* send the data block */
}

/**********************************************************/
```

```c
int Send_P_S(cpacket,dpacket)
register struct cmnd_pac *cpacket;
register struct data_pac *dpacket;
{
    register struct sdb0004 *PortStatPack;
    register char Portnum;
    char *movmem();

if (!CheckPort(Portnum = cpacket->cb.cb0004.port_no,0,0,0))
       return(INVALID_PORT);  /* invalid port number */

PortStatPack = &(dpacket->db.db0004);
     movmem(&(Ports[Portnum].port_no),&(PortStatPack->port_no),
         sizeof(struct Port));

return(0);          /* send the data block */
}

/****************************************************************/ int Time_Slave(cpacket,dpacket)
register struct cmnd_pac *cpacket;
register struct data_pac *dpacket;
{
long ProtocolTime();

register struct sdb0006 *TimePack;

TimePack = &(dpacket->db.db0006);
    TimePack->datetime = (PTime = ProtocolTime()) / 60;
    TimePack->seconds = PTime % 60;
    return(0);
}

/****************************************************************/ define tsite tshortl int Set_Site_ID(cpacket)
register struct cmnd_pac *cpacket;
{ if (SlaveLocked) return(UNIT_LOCKED);
    if ((tsite = cpacket->cb.cb0007.site_id) > 999)
       return(SITEID_RANGE);
    SiteID = tsite;
/*     sprintf(sid,fsite_id,SiteID);Remove 4-9-90*/
    return(0);
}

/****************************************************************/
```

```c
int Set_S_Time(cpacket,dpacket)
register struct cmnd_pac *cpacket;
register struct data_pac *dpacket;
{
long ProtocolTime();

register struct sdb0008 *TimePack;

if (SlaveLocked) return(UNIT_LOCKED);

get_time(&ttime);     /* initialize the time structure from
the hardware clock */ offset1 = cpacket->cb.cb0008.tim_offset;

curtime = ProtocolTime();

if ((offset1 + (curtime / 60)) < 0) return(TIME_RANGE);

/* Compute the ProtocolTime that is desired */

PTime = (((curtime / 60) + offset1) * 60) +
cpacket->cb.cb0008.seconds;

Ptime_Offset = PTime - ((IscoTime(&ttime)* 60) + ttime.sec);

/* initialize variables used in time PartTimeChange()
operations */
    /* offset used also in PartTimeChange() */
        curtime = curtime / 60;

/* Need to update the partitions here dependent upon update_time
field */

PTime = ProtocolTimeMin();

PartTimeChange(cpacket->cb.cb0008.update_time);   /* Do a
time change on the active partitions */

TimePack = &(dpacket->db.db0008);
    OldPTime = TimePack->datetime = (PTime = ProtocolTime()) /
60;
    TimePack->seconds = PTime % 60;
    return(0);
}

/***********************************************************/ define pw1 tlong1
define pw2 tlong2
```

```c
int Set_Psswrd(cpacket)
register struct cmnd_pac *cpacket;
{
    register char match;

pw1 = cpacket->cb.cb0009.p_word;
    pw2 = cpacket->cb.cb0009.new_word;
    match = ((pw1 == Slavepassword) || (pw1 == UNIVERSAL_PW));
    if (!match) {
        SlaveLocked = 1;
        return(INVALID_PWORD);
    }
       else if (SlaveLocked)
           SlaveLocked = 0;
    else
        Slavepassword = pw2;

return(0);

}

/**********************************************************/ int Create_MP(cpacket,dpacket)
register struct cmnd_pac *cpacket;
register struct data_pac *dpacket;
{
  register char PartNum;
  register short size;

if (SlaveLocked) return(UNIT_LOCKED);
  if ((PartNum = cpacket->cb.cb000A.partition_num) >
(MAX_PARTITIONS - 1))
      return(BAD_PARTITION);
  if (PartNum < Num_Partitions) return(ALREADY_EXISTS);
  if (PartNum != Num_Partitions) return(NOT_NEXT);
  if (((size = cpacket->cb.cb000A.part_siz) > Blks_Avail()) ||
!size) return(PARTITION_SIZE);
  CInit_Part(&Partit[PartNum],PartNum,size,logging_alloc);   /*
clear out the partition and init the size */
  logging_alloc += (size << 7);
  Num_Partitions++;
  dpacket->db.db000A.mem_avail = Blks_Avail();
  return(0);
}

/**********************************************************/ int Delete_MP(cpacket)
register struct cmnd_pac *cpacket;
{
  register char PartNum;
  register unsigned int numbytes;
```

```c
    if (SlaveLocked) return(UNIT_LOCKED);
    if ((PartNum = cpacket->cb.cb000B.partition_num) >
(Num_Partitions - 1))
        return(PART_NOT_EXIST);
    if (PartNum != (Num_Partitions - 1)) return(LESSOR_PART);

logging_alloc = Partit[PartNum].PartAddr;

Num_Partitions--;

return(0);
}

/**********************************************************/ int Change_PP(cpacket,dpacket)
register struct cmnd_pac *cpacket;
register struct data_pac *dpacket;
{
    register char PartNum;
    register unsigned char type;
    register short size;
    register struct scb000C *Tpac;

if (SlaveLocked) return(UNIT_LOCKED);
    if ((PartNum = cpacket->cb.cb000C.partition_num) >
(MAX_PARTITIONS - 1))
        return(BAD_PARTITION);
    if (PartNum > (Num_Partitions - 1)) return(PART_NOT_EXIST);
    Tpac = &(cpacket->cb.cb000C);
    if ((type = Tpac->type) > SCRATCH_PAD)
return(BAD_LOGGING_TYPE);
    if (Tpac->default_flag) {   /* if not take defaults, check for
valid width, port, etc. */
        if (type < SCRATCH_PAD) {
            /* Check for existence of port */
            if (!CheckPort(Tpac->port_no,0,0,0))
return(INVALID_PORT);
            if (CheckPort(Tpac->port_no,2,1,1)) { /* check for
rainfall port */
                if (Tpac->d_width != 1) return(DATA_RANGE);
            }
            else {
                if (Tpac->d_width != 2) return(DATA_RANGE);
            }
        }
    }
    else if (type < SCRATCH_PAD) {
        Tpac->d_width = 2;
        Tpac->port_no = type;    /* Ends up being level port for
time-driven, sampler port for event-driven */
    } if (type == TIME_DRIVEN) {
        if (Tpac->port_no == 1) return(MISMATCH_TYPE_PORT);
        switch ((unsigned short)Tpac->d_interval) {
```

```
                case 1:
                case 2:
                case 5:
                case 10:
                case 15:
                case 30:
                case 60:
                case 120:
                    break;
                default:
                    return(BAD_INTERVAL);
            }
        }
        else if (type == EVENT_DRIVEN) {
            if (!Tpac->port_no) return(MISMATCH_TYPE_PORT);
        }

RInit_part(&Partit[PartNum],Tpac);
        return(0);
}

/****************************************************/ int Request_PS(cpacket,dpacket)
register struct cmnd_pac *cpacket;
register struct data_pac *dpacket;
{
  register char PartNum;
  register struct Partition *Part;
  char *movmem();
  long ProtocolTime();

if ((PartNum = cpacket->cb.cb000D.partition_num) >
(MAX_PARTITIONS - 1))
       return(BAD_PARTITION);
  if (PartNum > (Num_Partitions - 1)) return(PART_NOT_EXIST);
  (Part = &Partit[PartNum])->Current_time = (PTime =
ProtocolTime()) / 60;
  Part->Current_Seconds = PTime % 60;
  movmem(Part,&(dpacket->db.db000D.part_num),46); /* copy the
partition information into the data packet */
  dpacket->db.db000D.partition_num = (unsigned char)PartNum;
  dpacket->db.db000D.partition_ads = (unsigned
long)Part->PartAddr;
  dpacket->db.db000D.partition_siz = (unsigned
long)(Part->Num_Blocks);
  dpacket->db.db000D.part_table_ads = (unsigned long)Part;
  dpacket->db.db000D.part_table_typ = 0;
  return(0);
}

/****************************************************/ int Send_Dblks(cpacket,dpacket)
register struct cmnd_pac *cpacket;
```

```c
register struct data_pac *dpacket;
{
  register char PartNum;
  register unsigned short fblock, lblock;
  register struct Partition *Part;
  char *movmem();

if ((PartNum = cpacket->cb.cb000E.partition_num) >
(MAX_PARTITIONS - 1))
      return(BAD_PARTITION);
  if (PartNum > (Num_Partitions - 1)) return(PART_NOT_EXIST);
  if ((Part = &Partit[PartNum])->logging_type == UNINITIALIZED)
return(UNINIT_PART);
  fblock = cpacket->cb.cb000E.first_blk;
  lblock = cpacket->cb.cb000E.last_blk;

if ((fblock > lblock) || (lblock >= Part->Num_Blocks))
return(BLOCK_NUMBER_RANGE);
  while (1) {
      dpacket->address = fblock;
      movmem(Part->PartAddr + (fblock << 7),&(dpacket->db),128);

if (Abort_Flg || (fblock == lblock)) break;
      SendDP(dpacket,0,0);
      /* cannot call switch_it here because of registerized
variables */
      /* if needed, the switch_it() routine could be modified to
save the registers in question */
      /* switch_it(); */      /* allow forground task to get some
time */
      Update_Parts();         /* we should update the partitions
between packets if necessary */
      fblock++;
  }
  if (fblock != lblock) {    /* must have been aborted */
      fillmem(&(dpacket->db),128,0); /* clear the body */
      SendDP(dpacket,CMD_ABORTED,1);    /* send the CMD_ABORTED
response */
      Abort_Flg = 0;
              /* Now, respond to the Abort command */
      fblock = cpacket->command;    /* remember the command and ID
*/
      lblock = cpacket->commandid;
      get_command(cpacket);      /* get the abort command */
      InitDP(cpacket,dpacket);  /* copy the command ID, etc */
      dpacket->db.db0000.command = fblock;
      dpacket->db.db0000.commandid = lblock;
  }
  return(0);     /* Note that this return will either be
returning the last data packet of the block or a response to the
Abort command */
}

/***********************************************************/
```

```
#ifdef DIAGS
int Run_Diags()
{
  return(NOT_IMPLEMENTED);
}

/**********************************************************/ int Request_DS()
{
  return(NOT_IMPLEMENTED);
}
#endif

/**********************************************************/ int Set_MP_Name(cpacket,dpacket)
register struct cmnd_pac *cpacket;
register struct data_pac *dpacket;
{
  register char PartNum;
  char *movmem();

if (SlaveLocked) return(UNIT_LOCKED);
  if ((PartNum = cpacket->cb.cb0011.partition_num) >
(MAX_PARTITIONS - 1))
      return(BAD_PARTITION);
  if (PartNum > (Num_Partitions - 1)) return(PART_NOT_EXIST);
  movmem(cpacket->cb.cb0011.part_name,Partit[PartNum].Name,10);
/* copy the name into the buffer area */
  return(0);
}

/**********************************************************/ int Writ_Memory(cpacket)
register struct cmnd_pac *cpacket;
{
  register struct scb0012 *cp;
  char *movmem();

if (SlaveLocked) return(UNIT_LOCKED);
  cp = &(cpacket->cb.cb0012);

movmem(cp->msg,(char *)cp->ads,cp->cnt);
  return(0);
}

/**********************************************************/ int Read_Memory(cpacket,dpacket)
register struct cmnd_pac *cpacket;
```

```c
register struct data_pac *dpacket;
{
  register struct scb0013 *cp;
  register char *dest;
  char *movmem();

cp = &(cpacket->cb.cb0013);

dest = (char *)&dpacket->db;

movmem((char *)cp->ads,dest,cp->cnt);

return(0);
}

/**********************************************/ int Exec_Memory(cpacket)
register struct cmnd_pac *cpacket;
{
  int (*indsub)();   /* pointer to a function that
returns an int */
  void Putit();

if (SlaveLocked) return(UNIT_LOCKED);

Putit(cpacket->cb.cb0014.ads,&indsub);     /*
get the address of the routine to execute */

(*indsub)(0);    /* make the call */
  return(0);
}

/**********************************************/ int Set_Xmt_TM(cpacket,dpacket)
register struct cmnd_pac *cpacket;
register struct data_pac *dpacket;
{
  if (SlaveLocked) return(UNIT_LOCKED);
  Xmit_Delay = cpacket->cb.cb0016.xmt_delay;
  return(0);
}

/**********************************************/ int Set_Dscrpt(cpacket,dpacket)
register struct cmnd_pac *cpacket;
register struct data_pac *dpacket;
{
```

```c
   if (SlaveLocked) return(UNIT_LOCKED);
   strncpy(SiteDescrip,cpacket->cb.cb0017.description,17);
   return(0);
}

/*********************************************************/ int No_Op()
{
   return(0);
}

/*********************************************************/ int Load_MP(cpacket)
struct cmnd_pac *cpacket;
{
  register struct Partition *Partptr;
  register char PartNum;
  register char NumChars;
  register unsigned char *WriteAddr;
   char *movmem();

if (SlaveLocked) return(UNIT_LOCKED);
   if ((PartNum = cpacket->cb.cb0019.partition_num) >
(MAX_PARTITIONS - 1))
       return(BAD_PARTITION);
   if (PartNum > (Num_Partitions - 1)) return(PART_NOT_EXIST);
   Partptr = &Partit[PartNum];
   if (Partptr->logging_type == UNINITIALIZED)
return(UNINIT_PART);
   if (Partptr->logging_type != SCRATCH_PAD) return(NOT_SCRATCH);
   NumChars = cpacket->cb.cb0019.bit_flags & 0xf;
   if (cpacket->cb.cb0019.bit_flags & 0x10)  /* check for storage
type */
      WriteAddr = (unsigned char *)(Partptr->PartAddr +
cpacket->cb.cb0019.LoadOffset);
   else
      WriteAddr = (unsigned char *)PAddr(Partptr);
   if ((WriteAddr) >= (Partptr->PartAddr + (Partptr->Num_Blocks <<
7))) return(ADDRESS_RANGE);
   if ((WriteAddr + NumChars) > (Partptr->PartAddr +
(Partptr->Num_Blocks << 7))) return(PART_OVERFLOW);

movmem(cpacket->cb.cb0019.Data,WriteAddr,NumChars);  /* copy
the data into the area */
   WriteAddr += NumChars;  /* Compute the ending address */
   WriteAddr -= (unsigned int)Partptr->PartAddr;  /* now, make it
relative to start of partition */
   Partptr->Current_Block = ((unsigned long)WriteAddr >> 7);  /*
convert it into block and offset */
   Partptr->Block_Offset = (unsigned long)WriteAddr & 127;
```

```c
  Partptr->Time_Last_Storage = ProtocolTimeMin();
  return(0);
}

/*******************************************************/ int Send_Lst()
{
  SendDP(&LastPacket,LastPacket.response,0);
  return(0);
}

/*******************************************************/ int Lock_UT()
{
      SlaveLocked = 1;
      return(0);
}

/*******************************************************/ int Read_SI(cpacket,dpacket)
register struct cmnd_pac *cpacket;
register struct data_pac *dpacket;
{
void copy_vol_units();

copy_vol_units();

dpacket->db.db001C.volume = SampFlg ? sampler_initl : 0;
      strncpy(dpacket->db.db001C.units,Volunits,6);
      return(0);
}

/*******************************************************/ int Set_SI(cpacket)
register struct cmnd_pac *cpacket;
{
  register char cntr;
void copy_vol_units();

copy_vol_units();
```

```c
    if (SlaveLocked) return(UNIT_LOCKED);
    if (cpacket->cb.cb001D.volume > 50000) return (NUMBER_RANGE);
    for (cntr = 0; cntr < 6; cntr++)   /* compare the units */
        if (cpacket->cb.cb001D.units[cntr] !=
    Volunits[cntr]) return(INVALID_UNITS);
    sampler_init1 = cpacket->cb.cb001D.volume;
    SampFlg = sampler_init1 == 0 ? 0 : 1;   /* either turn on or off
*/
    return(0);
}

/**********************************************/ int Rd_SampEStat(cpacket,dpacket)
register struct cmnd_pac *cpacket;
register struct data_pac *dpacket;
{
  char *movmem();

movmem(&SamplerEnab.PortNum,&(dpacket->db.db0020.PortNum),
    (unsigned char *)(&SamplerEnab.Rainbuf.Readings[0]) -
    &SamplerEnab.PortNum);
    dpacket->db.db0020.TotTimeRecords = SupportedTRecords;
    dpacket->db.db0020.EnableState = SEnableState();
    return(0);
}

/**********************************************/ int St_SampEStat(cpacket)
register struct cmnd_pac *cpacket;
{ register struct scb0021 *command;
    register char temprecs;
    char *movmem();

if (SlaveLocked) return(UNIT_LOCKED);

command = &cpacket->cb.cb0021;

switch (command->OpMode) {    /* Check Operating Mode with
port number */
        case 0:  /* On */
            EnableSampler();
            break;
        case 1:   /* Off */
            DisableSampler();
            break;
        case 3: /* Time Only */
            break;
        case 4: /* Rainfall Only */
        case 7: /* Rainfall AND Time */
```

```c
        case 8: /* Rainfall OR Time */
        case 9:
        case 10:
              return(INVALID_PORT);
              break;
        case 2:
        case 5:
        case 6:
              if (CheckPort(command->PortNum,0,0,0)) {   /* Check
for the existence of the port */
                     /* Now, check to see if it is a FLOW type */
                     if (!CheckPort(command->PortNum,1,2,0))
return(INVALID_PORT);  /* if port is other than flow port, return
error */
              }
              break;
        default:
              break;   /* Should probably return an error here
*/
      }
      /* Copy stuff over up to the InUseTimeRecords */ movmem(&(command->PortNum),&SamplerEnab.PortNum,
&SamplerEnab.InUseTimeRecords - &SamplerEnab.PortNum);
      fillmem(&SamplerEnab.Rainbuf,sizeof(struct RainBuffer),0);
/* clear the RainBuffer memory */
      SamplerEnab.Rainbuf.RainTripPoint = command->RainTripPoint;
      SamplerEnab.Rainbuf.RainInterval = command->ReadingInterval;
      return(0);
}

/*********************************************************/ int Rd_TimeRecords(cpacket,dpacket)
struct cmnd_pac *cpacket;
register struct data_pac *dpacket;
{
      register char NumRecs;
      char *movmem();

NumRecs = dpacket->db.db0022.NumberofRecs =
SamplerEnab.InUseTimeRecords; /* The number of records in this
packet */ movmem(SampETimes,dpacket->db.db0022.TimeRecords,
sizeof(TimeRec)*NumRecs);   /* an array of time records */ return(0);
}

/*********************************************************/
```

```c
int St_TimeRecords(cpacket)    /* Set Sampler Enable Time Records */
register struct cmnd_pac *cpacket;
{
    register char Recs;

register char offset;
    char *movmem();

if (SlaveLocked) return(UNIT_LOCKED);

if ((Recs = cpacket->cb.cb0023.NumberOfRecords) > 3) return(NUMBER_RANGE);

if ((Recs + (offset = cpacket->cb.cb0023.TableOffset)) > SupportedTRecords) return(NUMBER_RANGE);

/* copy the data into the local time record area */
    if (Recs) { movmem(cpacket->cb.cb0023.TimeRecords,&SampETimes[offset],
sizeof(TimeRec) * Recs);
        Recs += offset;
        if (Recs > SamplerEnab.InUseTimeRecords)
SamplerEnab.InUseTimeRecords = Recs;    /* The number of time records in use */
    }
    NewMin = 1;    /* flag that it is time to look at the time condition */
    return(0);
}

/*****************************************************/ int Rst_SampEnab(cpacket,dpacket)
register struct cmnd_pac *cpacket;
register struct data_pac *dpacket;
{ if (SlaveLocked) return(UNIT_LOCKED);

fillmem(&SamplerEnab,sizeof(SamplerEnab),0); /* clear the sampler enable structure */
    fillmem(SampETimes,sizeof(SampETimes),0);  /* Clear the array entries */

EnableSampler();

return(0);
}

/*****************************************************/
```

```c
int Rst_Partition(cpacket)
register struct cmnd_pac *cpacket;
{ register struct Partition *partptr;

register char tmp;

if (SlaveLocked) return(UNIT_LOCKED);

if ((tmp = cpacket->cb.cb0025.PartitionNum) >=
Num_Partitions) return(INVALID_PART);   /* The partition to Reset
*/ partptr = &Partit[tmp];

tmp = partptr->Recording_Mode;

if ((tmp == ROLLOVERMODE) || (tmp > RAINFALLSLATE)) return
(INVALID_PART);

if (tmp == TIMESLATE) {
        partptr->Triggerinfo.SlateTime =
cpacket->cb.cb0025.StartingTime;   /* The NEW starting time for
the Time Trigger */
    }

/* Now, release the hold flag on the partition and do time
change if necessary */

RestartPartPtr = partptr;   /* Global to pass to RestartPart
since ovcall1 does not pass parameters */ if (RestartPart()) Reset_Part(partptr);
    return(0);
}

/***************************************************************/ int Unlatch_SE()
{ if (SlaveLocked) return(UNIT_LOCKED);

ResetLatch();

return(0);
}

/***************************************************************/
```

```c
int (*CommandTbl[])() = {     /* Since this is static (READ-ONLY)
it may remain in the Code Segment */
            Abort_Cmd,      /* 0 */
            Send_Stat,      /* 1 */
            Ret_Cmnds,      /* 2 */
            End_Conv,  /* 3 */
            Send_P_S,  /* 4 */
            0,              /*Adjust_L    5 */
            Time_Slave,     /* 6 */
            Set_Site_ID,    /* 7 */
            Set_S_Time,     /* 8 */
            Set_Psswrd,     /* 9 */
            Create_MP,      /* a */
            Delete_MP,      /* b */
            Change_PP,      /* c */
          . Request_PS,     /* d */
            Send_Dblks,     /* e */
#ifdef DIAGS
            Run_Diags,      /* f */
            Request_DS,     /* 10 */
#else
            0,         /* f */
            0,         /* 10 */
#endif
            Set_MP_Name,    /* 11 */
            Writ_Memory,    /* 12 */
            Read_Memory,    /* 13 */
            Exec_Memory,    /* 14 */
            0,              /* Send_Fctab     15 */
            Set_Xmt_TM,     /* 16 */
            Set_Dscrpt,     /* 17 */
            No_Op,          /* 18 */
            Load_MP,   /* 19 */
            Send_Lst,  /* 1a */
            Lock_UT,   /* 1b */
            Read_SI,   /* 1c */
            Set_SI,         /* 1d */
            0,         /* 1e Alarm */
            0,         /* 1f Alarm */
            Rd_SampEStat,   /* 20 */
            St_SampEStat,   /* 21 */
            Rd_TimeRecords,    /* 22 */
            St_TimeRecords,    /* 23 */
            Rst_SampEnab,   /* 24 */
            Rst_Partition,  /* 25 */
            Unlatch_SE      /* 26 */
};

/*    MAY 15, 1990    LF14.C    VAQ03 */ include "type3240.h"
include "cmndset0.h"
#include "c_packet.h"
#include "d_packet.h"
#include "protocol.h"
``` define LatchMode (SamplerEnab.ModeFlags & 0x4)

```c
extern char             NewMin;
extern char             OldTimeCondition;
extern struct Partition Partit[3];
extern char             plotterhalt;
extern struct Port      Ports[2];
extern long             PTime;
extern unsigned long    RestartNumReadings;
extern struct Partition *RestartPartPtr;
extern char             SampHist[3];
extern TimeRec          SampETimes[SupportedTRecords];
extern struct SamplerEnable SamplerEnab;
extern unsigned int     SEDuration;
extern char             se_latch_flag;
extern char             se_pl_en_flag;
extern unsigned long    SEStartTime;
extern long             StartOfDay;
extern long             StartOfWeek;
extern struct Partition *TempPart;

/*   #include "softrev.h"   */ extern void             DisableSampler();
extern void             EnableSampler();

char FlowCondition(char,long *,char *);
```

/**********************************************************/

```c
void CheckCondition(Pptr)
struct Partition *Pptr;
{
void DecEndptr();
char FlowCondition();

char Mode;
char ConditionTrue;

ConditionTrue = 0;

if ((Mode = Pptr->Recording_Mode) == 0) return;

if (Pptr->SlateModeBits & 1) return; /* check if already full */
    if (Pptr->ConditionStartTime) return; /* check if condition satisfied */
```

```
    switch(Mode) {
        case 1: /* Standard Slate - condition always true */
            ConditionTrue = 1;
            break;
        case 2: /* Level Slate */
            break;
        case 3: /* Time Slate */
            if (PTime >= Pptr->Triggerinfo.SlateTime)
                ConditionTrue = 1;
            break;
        case 4: /* Flow Slate */
            if
(FlowCondition(0,(long*)&Pptr->Triggerinfo.SlateFlow,Pptr->Hyst))
                ConditionTrue = 1;
            break;
        case 5: /* Rainfall Triggered Slate */
            break;
    }
    if (ConditionTrue) {   /* Note that ConditionTrue is not set
if rainfall condition was met */
                    /* This is because these fields are
previously set */
        Pptr->ConditionStartTime = PTime;
        Pptr->End_Block = Pptr->Current_Block;
        Pptr->EndBlock_Offset = Pptr->Block_Offset;
    }
}

/*****************************************************/ int CheckHaltedSlate()

{ struct Partition *Pptr;

Pptr = TempPart;

/* Return immediately if slate mode and the partition is
halted */
    if (Pptr->Recording_Mode > 0) {
        if (Pptr->SlateModeBits & 1) return(1);
        if (!(Pptr->ConditionStartTime)) CheckCondition(Pptr);
    }
    return(0);
}

/*****************************************************/
```

```c
void CheckSampE()

{
char FlowCondition();
char TimeCondition();

char TriggState=0;
char Portnum;

Portnum = SamplerEnab.PortNum;

if(SamplerEnab.OpMode==0)
        {
        se_latch_flag=off;
        se_pl_en_flag=on;
        EnableSampler();
        }
    else if(SamplerEnab.OpMode==1)
        {
        se_latch_flag=off;
        se_pl_en_flag=on;
        DisableSampler();
        }
    else {
        switch (SamplerEnab.OpMode) {
            case 2:         /* Level/Flow Only */
                TriggState =
FlowCondition(Portnum,&SamplerEnab.Flow_or_Level,SampHist);
                break;
            case 3:         /* Time Only */
                TriggState = TimeCondition();
                break;
            case 4:         /* Rainfall Only */
                break;
            case 5:         /* Level/Flow and Time */
                TriggState =
FlowCondition(Portnum,&SamplerEnab.Flow_or_Level,SampHist) &&
TimeCondition();
                break;
            case 6:         /* Level/Flow or Time */
                TriggState =
FlowCondition(Portnum,&SamplerEnab.Flow_or_Level,SampHist) ||
TimeCondition();
                break;
            case 7:         /* Rainfall and Time */
                break;
            case 8:         /* Rainfall or Time */
                break;
            case 9:         /* Rainfall and Level */
                break;
            case 10:  /* Rainfall or Level */
                break;

}
```

```
            if(TriggState && LatchMode) se_latch_flag=on;

if(se_latch_flag==on || TriggState) EnableSampler();
            else DisableSampler();

if(SamplerEnab.PlotterControl==0 || se_latch_flag==on
                || TriggState) se_pl_en_flag=on;
            else se_pl_en_flag=off;

}
}

/************************************************/ char FlowCondition(Portnum,FloPtr,Hptr)

char Portnum;
long *FloPtr;
char *Hptr;
{ if (Ports[Portnum].typeopts.cur_flow >= *FloPtr )
        {
        if (Hptr[1])
                {
                Hptr[0] = 0;
                return(1);
                }
        else if(Hptr[0] < 15)
                    {
                    (Hptr[0])++;
                    return(0);
                    }
               else
                    {
                    Hptr[1] = 1;
                    Hptr[0] = 0;
                    return(1);
                    }
        }
else
        {
        if(Hptr[1] == 0)
                {
                Hptr[0] = 0;
                return(0);
                }
        else if(Hptr[0] < 15)
```

```
            {
            (Hptr[0])++;
            return(1);
            }
        else
            {
            Hptr[1] = 0;
            Hptr[0] = 0;
            return(0);
            }
        }
}
```

/****************************************************/

```
void LocalIncptr(Pptr)

/* Duplicate of one in protocol.c but that is in another overlay
 */
register struct Partition *Pptr;
/* This routine increments the Block_Offset and Current_Block
fields as necessary */
{
    if ((Pptr->Block_Offset += Pptr->data_width) > 127) {
        Pptr->Block_Offset -= 128;
        if (++(Pptr->Current_Block) >= Pptr->Num_Blocks) {
            Pptr->Current_Block = 0;
            if (Pptr->Rollover < 255) Pptr->Rollover++;
        }
    }
}
```

/****************************************************/

```
void ResetLatch()

{
    se_latch_flag=off;
}
```

/****************************************************/

```c
char RestartPart()

{
void StoreDeleteRec();

struct Partition *pptr;

pptr = RestartPartPtr;

pptr->SlateModeBits &= 0xFE;
    pptr->ConditionStartTime = 0;
    pptr->End_Block = 0;
    pptr->EndBlock_Offset = 0;

/* Calculate the number of readings to jump ahead */
    RestartNumReadings = (PTime - pptr->Time_Last_Storage) /
pptr->time_interval;

/* if greater than the number of readings in the partition,
reset it */
    if (RestartNumReadings >= ((128 / pptr->data_width) *
pptr->Num_Blocks)) return(1);

while (RestartNumReadings--) {
        pptr->Time_Last_Storage += pptr->time_interval;
        StoreDeleteRec(pptr);
        LocalIncptr(pptr);
    }
    return(0);
}
```

```
/****************************************************/ char SEnableState()
{
char inbit();

return(!inbit(port6c,4));
}
```

```
/****************************************************/
```

```c
void StoreDeleteRec(Pptr)

struct Partition *Pptr;

{
unsigned char *cptr;

cptr = (unsigned char *)(Pptr->PartAddr +
(Pptr->Current_Block << 7) + Pptr->Block_Offset);

if (Pptr->data_width == 2)
        *(int*)cptr=0xfffc;
    else
        *cptr=0xfc;
}
```

/****************************************************/

```c
char TimeCondition()

{
char TimeEntryTrue();

char count;
TimeRec *Tr;
    if (!NewMin) return(OldTimeCondition);

NewMin = 0;

StartOfDay = PTime - (PTime % 1440);    /* Calculate Start
of Day */
    StartOfWeek = PTime - 1440;   /* Since Jan 1, 1977 was a
Saturday, subtract 1440 minutes */
    StartOfWeek = StartOfWeek - (StartOfWeek % 10080) + 1440;/*
Calculate Start of Week */ count = SamplerEnab.InUseTimeRecords;   /* The number of
time records in use */

Tr = SampETimes;

while (count--) {
        if (TimeEntryTrue(Tr++)) return(OldTimeCondition = 1);
    } return(OldTimeCondition = 0);
}
```

```c
/****************************************************/ char TimeEntryTrue(Tr)

TimeRec *Tr;
{ if (Tr->Cyclic.ZeroBits) {  /* Check for actual time record
- zero bit field is non-zero */
        SEStartTime = Tr->Actual.StartTime;
        SEDuration = Tr->Actual.Duration;
    }
    else {
        SEDuration = Tr->Cyclic.Duration;
        if (Tr->Cyclic.StartTime & 0x8000) /* If high bit is
set, this is a Daily time record */
            SEStartTime = (Tr->Cyclic.StartTime & 0x7FFF) +
StartOfDay;
        else
            SEStartTime = Tr->Cyclic.StartTime + StartOfWeek;
    } if (PTime < SEStartTime) return(0);
    if (SEDuration == 0xFFFF) return(1);
    return((char)(PTime < (SEStartTime + SEDuration)));
}

/****************************************************/ void UpdateHaltFlag()

{ struct Partition *Pptr;

Pptr = TempPart;

/* Check if we need to halt a slate mode partition */
    if (Pptr->Recording_Mode > 0) {
        if (!(Pptr->SlateModeBits & 1)) { /* check if already
full */
            if (Pptr->ConditionStartTime) { /* check if
condition satisfied */
                if ((Pptr->End_Block == Pptr->Current_Block)
&& (Pptr->Block_Offset == Pptr->EndBlock_Offset))
Pptr->SlateModeBits |= 1;
            }
        }
    }

}
```

```c
/*    JULY 09, 1990    LF15.C    VAS07 */ include "type3240.h"
include "d_packet.h"
#include "protocol.h"

const char day_tab[2][13] = {
    { 0, 31, 28, 31, 30, 31, 30, 31, 31, 30, 31, 30, 31 },
    { 0, 31, 29, 31, 30, 31, 30, 31, 31, 30, 31, 30, 31 }
};

extern char         century;
char                char_to_error;
char                ck_sum_error;
extern float        flow;
extern const struct menus line_two;
extern char         Modem_off_count;
char                pkt_flag_error;
extern struct Port  Ports[2];
extern char         s[41];
extern struct tm_date sys_tm_dt;
unsigned char       tx_count;
char                tx_data[140];
char                *tx_ptr;
char                Volunits[6];
extern char         volume_units;

int sprintf(char *,const char *,...);

/****************************************************************/ long ISCO_time(year,month,day,hour,minute)      /* return ISCO date */
int year, month, day, hour, minute;             /* from month,day,year,hour,minute */
{
    int i, leap;
    long ISCO_day;
    if (year < 77) return(-1);
    leap = year % 4 == 0;
    for (i = 1; i < month; i++)
       day += day_tab[leap][i];
    ISCO_day = day - 1;
    for (i = year - 1; i >= 1977; i--) {
```

```
        leap = i % 4 == 0;
        ISCO_day += 365 + leap;
     }
     return((ISCO_day * 1440) + (60 * hour) + minute);
}
```

/****************************************************/
/*

```c
void std_time(ISCO_tme,year,month,day,hour,minute)
long ISCO_tme;
int *year, *month, *day, *hour, *minute;
{ int i, leap;

*minute = ISCO_tme % 60;
     ISCO_tme /= 60;
     *hour = ISCO_tme % 24;
     ISCO_tme /= 24;
     *year = 77;
     leap = *year % 4 == 0;
     while (ISCO_tme >= (long)(365 + leap)) {
        (*year)++;
        ISCO_tme -= (365 + leap);
        leap = *year % 4 == 0;
     };
     for (i = 1; ISCO_tme > day_tab[leap][i]; i++)
        ISCO_tme -= day_tab[leap][i];
     *month = i;
     *day = ISCO_tme + 1;
}
```

*/

/****************************************************/

```c
void copy_vol_units()
{
int index;
int index1=0;

for(index=0;index<6;index++)
     Volunits[index]=0x20;
index=line_two.position[3][volume_units-1]-
     line_two.position[3][0] + 3;
while(line_two.text[3][index]!=0x20)
     Volunits[index1++]=line_two.text[3][index++];
}
```

```
/*******************************************************/
/*
char *movmem(dst,src,numb)
char *dst;
char *src;
int  numb;
{
char *tmp;

tmp = dst;
  while(numb)
   {
   *tmp++ = *src++;
   --numb;
   }
return(dst);
}

*/

/*******************************************************/ long IscoTime(tptr)

struct timestruct *tptr;
{
return(ISCO_time(tptr->year,tptr->month,tptr->day,
     tptr->hour,tptr->min));
}

/*******************************************************/

/*
void fillmem(dst,numb,byte)

char *dst;
int  numb;
char byte;
{
  while(numb)
   {
   *dst++ = byte;
   --numb;
   }
}
```

```c
*/

/**********************************************/ void get_time(tptr)

struct timestruct *tptr;
{
tptr->year=(unsigned int)sys_tm_dt.cent * 100 + sys_tm_dt.year;
tptr->month=(unsigned int)sys_tm_dt.month;
tptr->day=(unsigned int)sys_tm_dt.day;
tptr->hour=(unsigned int)sys_tm_dt.hour;
tptr->min=(unsigned int)sys_tm_dt.min;
tptr->sec=(unsigned int)sys_tm_dt.sec;
}

/**********************************************/ void set_time(dt)

struct timestruct *dt;
{
output(port2g,(dt->year)%100);
century = (dt->year) / 100;
output(port2e,dt->month);
output(port2f,dt->day);
output(port2b,dt->hour);
output(port2c,dt->min);
output(port2d,dt->sec);
}

/**********************************************/ void StartTransmit(dpacket)

struct data_pac *dpacket;
{
char *movmem();
void enable_tx();
```

```
while(tx_count!=0);
movmem(dpacket,tx_data,140);
tx_ptr = tx_data;
tx_count = 140;
enable_tx();
}
```

/****************************************************/

```
void EnableSampler()

{
void outbit();

outbit(port6c,4,0);
}
```

/****************************************************/

```
void DisableSampler()

{
void outbit();

outbit(port6c,4,1);
}
```

/****************************************************/

```
void EndConv()

{
Modem_off_count=12;
}
```

```c
void Update_1f_Ports()

{
Ports[0].port_no = 0;
Ports[0].type = 2;
Ports[0].sub_type = 0;
Ports[0].err_flag = 0;
Ports[0].typeopts.cur_flow = flow * 100.0;
Ports[0].FlowMult = 1;
Ports[0].FlowPowerOf10 = 0;
Ports[0].Pad = 0;

Ports[1].port_no = 1;
Ports[1].type = 1;
Ports[1].sub_type = 0;
Ports[1].err_flag = 0;
Ports[1].typeopts.cur_flow = 0;
Ports[1].FlowMult = 0;
Ports[1].FlowPowerOf10 = 0;
Ports[1].Pad = 0;
}
```

```c
int do_tx_gen_error()
{
int index;
void enable_tx();
void sdisplay();

if(char_to_error || ck_sum_error || pkt_flag_error)
    {
    while(tx_count!=0);
    tx_ptr=tx_data;
    for(index=0;index<140;index++)
        {
        *tx_ptr=0;
        tx_ptr++;
```

```
/*   AUGUST 06, 1990    LFO.C    VAU17 */ define         maska 0x0FFF
define         maskov 0x1000
#define         maskpol 0x2000
#define         off 0
#define         on 1
#define         port2a 0x20     /* .01 sec */
#define         port2b 0x21     /* hours   */
#define         port2c 0x22     /* minutes */
#define         port2d 0x23     /* seconds */
#define         port3 0x31
#define         port4 0x41
#define         port5a 0x50
#define         port5b 0x51
#define         port5c 0x52
#define         port6a 0x60
#define         port6b 0x61
#define         port6c 0x62
#define         pos1 0
#define         pos2 6
#define         pos3 13
#define         pos4 18
#define         pos5 28
#define         pos6 31
#define         pos7 34
#define         pos10 38
#define         pos11 40
#define         pos12 46
#define         pos13 53
#define         pos14 68
#define         pos15 69
#define         pos16 76
#define         pos20 33
include        <MATH.H> unsigned int    auto_zero_time;
extern char     az_step;
char            baud;
extern char     BBR_bu;
extern char     bkup_key1;
extern char     bkup_key2;
char            blank[41]=
"                                        ";
unsigned char   cal_delay;
int             calib_index;
extern char     calib_print_flag;
extern char     calib_step;
extern char     commandrdy;
extern char     diag_menu_nbr;
unsigned int    dump_delay;
float           flow;
unsigned int    flow_calc_time=23;
```

```
float           flow_total=0.0;
char            gate_control_time1;
char            gate_control_time2=3;
char            gate_move_flag=1;
int             head;
int             head_count;
int             head_count2;
long            head_total;
long            head_total2;
int             head2;
int             lvdt;
unsigned char   lvdt_count;
unsigned char   lvdt_read_delay;
unsigned char   menu_number;
extern char     Modem_off_count;
extern char     Modem_on_count;
char            one_sec_flag;
int             pass_count;
extern char     power_up_flag;
char            print_count;
char            print_done;
char            print_mask=0x20;
unsigned int    print_time;
char            prior_req;
unsigned int    pulse_time;
unsigned char   purge_delay;
char            purge_flag;
char            purge_step=1;
unsigned int    purge_time;
extern char     rx_to30;
char            s[41];
extern int      sp_bu;
char            stop_gate;
char            sw_value[24];
char            sx[252];
char            sy[252];
char            time1ms=0;
unsigned int    tot_time=0;
char            Xcount;
int             zero_offset;

const int       head_lim[3][32]={

{0,315,819,993,1174,1388,1582,1820,2072,2318,2614,2911,3203,
3490,3781,4072,4364,4655,4951,5243,5534,5826,6074,6318,6563,6761,
6958,7155,7348,7546,7739,8192},
{000,000,120,180,200,240,320,420,460,500,520,560,580,
600,620,660,720,780,840,920,1000,1080,1160,1200,1280,
1400,1600,1700,1800,2000,2200,2200},
{120,120,280,320,360,480,620,760,820,880,920,960,980,
1000,1020,1080,1200,1360,1480,1620,1760,1900,2000,2100,
2200,2300,2400,2600,3000,4096,4096,4096}};

int             gage_block_act[32]={
0,315,819,993,1174,1388,1582,1820,2072,2318,2614,2911,3203,
3490,3781,4072,4364,4655,4951,5243,5534,5826,6074,6318,6563,6761,
6958,7155,7348,7546,7739,8192};
```

```
const char        msg[34][11]={
                  {"open      "},
                  {"A1        "},
                  {"A2        "},
                  {"A3*       "},
                  {"A4        "},
                  {"A5        "},
                  {"A6        "},
                  {"A7        "},
                  {"A8*       "},
                  {"A9        "},
                  {"A10       "},
                  {"A11       "},
                  {"A12       "},
                  {"B1*       "},
                  {"B2        "},
                  {"B3        "},
                  {"B4        "},
                  {"B5        "},
                  {"B6        "},
                  {"C1*       "},
                  {"C2        "},
                  {"C3        "},
                  {"C4        "},
                  {"C5        "},
                  {"D1*       "},
                  {"D2        "},
                  {"D3        "},
                  {"D4*       "},
                  {"D5        "},
                  {"D6*       "},
                  {"CLOSED    "},
                  {"          "},
                  {"GAUGE=    "},
                  {"LEARNING  "}};

int sprintf(char *,const char *,...);

void main()
{
void auto_zero();
void calib();
void calib_print();
void check_proto();
void clear_print();
void display_diag_menu();
```

```c
void display_menu();
void do_flow_calc();
void do_gate_control();
void do_initialization();
void do_print();
void do_rep_gen();
void do_sample();
void do_2312();
void do_tx_gen_error();
void do_typeD();
void dump();
void gate_hold();
void get_head();
void get_lvdt();
void lvdt_head_print();
void plotter_check();
void prn_prgm();
void prior_check();
void purge();
void rg_print();
void sdisplay();
int sprintf();
void super_bubble();
void switch_stuff();
void time_display();
void time_keeper();
void totalize();

/* sprintf(s,"%5d",pass_count++);
sdisplay(8,s); */

/*sprintf(s,"%3d%3d",Xcount,baud);
sdisplay(8,s); 6-28  should these variables be eliminated? */

/*sprintf(s,"%3d%3d",Modem_on_count,Modem_off_count);
sdisplay(7,s);
sprintf(s,"%3d",rx_to30);
sdisplay(49,s);*/ if(power_up_flag) do_initialization();

if(one_sec_flag)  time_keeper();

prior_check();

plotter_check();

switch_stuff();

if(print_done) clear_print();

if(menu_number==20) time_display();

if(prior_req==1) auto_zero();

if(!diag_menu_nbr) display_menu();
else display_diag_menu();
```

```
do_2312();

do_typeD();

/*do_tx_gen_error();*/ check_proto();

if(calib_step==0)
    {
if((gate_move_flag==on||lvdt_count>=20) && prior_req<2 &&
    lvdt_read_delay==0 && diag_menu_nbr<19)
    get_lvdt();
get_head();

if(lvdt_count<20 && prior_req<2 &&
    gate_control_time1==0 && lvdt_read_delay==0 &&
    diag_menu_nbr<19)
    do_gate_control();

if(flow_calc_time>=2) do_flow_calc();

if(tot_time>=2) totalize();

do_print();

if(prior_req==2) purge(head);

super_bubble();

if(prior_req==3) do_sample();

do_rep_gen();

rg_print();

prn_prgm();

} if(calib_print_flag) calib_print();

}    /*  END MAIN    */ void main1()
{
sprintf(s,"%2X %2X %4x %2x",bkup_key1,bkup_key2,
    sp_bu,BBR_bu);
sdisplay(64,s);
}
```

```c
/*      JULY 20, 1990       LF1.C       vAU05 */
/*      void calib()
        void calib_print()
        void digit_key_value(value)
        void do_flow_calc()
        void do_gate_control()
        void do_print()
        void get_head()
        void get_lvdt()
        int  read_head()
        void pump_control()
        void purge(head1)
        void switch_stuff()
*/ define              maska 0x0FFF
define              maskov 0x1000
#define              maskpol 0x2000
#define              off 0
#define              on 1
#define              port4 0x41
#define              port5a 0x50
#define              port5b 0x51
#define              port5c 0x52
#define              port6b 0x61
#define              port6c 0x62
#define              pos2 6
#define              pos3 13
define              pos5 28 char                       a_d_to;
extern unsigned int        auto_zero_time;
int                        avg_head;
extern char                az_step;
extern char                blank[41];
char                       bottle_num_timer;
char                       bottle_print_req;
extern char                buzz_time;
extern char                cable_len;
extern unsigned char       cal_delay;
unsigned char              calib_delay;
extern int                 calib_index;
char                       calib_print_flag;
extern char                calib_rounds;
char                       calib_step;
int                        calib_temp[8];
extern char                change_flag1;
extern char                change_flag4;
extern char                clear_flag;
char                       decimal_flag;
extern char                diag_menu_nbr;
extern char                digit_key_enable;
char                       digit_value=99;
```

```c
extern char              DMAF;
extern unsigned int      dump_delay;
char                     event_mark;
unsigned int             fast_sol_time;
extern float             flow;
extern unsigned int      flow_calc_time;
float                    flow_print;
int                      flow_print_count;
extern float             flow_total;
extern int               gage_block_act[32];
extern char              gate_control_time2;
extern char              gate_move_flag;
unsigned char            gate_move_time1;
unsigned char            gate_move_time2=10;
int                      gate_position;
char                     gh_step;
extern int               head;
extern char              head_avg_control;
extern int               head_count;
extern int               head_count2;
int                      head_count3;
extern const int         head_lim[3][32];
extern long              head_total;
extern long              head_total2;
long                     head_total3;
extern int               head2;
extern int               hl_index[7];
char                     lh_print_flag;
extern int               lvdt;
int                      lvdt2;
int                      lvdt3;
extern unsigned char     lvdt_count;
extern char              lvdt_disp;
char                     lvdt_power_flag;
char                     man_purge;
extern unsigned char     menu_number;
extern int               menu_timeout;
unsigned int             min_sol_time;
extern char              mode_letter;
extern const char        msg[34][11];
int                      old_flow_graph;
extern char              old_prgm_step;
char                     one_hour_flag;
char                     paper_adv_flag;
extern char              paper_out_flag;
extern int               plotter_full_scale;
extern char              plotter_mode;
char                     plotter_ovrg_flag;
extern char              plotter_speed;
extern char              plotter_text_type;
char                     plus_flag;
char                     power_up_flag;
extern char              pp_step;
char                     prev_line_bot_flag;
int                      prev_lvdt;
extern char              prgm_step;
```

```
extern char            print_count;
extern char            print_done;
char                   print_flag1;
char                   print_flag2;
int                    print_freq=10;
extern char            print_mask;
extern int             print_offset;
char                   print_text_pos;
extern unsigned int    print_time;
extern char            prior_req;
extern unsigned int    pulse_time;
char                   pump_flag;
extern unsigned char   purge_delay;
unsigned char          purge_delay1;
extern char            purge_flag;
extern char            purge_step;
extern char            purge_time_min;
extern char            purge_time_sec;
char                   purge_type;
extern char            report_gen;
extern char            rg_print_step;
extern char            rg_step;
extern char            rg_vol_print_flag;
extern char            s[41];
extern char            samp_delay;
extern char            samp_req;
unsigned int           sb_time;
extern char            se_pl_en_flag;
int                    start_gate_value;
unsigned int           start_sol_time;
extern char            stop_gate;
extern char            sw_value[24];
extern char            sx[252];
extern char            sy[252];
extern char            temp[8];
extern char            text_print_flag;
extern char            volume_units;
extern char            Vp_power_flag;
extern int             zero_offset;

const float volume_conversion[6]={
7.481,1.0,264.2,325872,0.2642,1000000.0};

int sprintf(char *,const char *,...);
```

/****************************************************************/

```c
void calib()

{
    int delta_lvdt;
    int move_value;
    int t1;

int find_delta();
    int get_lvdt_act();
    int get_lvdt_std();
    void outbit();
    void pulse_sol();
    void sdisplay();
    int sprintf();
    void toutbit();

outbit(port5c,6,1);        /*Turn on LVDT power.  */
    menu_timeout=0;

switch (calib_step)
        { case 1:
    calib_delay=3;
    calib_step=2;
    break;

case 2:
    if(calib_delay==0)
        {
        calib_step=3;
        calib_delay=8;
        }
    break;

/* Open gate */
case 3:
    prev_lvdt=get_lvdt_act();
    calib_step=4;
    break;

case 4:
    outbit(port5b,0,1);
    if(calib_delay==0) calib_step=5;
    break;

case 5:
    calib_delay=2;
    if(get_lvdt_act() - prev_lvdt<10) calib_step=6;
    else calib_step=3;
    break;

/* Fill air line */
case 6:
    outbit(port5b,0,0);
```

```
            prev_lvdt=get_lvdt_act();
            min_sol_time=30 * temp[0];
            calib_step=7;
            break;

case 7:
            pulse_sol(min_sol_time);
            calib_delay=3 * temp[0];
            calib_step=8;
            break;

case 8:
            if(calib_delay==0) calib_step=9;
            break;

case 9:
            if(prev_lvdt-get_lvdt_act()>200) calib_step=10;
            else
                {
                min_sol_time+=10;
                calib_step=7;
                }
            break;

case 10:
            min_sol_time=6;
            calib_step=11;
            break;

/* Find time to move 10 counts */
    case 11:
            prev_lvdt=get_lvdt_act();
            pulse_sol(min_sol_time);
            calib_delay=3 * temp[0];
            calib_step=12;
            break;

case 12:
            if(calib_delay==0) calib_step=13;
            break;

case 13:
            delta_lvdt=find_delta(prev_lvdt);
            calib_step=11;
            if(delta_lvdt<2) min_sol_time+=5;
            else if(delta_lvdt < 10)
                min_sol_time+=2;
            else if(delta_lvdt > 25) min_sol_time-=1;
            else
                {
                calib_step=14;
                start_sol_time=min_sol_time+2;
                }
                break;

/* Find time to move 25-40 counts */
```

```
case 14:
    prev_lvdt=get_lvdt_act();
    pulse_sol(start_sol_time);
    calib_delay=3 * temp[0];
    calib_step=15;
    break;

case 15:
    if(calib_delay==0) calib_step=16;
    break;

case 16:
    delta_lvdt=find_delta(prev_lvdt);
    calib_step=14;
    if(delta_lvdt < 25) start_sol_time+=2;
    else if(delta_lvdt > 40) start_sol_time-=5;
    else
        {
        calib_step=17;
        fast_sol_time=start_sol_time+10;
        }
    break;

/* Find time to move 200-300 counts */
case 17:
    prev_lvdt=get_lvdt_act();
    pulse_sol(fast_sol_time);
    calib_delay=3 * temp[0];
    calib_step=18;
    break;

case 18:
    if(calib_delay==0) calib_step=19;
    break;

case 19:
    delta_lvdt=find_delta(prev_lvdt);
    if(delta_lvdt < 200)
            {
            fast_sol_time+=10;
            calib_step=17;
            }
    else
            {
            calib_step=20;
            menu_number++;
            }
    break;

/* Open gate */
case 20:
    calib_index=0;
    outbit(port5b,0,1);
    buzz_time=10;
    calib_delay=1;
    calib_step=21;
    break;
```

```
case 21:
    if(calib_delay==0) calib_step=20;
    break;

case 30:
    outbit(port5b,0,0);
    start_gate_value=get_lvdt_act();
    pulse_time=start_sol_time;
    calib_step=31;
    break;

case 31:    /* Move within 1000 counts */
    calib_delay=3 * temp[0];
    if(get_lvdt_act() - gage_block_act[hl_index[calib_rounds]] >
        1000)
        {
        prev_lvdt=get_lvdt_act();
        pulse_sol(fast_sol_time);
        calib_step++;
        }
    else calib_step=35;
    break;

case 32:
    if(calib_delay==0) calib_step++;
    break;

case 33:
    delta_lvdt=find_delta(prev_lvdt);
    calib_step=31;
    if(delta_lvdt > 300) fast_sol_time-=5;
    else if(delta_lvdt < 200) fast_sol_time+=5;
        else
        {
        calib_step=35;
        calib_delay=3 * temp[0];
        }
    break;

/* Close in with 20-40 count steps */
case 35:
    prev_lvdt=get_lvdt_act();
    pulse_sol(pulse_time);
    calib_step++;
    break;

case 36:
    if(calib_delay==0) calib_step++;
    break;

case 37:
    delta_lvdt=find_delta(prev_lvdt);
    if(delta_lvdt > 40) pulse_time--;
    else if(delta_lvdt < 21) pulse_time++;
    if(pulse_time < min_sol_time)
        pulse_time=min_sol_time;
```

```
        move_value=start_gate_value - get_lvdt_act();
        if(delta_lvdt < 6 && move_value>50)
            calib_step++;
        else calib_step=35;
        calib_delay=temp[0];
        break;

/* Make sure gate is touching block by giving one more pulse */
case 38:
        prev_lvdt=get_lvdt_act();
        pulse_sol(pulse_time);
        calib_delay=3 * temp[0];
        calib_step++;
        break;

case 39:
        if(calib_delay==0) calib_step++;
        break;

case 40:
        calib_delay=3 * temp[0];
        delta_lvdt=find_delta(prev_lvdt);
        if(delta_lvdt > 8) calib_step=35;
        else
            {
            calib_step++;
            buzz_time=80;
            }
        break;

case 41:  t1=get_lvdt_act();
        if(t1>=head_lim[0][hl_index[calib_rounds]])
            calib_temp[calib_rounds]=(t1 - head_lim[0]
                [hl_index[calib_rounds]] + 1) / 3;
        else calib_temp[calib_rounds]=500 + (head_lim[0]
            [hl_index[calib_rounds]] - t1 + 1) / 3;
        change_flag1=on;
        menu_number++;
        calib_step++;
        break;

default:
        break;
    } /* end switch */

}
```

```c
/*****************************************************************/ void calib_print()
{
int index;

void sdisplay();
void splot();
int sprintf();
void time_date_fmt();

if(text_print_flag==0)
     {
     switch(calib_print_flag)
         {
     case 1:
         sprintf(s,"    ");
         splot(s);
         calib_print_flag=2;
         break;

case 2:
         time_date_fmt();
         splot(s);
         calib_print_flag=3;
         break;

case 33:
         calib_print_flag=0;
         gate_move_flag=1;
         break;
     default:
         for(index=0;index<10;index++)
             s[index]=msg[calib_print_flag - 2][index];
         sprintf(&s[10],"= %4d",
             gage_block_act[33-calib_print_flag]);
         splot(s);
         calib_print_flag++;
         }     /*End switch*/
     }         /*End If     */
}

/*****************************************************************/ void digit_key_value(value)
char value;

{
```

```c
if(digit_value>=10 && digit_key_enable==on)
    digit_value=value;
}
```

```
/****************************************************/ void do_flow_calc()

{ int calc_av_head();
float flow_calc();
void sdisplay();
int sprintf();
flow_calc_time-=2;
avg_head=calc_av_head();
if(purge_delay==0 && samp_delay==0 &&
    prior_req<2)
    flow=flow_calc(lvdt,avg_head);
flow_print+=flow;
flow_print_count++;
}

/****************************************************/ void do_gate_control()

{
int calc_av_head2();
void gate_control();

gate_control(lvdt,calc_av_head2());
}

/****************************************************/
```

```c
void do_print()

{
char inbit();
int end;
int flow_avg1;
int flow_avg2;
int flow_graph;
int index;
char pl_ovrg_flag2;
int start;

void print_scale();
void print_text_A();
void print_text_B();
void print_text_C();
void print_text_bottle();
void starprint();

if(se_pl_en_flag==on)
    {
    print_flag1=on;
    if(print_flag2==0) print_flag2=1;
    }
if(print_time>=print_freq && plotter_mode==2 && rg_print_step==0
    && flow_print_count>0 && pp_step==0 && pump_flag==off)
    {
    print_time-=print_freq;
    switch(plotter_speed)
        {
    case 1:
        print_freq=100;
        break;
    case 2:
        print_freq=50;
        break;
    case 3:
        print_freq=25;
        break;
    default:
        if(print_freq>12) print_freq=12;
        else print_freq=13;
        break;
        }
    flow_graph=(flow_print / (float)flow_print_count) /
        (float)plotter_full_scale * 240.0 + 2.5;
    if(flow_graph>482) flow_graph=482;
    if(flow_graph>242)
        {
        flow_graph-=240;
        pl_ovrg_flag2=on;
        if(plotter_ovrg_flag==off)
            {
            flow_avg1=242;
            flow_avg2=2;
            }
        else
```

```
            {
            flow_avg1=(old_flow_graph + flow_graph + 1)/2;
            flow_avg2=flow_avg1;
            }
        }
else
        {
        pl_ovrg_flag2=off;
        if(plotter_ovrg_flag==off)
            {
            flow_avg1=(old_flow_graph + flow_graph + 1)/2;
            flow_avg2=flow_avg1;
            }
        else
            {
            flow_avg1=2;
            flow_avg2=242;
            }
        }
if(old_flow_graph<flow_avg1)
        {
        start=old_flow_graph;
        end=flow_avg1;
        }
else
        {
        start=flow_avg1;
        end=old_flow_graph;
        }
print_mask=print_mask << 1;
for(index=start;index<=end;index++)
        sx[index]=sx[index] | print_mask;
print_mask=print_mask >> 1;
if(flow_graph>flow_avg2)
        {
        start=flow_avg2;
        end=flow_graph;
        }
else
        {
        start=flow_graph;
        end=flow_avg2;
        }
if(event_mark==2)
        {
        for(index=2;index<=6;index++)
                sx[index]=sx[index] | print_mask;
        start=68;
        end=242;
        event_mark=0xFE;
        bottle_print_req=on;
        }
for(index=start;index<=end;index++)
        sx[index]=sx[index] | print_mask;
old_flow_graph=flow_graph;
plotter_ovrg_flag=pl_ovrg_flag2;
flow_print=0.0;
flow_print_count=0;
```

```
if(print_flag2==4)
    {
switch(plotter_text_type)
    {
case 1:
    print_text_A(2);
    break;
case 2:
    print_text_B();
    break;
case 3:
    print_text_C();
    break;
case 4:
    print_scale();
    break;
default:
    break;
    }
    }
else if(print_flag2==1)
    {
    print_flag2=2;
    paper_adv_flag=on;
    starprint(off,sx);
    print_text_A(print_count);
    }
if(print_text_pos==0)
    {
    for(index=0;index<240;index++)
    sx[index+2+print_offset]=sx[index+2+print_offset] |
        sy[index];
    }
plotter_text_type=0;
print_mask = print_mask >> 1;
if(++print_count>=6)
    {
    print_count = 0;
    print_mask = 0x20;
    }
print_text_pos++;
if(print_text_pos>2 && print_text_pos<6
    && prev_line_bot_flag==off && bottle_num_timer==0
    && bottle_print_req==on)
    {
    prev_line_bot_flag=on;
    bottle_print_req=off;
    print_text_bottle();
    }
else prev_line_bot_flag=off;
if(print_flag1==off)
    {
    print_flag2=0;
    print_done=on;
    }
else
    {
    while(DMAF);
```

```
                if(!paper_out_flag && !Vp_power_flag)
                    starprint(on,sx);
                else print_done=on;
                }
            print_flag1=off;
            if(print_flag2==2 || print_flag2==3)
                print_flag2++;
            }
        rg_vol_print_flag=off;
        }
}
```

/*****************************************************/

```
void get_head()          /* Read head */

{
int disp_head;

int read_head();
char inbit();
int inword();
void sdisplay();
int sprintf();

if(sb_time>(3 * gate_move_time2) && az_step==0)
    head=read_head() - zero_offset + 5;
head_total+=head;
head_count++;
head_total2+=head;
head_count2++;
head_total3+=head;
head_count3++;
if(menu_number==20 && lvdt_disp==2)
    {
    if(head_avg_control==2) disp_head=avg_head;
    else disp_head=head;
    sprintf(s,"H=%4d",disp_head);
    sdisplay(33,s);
    }
}
```

/*****************************************************/

```c
void get_lvdt()

{
int old_lvdt;
int delta_lvdt;

int get_lvdt_std();
void outbit();
void sdisplay();
int sprintf();

if(gate_move_flag==on && lvdt_count<20) lvdt_count=20;
if(lvdt_count>=22 && lvdt_power_flag==on)
     {
     lvdt_count=0;
     old_lvdt=lvdt;
     lvdt=get_lvdt_std();
     if(gate_move_flag==on)
           {
           gate_move_flag=off;
           delta_lvdt=old_lvdt - lvdt;
           if(head>1000)gate_control_time2=5;
           if(delta_lvdt<0) delta_lvdt=-delta_lvdt;
           if(delta_lvdt<10 && gate_control_time2<60)
              gate_control_time2++;
           else if(delta_lvdt>10 && gate_control_time2>3)
              gate_control_time2/=2;
           }
     outbit(port5c,6,0);
     lvdt_power_flag=off;
     }
 else
     {
     outbit(port5c,6,1);
     lvdt_power_flag=on;
     if(menu_number==20 && lvdt_disp==2)/*xxxxx*/
           {
           sprintf(s,":");
           sdisplay(27,s);
           }
     }
}

/*****************************************************/ int read_head()

{
int x;
int zero_head;
```

```
char inbit();
int inword();
void outbit();

a_d_to=0;
outbit(port5a,7,1);
while(inbit(port6b,5))
     if(a_d_to>=3) return(head + zero_offset);
x=inword(port4);
zero_head=x & maska;
if(~x & maskpol) zero_head=-zero_head;
return(zero_head);
}
```

```
/****************************************************/ void purge(head1)

int head1;

{
int get_lvdt_std();
void outbit();
void toutbit();
void sdisplay();
int sprintf();

mode_letter=0x46;
switch (purge_step)
     {
case 1:   purge_delay=2;
          purge_step=2;
          outbit(port5c,6,1);
          head2=head1;
          break;

case 2:   if(purge_delay==0) purge_step=10;
          break;

case 10:  lvdt2=get_lvdt_std();
          toutbit(port5b,1,1000);
          purge_delay=gate_move_time2;
          purge_step=11;
          break;

case 11:  if(purge_delay==0) purge_step=12;
          break;

case 12:  /* close gate until it stops */
          lvdt3=get_lvdt_std();
```

```c
            if(lvdt2 - lvdt3 < 100)
                {
                purge_step=13;
                if(purge_type==0) purge_delay=60;
                else purge_delay=120;
                }
            else purge_step=10;
            break;

case 13: if(purge_delay==0) purge_step=14;
         if(head1>800 && purge_type==0)
                purge_step=14;
         else if(head1>1000) purge_step=14;
         break;

case 14: /* open gate */
         purge_delay=120;
         purge_step=15;
         break;

case 15: purge_delay1=gate_move_time2;
         lvdt2=get_lvdt_std();
         purge_step=16;
         break;

case 16:
         outbit(port5b,0,1);
         if(purge_delay1==0) purge_step=17;
         break;

case 17: if(get_lvdt_std() - lvdt2<10||purge_delay==0)
                purge_step=18;
         else purge_step=15;
         break;

case 18: purge_delay=120;
         outbit(port5b,0,0);
         purge_step=19;
         break;

case 19: if(purge_delay==0 || head1<head2+50)
                purge_step=20;
         break;

case 20: /* Pressurize line */
         purge_delay1=gate_move_time2;
         toutbit(port5b,1,500);
         purge_step=21;
         break;

case 21: if(purge_delay1==0) purge_step=22;
         break;

case 22: lvdt2=get_lvdt_std();
         toutbit(port5b,1,1000);
         gate_move_time1=0;
         purge_delay=5;
```

```
                purge_delay1=0;
                purge_step=24;
                break;

case 23:        lvdt2=get_lvdt_std();
                purge_delay1=1;
                purge_step=24;
                break;

case 24:        /*  look for gate starting to move */
                if(purge_delay==0) purge_step=25;
                else if(purge_delay1==0)
                    {
                    lvdt3=get_lvdt_std();
                    if(lvdt2 - lvdt3 > 10) purge_step=25;
                    else purge_step=23;
                    }
                break;

case 25:        /*  look for gate stopping */
                purge_delay=10;
                purge_step=26;
                break;

case 26:        lvdt2=get_lvdt_std();
                purge_delay1=1;
                purge_step=27;
                break;

case 27:        if(purge_delay==0) purge_step=28;
                else if(purge_delay1==0)
                    {
                    lvdt3=get_lvdt_std();
                    if(lvdt2 - lvdt3 < 20) purge_step=28;
                    else purge_step=26;
                    }
                break;

default:        gate_move_time2=gate_move_time1;
                if(gate_move_time2<cable_len*2)
                    gate_move_time2=cable_len*2;
                if(gate_move_time2>30) gate_move_time2=30;
                purge_flag=0;
                purge_step=1;
                purge_delay=12 * gate_move_time2;
                if(purge_type==0) purge_type=1;
                else purge_type=0;
                purge_time_sec=0;
                purge_time_min=0;
                prior_req=0;
                break;

}   /*end switch*/
}   /*end function*/

/*************************************************************/
```

```c
void switch_stuff()

{
int auto_zero();
void check_lock();
void cursor_control();
void digit_key_value();
void sdisplay();
void starprint();
int sprintf();

if(sw_value[0]==5)   /*  NUMBER 7  */
    {
    sw_value[0]=6;
    digit_key_value(7);
    } if(sw_value[1]==5)   /*  NUMBER 8  */
    {
    sw_value[1]=6;
    digit_key_value(8);
    } if(sw_value[2]==5)   /*  NUMBER 9  */
    {
    sw_value[2]=6;
    digit_key_value(9);
    } if(sw_value[3]==5)    /*  GO TO PROGRAM STEP  */
    {
    sw_value[3]=6;
    if(menu_number==20)
        menu_number=19;
    menu_timeout=0;
    } if(sw_value[4]==5)   /*  NUMBER 4  */
    {
    sw_value[4]=6;
    digit_key_value(4);
    } if(sw_value[5]==5)   /*  NUMBER 5  */
    {
    sw_value[5]=6;
    digit_key_value(5);
    } if(sw_value[6]==5)   /*  NUMBER 6  */
    {
    sw_value[6]=6;
    digit_key_value(6);
    } if(sw_value[7]==5)   /*  EXIT PROGRAM  */
    {
```

```c
    sw_value[7]=6;
    cursor_control(0,off);
    if(diag_menu_nbr)
          {
          menu_number=0;
          diag_menu_nbr=0;
          }
    else if(change_flag4==on) menu_number=30;
          else
               {
               calib_step=0;
               menu_number=0;
               check_lock();
               }
    } if(sw_value[8]==5)   /*  NUMBER 1  */
    {
    sw_value[8]=6;
    digit_key_value(1);
    } if(sw_value[9]==5)   /*  NUMBER 2  */
    {
    sw_value[9]=6;
    digit_key_value(2);
    } if(sw_value[10]==5) /*  NUMBER 3  */
    {
    sw_value[10]=6;
    digit_key_value(3);
    } if(sw_value[11]==5)      /*  CLEAR ENTRY  */
    {
    sw_value[11]=6;
    clear_flag=on;
    } if(sw_value[13]==5)      /*  NUMBER 0  */
    {
    sw_value[13]=6;
    digit_key_value(0);
    } if(sw_value[15]==5)      /*  ENTER PROGRAM STEP  */
    {
    sw_value[15]=6;
    if(diag_menu_nbr) diag_menu_nbr++;
    else if(menu_number==20) menu_number=1;
          else if(menu_number==21 || menu_number==22)
               {
               if(prgm_step>11) menu_number=19;
               else
                    {
```

```
                    menu_number=prgm_step;
                    old_prgm_step=prgm_step;
                    cursor_control(0,off);
                    digit_key_enable=off;
                    }
                }
            else menu_number++;
        menu_timeout=0;
        } if(sw_value[16]>=5)
    {
    sw_value[16]=6;
    plus_flag=on;
    } if(sw_value[17]>=5)        /*   DECIMAL POINT   */
    {
    sw_value[17]=6;
    decimal_flag=1;
    } if(sw_value[18]>=5)        /*   PAPER ADVANCE */
    {
    if(paper_adv_flag==off)
        {
        starprint(off,sx);
        paper_adv_flag=on;
        }
    sw_value[18]=6;
    } if(sw_value[19]>=5)        /*   PRINT PROGRAM      */
    {
    sw_value[19]=6;
    if(pp_step==0 && menu_number==20) pp_step=1;
    } if(sw_value[20]==5)    /*  Manual Sample */
    {
    sw_value[20]=6;
    samp_req=on;
    } if(sw_value[21]==5)        /*   GATE FLUSH    */
    {
    sw_value[21]=6;
    if(purge_flag==off) purge_flag=on;
    else purge_step=28;
    } if(sw_value[22]>=5)        /*   MANUAL-PURGE   */
    {
    sw_value[22]=6;
    man_purge=on;
    }
```

```
if(sw_value[23]==5)        /*  PRINT REPORT   */
    {
    sw_value[23]=6;
    if(report_gen==1 && rg_print_step==0 && rg_step==1)
        rg_print_step=1;
    }

}
/*     JULY 09, 1990      LF2.C       VT01 */
```

```
#define         maska 0x0FFF
define         maskov 0x1000
#define         maskpol 0x2000
#define         off 0
#define         on 1
#define         port2a 0x20    /*   .01 second  */
#define         port2b 0x21    /*   hour        */
#define         port2c 0x22    /*   minute      */
#define         port2d 0x23    /*   seconds     */
#define         port2e 0x24    /*   month       */
#define         port2f 0x25    /*   day         */
#define         port2g 0x26    /*   year        */
#define         port3 0x31
#define         port5a 0x50
#define         port5b 0x51
#define         port5c 0x52
#define         port6b 0x61
#define         pos1 0
#define         pos3 13
#define         pos4 18
#define         pos5 28
#define         pos6 31
#define         pos13 53
#define         pos14 68
#define         pos15 69
define         pos20 33 extern char             a_d_to;
int                     av_head3;
char                    beep_number;
extern unsigned char    cal_delay;
char                    change_flag1;
char                    change_flag3;
char                    change_flag4;
extern const char       char_pattern0[97];
extern const char       char_pattern1[280];
char                    clear_flag;
char                    digit_key_enable;
extern char             digit_value;
extern float            flow;
extern float            flow_total;
char                    fl_rt_unts_col=1;
```

```
char                     fl_rt_unts_row;
extern int               gage_block_act[32];
extern char              gate_control_time1;
extern char              gate_control_time2;
extern char              gate_move_flag;
extern unsigned char     gate_move_time2;
extern int               gate_position;
int                      ghp_time_dn;
int                      ghp_time_up;
extern char              gh_step;
extern int               head_count2;
extern int               head_count3;
extern const int         head_lim [3][32];
int                      head_print_time;
extern long              head_total3;
extern char              lh_print_flag;
char                     lock_flag=1;
char                     lock_timer;
extern char              lvdt_disp;
extern unsigned char     lvdt_read_delay;
char                     menu_flash_time;
extern unsigned char     menu_number;
int                      menu_time=300;
extern const char        month_name[36];
extern const char        msg[34][11];
char                     old_menu_value;
char                     old_prgm_step=1;
char                     pass_digit_count;
int                      pass_number;
char                     prgm_step=1;
char                     prog_unlock_flag;
unsigned char            reentry_menu_number;
unsigned char            reentry_menu_number2;
extern char              s[41];
int                      scd_lvdt;
extern char              sw_value[24];
extern char              sx[252];
extern char              sy[252];
char                     temp[8];
char                     temp_reentry;
char                     text_print_flag;
char                     volume_units=2;
extern int               zero_offset;

struct     table{
    int gate_pos[32];
    int head_ht[32][10];
    float flow_val[32][11];
      };

extern const struct table flow_table;

struct menus{
    int position[20][6];
    char text[20][44];};
extern const struct menus line_two;
```

```c
const float flow_conversion[3][4]={
{1.0,60.0,694.44,448.83},
{1585.3,4.4033,0.18347,15.853},
{0.0052,0.0167,226.25,0.1247}};

int sprintf(char *,const char *,...);
```

/****************************************************/

```c
void display_line_two(entry_number)
char entry_number;

{
void sdisplay();

sdisplay(line_two.position[entry_number][0]-3,
     &line_two.text[entry_number][0]);
}
```

/****************************************************/

```c
int find_delta(fst_lvdt)
int fst_lvdt;
{
int get_lvdt_act();
void sdisplay();
int delta_lvdt;
int sprintf();

delta_lvdt=fst_lvdt - get_lvdt_act();
sprintf(s,"%4d",delta_lvdt);
sdisplay(60,s);
return(delta_lvdt);
}
```

/****************************************************/

```c
void flash_menu_item(entry_number,position)
char entry_number;
char position;
```

```
{
char char_count=0;
char index;
void sdisplay();

position--;
index=line_two.position[entry_number][position] -
        line_two.position[entry_number][0];
if(menu_flash_time > 90)
    {
    menu_flash_time=0;
    sdisplay(line_two.position[entry_number][0]-3,
            &line_two.text[entry_number][0]);
    }
else if(menu_flash_time > 30 && menu_flash_time < 60)
    {
    menu_flash_time=60;
    while(line_two.text[entry_number][index+3] != 0x20 &&
          line_two.text[entry_number][index+3] != 0)
        {
        s[char_count++]=0x20;
        index++;
        }
    s[char_count]=0;
    sdisplay(line_two.position[entry_number][position],s);
    }
}

/************************************************************/ float flow_calc(lvdt4,head3)

int lvdt4;
int head3;

{
    char i=0;
    char j=0;
    char k=0;
    float ratio1,ratio2,ratio3,tmp1,tmp2,flow2;
    int head_tmp[12];

void sdisplay();
    int sprintf();

if(head3<120)
        head3=120;
```

```
while(flow_table.gate_pos[i]<=lvdt4)
     i++;
ratio1=lvdt4-flow_table.gate_pos[i-1];
ratio1=ratio1/(flow_table.gate_pos[i]-
          flow_table.gate_pos[i-1]);

for(j=0;j<=9;j++)
     head_tmp[j+1]=flow_table.head_ht[i-1][j];
head_tmp[0]=120;
head_tmp[11]=4096;
j=0;
while(head_tmp[j]<=head3)
     j++;
ratio2=head3-head_tmp[j-1];
ratio2=ratio2/(head_tmp[j]-head_tmp[j-1]);

for(k=0;k<=9;k++)
     head_tmp[k+1]=flow_table.head_ht[i][k];
k=0;
while(head_tmp[k]<=head3)
     k++;
ratio3=head3-head_tmp[k-1];
ratio3=ratio3/(head_tmp[k]-head_tmp[k-1]);
j--;
k--;
if(j==0)
     tmp1=0.0;
else
     tmp1=flow_table.flow_val[i-1][j-1];

tmp1=(flow_table.flow_val[i-1][j]-
      tmp1)*ratio2+tmp1;

if(k==0)
     tmp2=0.0;
else
     tmp2=flow_table.flow_val[i][k-1];

tmp2=(flow_table.flow_val[i][k]-
      tmp2)*ratio3+tmp2;

flow2=(tmp2-tmp1)*ratio1+tmp1;

return(flow2);
}
```

/**************************************************/

/* Control the gate position to keep the head within the
   proper range above the gate.  */

```
void gate_control(lvdt5,head4)
    int lvdt5;
    int head4;
{
    void sdisplay();
    int sprintf();

void toutbit();
    int i=0;
    float propor;
    int lower_gate_lim;
    unsigned int lower_head_lim;
    int upper_gate_lim;
    unsigned int upper_head_lim;
    int ave_head_lim;
    int gate_time;

if(head4<0) head4=0;
    lower_gate_lim = head_lim[0][2];
    upper_gate_lim = head_lim[0][30];
    gate_control_time1=gate_control_time2;

while(head_lim[0][i]<=lvdt5)
        i++;
/*  sprintf(s,"%3d",i);
    sdisplay(pos20,s);*/
    propor=lvdt5-head_lim[0][i-1];
    propor=propor/(head_lim[0][i]-head_lim[0][i-1]);
/*  sprintf(s,"%6.4f",propor);
    sdisplay(pos14,s);*/
    lower_head_lim=(head_lim[1][i]-head_lim[1][i-1])*propor;
    lower_head_lim+=head_lim[1][i-1];
    upper_head_lim=((head_lim[2][i]-head_lim[2][i-1])*propor)+
     head_lim[2][i-1];
    ave_head_lim=(upper_head_lim+lower_head_lim)/2;

/*  if(display_mode==0)
        {
        sprintf(s,"%4d",lower_head_lim);
        sdisplay(pos3,s);
        sprintf(s,"%4d",upper_head_lim);
        sdisplay(pos13,s);
        sprintf(s,"%4d",ave_head_lim);
        sdisplay(pos4,s);
        }*/ if(head4<lower_head_lim && lvdt5>lower_gate_lim)
        {
        gate_time=(ave_head_lim-head4);
        if(gate_time>200 || gate_time<1)
            gate_time=200;
        toutbit(port5b,1,gate_time);
        gate_move_flag=1;
        lvdt_read_delay=gate_move_time2;
        }
    else if(head4>upper_head_lim && lvdt5<upper_gate_lim)
        {
```

```
        gate_time=(head4-ave_head_lim);
        if(gate_time>1000 || gate_time<1)
            gate_time=1000;
        toutbit(port5b,0,gate_time);
        gate_move_flag=1;
        lvdt_read_delay=gate_move_time2;
        } if(lvdt5<lower_gate_lim-100) /*Keep gate above lowest step*/
    {
    toutbit(port5b,0,20);
    gate_move_flag=1;
    lvdt_read_delay=gate_move_time2;
    }
}
```

```
/**********************************************************/ void gate_close(time)
int time;
{
void sdisplay();
int sprintf();
void toutbit();

toutbit(port5b,1,time);
sprintf(s,"%3d",time);
sdisplay(74,s);
cal_delay=25;
while(cal_delay);
}
```

```
/**********************************************************/ void gate_hold()
{
int fst_lvdt;
int gate_move;
int lvdt_diff;

int calc_av_head2();
float flow_calc();
void gate_close();
void gate_open();
void get_head();
```

```
int get_lvdt_act();
int get_lvdt_std();
void outbit();
int pulse_adjust();
void sdisplay();
int sprintf();

outbit(port5c,6,1);
sprintf(s,"TRGT LVDT=%4d",gage_block_act[gate_position]);
sdisplay(50,s);
sdisplay(65,&msg[31-gate_position][0]);
get_lvdt_act();
get_head();
if(head_count2>8)
    {
    flow=flow_calc(get_lvdt_std(),calc_av_head2());
    sprintf(s,"FL=%5.1f",flow);
    sdisplay(25,s);
    } fst_lvdt=get_lvdt_act();
lvdt_diff=fst_lvdt - gage_block_act[gate_position];
if(lvdt_diff>2)
    {
    gate_close(ghp_time_dn);
    scd_lvdt=get_lvdt_act();
    gate_move=fst_lvdt - scd_lvdt;
    sprintf(s,"%3d",gate_move);
    sdisplay(77,s);
    ghp_time_dn+=pulse_adjust(lvdt_diff,gate_move);
    if(ghp_time_dn<1) ghp_time_dn=1;
    if(ghp_time_dn > 50) ghp_time_dn=50;
    }
if(lvdt_diff<-3)
    {
    gate_open(ghp_time_up);
    lvdt_diff=-lvdt_diff;
    scd_lvdt=get_lvdt_act();
    gate_move=scd_lvdt - fst_lvdt;
    sprintf(s,"%3d",gate_move);
    sdisplay(37,s);
    ghp_time_up+=pulse_adjust(lvdt_diff,gate_move);
    if(ghp_time_up<1) ghp_time_up=1;
    if(ghp_time_up > 50) ghp_time_up=50;
    }
}
```

/****************************************************************/

```c
void gate_open(time)
int time;
{
void sdisplay();
void toutbit();
int sprintf();

toutbit(port5b,0,time);
sprintf(s,"%3d",time);
sdisplay(34,s);
cal_delay=25;
while(cal_delay);
}
```

/**********************************************/

```c
int get_lvdt_act()

{
    int x;
    int lvdt6;
    void sdisplay();
    char inbit();
    int inword();
    void outbit();
    int sprintf();

outbit(port5a,6,1);
    a_d_to=0;
    while(!inbit(port6b,4));
    while(inbit(port6b,4))
        if(a_d_to>=3) return(4096);
    x=inword(port3);
    lvdt6=x&maska;
    if(x&maskpol)
        lvdt6+=4096;
    else lvdt6=4095-lvdt6;
    outbit(port5a,6,0);

/*    if(display_mode>=1)
        {
        sprintf(s,"%6d",lvdt6);
        if(x&maskov)
            s[0]='^';
        if(display_mode==1)
            sdisplay(pos15,s);
        else sdisplay(0,s);
        }*/ return(lvdt6);
}
```

```c
/****************************************************/ int get_lvdt_std()

{
    int lvdt7;
    int i=0;
    float ratio;
    void sdisplay();
    int get_lvdt_act();
    int sprintf();

lvdt7=get_lvdt_act();

while(gage_block_act[i]<=lvdt7)
        i++;
    ratio=lvdt7-gage_block_act[i-1];
    ratio=ratio/(gage_block_act[i] - gage_block_act[i-1]);
    lvdt7=(head_lim[0][i] - head_lim[0][i-1]) * ratio +
            head_lim[0][i-1] + 0.5;

if(menu_number==20 && lvdt_disp==2)/*xxxx*/
        {
        sprintf(s,"L=%4d",lvdt7);
        sdisplay(26,s);
        } return(lvdt7);
}

/****************************************************/ void lvdt_head_print()
{
int calc_av_head();
void time_date_fmt();
void splot();

switch(lh_print_flag)
    {
case 0:
    break;

case 1:
    time_date_fmt();
    splot(s);
    head_print_time=0;
```

```
              lh_print_flag=2;
              break;

case 2:
              if(head_print_time>=5)
                 {
                 sprintf(s,"ZERO OFFSET=%4d",zero_offset);
                 splot(s);
                 calc_av_head();
                 head_count3=0;
                 head_total3=0;
                 head_print_time=0;
                 lh_print_flag=3;
                 }
              break;

case 13:
              if(head_print_time>=5)
                 {
                 sprintf(s,"COUNTS=%4d,AV HEAD=%4d",head_count3,av_head3);
                 splot(s);
                 lh_print_flag++;
                 }
              break;

case 14:
              if(head_print_time>=10)
                 {
                 sprintf(s,"    ");
                 splot(s);
                 lh_print_flag=0;
                 }
              break;

default:
              if(head_print_time>=30)
                 {
                 head_print_time-=30;
                 lh_print_flag++;
                 sprintf(&s[12],"HEAD=%4d",calc_av_head());
                 sprintf(s,"LVDT=%4d",scd_lvdt);
                 s[9]=0x20;
                 s[10]=0x20;
                 s[11]=0x20;
                 splot(s);
                 av_head3=head_total3 / head_count3;
                 }
           }
}

/*******************************************************/ int pulse_adjust(lvdt_diff,gate_move)
int lvdt_diff;
int gate_move;
```

```c
{
int time1;

time1=0;
if(lvdt_diff>300)
    {
    if(gate_move<50) time1=1;
    else if(gate_move>60) time1=-1;
    }
else
    {
    if(lvdt_diff>10)
        {
        if(gate_move<10) time1=1;
        else
            {
            time1=-1;
            if(gate_move>20) time1=-2;
            }
        }
    else
        {
        if(gate_move<1) time1=1;
        else
            {
            if(gate_move>3) time1=-1;
            if(gate_move>10) time1=-2;
            }
        }
    }
return(time1);
}
```

```
/*************************************************/ void pulse_sol(sol_time)
unsigned int sol_time;

{
void sdisplay();
int sprintf();
void toutbit();

toutbit(port5b,1,sol_time);
sprintf(s,"%4d",sol_time);
sdisplay(50,s);
cal_delay=25;
while(cal_delay);
}
```

```c
/****************************************************/ void splot(text_ptr)
char *text_ptr;

{
void starprint();
void text_to_dot();

text_to_dot(text_ptr);
text_print_flag=on;
starprint(on,sy);
}

/****************************************************/ void time_date_fmt()

{
char inbyte();
int sprintf();

inbyte(port2a);
sprintf(s,"%02d",inbyte(port2b));
sprintf(&s[2],":");
sprintf(&s[3],"%02d",inbyte(port2c));
sprintf(&s[5],":");
sprintf(&s[6],"%02d",inbyte(port2d));
sprintf(&s[8]," ");
sprintf(&s[10],"%02d",inbyte(port2e));
sprintf(&s[12],"/");
sprintf(&s[13],"%02d",inbyte(port2f));
sprintf(&s[15],"/");
sprintf(&s[16],"%02d",inbyte(port2g));
}

/****************************************************/ void time_date_transfer(position)
int position;

{
int index;
```

```
void text_to_dot();
void time_date_fmt();

time_date_fmt();
text_to_dot(s);
for(index=0;index<120;index++)

sx[index + position] = sx[index + position] | sy[index];
}

/**********************************************************/

/*   This function converts ASCII text to a 5 X 7
     dot pattern for the plotter.  It can handle a
     maximum of 40 ASCII characters as input.  Output
     is in string sy.        */ void text_to_dot(text_ptr)
char *text_ptr;

{
char *cptr;     /*  pointer to character patterns  */
int index;
char *syptr;    /*  pointer to output to plotter  */ for(index=0;index<240;index++)       /*   Clear output string  */
    sy[index]=0;

syptr=sy;                            /*   Set output pointer to  */
while(*text_ptr!=0)                  /*   starting position      */
    {
    cptr=char_pattern0;
    while(*cptr!=0)
        {
        if(*text_ptr==*cptr)
            {
            cptr++;
            goto copy;
            }
        else cptr+=6;
        } cptr=char_pattern1 + (*text_ptr - 0x28) * 5;
    copy:  for(index=0;index<5;index++)
            {
            *syptr=*cptr;
            syptr++;
            cptr++;
```

```
            }
    *syptr=0;
    syptr++;
    text_ptr++;
    }   /* end while */
}

/**********************************************************/ void time_display()

{
char monthx;

char inbyte();
void sdisplay();

inbyte(port2a);
if(inbyte(port2d) % 10 >=8)
     {
     monthx=(inbyte(port2e) - 1) * 3;
     sprintf(s,"%02d",inbyte(port2f));
     s[2]=month_name[monthx];
     s[3]=month_name[monthx+1];
     s[4]=month_name[monthx+2];
     sprintf(&s[5],"%02d ",inbyte(port2g));
     }
else
     {
     sprintf(s,"%02d",inbyte(port2b));
     sprintf(&s[2],":");
     sprintf(&s[3],"%02d",inbyte(port2c));
     sprintf(&s[5],":");
     sprintf(&s[6],"%02d",inbyte(port2d));
     }
sdisplay(70,s);
}

/**********************************************************/ void update_value(digit_val,temp_num)
char digit_val;
char temp_num;

{
void check_report_gen();
```

```
if(digit_value < digit_val && digit_value>0)
    temp[temp_num]=digit_value;
digit_value=99;
if(sw_value[12]==5)
    {
    sw_value[12]=6;
    if(--temp[temp_num]==0)
        temp[temp_num]=digit_val-1;
    }
if(sw_value[14]==5)
    {
    sw_value[14]=6;
    if(++temp[temp_num]==digit_val)
        temp[temp_num]=1;
    }
if(clear_flag==on)
    {
    temp[temp_num]=old_menu_value;
    clear_flag=off;
    }
if(old_menu_value==temp[temp_num])
    change_flag1=off;
else
    {
    change_flag1=on;
    if(lock_flag==1 && prog_unlock_flag==off)
        menu_number=35;
    check_report_gen();
    }
}

/*   AUGUST 02, 1990   LF4.C    VAU17 */ typedef char *STRING;

define            off 0
#define            on 1
#define            port2a 0x20    /* .01 second */
#define            port2b 0x21    /* hour   */
#define            port2c 0x22    /* minute */
#define            port2d 0x23    /* second */
#define            port2e 0x24    /* month  */
#define            port2f 0x25    /* day    */
#define            port2g 0x26    /* year   */
define            port6c 0x62 struct              menus{
    int position[20][6];
    char text[20][44];};

extern char         beep_number;
extern char         cable_len;
extern char         calib_mode;
extern char         calib_step;
```

```
extern int            calib_temp[8];
char                  century=19;
extern char           change_flag1;
extern char           change_flag3;
extern char           change_flag4;
extern char           clear_flag;
int                   cursor_position;
extern char           decimal_flag;
char                  diag_menu_nbr;
char                  digit_count;
extern char           digit_key_enable;
extern char           digit_value;
char                  fault_msg_number;
char                  fault_msg_time;
extern float          flow;
extern const float    flow_conversion[3][4];
unsigned int          flow_per_pulse=10;
extern const char     flow_plot_dec[3][4];
extern const char     flow_plot_digits[3][4];
extern const float    flow_plot_max[3][4];
extern const float    flow_plot_min[3][4];
extern float          flow_total;
extern char           fl_rt_unts_col;
extern char           fl_rt_unts_row;
float                 interval_mult;
extern const STRING   line_one[74];
extern const struct menus line_two;
extern char           lock_flag;
extern char           lock_timer;
char                  max_digit_count;
char                  menu_active;
extern char           menu_flash_time;
extern unsigned char  menu_number;
extern int            menu_time;
int                   menu_timeout;
char                  mode_letter;
char                  month_length[12]=
{31,28,31,30,31,30,31,31,30,31,30,31};
extern char           old_menu_value;
extern char           old_prgm_step;
extern char           paper_out_flag;
extern char           pass_digit_count;
extern int            pass_number;
char                  plotter_jammed_flag;
char                  plotter_mode=1;
int                   plotter_full_scale=50; /* in gpm */
char                  plotter_speed=1;
extern char           plus_flag;
char                  post_menu_delay;
extern char           prgm_step;
extern char           prog_unlock_flag;
extern int            purge_time1;
extern unsigned char  reentry_menu_number;
extern unsigned char  reentry_menu_number2;
extern char           report_gen;
extern char           report_gen_lock_out;
```

```
char                    reset_tot=2;
extern char             s[41];
char                    sampler_init=1;
int                     samp_time_min;
char                    samp_time_sec;
float                   samp_vol;
float                   samp_vol_limit;
char                    sb_freq=1;
int                     SiteID=1;
extern char             temp[8];
int                     tempc;
unsigned int            tempx;
float                   tempy;
extern char             temp_reentry;
int                     time_per_pulse=60;
extern const float      volume_conversion[6];
extern char             volume_units;
extern char             Vp_power_flag;

int sprintf(char *,const char *,...);

void step_setup3(char,char);

void menu_select(char,char,char);

/*****************************************************/ void check_lock()

{
if(prog_unlock_flag==on)
    lock_timer=30;
}

/*****************************************************/ void display_hr_min(pos_1,pos_2)
int pos_1;
int pos_2;
```

```
{
void sdisplay();

sprintf(s,"%02d",tempc/60);
sdisplay(pos_1,s);
sprintf(s,"%02d",tempc%60);
sdisplay(pos_2,s);
}

/****************************************************/ void display_menu()

{ int calc_calib_check_digit();
void calib_diff_calc();
void check_lock();
void check_min_max();
void check_report_gen();
void clear_display();
void cursor_control();
void digit_wait();
void digit_wait1();
void digit_wait2();
void digit_wait4();
void display_hr_min();
void display_line_two();
void display_menu2();
void display_units();
void flash_menu_item();
char inbit();
char inbyte();
void menu_select();
void plotter_time_align();
void print_formt_flow();
void print_formt_vol();
void range_display();
void screen_fill();
void step_setup1();
void step_setup2();
void step_setup3();
void step_setup4();
void sdisplay();
void sdisplay1();
void update_value();
if(menu_number!=20 && menu_timeout>120) menu_number=0;
switch(menu_number)
{
case 0:          /*  NORMAL DISPLAY  */
    plus_flag=off;
    decimal_flag=0;
    clear_display();
    cursor_control(0,off);
    sdisplay(0,line_one[0]);
```

```
        menu_time=0;
        post_menu_delay=20;
        diag_menu_nbr=0;
        menu_number=20;
        break;

case 1:         /*   START STEP 1   */
        old_menu_value=fl_rt_unts_col;
        temp[0]=fl_rt_unts_row;
        temp[1]=fl_rt_unts_col;
        step_setup1();
        report_gen_lock_out=on;
        menu_active=on;
        menu_number=23;
        break;

case 2:         /*   START STEP 2   */
        old_menu_value=sampler_init;
        temp[0]=sampler_init;
        tempx=flow_per_pulse;
        tempc=time_per_pulse;
        step_setup1();
        report_gen_lock_out=off;
        menu_number=43;
        break;

case 3:         /*   START STEP 3   */
        old_menu_value=plotter_mode;
        temp[0]=plotter_mode;
        step_setup1();
        report_gen_lock_out=off;
        menu_number=55;
        break;

case 4:         /*   START STEP 4   */
        temp[4]=0;
        report_gen_lock_out=on;
        menu_number=71;
        break;

case 5:         /*   START STEP 5   */
        tempx=SiteID;
        tempc=SiteID;
        step_setup1();
        digit_count=0;
        report_gen_lock_out=on;
        menu_number=88;
        break;

case 6:         /*   START STEP 6   */
        old_menu_value=reset_tot;
        temp[0]=reset_tot;
        step_setup1();
        report_gen_lock_out=on;
        menu_number=91;
        break;
```

```c
case 7:         /*   START STEP 7   */
    old_menu_value=report_gen;
    temp[0]=report_gen;
    step_setup1();
    report_gen_lock_out=off;
    menu_number=94;
    break;

case 8:         /*   START STEP 8   */
    step_setup1();
    report_gen_lock_out=off;
    menu_number=126;
    break;

case 9:         /*  START STEP 9   */
    old_menu_value=sb_freq;
    temp[0]=sb_freq;
    step_setup1();
    report_gen_lock_out=off;
    menu_number=135;
    break;

case 10:        /*   START STEP 10 */
    calib_diff_calc();
    step_setup1();
    report_gen_lock_out=off;
    menu_number=202;
    break;

case 11:        /*   START STEP 11 */
    step_setup1();
    menu_number=189;
    old_menu_value=lock_flag;
    report_gen_lock_out=off;
    temp[0]=lock_flag;
    break;

case 19:        /*   ENTER PRGM STEP NUMBER  */
    clear_display();
    sdisplay(0,line_one[1]);
    sprintf(s,"%2d",old_prgm_step);
    sdisplay(36,s);
    cursor_control(36,on);
    menu_number=21;
    digit_key_enable=on;
    prgm_step=old_prgm_step;
    menu_active=on;
    break;

case 20:        /*   REFRESH NORMAL  */
    menu_timeout=0;
    if(menu_time>=300)
        menu_number=0;
    if(post_menu_delay==0) menu_active=off;
    if(lock_timer==0)
        {
```

```
            prog_unlock_flag=off;
            if(lock_flag==1)
                {
                sprintf(s,"L");
                sdisplay(39,s);
                }
            } print_formt_vol(0,flow_total,on);
    sdisplay(40,s);

print_formt_flow(0,flow,on,on);
    sdisplay(56,s);

if(fault_msg_time < 1)
        {
        if(Vp_power_flag && fault_msg_number==0)
            menu_number=207;
        else if(plotter_mode==2 && paper_out_flag &&
            fault_msg_number==1) menu_number=187;
        else if(plotter_jammed_flag &&
            fault_msg_number==2) menu_number=208;
        else if(calc_calib_check_digit() != calib_temp[7] &&
            fault_msg_number==3) menu_number=209;
        if(++fault_msg_number > 3) fault_msg_number=0;
            } if(plus_flag) menu_number=182;
        s[0]=mode_letter;
        s[1]=0;
        sdisplay(79,s);
        mode_letter=0x20;
        break;

case 21:        /*  WAIT FOR 1ST DIGIT OF PRGM STEP  */
        if(digit_value<10)
            {
            prgm_step=digit_value;
            digit_value=99;
            sprintf(s," ");
            sdisplay(37,s);
            sprintf(s,"%ld",prgm_step);
            sdisplay(36,s);
            menu_number=22;
            }
        break;

case 22:
        if(digit_value<10)  /*  WAIT FOR 2ND DIGIT OF PRGM STEP  */
            {
            sprintf(s,"%ld",digit_value);
            sdisplay(37,s);
            prgm_step=prgm_step * 10 + digit_value;
            digit_value=99;
            digit_key_enable=off;
            }
```

```
        if(clear_flag==on)
            {
            clear_flag=off;
            menu_number=19;
            }
        break;

case 23:        /* STEP 1.0 */
    step_setup2(2,temp[0]);
    break;

case 24:        /* WAIT FOR MENU SELECTION */
    menu_select(temp[0],1,6);
    break;

case 25:        /* AFTER 'PROGRAM ENTER' */
    digit_key_enable=off;
    if(temp[1]==5)
            {
            if(++temp[0]>2)
                temp[0]=0;
            if(temp[0]==f1_rt_unts_row)
                change_flag3=off;
            else change_flag3=on;
            old_menu_value=5;
            menu_number=23;
            }
    else menu_number=26;
    break;

case 26:        /* STEP 1.1 */
    step_setup3(volume_units,2);

case 27:
    step_setup2(3,3);
    break;

case 28:        /* WAIT FOR MENU SELECTION */
    menu_select(3,2,7);
    break;

case 29:        /* END OF STEP 1 */
    digit_key_enable=off;
    if(volume_units!=temp[2] && sampler_init==2)
        menu_number=40;
    else menu_number=59;
    volume_units=temp[2];
    break;

case 30:        /* 'EXIT PROGRAM' */
    sdisplay(0,line_one[4]);
    sdisplay(40,line_one[5]);
    digit_key_enable=on;
    menu_number=31;
    break;
```

```
case 31:         /*  WAIT FOR '0' OR '1'  */
    if(digit_value==0)
        {
        calib_step=0;
        menu_number=0;
        check_lock();
        }
    if(digit_value==1) menu_number=reentry_menu_number;
    digit_value=99;
    break;

case 32:
    menu_number=30;
    break;

case 35:         /*  ENTER PASSNUMBER  */
    pass_digit_count=0;
    pass_number=0;
    temp_reentry=reentry_menu_number;
    change_flag4=off;

case 36:
    clear_display();
    sdisplay(0,line_one[6]);
    cursor_control(17,on);
    if(pass_number!=0)
        {
        sprintf(s,"%d",pass_number);
        sdisplay(17,s);
        }
    digit_key_enable=on;
    reentry_menu_number=36;
    menu_number=37;
    break;

case 37:         /*  WAIT FOR 4 DIGITS  */
    if(digit_value<10 && pass_digit_count < 4)
        {
        pass_number=pass_number*10+digit_value;
        pass_digit_count++;
        sprintf(s,"%d",pass_number);
        sdisplay(17,s);
        change_flag4=on;
        }
    if(clear_flag==on)
        {
        clear_flag=off;
        pass_number=0;
        pass_digit_count=0;
        menu_number=36;
        }
    digit_value=99;
    break;

case 38:         /*  CHECK PASSNUMBER VALIDITY  */
    digit_key_enable=off;
```

```
            cursor_control(0,off);
            if(pass_number==3240)
                    {
                    reentry_menu_number=temp_reentry;
                    menu_number=reentry_menu_number;
                    prog_unlock_flag=on;
                    }
            else if(pass_number==6850) diag_menu_nbr=1;
                else
                        {
                        clear_display();
                        sdisplay(0,line_one[7]);
                        beep_number=10;
                        menu_number=39;
                        }
            break;

case 39:
            if(beep_number==0)
                menu_number=reentry_menu_number2;
            break;

case 40:        /* DISPLAY 'CAUTION: SAMPLER...' */
            clear_display();
            sdisplay(0,line_one[8]);
            sdisplay(40,line_one[9]);
            menu_number=41;
            sampler_init=1;

case 41:        /* WAIT FOR 'ENTER/ */
            break;

case 42:
            menu_number=59;
            break;

case 43:        /* STEP 2.0 */
            step_setup2(10,4);
            break;

case 44:        /* WAIT FOR MENU SELECTION */
            menu_select(4,0,4);
            break;

case 45:
            change_flag3=change_flag4;
            if(temp[0]==2) menu_number=46;
            else if(temp[0]==3) menu_number=50;
                else menu_number=162;
            break;

case 46:        /* STEP 2.1 */
            menu_number=47;
            tempy=0.0;
            digit_count=0;
            change_flag1=off;
```

```
        reentry_menu_number2=46;
        break;

case 47:
        clear_display();
        sdisplay(0,line_one[11]);
        reentry_menu_number=47;
        cursor_position=61;
        range_display(12,63);
        break;

case 48:         /*  WAIT FOR DIGITS  */
        digit_wait1(61);
        break;

case 49:
        decimal_flag=0;
        if(change_flag1==on)
            {
            tempy=tempy/interval_mult;
            if(tempy>60000.0) tempy=60000.0;
            tempx=tempy;
            }
        if(tempx<10 || tempx>50000)
            {
            tempx=flow_per_pulse;
            menu_number=46;
            }
        else menu_number=162;
        break;

case 50:         /*  STEP 2.2  */
        digit_count=0;
        change_flag1=off;
        reentry_menu_number2=50;
        cursor_position=66;
        tempc=time_per_pulse;
        menu_number=51;
        break;

case 51:
        clear_display();
        sdisplay(0,line_one[13]);
        sdisplay(40,line_one[14]);
        reentry_menu_number=51;
        digit_key_enable=on;
        display_hr_min(66,74);
        menu_number=52;
        break;

case 52:         /*  WAIT FOR 4 DIGITS  */
        digit_wait4(66,74,50);
        break;

case 53:
        if(tempc>1440) menu_number=50;
```

```
        else menu_number=162;
        break;

case 54:         /* END OF STEP 2 */
    digit_key_enable=off;
    if(temp[0]!=sampler_init)
        {
        samp_vol=0.0;
        samp_time_min=0;
        samp_time_sec=0;
        }
    samp_vol_limit=(float)tempx * interval_mult *
        volume_conversion[volume_units-1];
    sampler_init=temp[0];
    flow_per_pulse=tempx;
    time_per_pulse=tempc;
    menu_number=3;
    break;

case 55:         /* STEP 3.0 */
    step_setup2(15,5);
    break;

case 56:         /* WAIT FOR MENU SELECTION */
    menu_select(5,0,3);
    break;

case 57:
    change_flag3=change_flag4;
    if(temp[0]==2) menu_number=63;
    else menu_number=70;
    break;

case 59:
    if((fl_rt_unts_row!=temp[0]||fl_rt_unts_col!=temp[1])&&
        plotter_mode==2) menu_number=60;
    else menu_number=2;
    fl_rt_unts_row=temp[0];
    fl_rt_unts_col=temp[1];
    break;

case 60:         /* CAUTION: PLOTTER TURNED OFF */
    clear_display();
    sdisplay(0,line_one[20]);
    sdisplay(40,line_one[9]);
    plotter_mode=1;
    menu_number=61;

case 61:         /* WAIT FOR 'ENTER' */
    break;

case 62:
    menu_number=2;
    break;
```

```
case 63:        /*  STEP 3.1  */
    step_setup4((long)plotter_full_scale,
        flow_plot_min[fl_rt_unts_row][fl_rt_unts_col-1],
        flow_plot_max[fl_rt_unts_row][fl_rt_unts_col-1],52);
    break;

case 64:
    screen_fill(16,flow_plot_dec[fl_rt_unts_row]
        [fl_rt_unts_col-1],flow_plot_min[fl_rt_unts_row]
        [fl_rt_unts_col-1],flow_plot_max[fl_rt_unts_row]
        [fl_rt_unts_col-1],17,52);
    break;

case 65:  /*  WAIT FOR DIGITS  */
    digit_wait2(flow_plot_dec[fl_rt_unts_row]
        [fl_rt_unts_col-1],52,flow_plot_digits
        [fl_rt_unts_row][fl_rt_unts_col-1]);
    break;

case 66:        /*  CHECK VALUE AGAINST MIN AND MAX  */
    check_min_max(flow_plot_min[fl_rt_unts_row]
        [fl_rt_unts_col-1],flow_plot_max
        [fl_rt_unts_row][fl_rt_unts_col-1]);
    break;

case 67:        /*  STEP 3.2  */
    step_setup3(plotter_speed,1);
    break;

case 68:
    step_setup2(18,6);
    break;

case 69:
    menu_select(6,1,5);
    break;

case 70:        /*  END OF STEP 3  */
    digit_key_enable=off;
    plotter_mode=temp[0];
    plotter_full_scale=tempy;
    plotter_speed=temp[1];
    if(change_flag4==on) plotter_time_align();
    menu_number=4;
    break;

default:
    display_menu2();
    break;

}       /* End Switch */
}
```

```c
/****************************************************************/ void digit_wait(cursor_pos,temp_num,digit_num)
int cursor_pos;
int temp_num;
int digit_num;

{
void check_report_gen();
void cursor_control();
void sdisplay();

if(change_flag1==off) cursor_position=cursor_pos;
    if(digit_value<10)
        {
        if(change_flag1==off) temp[temp_num]=0;
        temp[temp_num]=temp[temp_num] * 10 + digit_value;
        change_flag1=on;
        digit_value=99;
        cursor_position++;
        if(++digit_count>=digit_num) digit_key_enable=off;
        if(lock_flag==on && prog_unlock_flag==off)
            menu_number=35;
        check_report_gen();
        }
    sprintf(s,"%-*d",digit_num,temp[temp_num]);
    sdisplay(cursor_pos,s);
    cursor_control(cursor_position,on);
    if(clear_flag==on)
        {
        clear_flag=off;
        change_flag1=off;
        temp[temp_num]=old_menu_value;
        digit_key_enable=on;
        digit_count=0;
        }
    change_flag4=change_flag1 | change_flag3;
}

/****************************************************************/ void digit_wait1(position)
int position;

{
```

```c
char tempa;
float tempb;
void check_report_gen();
void sdisplay();
void cursor_control();

if(digit_value<10 && digit_count < max_digit_count)
    {
    if(decimal_flag>0)
        {
        tempb=digit_value;
        for(tempa=decimal_flag;tempa>0;tempa--)
            tempb=tempb/10.0;
        tempy=tempy + tempb;
        decimal_flag++;
        }
    else tempy=tempy * 10.0 + digit_value;
    digit_count++;
    change_flag1=on;
    if(lock_flag==on && prog_unlock_flag==off)
        menu_number=35;
    check_report_gen();
    }
if(change_flag1==on)
    {
    if(tempy>=1)
        {
        if(decimal_flag>0)
            sprintf(s,"%-7.*f",decimal_flag-1,tempy);
        else sprintf(s,"%-7.0f",tempy);
        }
    else sprintf(s,"%-6.*f",digit_count,tempy);
    sdisplay(position,s);
    }
cursor_control(cursor_position+digit_count,on);
digit_value=99;
if(clear_flag==on)
    {
    clear_flag=off;
    menu_number-=2;
    }
change_flag4=change_flag1 | change_flag3;
}
```

/********************************************************/

```c
void digit_wait2(dec_places,disp_pos,num_digits)
int dec_places;
```

```
int disp_pos;
int num_digits;

{
char tempa;
float tempb;
void cursor_control();
void sdisplay();
if(dec_places==0) decimal_flag=0;
if(digit_value<10)
      {
      if(change_flag1==off)
            {
            tempy=0.0;
            sprintf(s,"        ");
            sdisplay(disp_pos,s);
            }
      if(decimal_flag>0)
            {
            tempb=digit_value;
            for(tempa=decimal_flag;tempa>0;tempa--)
                  tempb=tempb/10.0;
            tempy+=tempb;
            decimal_flag++;
            }
      else tempy=tempy*10.0+digit_value;
      change_flag1=on;
      digit_value=99;
      if(lock_flag==on && prog_unlock_flag==off)
            menu_number=35;
      if(++digit_count>=num_digits)
            digit_key_enable=off;
      }
sprintf(s,"%-1.*f",dec_places,tempy);
sdisplay(disp_pos,s);
if(decimal_flag==1 && digit_count==1 &&
      cursor_position==disp_pos) cursor_position++;
if(decimal_flag==1 && digit_count==0 &&
      cursor_position==disp_pos) cursor_position+=2;
cursor_control(cursor_position+digit_count,on);
if(clear_flag==on)
      {
      clear_flag=off;
      menu_number-=2;
      }
change_flag4=change_flag1 | change_flag3;
}
```

/**********************************************************/

```c
void digit_wait4(pos_1,pos_2,mn_num)
int pos_1;
int pos_2;
int mn_num;

{
void check_report_gen();
void cursor_control();
void display_hr_min();

if(digit_value<10)
      {
      if(change_flag1==off) tempc=0;
      if(digit_count==0)
            tempc=digit_value*600;
      else if(digit_count==1)
            {
            tempc+=digit_value*60;
            cursor_position=pos_2-2;
            }
            else if(digit_count==2)
                  tempc+=digit_value*10;
                  else tempc+=digit_value;
      digit_value=99;
      change_flag1=on;
      display_hr_min(pos_1,pos_2);
      if(++digit_count>=4) digit_key_enable=off;
      if(lock_flag==on && prog_unlock_flag==off)
            menu_number=35;
      check_report_gen();
      }
 cursor_control(cursor_position+digit_count,on);
 if(clear_flag==on)
      {
      clear_flag=off;
      menu_number=mn_num;
      }
 change_flag4=change_flag1 | change_flag3;
 }
```

/***********************************************************/

```c
void display_units(entry_number,position)
int entry_number;
int position;

{
int index;
```

```
int char_count=1;
void sdisplay1();

index=line_two.position[entry_number][position-1] -
      line_two.position[entry_number][0] + 3;
s[0]=0x20;
while(line_two.text[entry_number][index] != 0x20)
     {
     s[char_count++]=line_two.text[entry_number][index];
     index++;
     }
s[char_count]=0;
sdisplay1(s);
}
```

```
/****************************************************/ void menu_select(line_num,temp_num,max_entry)
char line_num;
char temp_num;
char max_entry;

{
void flash_menu_item();
void update_value();

flash_menu_item(line_num,temp[temp_num]);
digit_key_enable=on;
update_value(max_entry,temp_num);
change_flag4=change_flag1 | change_flag3;
}
```

```
/****************************************************/ void range_display(line_num,cursor_pos2)
int cursor_pos2;
int line_num;

{
float tempz;

void display_units();
void sdisplay();
void sdisplay1();
```

```
if(volume_units==1)
    {
    sprintf(s,"10 - 50000)");
    interval_mult=1;
    max_digit_count=5;
    }
else if(volume_units==2)
    {
    sprintf(s,"100 - 500000)");
    interval_mult=10;
    max_digit_count=6;
    }
    else if(volume_units==3)
        {
        sprintf(s,"1 - 5000)");
        interval_mult=.1;
        max_digit_count=4;
        }
        else if(volume_units==4 || volume_units==6)
            {
            sprintf(s,".0001 - .5)");
            interval_mult=.00001;
            max_digit_count=4;
            if(change_flag1==off) decimal_flag=1;
            cursor_position=cursor_pos2;
            }
            else if(volume_units==5)
                {
                sprintf(s,"1000 - 5000000)");
                interval_mult=100;
                max_digit_count=7;
                }
sdisplay1(s);
sdisplay(40,line_one[line_num]);
tempz=tempx * interval_mult;
if(tempz>=1)
sprintf(s,"%-7.0f",tempz);
else sprintf(s,"%4.4f",tempz);
sdisplay1(s);
display_units(3,volume_units);
menu_number++;
digit_key_enable=on;
}
```

/*****************************************************************/

```
void step_setup1()

{
```

```
void cursor_control();

cursor_control(0,off);
change_flag1=off;
change_flag3=off;
change_flag4=off;
reentry_menu_number2=menu_number;
}
```

```
/*****************************************************/ void step_setup2(line_one_num,line_two_num)
int line_one_num;
int line_two_num;

{
void clear_display();
void display_line_two();
void sdisplay();

clear_display();
sdisplay(0,line_one[line_one_num]);
display_line_two(line_two_num);
menu_flash_time=0;
reentry_menu_number=menu_number;
menu_number++;
}
```

```
/*****************************************************/ void step_setup3(var_name,temp_num)
char temp_num;
char var_name;

{
void cursor_control();

old_menu_value=var_name;
temp[temp_num]=var_name;
```

```c
cursor_control(0,off);
change_flag1=off;
change_flag3=change_flag4;
change_flag4=off;
reentry_menu_number2=menu_number;
menu_number++;
}
/*****************************************************/ void step_setup4(perm_var,min_val,max_val,cursor_pos)
long perm_var;
int cursor_pos;
float min_val;
float max_val;

{
digit_count=0;
change_flag1=off;
decimal_flag=0;
reentry_menu_number2=menu_number;
tempy=perm_var;
tempy=tempy / flow_conversion[fl_rt_unts_row]
    [fl_rt_unts_col-1];
if(tempy<min_val) tempy=min_val;
else if(tempy>max_val) tempy=max_val;
if(max_val<1.0)
    {
    cursor_position=cursor_pos+2;
    decimal_flag=1;
    }
else cursor_position=cursor_pos;
menu_number++;
}

/*****************************************************/ void screen_fill(first_line,dec_places,min_val,max_val,
    second_line,disp_pos)
int dec_places;
int first_line,second_line,disp_pos;
float min_val,max_val;

{
void clear_display();
void sdisplay();
void sdisplay1();
void display_units();
```

```
clear_display();
sdisplay(0,line_one[first_line]);
sprintf(s,"%-1.*f",dec_places,min_val);
sdisplay1(s);
sprintf(s," - %1.*f)",dec_places,max_val);
sdisplay1(s);
sdisplay(40,line_one[second_line]);
display_units(fl_rt_unts_row,fl_rt_unts_col);
sprintf(s,"%-1.*f",dec_places,tempy);
sdisplay(disp_pos,s);
reentry_menu_number=menu_number;
digit_key_enable=on;
menu_number++;
}
```

/****************************************************/

```
void screen_fill2(first_line,dec_places,disp_pos)
int dec_places;
int first_line,disp_pos;

{
void clear_display();
void sdisplay();
void sdisplay1();
void display_units();

clear_display();
sdisplay(0,line_one[first_line]);
sprintf(s,"%-1.*f   ",dec_places,tempy);
sdisplay(disp_pos,s);
display_units(fl_rt_unts_row,fl_rt_unts_col);
reentry_menu_number=menu_number;
digit_key_enable=on;
menu_number++;
}
```
/****************************************************/

```
void check_min_max(min_val,max_val)
float max_val;
float min_val;

{
if(tempy<min_val || tempy>max_val)
```

```
    menu_number-=3;
else menu_number++;
tempy=tempy * flow_conversion[fl_rt_unts_row]
    [fl_rt_unts_col-1];
}

/*   AUGUST 02, 1990    LF5.C    VAU17 */ include "type3240.h"
typedef char *STRING;

extern char              beep_number;
char                     cable_len=3;
char                     calib_mode=2;
extern char              calib_print_flag;
char                     calib_rounds;
extern char              calib_step;
extern int               calib_temp[8];
extern char              century;
extern char              change_flag1;
extern char              change_flag3;
extern char              change_flag4;
extern char              clear_flag;
char                     clear_report=2;
extern int               cursor_position;
extern const char        day_tab[2][13];
extern char              decimal_flag;
extern char              digit_count;
extern char              digit_key_enable;
extern char              digit_value;
extern const float       flow_conversion[3][4];
extern char              fl_rt_unts_col;
extern char              fl_rt_unts_row;
extern float             flow_total;
int                      int_str_yr=1990;
char                     int_str_mnth=1;
char                     int_str_day=1;
char                     int_str_hr;
char                     int_str_min;
extern float             interval_mult;
extern const STRING      line_one[74];
extern const struct menus line_two;
extern char              lock_flag;
extern unsigned char     menu_number;
extern int               menu_timeout;
extern char              month_length[12];
struct timestruct        new_time_val;
extern char              old_menu_value;
extern char              prog_unlock_flag;
char                     purge_time_min;
char                     purge_time_sec;
int                      purge_time1=15;
extern unsigned char     reentry_menu_number;
extern unsigned char     reentry_menu_number2;
```

```
char                    report_gen=2;
int                     report_interval=10;
char                    report_interval_units=1;
extern char             reset_tot;
extern char             rg_print_step;
extern char             rg_step;
extern char             s[41];
extern char             sb_freq;
extern int              SiteID;
extern struct tm_date   sys_tm_dt;
extern char             temp[8];
extern int              tempc;
int                     tempd;
extern unsigned int     tempx;
extern float            tempy;
extern unsigned int     tot_time;
extern const float      volume_conversion[6];
extern char             volume_units;
extern int              xmit_full_scale;

int sprintf(char *,const char *,...);

void step_setup3(char,char);

void menu_select(char,char,char);

/***********************************************************/ void display_menu2()

{ int calc_calib_check_digit();
void calc_gb_act();
void calib();
void calib_diff_calc();
void check_lock();
void check_min_max();
void check_report_gen();
void clear_display();
void cursor_control();
void digit_wait();
void digit_wait1();
void digit_wait2();
void digit_wait4();
void display_calib_const();
void display_hr_min();
```

```c
void display_line_two();
void display_menu3();
void flash_menu_item();
char inbyte();
void menu_select();
void plotter_time_align();
void range_display();
char rg_time_check();
void screen_fill2();
void Set_Time();
void step_setup1();
void step_setup2();
void step_setup3();
void step_setup4();
void sdisplay();
void sdisplay1();
void update_value();

switch(menu_number)
{
case 71:        /* STEP 4.0      */
    cursor_control(0,off);
    inbyte(port2a);
    tempx=(int)century * 100 + inbyte(port2g);
    tempc=tempx;
    temp[0]=inbyte(port2e);
    temp[1]=inbyte(port2f);
    temp[2]=inbyte(port2b);
    temp[3]=inbyte(port2c);
    step_setup1();
    menu_number=72;
    break;

case 72:
    clear_display();
    sdisplay(0,line_one[19]);
    reentry_menu_number=72;
    sprintf(s,"%d",tempc);
    sdisplay(46,s);
    sprintf(s,"%-2d",temp[0]);
    sdisplay(54,s);
    sprintf(s,"%-2d",temp[1]);
    sdisplay(61,s);
    sprintf(s,"%-2d",temp[2]);
    sdisplay(66,s);
    sprintf(s,"%-2d",temp[3]);
    sdisplay(73,s);
    digit_key_enable=on;
    digit_count=0;
    menu_number=73+temp[4];
    break;

case 73:  /* WAIT FOR YEAR DIGITS  */
    if(change_flag1==off) cursor_position=46;
```

```c
        if(digit_value<10)
            {
            if(change_flag1==off)
                {
                tempc=0;
                sprintf(s,"    ");
                sdisplay(46,s);
                }
            tempc=tempc * 10 + digit_value;
            change_flag1=on;
            digit_value=99;
            cursor_position++;
            if(++digit_count>=4) digit_key_enable=off;
            if(lock_flag==on && prog_unlock_flag==off)
                menu_number=35;
            check_report_gen();
            }
        sprintf(s,"%d",tempc);
        sdisplay(46,s);
        cursor_control(cursor_position,on);
        if(clear_flag==on)
            {
            clear_flag=off;
            change_flag1=off;
            tempc=tempx;
            digit_key_enable=on;
            digit_count=0;
            }
        change_flag4=change_flag1;
        break;

case 74:
        if(tempc<1989 || tempc>2100)
            {
            tempc=tempx;
            change_flag1=off;
            menu_number=72;
            }
        else
            {
            menu_number=75;
            change_flag3=change_flag4;
            }
        break;

case 75:   /*  MONTH  */
        temp[4]=3;
        digit_key_enable=on;
        digit_count=0;
        change_flag1=off;
        old_menu_value=inbyte(port2e);
        temp[0]=old_menu_value;
        menu_number=76;
        break;
```

```c
case 76:
    digit_wait(54,0,2);
    break;

case 77:
    if(temp[0]<1 || temp[0]>12) menu_number=75;
    else
        {
        menu_number=78;
        change_flag3=change_flag4;
        }
    break;

case 78:  /*  DAY    */
    temp[4]=6;
    digit_key_enable=on;
    digit_count=0;
    change_flag1=off;
    old_menu_value=inbyte(port2f);
    temp[1]=old_menu_value;
    menu_number=79;
    break;

case 79:
    digit_wait(61,1,2);
    break;

case 80:
    if(temp[1]<1 || temp[1]>month_length[temp[0]-1])
        menu_number=78;
    else if(temp[0]==2 && tempc%4!=0 && temp[1]>28)
        menu_number=78;
        else
            {
            menu_number=81;
            change_flag3=change_flag4;
            }
    break;

case 81:  /*  HOUR   */
    temp[4]=9;
    digit_key_enable=on;
    digit_count=0;
    change_flag1=off;
    old_menu_value=inbyte(port2b);
    temp[2]=old_menu_value;
    menu_number=82;
    break;

case 82:
    digit_wait(66,2,2);
    break;

case 83:
    if(temp[2]<0 || temp[2]>23)
        menu_number=81;
```

```
            else
                {
                menu_number=84;
                change_flag3=change_flag4;
                }
            break;

case 84:  /*   MINUTE  */
            temp[4]=12;
            digit_key_enable=on;
            digit_count=0;
            change_flag1=off;
            old_menu_value=inbyte(port2c);
            temp[3]=old_menu_value;
            menu_number=85;
            break;

case 85:
            digit_wait(73,3,2);
            break;

case 86:
            if(temp[3]<0 || temp[3]>59)
                    menu_number=84;
            else menu_number=87;
            break;

case 87:  /*   END OF STEP 4.0  */
            new_time_val.year = tempc;
            new_time_val.month = temp[0];
            new_time_val.day = temp[1];
            new_time_val.hour = temp[2];
            new_time_val.min = temp[3];
            new_time_val.sec = 0;
            Set_Time(&new_time_val);
            if(change_flag4==on) plotter_time_align();
            digit_key_enable=off;
            menu_number=5;
            break;

case 88:  /*   STEP 5.0  */
            clear_display();
            sdisplay(0,line_one[21]);
            sdisplay(40,line_one[22]);
            sprintf(s,"%3d",tempc);
            sdisplay1(s);
            digit_key_enable=on;
            reentry_menu_number=88;
            menu_number=89;
            break;

case 89:  /*   WAIT FOR 3 DIGITS   */
            if(digit_value<10)
                    {
                    if(change_flag1==off) tempc=0;
                    tempc=tempc * 10 + digit_value;
```

```c
            change_flag1=on;
            digit_value=99;
            if(++digit_count>=3) digit_key_enable=off;
            if(lock_flag==on && prog_unlock_flag==off)
                menu_number=35;
            check_report_gen();
            }
     sprintf(s,"%-3d",tempc);
     sdisplay(54,s);
     cursor_control(54+digit_count,on);
     if(clear_flag==on)
            {
            clear_flag=off;
            change_flag1=off;
            tempc=tempx;
            digit_key_enable=on;
            digit_count=0;
            }
     change_flag4=change_flag1;
     break;

case 90:  /*   END OF STEP 5  */
     if(tempc<1 || tempc>999) menu_number=5;
     else
            {
            SiteID=tempc;
            menu_number=6;
            }
     break;

case 91:  /*   STEP 6.0  */
     step_setup2(23,7);
     break;

case 92:
     menu_select(7,0,3);
     break;

case 93:  /*   END OF STEP 6  */
     digit_key_enable=off;
     reset_tot=temp[0];
     if(reset_tot==1)
            {
            flow_total=0.0;
            tot_time=0;
            reset_tot=2;
            }
     menu_number=7;
     break;

case 94:  /*   STEP 7.0  */
     if(report_gen==1) step_setup2(24,8);
     else
            {
            int_str_yr=sys_tm_dt.cent * 100 + sys_tm_dt.year;
            int_str_mnth=sys_tm_dt.month;
```

```
                int_str_day=sys_tm_dt.day;
                int_str_hr=sys_tm_dt.hour;
                step_setup2(24,13);
                }
            break;

case 95:
            if(report_gen==1) menu_select(8,0,4);
            else menu_select(13,0,3);
            break;

case 96:  /*   STEP 7.1   */
            if(temp[0]==2)
                {
                if(report_gen==1) rg_print_step=1;
                report_gen=temp[0];
                menu_number=8;
                }
            else if(temp[0]==1) menu_number=99;
                else step_setup3(clear_report,1);
            temp[1]=clear_report;
            break;

case 97:
            step_setup2(25,7);
            break;

case 98:
            menu_select(7,1,3);
            break;

case 99:  /*   STEP 7.2   */
            step_setup3(report_interval_units,2);
            break;

case 100:
            step_setup2(26,9);
            break;

case 101:
            menu_select(9,2,4);
            break;

case 102:  /*   STEP 7.3   */
            tempx=report_interval;
            tempc=report_interval;
            change_flag1=off;
            change_flag3=change_flag4;
            change_flag4=off;
            reentry_menu_number2=menu_number;
            digit_count=0;
            menu_number=103;
            break;

case 103:
            clear_display();
```

```
            sdisplay(0,line_one[26+temp[2]]);
            sprintf(s,"%4d",tempc);
            sdisplay(40,s);
            if(temp[2]==1) sprintf(s,"HOURS");
            else if(temp[2]==2) sprintf(s,"DAYS");
                else sprintf(s,"MONTHS");
            sdisplay(45,s);
            digit_key_enable=on;
            reentry_menu_number=103;
            menu_number=104;
            break;

case 104:  /*    WAIT FOR 4 DIGITS    */
            if(digit_value<10)
                {
                if(change_flag1==off) tempc=0;
                tempc=tempc * 10 + digit_value;
                change_flag1=on;
                digit_value=99;
                if(++digit_count>=4) digit_key_enable=off;
                if(lock_flag==on && prog_unlock_flag==off)
                    menu_number=35;
                }
            sprintf(s,"%-4d",tempc);
            sdisplay(40,s);
            cursor_control(40+digit_count,on);
            if(clear_flag==on)
                {
                clear_flag=off;
                change_flag1=off;
                tempc=tempx;
                digit_key_enable=on;
                digit_count=0;
                }
            change_flag4=change_flag1|change_flag3;
            break;

case 105:
            if(tempc<1 || tempc>9999) menu_number=102;
            else menu_number=106;
            break;

case 106:  /*    STEP 7.4    */
            tempx=int_str_yr;
            tempd=tempx;
            temp[3]=int_str_mnth;
            temp[4]=int_str_day;
            temp[5]=int_str_hr;
            temp[6]=int_str_min;
            temp[7]=0;
            change_flag1=off;
            change_flag3=change_flag4;
            change_flag4=off;
            reentry_menu_number2=106;
            menu_number=107;
            break;
```

```c
case 107:
    clear_display();
    sdisplay(0,line_one[30]);
    sdisplay(40,line_one[31]);
    sprintf(s,"%4d",tempd);
    sdisplay(43,s);
    sprintf(s,"%-2d",temp[3]);
    sdisplay(55,s);
    sprintf(s,"%-2d",temp[4]);
    sdisplay(63,s);
    sprintf(s,"%-2d",temp[5]);
    sdisplay(70,s);
    sprintf(s,"%-2d",temp[6]);
    sdisplay(78,s);
    reentry_menu_number=107;
    digit_key_enable=on;
    digit_count=0;
    menu_number=108+temp[7];
    break;

case 108:   /*  WAIT FOR YEAR DIGITS  */
    if(change_flag1==off) cursor_position=43;
    if(digit_value<10)
        {
        if(change_flag1==off)
            {
            tempd=0;
            sprintf(s,"    ");
            sdisplay(43,s);
            }
        tempd=tempd * 10 + digit_value;
        change_flag1=on;
        digit_value=99;
        cursor_position++;
        if(++digit_count>=4) digit_key_enable=off;
        if(lock_flag==on && prog_unlock_flag==off)
            menu_number=35;
        }
    sprintf(s,"%d",tempd);
    sdisplay(43,s);
    cursor_control(cursor_position,on);
    if(clear_flag==on)
        {
        clear_flag=off;
        change_flag1=off;
        tempd=tempx;
        digit_key_enable=on;
        digit_count=0;
        }
    change_flag4=change_flag1 | change_flag3;
    break;

case 109:
    if(tempd<1989 || tempd>2100)
        {
        tempd=tempx;
```

```
                change_flag1=off;
                menu_number=107;
                }
        else
                {
                menu_number=110;
                change_flag3=change_flag4;
                }
        break;

case 110:   /*  MONTH  */
        temp[7]=3;
        digit_key_enable=on;
        digit_count=0;
        change_flag1=off;
        old_menu_value=int_str_mnth;
        temp[3]=old_menu_value;
        menu_number=111;
        break;

case 111:
        digit_wait(55,3,2);
        break;

case 112:
        if(temp[3]<1 || temp[3]>12) menu_number=110;
        else
                {
                menu_number=113;
                change_flag3=change_flag4;
                }
        break;

case 113:   /*  DAY     */
        temp[7]=6;
        digit_key_enable=on;
        digit_count=0;
        change_flag1=off;
        old_menu_value=int_str_day;
        temp[4]=old_menu_value;
        menu_number=114;
        break;

case 114:
        digit_wait(63,4,2);
        break;

case 115:
        if(temp[4]<1 || (temp[4]>28 && temp[2]==3) ||
          (tempd%4==0 && temp[4]>day_tab[1][temp[3]]) ||
          (tempd%4!=0 && temp[4]>day_tab[0][temp[3]]))
                menu_number=113;
        else
                {
                menu_number=116;
```

```
                change_flag3=change_flag4;
                }
        break;

case 116:  /*  HOUR   */
        temp[7]=9;
        digit_key_enable=on;
        digit_count=0;
        change_flag1=off;
        old_menu_value=int_str_hr;
        temp[5]=old_menu_value;
        menu_number=117;
        break;

case 117:
        digit_wait(70,5,2);
        break;

case 118:
        if(temp[5]<0 || temp[5]>23)
                menu_number=116;
        else
                {
                menu_number=119;
                change_flag3=change_flag4;
                }
        break;

case 119:  /*  MINUTE */
        temp[7]=12;
        digit_key_enable=on;
        digit_count=0;
        change_flag1=off;
        old_menu_value=int_str_min;
        temp[6]=old_menu_value;
        menu_number=120;
        break;

case 120:
        digit_wait(78,6,2);
        break;

case 121:
        if(temp[6]<0 || temp[6]>59)
                menu_number=119;
        else if(rg_time_check(tempd,temp[3],temp[4],temp[5],
                temp[6],temp[2],tempc,off) >=2) menu_number=122;
                else menu_number=106;
        break;

case 122: /*   END OF STEP 7  */
        cursor_control(0,off);
        if(temp[0]==3)
                {
                temp[0]=1;
```

```
                if(temp[1]==1)
                    {
                    rg_step=2;
                    temp[1]=2;
                    }
                else rg_print_step=1;
                }
        report_gen=temp[0];
        clear_report=temp[1];
        report_interval_units=temp[2];
        report_interval=tempc;
        int_str_yr=tempd;
        int_str_mnth=temp[3];
        int_str_day=temp[4];
        int_str_hr=temp[5];
        int_str_min=temp[6];
        digit_key_enable=off;
        menu_number=8;
        break;

case 123:
case 124:
case 125:
case 126:       /*  STEP 8.0  */
        digit_count=0;
        reentry_menu_number2=126;
        cursor_position=40;
        tempc=purge_time1;
        menu_number=127;
        break;

case 127:
        clear_display();
        sdisplay(0,line_one[33]);
        sdisplay(40,line_one[34]);
        reentry_menu_number=127;
        digit_key_enable=on;
        display_hr_min(40,50);
        menu_number=128;
        break;

case 128:       /*  WAIT FOR 4 DIGITS  */
        digit_wait4(40,50,126);
        break;

case 129:
        if(tempc<15 || tempc>1440) menu_number=126;
        else menu_number=134;
        break;

case 130:
case 131:
case 132:
case 133:

case 134: /*    END OF STEP 8   */
```

```c
        digit_key_enable=off;
        purge_time_min=0;
        purge_time_sec=0;
        purge_time1=tempc;
        menu_number=9;
        break;

case 135: /*   STEP 9.0   */
        step_setup2(37,18);
        break;

case 136:
        menu_select(18,0,7);
        break;

case 137:
        digit_key_enable=off;
        sb_freq=temp[0];
        menu_number=10;
        break;

case 138: /*   STEP 10.2 */
        step_setup2(38,12);
        break;

case 139:
        menu_select(12,1,3);
        break;

case 140:
        digit_key_enable=off;
        change_flag3=change_flag4;
        change_flag1=off;
        change_flag4=off;
        if(temp[1]==1) menu_number=141;
        else menu_number=192;
        break;

case 141: /*   STEP 10.3 */
        if(lock_flag==1 && prog_unlock_flag==off)
            menu_number=35;
        else menu_number=142;
        reentry_menu_number=142;
        reentry_menu_number2=138;
        break;

case 142:
        clear_display();
        sdisplay(0,line_one[55]);
        calib_rounds=0;
        calib_step=1;
        reentry_menu_number=142;
        change_flag4=change_flag3;
        menu_number=143;
        break;
```

```
case 143:
    calib();
    break;

case 144:
    clear_display();
    sdisplay(0,line_one[39]);
    s[0]=0x41+calib_rounds;
    s[1]=0;
    sdisplay(11,s);
    reentry_menu_number=144;
    menu_number=145;
    break;

case 145:
    change_flag4=change_flag1 | change_flag3;
    calib();
    break;

case 146:
    clear_display();
    sdisplay(0,line_one[57]);
    s[0]=0x41+calib_rounds;
    s[1]=0;
    sdisplay(17,s);
    calib_step=30;
    reentry_menu_number=146;
    menu_number=147;
    break;

case 147:
    change_flag4=change_flag1 | change_flag3;
    calib();
    break;

case 148:
    if(++calib_rounds>=7) menu_number=149;
    else menu_number=144;
    break;

case 149:
    clear_display();
    sdisplay(0,line_one[56]);
    calib_temp[7]=calc_calib_check_digit();
    display_calib_const(on);
    reentry_menu_number=149;
    menu_number=150;
    break;

case 150:
    change_flag4=change_flag1 | change_flag3;
    menu_timeout=0;
    break;

case 151:
    menu_number=160;
```

```
        break;
case 160: /*   END OF STEP 10 */
    xmit_full_scale=tempy;
    cable_len=temp[0];
    calib_mode=temp[1];
    calib_step=0;
    calc_gb_act();
    calib_diff_calc();
    if(decimal_flag==1)
        {
        calib_print_flag=1;
        decimal_flag=0;
        }
    menu_number=11;
    break;

case 161: /*   CHECK REPORT GEN LOCK OUT      */
    cursor_control(0,off);
    clear_display();
    sdisplay(0,line_one[42]);
    sdisplay(40,line_one[43]);
    beep_number=10;
    menu_number=39;
    break;

default:
    display_menu3();
    break;

}   /* End Switch */
}

/*   JULY 27, 1990   LF6.C    VAU13 */ include "type3240.h"
define MinPurgeFlow 0.25 extern char             auto_zero_control;
extern unsigned int     auto_zero_time;
char                    az_count;
char                    az_delay;
char                    az_step;
char                    bottle_count;
extern char             bottle_num_timer;
extern unsigned char    calib_delay;
extern char             century;
extern unsigned int     dump_delay;
char                    event_hour;
char                    event_mark2;
char                    event_min;
extern char             fault_msg_time;
extern float            flow;
```

```
extern const float      flow_conversion[3][4];
extern const char       flow_plot_dec[3][4];
extern char             fl_rt_unts_col;
extern char             fl_rt_unts_row;
extern unsigned int     flow_calc_time;
extern float            flow_total;
extern char             gate_control_time1;
extern unsigned char    gate_move_time1;
extern unsigned char    gate_move_time2;
extern int              head;
extern int              head_print_time;
extern int              int_str_yr;
extern char             int_str_mnth;
extern char             int_str_day;
extern char             int_str_hr;
extern char             int_str_min;
extern const struct menus line_two;
extern char             lock_timer;
extern unsigned char    lvdt_count;
extern unsigned char    lvdt_read_delay;
int                     lvdt2x;
struct tm_date          max_fst;
struct tm_date          max_lst;
extern unsigned char    menu_number;
extern int              menu_time;
extern int              menu_timeout;
struct tm_date          min_fst;
struct tm_date          min_lst;
extern char             mode_letter;
const char              month_name[36]=
"JANFEBMARAPRMAYJUNJULAUGSEPOCTNOVDEC";
extern char             month_length[12];
long                    offset;
int                     old_az_time;
int                     old_az_value;
int                     old_offset_val;
extern char             one_hour_flag;
char                    one_min_flag;
extern char             one_sec_flag;
extern char             paper_out_flag;
extern int              plotter_full_scale;
extern char             plotter_speed;
char                    plotter_text_type;
int                     plotter_time;
extern char             post_menu_delay;
extern char             print_count;
extern char             print_mask;
int                     print_offset;
extern char             print_text_pos;
extern unsigned int     print_time;
extern char             prior_req;
unsigned int            pump_time_min;
char                    pump_time_sec;
extern unsigned char    purge_delay;
extern unsigned char    purge_delay1;
extern char             purge_flag;
```

```
extern char            purge_time_min;
extern char            purge_time_sec;
extern int             purge_time1;
extern int             report_interval;
extern char            report_interval_units;
extern char            report_gen;
struct report_data     rg_data1;
extern float           rg_flow_total;
struct tm_date         rg_int_end;
struct tm_date         rg_int_start;
float                  rg_last_flow;
int                    rg_max_count;
float                  rg_max_flow;
int                    rg_min_count;
float                  rg_min_flow;
char                   rg_print_step;
char                   rg_step;
extern char            rg_vol_print_flag;
extern char            rg_vol_print_time;
extern char            s[41];
extern char            sampler_init;
char                   samp_delay;
char                   samp_pulse_time;
char                   samp_req;
char                   samp_step=1;
extern int             samp_time_min;
extern char            samp_time_sec;
extern float           samp_vol;
extern float           samp_vol_limit;
extern unsigned int    sb_time;
extern char            SiteDescrip[18];
extern int             SiteID;
extern char            spc_msg_time;
extern char            sx[252];
extern char            sy[252];
struct tm_date         sys_tm_dt;
extern char            TCheckCondition;
extern char            text_print_flag;
extern int             time_per_pulse;
extern unsigned int    tot_time;
extern char            typeD_time;
extern char            x2312_tx_time;
extern const float     volume_conversion[6];
extern char            volume_units;
extern char            Vp_power_flag;
extern int             zero_offset;

int sprintf(char *,const char *,...);
```

/*********************************************************/

```
void auto_zero()
{
int diff;
```

```c
int new_az_value;

void outbit();
int read_head();
void sdisplay();
int sprintf();

if(auto_zero_control==1) az_step=5;
outbit(port5b,4,1);
mode_letter=0x41;
if(az_step==0) az_step=1;

switch(az_step)
    {
case 1:
    auto_zero_time=120;
    az_step=2;
    az_delay=0;
    az_count=0;
    break;

case 2:
    if(auto_zero_time==0) az_step=3;
    if(az_delay==0)
        {
        new_az_value=read_head();
        diff=new_az_value-old_az_value;
        if(diff<0) diff=-diff;
        if(diff<3) az_step=3;
        old_az_value=new_az_value;
        az_delay=5;
        offset=0;
        }
    break;

case 3:
    if(az_delay==0)
        {
        offset+=read_head();
        az_delay=1;
        az_count++;
        if(az_count>=16) az_step=4;
        }
    break;

case 4:
    offset+=8;
    zero_offset=offset / 16;
    az_step=5;
    diff=zero_offset-old_offset_val;
    if(diff<0) diff=-diff;
    if(diff>10) auto_zero_time=300;
    else if(diff>=6) auto_zero_time=600;
        else if( diff<3) auto_zero_time=old_az_time * 2;
            else auto_zero_time=old_az_time;
    if(auto_zero_time>3600) auto_zero_time=3600;
```

```c
        old_az_time=auto_zero_time;
        old_offset_val=zero_offset;
        break;

default:
        outbit(port5b,4,0);
        az_delay=10;
        prior_req=0;
        az_step=0;
        break;

}
}

/*****************************************************/ void clear_s()
{
int index;

for(index=0;index<41;index++)
    s[index]=0x20;
}

/*****************************************************/ void copy_text()

{
int index;
void text_to_dot();
text_to_dot(s);
for(index=0;index<240;index++)
    sx[index+2]=sx[index+2] | sy[index];
}

/*****************************************************/ void do_rep_gen()
{ char inbit();
void rg_data_accum();
```

```c
char rg_time_check();
void save_time();
void zero_rg_data();

if(report_gen==1)
    {
    switch(rg_step)
        { case 0:
        if(rg_time_check(int_str_yr,int_str_mnth,int_str_day,
        int_str_hr,int_str_min,1,0,off)<=1)
        {
        rg_step=1;
        zero_rg_data();
        save_time(&rg_int_start);
        }
    break;

case 1:
    if(one_min_flag==2)
        {
        one_min_flag=off;
        rg_data_accum(flow);
        save_time(&rg_int_end);
        if(rg_time_check(int_str_yr,int_str_mnth,int_str_day,
        int_str_hr,int_str_min,report_interval_units,
        report_interval,off)<=1 && !paper_out_flag &&
        !Vp_power_flag)
        rg_step=2;

}
    break;

case 2:
        rg_print_step=1;
        rg_step=3;
    break;

case 3:
        if(paper_out_flag || Vp_power_flag)
            {
            rg_print_step=0;
            rg_step=1;
            }
    break;

case 4:
        while(rg_time_check(int_str_yr,int_str_mnth,
            int_str_day,int_str_hr,int_str_min,
            report_interval_units,report_interval,off)<=1)
            rg_time_check(int_str_yr,int_str_mnth,
            int_str_day,int_str_hr,int_str_min,
            report_interval_units,report_interval,on);
        rg_step=0;
        break;
```

}
        }
}

/*******************************************************/ void do_sample()
{
int get_lvdt_std();
void outbit();
void toutbit();

outbit(port5c,6,1);
mode_letter=0x53;
if(head>1320 && samp_step>6 && get_lvdt_std()<6000)
    toutbit(port5b,0,500);
    switch(samp_step)
        {
        case 1:
            if(head>920) samp_step=8;
            else samp_step=2;
            break;
        case 2:
            samp_delay=2;
            samp_step=3;
            break;
        case 3:
            if(samp_delay==0) samp_step=4;
            break;
        case 4:
            lvdt2x=get_lvdt_std();
            toutbit(port5b,1,1000);
            samp_delay=gate_move_time2;
            samp_step=5;
            break;

case 5:
            if(samp_delay==0) samp_step=6;
            break;

case 6:
            if(lvdt2x-get_lvdt_std()<100) samp_step=7;
            else samp_step=4;
            samp_delay=60;
            break;
        case 7:
            if(head>520) samp_step=8;
```

```
            else if(samp_delay==0) samp_step=10;
            break;
    case 8:
            outbit(port5c,0,1);
            samp_pulse_time=5;
            samp_delay=60;
            samp_step=9;
            break;
    case 9:
            if(samp_delay==0) samp_step=10;
            break;
    default:
            samp_req=off;
            samp_step=1;
            samp_delay=30;
            prior_req=0;
            break;

}
}
```

/****************************************************/

```
void plotter_text_check()

{
char hour;
char inbyte();
int pl_test_time;

if(one_hour_flag)
        {
        one_hour_flag=off;
        inbyte(port2a);
        hour=inbyte(port2b);
        switch(plotter_speed)
                {
        case 1:
                if(hour%8==0) plotter_time=0;
                print_time=95;
                break;
        case 2:
                if(hour%4==0) plotter_time=0;
                print_time=45;
                break;
        case 3:
                if(hour%2==0) plotter_time=0;
```

```
            print_time=20;
            break;
        default:
            plotter_time=0;
            print_time=7;
            break;
        }
    print_count=2;
    print_mask=0x8;
    }
switch(plotter_speed)
    {
    case 2:
        pl_test_time=plotter_time*2;
        break;
    case 3:
        pl_test_time=plotter_time*4;
        break;
    case 4:
        pl_test_time=plotter_time*8;
        break;
    default:
        pl_test_time=plotter_time;
        break;
    } if(pl_test_time==3600 || pl_test_time==10800 ||
   pl_test_time==18000|| pl_test_time==25200)
     plotter_text_type=4;
else if(pl_test_time==0 || pl_test_time==14400)
     plotter_text_type=1;
     else if(pl_test_time==7200) plotter_text_type=2;
        else if(pl_test_time==21600) plotter_text_type=3;
}

/***********************************************************/ void plotter_time_align()

{
int speed_factor;
int time_sec;
void clear_print();
char inbyte();

inbyte(port2a);
time_sec=inbyte(port2c) * 60 + inbyte(port2d);
switch(plotter_speed)
    {
```

```
    case 1:
        plotter_time=(inbyte(port2b)%8) * 3600 + time_sec;
        speed_factor=1;
        break;
    case 2:
        plotter_time=(inbyte(port2b)%4) * 3600 + time_sec;
        speed_factor=2;
        break;
    case 3:
        plotter_time=(inbyte(port2b)%2) * 3600 + time_sec;
        speed_factor=4;
        break;
    default:
        plotter_time=time_sec;
        speed_factor=8;
        break;
}
plotter_time--;

clear_print();
time_sec+=300/speed_factor-5;
print_text_pos=(time_sec%(3600/speed_factor))/(600/speed_factor);
print_count=(time_sec%(600/speed_factor))*speed_factor/100;
if(plotter_speed==4)
    {
    while(time_sec>=25) time_sec-=25;
    if(time_sec>12) time_sec-=12;
    print_time=time_sec;
    }
else print_time=time_sec % (100/speed_factor);

print_mask=0x20 >> print_count;
}
```

/**************************************************/

```
void print_scale()

{
int index;
void text_to_dot();

print_text_pos=0;
for(index=0;index<=40;index++) s[index]=0x20;
for(index=0;index<=8;index++)
    s[index*4]=0x2B;
s[33]=0;
```

```
text_to_dot(s);
print_offset=22;
}
```

/****************************************************/

```
void print_text_A(bar_pos)
int bar_pos;

{
int index;
int month;
float tempf;

void print_formt_vol();
void text_to_dot();
char inbyte();

print_text_pos=0;
for(index=0;index<40;index++) s[index]=0x20;
inbyte(port2a);
s[0]=bar_pos+2;
sprintf(&s[1]," %2d",inbyte(port2b));
sprintf(&s[4],":%02d",inbyte(port2c));
sprintf(&s[7]," %2d",inbyte(port2f));
month=(inbyte(port2e)-1)*3;
s[10]=month_name[month];
s[11]=month_name[month+1];
s[12]=month_name[month+2];
sprintf(&s[13],"%2d",inbyte(port2g));
sprintf(&s[15]," TOTAL=");
if(rg_vol_print_flag) tempf=rg_flow_total;
else tempf=flow_total;
print_formt_vol(23,tempf,off);
s[39]=bar_pos+2;
s[40]=0;
text_to_dot(s);
print_offset=0;
}
```

/****************************************************/

```
void print_text_B()

{
```

```c
int index;
void text_to_dot();
char *strcpy();

print_text_pos=0;
for(index=0;index<40;index++) s[index]=0x20;
sprintf(s,"- ID=%-3d",SiteID);
strcpy(&s[8],SiteDescrip);
s[25]=0x20;
s[39]=0x2d;
s[40]=0;
text_to_dot(s);
print_offset=0;
}
```

```
/****************************************************/
```

```c
void print_text_C()

{
int index;

void print_formt_flow();
void text_to_dot();
char inbyte();

print_text_pos=0;
for(index=0;index<40;index++) s[index]=0x20;
inbyte(port2a);
sprintf(s,"-0%% %2d",inbyte(port2b));
sprintf(&s[7],":%02d",inbyte(port2c));
sprintf(&s[10],"   100%%=");
print_formt_flow(18,(float)plotter_full_scale,off,off);
s[35]=0x31;
s[36]=0x30;
s[37]=0x30;
s[38]=0x25;
s[39]=0x2d;
s[40]=0;
text_to_dot(s);
print_offset=0;
}
```

```
/****************************************************/
```

```c
void print_text_bottle()
{
int index;
void copy_text();
```

```c
for(index=0;index<40;index++) s[index]=0x20;
sprintf(&s[1],"B:%02d",bottle_count);
sprintf(&s[5]," %02d",event_hour);
sprintf(&s[8],":%02d",event_min);
copy_text();
}
```

```
/****************************************************/
```

```c
void rg_data_accum(flowa)
float flowa;

{
void save_time();

if(flowa>rg_max_flow)
      {
      rg_max_flow=flowa;
      rg_max_count=1;

save_time(&max_fst);
      }
else if(flowa==rg_max_flow && flowa>rg_last_flow)
      {
      rg_max_count++;
      save_time(&max_lst);
      } if(flowa<rg_min_flow)
      {
      rg_min_flow=flowa;
      rg_min_count=1;
      save_time(&min_fst);
      }
else if(flowa==rg_min_flow && flowa<rg_last_flow)
      {
      rg_min_count++;
      save_time(&min_lst);
      } rg_last_flow=flowa;

rg_data1.min_sum+=flowa;
if(++rg_data1.min_count>=60)
      {
      rg_data1.hour_sum+=rg_data1.min_sum / rg_data1.min_count;
      rg_data1.min_sum=0.0;
```

```c
        rg_data1.min_count=0;
        if(++rg_data1.hour_count>=24)
            {
            rg_data1.day_sum+=rg_data1.hour_sum /
                rg_data1.hour_count;
            rg_data1.hour_sum=0.0;
            rg_data1.hour_count=0;
            if(++rg_data1.day_count>=28 &&
                int_str_day==sys_tm_dt.day)
                {
                rg_data1.month_sum+=rg_data1.day_sum /
                    rg_data1.day_count;
                rg_data1.month_count++;
                rg_data1.day_sum=0.0;
                rg_data1.day_count=0;
                }
            }
        } if(event_mark2==1)
    {
    rg_data1.sample_count++;
    event_mark2=2;
    }
}

/*********************************************************/ char rg_time_check(year1,month1,day1,hour1,min1,units1,interval1,
    xfer_flag)
int year1;
int month1;
int day1;
int hour1;
int min1;
int units1;
int interval1;
int xfer_flag;

{
char status;
int test_val;

if(units1==0) min1+=interval1;
else if(units1==1) hour1+=interval1;
    else if(units1==2) day1+=interval1;
```

```
        else month1+=interval1;

hour1+=min1/60;
min1%=60;
day1+=hour1/24;
hour1%=24;
while(day1>month_length[(month1-1)%12])
    {
    day1-=month_length[(month1-1)%12];
    if(year1%4==0 && month1%12==2) day1--;
    month1++;
    }
year1+=(month1-1)/12;
month1=(month1-1)%12 + 1;
test_val=sys_tm_dt.year + (int)sys_tm_dt.cent * 100;
if(year1<test_val) status=0;
else if(year1>test_val) status=2;
    else
        {
        if(month1<sys_tm_dt.month) status=0;
        else if(month1>sys_tm_dt.month) status=2;
            else
                {
                if(day1<sys_tm_dt.day) status=0;
                else if(day1>sys_tm_dt.day) status=2;
                    else
                        {
                        if(hour1<sys_tm_dt.hour) status=0;
                        else if(hour1>sys_tm_dt.hour) status=2;
                            else
                                {
                                if(min1<sys_tm_dt.min) status=0;
                                else if(min1>sys_tm_dt.min) status=2;
                                    else status=1;
                                }
                        }
                }
        } if(xfer_flag)
    {
    int_str_yr=year1;
    int_str_mnth=month1;
    int_str_day=day1;
    int_str_hr=hour1;
    int_str_min=min1;
    } return(status);

}
```

```
/****************************************************/ void samp_time_check()

{
void outbit();

if(++samp_time_sec>=60)
     {
     samp_time_sec=0;
     if(++samp_time_min>=time_per_pulse)
          {
          samp_time_min=0;
          samp_req=on;
          }
     }
}

/****************************************************/ void save_sys_time(tdptr)
struct tm_date *tdptr;

{
char inbyte();

inbyte(port2a);
tdptr->cent=century;
tdptr->year=inbyte(port2g);
tdptr->month=inbyte(port2e);
tdptr->day=inbyte(port2f);
tdptr->hour=inbyte(port2b);
tdptr->min=inbyte(port2c);
tdptr->sec=inbyte(port2d);
if(one_min_flag==1) one_min_flag=2;
}

/****************************************************/ void save_time(tdptr)
struct tm_date *tdptr;
```

```
{
*tdptr=sys_tm_dt;
}
```

/****************************************************/

```
void tm_dt_to_text(position,sptr,at_flag)
int position;
struct tm_date *sptr;
int at_flag;

{
int month;

sprintf(&s[position],"%02d",sptr->day);
month=((sptr->month)-1)*3;
s[position+2]=month_name[month];
s[position+3]=month_name[month+1];
s[position+4]=month_name[month+2];
sprintf(&s[position+5],"%02d",sptr->year);
if(at_flag==0)
    {
    sprintf(&s[position+7]," %02d:%02d",sptr->hour,sptr->min);
    s[position+13]=0x20;
    }
else sprintf(&s[position+7]," AT %02d:%02d",
    sptr->hour,sptr->min);
}
```

/****************************************************/

```
void time_keeper()

{
void outbit();
void plotter_text_check();
void samp_time_check();
void save_sys_time();

one_sec_flag--;
save_sys_time(&sys_tm_dt);
```

```c
if(auto_zero_time!=0) auto_zero_time--;
if(az_delay!=0) az_delay--;
flow_calc_time++;
tot_time++;
print_time++;
sb_time++;
head_print_time++;
menu_time++;
plotter_time++;
plotter_text_check();
gate_move_time1++;
if(purge_delay!=0) purge_delay--;
if(purge_delay1!=0) purge_delay1--;
if(dump_delay!=0) dump_delay--;
if(gate_control_time1!=0) gate_control_time1--;
if(lock_timer!=0) lock_timer--;
if(spc_msg_time!=0) spc_msg_time--;
if(fault_msg_time!=0) fault_msg_time--;
if(bottle_num_timer !=0) bottle_num_timer--;
if(samp_delay!=0) samp_delay--;
if(samp_pulse_time != 0)
    {
    samp_pulse_time--;
    if(samp_pulse_time==0) outbit(port5c,0,0);
    }
if(sampler_init==3) samp_time_check();
if(++purge_time_sec>=60)
    {
    purge_time_sec=0;
    if(++purge_time_min>=purge_time1 && flow>MinPurgeFlow)
        purge_flag=on;
    }
if(post_menu_delay!=0) post_menu_delay--;
if(lvdt_read_delay!=0) lvdt_read_delay--;
else lvdt_count++;
if(calib_delay!=0) calib_delay--;
x2312_tx_time++;
typeD_time++;
menu_timeout++;
if(pump_time_sec>60)
    {
    pump_time_sec-=60;
    pump_time_min++;
    outbit(port5b,0,0);
    outbit(port5b,1,0);
    }
TCheckCondition=on;
if(rg_vol_print_time<105) rg_vol_print_time++;
}

/******************************************************/ void totalize()
```

```c
{
float flow_incr;
void outbit();

tot_time-=2;
flow_incr=flow/30.0;
flow_total+=flow_incr;
if(sampler_init==2)
    {
    samp_vol+=flow_incr;
    if(samp_vol>=samp_vol_limit)
        {
        samp_vol=0.0;
        samp_req=on;
        }
    }
}
```

```
/******************************************************/ void zero_rg_data()
{
rg_data1.month_sum=0.0;
rg_data1.day_sum=0.0;
rg_data1.hour_sum=0.0;
rg_data1.min_sum=0.0;
if(rg_vol_print_time<100)
    rg_data1.old_flow_vol=rg_flow_total;
else
    rg_data1.old_flow_vol=flow_total;
rg_data1.month_count=0;
rg_data1.day_count=0;
rg_data1.hour_count=0;
rg_data1.min_count=0;
rg_data1.sample_count=0;

rg_max_flow=0.0;
rg_last_flow=0.0;
rg_min_flow=1000;
rg_max_count=0;
rg_min_count=0;
}
^Z
        }
    tx_data[2]=0xAA;
    tx_data[3]=0x55;

if(ck_sum_error)
```

```c
            {
            tx_data[4]=0x03;
            tx_data[136]=0x03;
            ck_sum_error=0;
/*            sprintf(s,"CS");
            sdisplay(25,s);*/
            }
        else if(pkt_flag_error)
            {
            tx_data[4]=0x04;
            tx_data[136]=0x04;
            pkt_flag_error=0;
/*            sprintf(s,"PF");
            sdisplay(28,s);*/
            }
        else if(char_to_error)
            {
            tx_data[4]=0x05;
            tx_data[136]=0x05;
            char_to_error=0;
/*            sprintf(s,"TO");
            sdisplay(31,s);*/
            } tx_ptr=tx_data;
    tx_count=140;
    enable_tx();
    return(1);
    }
else return(0);
}

/*    AUGUST 07, 1990    LF16.C    VAU17 */ include "type3240.h"
typedef char *STRING;

char                    auto_zero_control=2;
extern unsigned int     auto_zero_time;
extern char             beep_number;
extern char             buzz_time;
extern int              calib_temp[8];
char                    clock_adj_control=1;
extern char             diag_menu_nbr;
extern char             digit_key_enable;
extern char             digit_value;
extern char             fl_rt_unts_col;
extern char             fl_rt_unts_row;
extern const float      flow_conversion[3][4];
extern int              gage_block_act[32];
char                    head_avg_control=1;
extern const int        head_lim[3][32];
int                     hl_index[7]=
    {28,23,18,12,7,4,2};
char                    interactive;
```

```
char                        key_pushed;
extern const STRING         line_one[74];
extern const struct menus   line_two;
extern char                 lvdt_disp;
extern int                  menu_time;
extern char                 paper_adv_flag;
extern char                 paper_out_flag;
extern char                 plotter_jammed_flag;
extern char                 power_up_flag;
extern int                  prev_lvdt;
const char                  PRESSKEY[]="PRESS ANY KEY";
extern char                 print_done;
char                        proto_enable=1;
extern unsigned int         pulse_time;
extern unsigned int         pump_time_min;
extern char                 report_gen;
extern struct tm_date       rg_int_end;
extern char                 rg_step;
extern char                 rx_count;
extern char                 rx_data0[28];
extern char                 *rx_ptr;
extern char                 s[41];
char                        sb_control=2;
extern unsigned int         start_sol_time;
extern char                 sw_value[24];
extern struct tm_date       sys_tm_dt;
extern char                 sx[252];
extern char                 sy[252];
extern char                 temp[8];
static char                 *testtype[]={
                            "RUNNING ALL TESTS FROM 6 - 2",
                         "ROM/RAM TEST, PRESS '4-EXIT' WHEN DONE",
                            "PLOTTER TEST",
                            "UART TEST",
                            "SAMPLER PORT TEST",
                            "DISPLAY TEST"};
extern char                 text_print_flag;
unsigned char               timrflash;
extern unsigned char        tx_count;
extern char                 tx_data[140];
extern char                 *tx_ptr;
extern const float          volume_conversion[6];
const char                  vol_dec_places[6]={1,0,3,6,0,6};
extern char                 volume_units;
extern char                 Vp_power_flag;
extern int                  zero_offset;

void menu_select(char,char,char);
int sprintf(char *,const char *,...);
void TestOP(char);
```

```c
/**********************************************************/ int calc_calib_check_digit()
{
int i;
int j;
int *ptr;
int sum;

ptr=calib_temp;
sum=*ptr;
ptr++;
for(i=1;i<=6;i++)
    {
    sum=sum + *ptr;
    ptr++;
    }
while(sum>1000) sum -= 1000;
i=sum / 100;
sum=sum - i * 100;
j=sum / 10;
i=i - j;
sum=sum - j * 10;
i=i + sum + 1;
if(i<0) i= -i;
while(i>=10) i -= 10;
return(i);
}

/**********************************************************/ void calib_diff_calc()
{
int index;
int t1;

for(index=0;index<=6;index++)
    {
    t1=hl_index[index];
    if(gage_block_act[t1]>=head_lim[0][t1])
        calib_temp[index]=(gage_block_act[t1] -
        head_lim[0][t1] + 1) / 3;
    else calib_temp[index]=500 + (head_lim[0][t1] -
        gage_block_act[t1] + 1) / 3;
    }
```

/****************************************************/

```c
void calc_gb_act()
{
float f1;
int i1;
int i2=1;

for(i1=0;i1<=6;i1++)
    {
    if(calib_temp[i1]>500)
        calib_temp[i1]=head_lim[0][hl_index[i1]] -
        (calib_temp[i1] - 500) * 3;
    else calib_temp[i1]=calib_temp[i1] * 3 +
        head_lim[0][hl_index[i1]];
    } for(i1=0;i1<=5;i1++)
    {
    while(i2<=hl_index[5-i1])
        {
    L1: f1=head_lim[0][i2] - head_lim[0][hl_index[6-i1]];
    f1=f1/(float)(head_lim[0][hl_index[5-i1]] -
            head_lim[0][hl_index[6-i1]]);
        f1=f1 * (calib_temp[5-i1] - calib_temp[6-i1]);
        gage_block_act[i2]=f1 + calib_temp[6-i1] + 0.5;
        i2++;
        if(i2==29 || i2==30) goto L1;
        }
    }
}
```

/****************************************************/

```c
void clear_print()
{
int index;

void starprint();
```

```
print_done=0;
if(paper_adv_flag==off)
    {
    if(text_print_flag==off)
        {
        for(index=0;index<252;index++) sx[index] = 0;
        sx[2] = 0x55;
        sx[242] = 0x55;
        }
    else if(text_print_flag==on)
        {
        for(index=0;index<252;index++) sy[index]=0;
        starprint(off,sy);
        text_print_flag=2;
        }
        else text_print_flag=off;
    }
else paper_adv_flag=off;
}
```

```
/****************************************************/ void Delay(tt)  /* tt delay in 100 msec */
unsigned char tt;
{ timrflash=tt * 10;
while(timrflash);
}
```

```
/****************************************************/ void display_calib_const(disp_f)
char disp_f;
{
int index;
void sdisplay();

for(index=0;index<=6;index++)
    sprintf(&s[index*4],"%03d-",calib_temp[index]);
sprintf(&s[28],"%ld",calib_temp[7]);
```

```c
if(disp_f) sdisplay(40,s);
}
```

```
/*******************************************************/
```

```c
void display_diag_menu()

{
int delta_lvdt;
int new_lvdt;

void clear_display();
void cursor_control();
int get_lvdt_std();
void menu_select();
void outbit();
void sdisplay();
void step_setup2();
void TestOP();
void toutbit();

switch(diag_menu_nbr)
    {
case 1:  /* CLOCK ADJUST */
    cursor_control(0,off);
    temp[0]=clock_adj_control;
    step_setup2(67,11);
    diag_menu_nbr++;
    break;

case 2:
    menu_select(11,0,3);
    clock_adj_control=temp[0];
    break;

case 3:  /* LVDT/HEAD DISPLAY */
    temp[0]=lvdt_disp;
    step_setup2(53,11);
    diag_menu_nbr++;
    break;

case 4:
    menu_select(11,0,3);
    lvdt_disp=temp[0];
    break;

case 5:  /* SUPER BUBBLE */
```

```
        temp[0]=sb_control;
        step_setup2(63,11);
        diag_menu_nbr++;
        break;

case 6:
        menu_select(11,0,3);
        sb_control=temp[0];
        break;

case 7:  /* HEAD AVERAGING */
        temp[0]=head_avg_control;
        step_setup2(64,11);
        diag_menu_nbr++;
        break;

case 8:
        menu_select(11,0,3);
        head_avg_control=temp[0];
        break;

case 9:  /* AUTO ZERO */
        temp[0]=auto_zero_control;
        step_setup2(65,11);
        diag_menu_nbr++;
        break;

case 10:
        menu_select(11,0,3);
        auto_zero_control=temp[0];
        break;

case 11:  /* ZERO PRESSURE TRANSDUCER */
        temp[0]=2;
        step_setup2(66,7);
        diag_menu_nbr++;
        break;

case 12:
        menu_select(7,0,3);
        if(temp[0]==1) auto_zero_time=2;
        break;

case 13:  /* DISPLAY PRESSURE TRANSDUCER ZERO OFFSET */
        clear_display();
        sdisplay(0,line_one[68]);
        diag_menu_nbr++;
        break;

case 14:
        sprintf(s,"%3d",zero_offset);
        sdisplay(19,s);
        break;

case 15:  /* DISPLAY AIR PUMP RUN TIME */
        clear_display();
```

```c
        sdisplay(0,line_one[69]);
        diag_menu_nbr++;
        break;

case 16:
        sprintf(s,"%5d",pump_time_min);
        sdisplay(17,s);
        break;

case 17:  /* DIAGNOSTICS */
        sdisplay(0,line_one[70]);
        sdisplay(40,line_one[71]);
        diag_menu_nbr++;
        break;

case 18:
        digit_key_enable=on;
        if(digit_value<7 && digit_value>0)
            {
            TestOP((char)(digit_value-1));
            diag_menu_nbr=17;
            }
        digit_value=99;
        break;

case 19:  /*  GAUGE BLOCK READ */
        clear_display();
        sdisplay(0,line_one[72]);
        sdisplay(40,line_one[73]);
        diag_menu_nbr++;
        break;

case 20:
        outbit(port5c,6,1);
        if(sw_value[14]>=5)   /* open gate */
            {
            sw_value[14]=6;
            outbit(port5b,0,1);
            }
        else outbit(port5b,0,0);

if(sw_value[12]>=5)   /* close gate */
            {
            sw_value[12]=6;
            outbit(port5b,1,1);
            }
        else outbit(port5b,1,0);

sprintf(s,"LVDT=%4d",get_lvdt_std());
        sdisplay(30,s);

if(sw_value[13]>=5)
            {
            sw_value[13]=6;
            diag_menu_nbr=22;
            }
        break;
```

```
case 22:
    clear_display();
    sdisplay(0,line_one[72]);
    toutbit(port5b,1,50);
    pulse_time=15;
    Delay(15);
    diag_menu_nbr++;
    break;

case 23:
    outbit(port5c,6,1);
    prev_lvdt=get_lvdt_std();
    toutbit(port5b,1,pulse_time);
    sprintf(s,"%4d",pulse_time);
    sdisplay(50,s);
    Delay(8);
    new_lvdt=get_lvdt_std();
    delta_lvdt=prev_lvdt - new_lvdt;
    sprintf(s,"LVDT=%4d",new_lvdt);
    sdisplay(30,s);
    sprintf(s,"%4d",delta_lvdt);
    sdisplay(60,s);
    if(delta_lvdt>40) pulse_time--;
    else if(delta_lvdt<21) pulse_time++;
    if(pulse_time<10) pulse_time=10;
    if(delta_lvdt<6) diag_menu_nbr++;
    break;

case 24:
    outbit(port5c,6,1);
    prev_lvdt=get_lvdt_std();
    Delay(20);
    toutbit(port5b,1,pulse_time);
    sprintf(s,"%4d",pulse_time);
    sdisplay(50,s);
    new_lvdt=get_lvdt_std();
    delta_lvdt=prev_lvdt - new_lvdt;
    sprintf(s,"LVDT=%4d",new_lvdt);
    sdisplay(30,s);
    sprintf(s,"%4d",delta_lvdt);
    sdisplay(60,s);
    if(delta_lvdt>8) diag_menu_nbr=23;
    else
        {
        buzz_time=80;
        diag_menu_nbr=19;
        }
    break;

default:
    diag_menu_nbr=1;
    break;

}
```

}

/****************************************************/

```
void do_initialization()
{
void plotter_time_align();
char rg_time_check();
void save_sys_time();

power_up_flag=off;
plotter_time_align();
save_sys_time(&sys_tm_dt);
if(rg_time_check((int)rg_int_end.cent*100+rg_int_end.year,
rg_int_end.month,rg_int_end.day,
     rg_int_end.hour,rg_int_end.min,0,5,off)==0 &&
     report_gen==1) rg_step=2;
menu_time=300;
}
```

/****************************************************/

```
void getkey()
{
char c;

key_pushed=0;
while(!key_pushed);
for(c=0;c<24;c++)
    if(sw_value[c]==5) sw_value[c]=6;
}
```

/****************************************************/

```
void print_formt_flow(position,flowb,end_f,end_blank)
int position;
```

```c
float flowb;
char end_f;
char end_blank;
{
int char_count;
int dec;
float disp_flow;
int index;

disp_flow=flowb /
    flow_conversion[fl_rt_unts_row][fl_rt_unts_col-1];
if(disp_flow<1) dec=3;
else if(disp_flow<10) dec=2;
    else if(disp_flow<100) dec=1;
        else dec=0;
char_count=sprintf(&s[position],"%4.*f ",dec,disp_flow);
index=(fl_rt_unts_col-1) * 8 + 3;
s[position+char_count]=line_two.text[fl_rt_unts_row][index];
s[position+char_count+1]=line_two.text[fl_rt_unts_row]
    [index+1];
s[position+char_count+2]=line_two.text[fl_rt_unts_row]
    [index+2];
if(end_blank)
    {
    s[position+char_count+3]=0x20;
    if(end_f) s[position+char_count+4]=0;
    }
else if(end_f) s[position+char_count+3]=0;
}

/****************************************************/ void print_formt_vol(position,vola,end_f)
int position;
float vola;
char end_f;
{
int char_count;
int index;

vola=vola / volume_conversion[volume_units-1];
char_count=sprintf(&s[position],"%0.*f ",
    vol_dec_places[volume_units-1],vola);
index=line_two.position[3][volume_units-1] -
    line_two.position[3][0] + 3;
while(line_two.text[3][index] != 0x20)
    s[position+char_count++]=line_two.text[3][index++];
```

```c
if(end_f) s[position+char_count]=0;
}
```

/****************************************************/

```c
void print_menu_selection(string_pos,line_num,entry_num)
int entry_num;
int line_num;
int string_pos;
{
int t1;

t1=line_two.position[line_num][entry_num-1] -
    line_two.position[line_num][0] + 3;
while(line_two.text[line_num][t1]!=0x20)
    {
    s[string_pos]=line_two.text[line_num][t1];
    t1++;
    string_pos++;
    }
s[string_pos]=0;
}
```

/****************************************************/

```c
char *TestRomRam()
{
void check_ram();
int check_rom();
void sdisplay();
sdisplay(40,"TESTING ROM...");
if(check_rom()) return("ROM CHECKSUM ERROR");
sdisplay(40,"TESTING RAM...");
check_ram();
return(0);

}
```

/****************************************************/

```c
char *TestPlotter()
{
char c;
char i;
```

```c
    char *ptr=s;

void clear_s();
    void fillmem();
    void splot();
    void starprint();

if(Vp_power_flag) return(line_one[60]);
    if(paper_out_flag) return(line_one[54]);

clear_s();
    splot(s);
    while(!print_done);
    print_done=0;
    starprint(off,sy);
    while(!print_done);
    print_done=0;

for(i=0;i<4;i++)
        for(c='0';c<='9';c++)
            *ptr++ = c;
    splot(s);
    while(!print_done);
    print_done=0;
    fillmem(sy,252,0);
    starprint(off,sy);
    while(!print_done);
    print_done=0;
    text_print_flag=off;
    if(plotter_jammed_flag) return(line_one[61]);

clear_s();
    ptr=s;
    for(c=':';c<='Z';c++)
        *ptr++ = c;
    splot(s);
    while(!print_done);
    print_done=0;
    fillmem(sy,252,0);
    starprint(off,sy);
    while(!print_done);
    print_done=0;
    text_print_flag=off;
    if(plotter_jammed_flag) return(line_one[61]);

return(0);
}

/****************************************************/ char *TestUart()
```

```
{
char *cptr;
char *rptr;

void clear_display();
void Delay();
void enable_tx();
void fillmem();
void getkey();
char *movmem();
void sdisplay();

proto_enable=0;

if(interactive)

{
    clear_display();
    sdisplay(0,"INSERT INTERROGATOR TEST PLUG");
    sdisplay(40,PRESSKEY);
    getkey();
    } movmem(PRESSKEY,tx_data,13);
tx_ptr=tx_data;
tx_count=13;
fillmem(rx_data0,13,0);
rx_ptr=rx_data0;
enable_tx();
while(tx_count != 0);
Delay(4);
cptr=PRESSKEY;
rptr=rx_data0;
while(*cptr)
    {
    if(*cptr != *rptr)
        {
        rx_ptr=rx_data0;
        rx_count=0;
        proto_enable=1;
        return("UART FAILED");
        }
    cptr++;
    rptr++;
    }
rx_ptr=rx_data0;
rx_count=0;
proto_enable=1;
return(0);
}
```

```
/******************************************************/ char *TestSampler()
{
char c;
char *ptr;
char x;
void clear_display();
void Delay();
void getkey();
char inbit();
void outbit();
void sdisplay();

if(interactive)
     {
     clear_display();
     sdisplay(0,"INSERT SAMPLER TEST PLUG");
     sdisplay(40,PRESSKEY);
     getkey();
     } clear_display();
sdisplay(0,"TESTING EVENTMARK I/O");
ptr="EVENTMARK I/O NOT WORKING";
for (c=0;c<10;c++)
     {
     outbit(port5c,0,1); /* Hi event mark out */
     Delay(1);
     x=inbit(port6a,0);
     outbit(port5c,0,0);
     if(x) return(ptr);
     Delay(1);
     if(!inbit(port6a,0)) return(ptr);
     } clear_display();
sdisplay(0,"TESTING SAMP EN/BOTTLE I/O");
ptr="SAMP EN/BOTTLE COUNT NOT WORKING";
for (c=0;c<10;c++)
     {
     outbit(port6c,4,1); /* LO sampler enable */
     Delay(1);
     x=inbit(port6a,1);
     outbit(port6c,4,0);
     if(!x) return(ptr);
     Delay(1);
     if(inbit(port6a,1)) return(ptr);
     } return(0);
}
```

```c
/*****************************************************/ char *TestDisplay()
{
char c;
void clear_display();
void cursor_control();
void Delay();
void getkey();
void putchr();
void sdisplay();

clear_display();
sdisplay(0,"ENTIRE DISPLAY WILL BLANK");
if(interactive)
     {
     sdisplay(40,PRESSKEY);
     getkey();
     }
else Delay(15);
clear_display();
Delay(20);

sdisplay(0,"ENTIRE DISPLAY WILL BE FILLED");
if(interactive)
     {
     sdisplay(40,PRESSKEY);
     getkey();
     }
else Delay(15);
for(c=1;c<=80;c++) putchr(0xff);
Delay(20);

clear_display();
sdisplay(0,"WALK CURSOR ACROSS DISPLAY");
if(interactive)
     {
     sdisplay(40,PRESSKEY);
     getkey();
     }
else Delay(15);
clear_display();
for(c=0;c<80;c++)
     {
     cursor_control(c,off);
     putchr(0xff);
     Delay(2);
     cursor_control(c,off);
     putchr(' ');
     } return(0);
}
```

```c
/*****************************************************/ char *(*tfunc[])() = {
    0,
    TestRomRam,
    TestPlotter,
    TestUart,
    TestSampler,
    TestDisplay};

/*****************************************************/ void runtest(type)
char type;
{
char *errmess;
void clear_display();
void Delay();
void getkey();
void sdisplay();
void sdisplay1();
clear_display();
sdisplay(0,testtype[type]);
Delay(10);
if(errmess=(*tfunc[type])())
    {
    clear_display();
    sdisplay(0,testtype[type]);
    sdisplay1(" FAILED...");
    sdisplay(40,errmess);
    beep_number=5;
    getkey();
    }
else if(!interactive)
    {
    clear_display();
    sdisplay1("PASSED...");
    Delay(5);
    }
}

/*****************************************************/ void TestOP(type)
char type;
```

```
{
void Delay();
void runtest();

interactive=1;
if(type) runtest(type);
else
    {
    interactive=0;
    clear_display();
    sdisplay(0,testtype[0]);
    Delay(20);
    runtest(5);
    runtest(4);
    runtest(3);
    runtest(2);
    runtest(1);
    }
}
^z
```

NAME CSTARTUP

| | | |
|---|---|---|
| | PUBLIC | BBR_bu |
| | PUBLIC | bkup_key1 |
| | PUBLIC | bkup_key2 |
| | PUBLIC | buzz_time |
| | PUBLIC | ckrom |
| | PUBLIC | display |
| | PUBLIC | DMAF |
| | PUBLIC | F24 |
| | PUBLIC | lng_adc |
| | PUBLIC | Modem_off_count |
| | PUBLIC | Modem_on_count |
| | PUBLIC | msg2 |
| | PUBLIC | msg5 |
| | PUBLIC | result |
| | PUBLIC | rx_count |
| | PUBLIC | rx_data0 |
| | PUBLIC | rx_ptr |
| | PUBLIC | rx_to30 |
| | PUBLIC | sp_bu |
| | PUBLIC | start |
| | PUBLIC | ckrdy |
| | PUBLIC | exit |
| | PUBLIC | prtr_run_time |
| | EXTERN | a_d_to |
| | EXTERN | baud |
| | EXTERN | beep_number |
| | EXTERN | blocktimer |
| | EXTERN | bottle_count |
| | EXTERN | bottle_num_timer |
| | EXTERN | cal_delay |

| | | | |
|---|---|---|---|
| EXTERN | char_to_error | | |
| EXTERN | ck_sum_error | | |
| EXTERN | clock_adj_control | | |
| EXTERN | commandrdy | | |
| EXTERN | conversation | | |
| EXTERN | event_hour | | |
| EXTERN | event_min | | |
| EXTERN | event_mark | | |
| EXTERN | event_mark2 | | |
| EXTERN | event_mark3 | | |
| EXTERN | flow_total | | |
| EXTERN | gage_block_act | | |
| EXTERN | key_pushed | | |
| EXTERN | main | | |
| EXTERN | main1 | | |
| EXTERN | menu_flash_time | | |
| EXTERN | one_hour_flag | | |
| EXTERN | one_min_flag | | |
| EXTERN | one_sec_flag | | |
| EXTERN | pkt_flag_error | | |
| EXTERN | plotter_jammed_flag | | |
| EXTERN | power_up_flag | | |
| EXTERN | print_done | | |
| EXTERN | proto_enable | | |
| EXTERN | pump_flag | | |
| EXTERN | pump_time_sec | | |
| EXTERN | rx_data1 | | |
| EXTERN | sb_time | | |
| EXTERN | sb_pulse_time | | |
| EXTERN | str2312_ptr | | |
| EXTERN | sw_value | | |
| EXTERN | time1ms | | |
| EXTERN | timrflash | | |
| EXTERN | tx_count | | |
| EXTERN | tx_data | | |
| EXTERN | tx_ptr | | |
| EXTERN | Xcount | | |
| EXTERN | tx1_enable_f | | |
| EXTERN | ?SCALL_HL_L10 | | |
| EXTERN | ?SEG_INIT_L07 | | |
| PAGE | | | |

| | | | |
|---|---|---|---|
| BBR: | EQU | 39h | ;mmu Bank Base Register |
| BBRVAL: | EQU | 00h | ;Bank base addr = 00000h |
| BCR1L: | EQU | 2Eh | ;DMA1 Byte Count Register Low |
| bdos: | EQU | 0005h | ;define sys entry point |
| CBAR: | EQU | 3Ah | ;mmu Common/Bank Area Reg |
| CBARVAL: | EQU | 85h | ;MMU com area reg = 8000h<br>;MMU bank area reg= 5000h |
| CBR: | EQU | 38h | ;mmu Common Base Register |
| CBRVAL: | EQU | 18h | ;Common base addr= 18000h |
| char_in: | EQU | 1 | ;define character input # |
| char_out: | EQU | 2 | ;define char output # |
| CNTLA0: | EQU | 0 | ;ASCI0 control register A |

```
CNTLA1:         EQU     1               ;ASCI1 control register A
CNTLB0:         EQU     2               ;ASCI0 control register B
CNTLB1:         EQU     3               ;ASCI1 control register B
CNTLA0VAL0:     EQU     64H             ;Transmitter, Receiver enabled;
                                        ; RTS Lo; 1 start, 8 data, 1 stop
CNTLA0VAL1:     EQU     74H             ;Transmitter, Receiver enabled;
                                        ; RTS Hi; 1 start, 8 data, 1 stop
CNTLA1VAL:      EQU     30H             ;
CNTLB0VAL:      EQU     02H             ;
CNTLB1VAL:      EQU     0Ch             ;
cr:             EQU     0Dh             ;define carriage return
ctrl_c:         EQU     'C'-40h         ;define end of file char
DCNTL:          EQU     32h             ;Dma/wait CoNTroL reg
DCNTLVAL:       EQU     30h             ;Memory wait = 0
                                        ;I/O wait = 4
                                        ;DMA sense = X
                                        ;DMA Ch 1 mode = X
DSTAT:          EQU     30h             ;Dma STATus register.
DSTATVAL:       EQU     0               ;DMA1En = disabled,
                                        ;DMA0En = disabled,
                                        ;DIE1 = disabled,
                                        ;DIE0 = disabled.
eof:            EQU     00h             ;lib routine end of file
ICR:            EQU     3Fh             ;I/O Control Register
IL:             EQU     33h             ;Interrupt vector Low
                                        ; register
ILVAL:          EQU     80h             ;Interrupt vector table
                                        ; address = 80h
INIT_DEST:      EQU     8000h
IN3OUT1:        EQU     93h             ;Port A = in
                                        ;Port B = in
                                        ;Port C0 = in
                                        ;Port C1 = out
IOPAGE:         EQU     80h             ;I/O PAGE = 3
ITC:            EQU     34h             ;Int/Trap Control reg
ITCVAL:         EQU     02h             ;Trap = disabled
                                        ;Int 2 = disabled
                                        ;Int 1 = enabled
                                        ;Int 0 = disabled
lf:             EQU     0Ah             ;define line feed
OUT4:           EQU     80h             ;Port A = out
                                        ;Port B = out
                                        ;Port C0 = out
                                        ;Port C1 = out
PORT1a:         EQU     10h
PORT1b:         EQU     11h
PORT2a:         EQU     20h
PORT2b:         EQU     21h
PORT2c:         EQU     22h
PORT5a:         EQU     50h
PORT5b:         EQU     51h
PORT5c:         EQU     52h
PORT5d:         EQU     53h
PORT6a:         EQU     60h
PORT6b:         EQU     61h
PORT6c:         EQU     62h
```

| | | | |
|---|---|---|---|
| PORT6d: | EQU | 63h | |
| RCR: | EQU | 36h | ;Refresh Control Register |
| RCRVAL: | EQU | 00h | ;Refresh = disabled |
| | | | ;Wait states = X |
| | | | ;Cycle select = X |
| RDR0: | EQU | 08H | |
| RLDR0H: | EQU | 0Fh | ;timer ReLoaD Register |
| | | | ; channel 0 High |
| RLDR0L: | EQU | 0Eh | ;timer ReLoaD Register |
| | | | ; channel 0 Low |
| RTCCRVAL: | EQU | 1Ch | ;RTC command reg: |
| | | | ; test bit = normal |
| | | | ; interrupt = enable |
| | | | ; run/stop = run |
| | | | ; format = 24 hour |
| | | | ; xtal = 32 khz |
| RTCMRVAL: | EQU | 3Ah | ;RTC interrupt mask reg: |
| | | | ; day = off |
| | | | ; hour = on |
| | | | ; min = on |
| | | | ; sec = on |
| | | | ; 1/10 s = off |
| | | | ; 1/100 s = on |
| | | | ; alarm = off |
| RTCMRV1: | EQU | 38H | ;RTC clock setting mask: |
| | | | ; day = off |
| | | | ; hour = on |
| | | | ; min = on |
| | | | ; sec = on |
| | | | ; 1/10 s = off |
| | | | ; 1/100 s = off |
| | | | ; alarm = off |
| STACK: | EQU | 0 | ;stack address |
| STACK1: | EQU | 0FE00H | |
| STAT0: | EQU | 4 | ;ASCI0 status register |
| STAT1: | EQU | 5 | ;ASCI1 status register |
| STAT0VAL0: | EQU | 08H | ;Rx interrupt enabled, |
| | | | ; Tx interrupt disabled. |
| STAT0VAL1: | EQU | 0 | ;Rx and Tx interrupts disabled. |
| TCR: | EQU | 10h | ;Timer Control Register |
| TCRVAL: | EQU | 11h | ;Timer int 1 = disabled |
| | | | ;Timer int 0 = enabled |
| | | | ;Timer out cntrl = inhib |
| | | | ;Timer down count 1 = dis |
| | | | ;Timer down count 0 = en |
| TDR0: | EQU | 6 | ;ASCI0 transmit data register |
| TDR1: | EQU | 7 | ;ASCI1 transmit data register |
| TMDR0H: | EQU | 0Dh | ;TiMer Data Register |
| | | | ; channel 0 High |
| TMDR0L: | EQU | 0Ch | ;TiMer Date Register |
| | | | ; channel 0 Low |
| TMDR1H: | EQU | 15h | ;TiMer Data Register |
| | | | ; channel 1 High |
| TMDR1L: | EQU | 14h | ;TiMer Data Register |
| | | | ; channel 1 Low |
| TMR0LVAL: | EQU | 153 | ;Timer 0 reload |

```
TMR0HVAL:       EQU    00            ; value = 1 msec
TSR0:           EQU    8             ;ASCI0 receive register
TSR1:           EQU    9             ;ASCI1 receive register
                PAGE RSEG FLIST
exit:           DEFD bankexit

ASEG

ORG 0
        di
        jp   RESET                   ;RESET vector.
                ORG 38h
        jp   INT0                    ;INT0 vector.
                ORG 66h
        jp   NMI                     ;NMI vector.
;
;
;
;
;       INTERRUPT VECTORS
;
                ORG    ILVAL
                DEFW   RTC           ;INT1
                DEFW   0             ;INT2
                DEFW   TIMER0        ;PRT0
                DEFW   TIMER1        ;PRT1
                DEFW   0             ;DMA0
                DEFW   DMA1          ;DMA1
                DEFW   0             ;CSI/O
                DEFW   SERIAL0       ;ASCI00
                DEFW   SERIAL1       ;ASCI01

RSEG DATA
;
AA_flag:        DEFS   1
bad_char_count:
                DEFS   1
BBR_bu:         DEFS   1
bkup_key1:      DEFS   1
bkup_key2:      DEFS   1
bottle_pulse_count:
                DEFS   1
buzz_off_time:  DEFS   1
buzz_time:      DEFS   1
DMAF:           DEFS   1
erase_val       DEFS   1
fst_int_f:      DEFS   1
init_f:         DEFS   1
Modem_off_count:
                DEFS   1
```

```
Modem_on_count:
               DEFS    1
pkt_flag_count:
               DEFS    1
prtr_run_time: DEFS    1
result:        DEFS    5
rst_keys:      DEFS    1
rx_count:      DEFS    1
rx_data0:      DEFS    28
rx_ptr:        DEFS    2
rx_to2         DEFS    1
rx_to3:        DEFS    1
rx_to30:       DEFS    1
sevF_count:    DEFS    1
sp_bu:         DEFS    2

RSEG    CSTART
               PAGE msg1:   DEFM    'TESTING RAM'
        DEFB    0
msg2:   DEFM    'RAM FAILED!'
        DEFB    0
msg3:   DEFM    'TESTING ROM'
        DEFB    0
msg4:   DEFM    'ROM FAILED!'
        DEFB    0
msg5:   DEFM    'RAM PASSED.'
        DEFB    0
msg6:   DEFM    'ROM PASSED.'
        DEFB    0
msg7:   DEFM    'POWER LOST/LOW BATTERY'
        DEFB    0
msg8:   DEFM    'UNABLE TO RESUME PROGRAM-PRESS ''4'' AND '
        DEFM    '''EXIT'' KEYS TO RESUME'
        DEFB    0
msg9:   DEFM    'RESTART'
        DEFB    0
;
RESET:  LD      SP,STACK1
        ld      a,IOPAGE
        out0    (ICR),a              ;Set internal I/O page (ICR).
        ld      a,ILVAL
        out0    (IL+IOPAGE),a        ;Set interrupt vector at 80h
                                     ; (IL).
        ld      a,DCNTLVAL
        out0    (DCNTL+IOPAGE),a     ;No mem waits
                                     ; 1 I/O wait (DCNTL).
        ld      a,ITCVAL
        out0    (ITC+IOPAGE),a       ;Enable INT1 interrupt (ITC).
        ld      a,RCRVAL
        out0    (RCR+IOPAGE),a       ;Disable RAM refresh
                                     ; cycle (RCR).
        ld      a,TCRVAL             ;Enable PRT0 (TCR).
        out0    (TCR+IOPAGE),a
```

```
        ld    a,CBARVAL
        outO  (CBAR+IOPAGE),a      ;Set up MMU (CBAR).
        ld    a,CBRVAL
        outO  (CBR+IOPAGE),a       ;Base address for
                                   ; com area 1 (CBR).
        ld    a,BBRVAL
        outO  (BBR+IOPAGE),a       ;Base address for bank (BBR).
        ld    a,TMROLVAL           ;Load tmr0 and reload
                                   ; reg for 1 ms.
        outO  (TMDROL+IOPAGE),a
        outO  (RLDROL+IOPAGE),a
        ld    a,TMROHVAL
        outO  (TMDROH+IOPAGE),a
        outO  (RLDROH+IOPAGE),a
        ld    a,OUT4               ;Initialize I/O ports.
        out   (PORT5d),a
        ld    a,IN3OUT1
        out   (PORT6d),a
        ld    a,0c2h               ;Turn on row 2 of keyboard.
        out   (PORT5a),a           ;Write appropriate data
                                   ; on outputs.
        ld    a,0h
        out   (PORT5b),a
        ld    a,0c2h
        out   (PORT5c),a
        ld    a,10h
        out   (PORT6c),a
        ld    a,RTCCRVAL           ;Initialize RTC chip.
        out   (PORT1b),a
        ld    a,RTCMRVAL
        out   (PORT1a),a
;
;
;       reset display
;
        ld    b,4
outres: call  ckrdy
        ld    a,38h                ;Reset display
        out   (0),a                ;Control word data
                                   ; size/format.
        dec   b
        jp    nz,outres            ;repeat 4 times.
        call  ckrdy
        ld    a,06h                ;Increment display mode.
        out   (0),a
        call  ckrdy
        ld    a,0ch                ;Display on; cursor, blink off
        out   (0),a
        call  ckrdy
        ld    a,01h                ;Clear display.
        out   (0),a
        ld    a,CNTLA0VAL1
        outO  (CNTLA0+IOPAGE),a
        ld    a,CNTLB0VAL
        outO  (CNTLB0+IOPAGE),A
        ld    a,CNTLA1VAL          ;Multiprocessor off, Rx
```

```
        out0  (CNTLA1+IOPAGE),a    ; disabled, Tx enabled,
                                   ; CKA1 disabled, Error
                                   ; reset, 7 data, no parity,
                                   ; 1 stop.
        ld    a,CNTLB1VAL          ;300 baud.
        out0  (CNTLB1+IOPAGE),a
        ld    a,STAT0VAL0
        out0  (STAT0+IOPAGE),a
        LD    A,0
        LD    (DMAF),A
        ld    hl,rx_data0
        ld    (rx_ptr),hl
        im    1
        jp    start

PAGE start:
        in    a,(PORT6c)           ;Read power fail input.
        bit   3,a                  ;OK?
        jr    nz,F15               ;Yes.
;
        ld    a,22H                ;Disable RAM.
        out   (PORT5c),a
        ld    hl,msg7              ;Display Power Fail message.
F16:    in    a,(2)                ;busy?
        bit   7,a
        jr    nz,F16               ;yes.
        ld    a,80H
        out   (0),a                ;Write command.
F17:    in    a,(2)                ;busy?
        bit   7,a
        jr    nz,F17               ;yes.
        ld    a,(hl)
        cp    0                    ;End of string character?
        jr    z,start              ;Yes.
        out   (1),a                ;Write character.
        inc   hl
        jr    F17
;
F15:    ld    a,0C2H               ;Enable RAM.
        out   (PORT5c),a
        in    a,(PORT6b)           ;Read and save hard reset
        ld    (rst_keys),a         ; keys.
;
        ld    hl,STACK1            ;Test top 8 bytes of ram.
        ld    c,8
F01:    ld    a,0AAH
        ld    (hl),a
        ld    a,(hl)
        cp    0AAH
        jp    nz,bad_ram
        ld    a,055H
        ld    (hl),a
        ld    a,(hl)
        cp    055H
```

```
        jr    nz,bad_ram
        ld    a,00
        ld    (hl),a
        ld    a,(hl)
        cp    00
        jr    nz,bad_ram
        ld    a,0FFH
        ld    (hl),a
        ld    a,(hl)
        cp    0FFH
        jr    nz,bad_ram
        dec   hl
        dec   c
        jr    nz,F01
;
        ld    hl,msg1            ;Output "TESTING RAM".
        ld    c,0
        call  display
;
        call  ram_cs             ;Do checksum on ram.
;
        ld    hl,8000H           ;Test all of ram.
        ld    bc,8000H
F03:    in    a,(PORT6c)         ;Read 12 V power fail.
        bit   3,a                ;OK?
        jp    z,start            ;No.
        ld    d,(hl)
        ld    a,0AAH
        ld    (hl),a
        ld    a,(hl)
        cp    0AAH
        jr    nz,bad_ram
        ld    a,055H
        ld    (hl),a
        ld    a,(hl)
        cp    055H
        jr    nz,bad_ram
        ld    a,00
        ld    (hl),a
        ld    a,(hl)
        cp    00
        jr    nz,bad_ram
        ld    a,0FFH
        ld    (hl),a
        ld    a,(hl)
        cp    0FFH
        jr    nz,bad_ram
        ld    (hl),d
        inc   hl
        dec   bc
        ld    a,b
        or    c
        jr    nz,F03
        call  ram_cs             ;Do checksum again.
        ld    a,e                ;First checksum to a.
        exx                      ;Last to e.
```

```
              cp   e                    ;Same?
              jr   nz,bad_ram           ;No.
              ld   a,d                  ;Last to a.
              exx                       ;First to d.
              cp   d                    ;Same?
              jr   nz,bad_ram           ;No.
              ld   hl,msg5
              ld   c,0
              call display
              ld   c,10
F13:          ld   b,0ffh
F10:          ld   a,0ffh               ;Delay.
F09:          dec  a
              jr   nz,F09
              dec  b
              jr   nz,F10
              dec  c
              jr   nz,F13
              jr   F02
;
bad_ram:      ld   hl,msg2              ;Display FAILED message.
F04:          in   a,(2)                ;busy?
              bit  7,a
              jr   nz,F04               ;yes.
              ld   a,80H
              out  (0),a                ;Write command.
F05:          in   a,(2)                ;busy?
              bit  7,a
              jr   nz,F05               ;yes.
              ld   a,(hl)
              cp   0                    ;End of string character?
              jr   z,F06                ;Yes.
              out  (1),a                ;Write character.
              inc  hl
              jr   F05
F06:          halt
F02:          ld   hl,msg3              ;Testing ROM.
              ld   c,0
              call display
              call ckrom
              ld   a,h                  ;Is sum zero?
              or   l
              jr   z,F08                ;Yes.
              ld   hl,msg4              ;ROM PASSED message.
              ld   c,0
              call display
              halt
F08:          ld   hl,msg6              ;ROM FAILED message.
              ld   c,0
              call display
              ld   c,10
F14:          ld   b,0ffh
F11:          ld   a,0ffh               ;Delay.
F12:          dec  a
              jr   nz,F12
              dec  b
```

```
            jr    nz,F11
            dec   c
            jr    nz,F14
;
;
            ld    a,(rst_keys)        ;Read keyboard.
            bit   0,a                 ;Is '4' key pressed?
            jr    z,F19               ;No.
            bit   3,a                 ;Is 'EXIT' key pressed?
            jr    z,F19               ;No.
F21:        ld    sp,STACK
            CALL  ?SEG_INIT_L07
            xor   a
            ld    (erase_val),a
            jr    L0000
F19:        ld    a,(bkup_key1)       ;key 1 set?
            cp    55h
            jr    nz,F20              ;no.
            ld    a,(bkup_key2)       ;key 2 set?
            cp    0AAh
            jr    nz,F20              ;no.
            jp    warm_start
F20:        ld    hl,msg8             ;Display 'unable to resume..'
            ld    c,0
            call  display
;
;
F22:        LD    HL,main1
            CALL  ?SCALL_HL_L10
;
;
F24:        ld    a,0C2H              ;Turn on row 2 of keyboard.
            out   (PORT5a),a
            in    a,(PORT6b)
            bit   0,a                 ;Is '4' key pressed?
            jr    z,F24               ;no.
            bit   3,a                 ;Is 'EXIT' key pressed?
            jr    z,F24               ;No.
            jr    F21
;
L0000:      ei                        ;Turn on interrupts.
            LD    HL,main
            CALL  ?SCALL_HL_L10
            LD    A,(DMAF)            ;Is DMA flag set?
            OR    A
            JR    NZ,L0000            ;Yes.
            slp
bankexit:
            jr    L0000 ckrdy:      in    a,(2)               ;busy?
            bit   7,a
            jp    nz,ckrdy            ;yes.
            ret
```

RSEG RCODE

```
TIMER0:     push af                     ;1 millisecond interrupt.
            in0  a,(TCR+IOPAGE)         ;Read TCR.
            in0  a,(TMDR0L+IOPAGE)      ;Read TMDR0L to
                                        ; clear interrupt.
            ld   a,(time1ms)            ;Is time zer0?
            or   a
            jr   z,L1                   ;Yes.
            dec  a                      ;Decrease time.
            ld   (time1ms),a
L1:         pop  af
            ei
            ret TIMER1:     push af
            in   a,(PORT5c)             ;Reset divider.
            or   02h
            out  (PORT5c),a
            in0  a,(TCR+IOPAGE)         ;Clear interrupt.
            in0  a,(TMDR1L+IOPAGE)
            ld   a,TCRVAL               ;Turn off timer 1.
            out0 (TCR+IOPAGE),a
            pop  af
            ei
            ret RTC:        push af                     ;10 mS, 1 Sec, 1 Min and 1 Hr
            push bc                     ; interrupt.
            push de
            push hl
            push ix
            push iy
;
;     POWER FAIL
;
            in   a,(PORT6c)             ;Read 12 V power fail.
            bit  3,a                    ;Ok?
            jp   nz,B99                 ;Yes.
            ld   (sp_bu),sp             ;Save stack pointer
            in0  a,(BBR + IOPAGE)       ; and bank page.
            ld   (BBR_bu),a
            xor  a                      ;Turn off outputs.
            out  (PORT5a),a
            out  (PORT5b),a
            ld   a,55h                  ;Set power down flags.
            ld   (bkup_key1),a
            ld   a,0AAh
            ld   (bkup_key2),a
```

```
            call ckrdy              ;Clear display.
            ld   a,01
            out  (0),a
            ld   hl,msg7            ;Display "power fail" msg.
            ld   c,0
            call display
            ld   a,22h              ;Disable RAM.
            out  (PORT5c),a
            ld   a,01               ;Open gate.
            out  (PORT5b),a
;
warm_start:
            ld   b,250
A11:        in   a,(PORT6c)         ;Read 12V power state.
            bit  3,a                ;ok?
            jr   z,A11              ;No.
            dec  b                  ;250 times?
            jr   nz,A11             ;No.
;
            ld   a,0C2H             ;Turn RAM back on.
            out  (PORT5c),a
            ld   a,0C0H
            out  (PORT5a),a
            xor  a                  ;Close gate.
            out  (PORT5b),a
            ld   a,1
            ld   (power_up_flag),a
            ld   a,(BBR_bu)         ;Restore bank page.
            out0 (BBR + IOPAGE),a
            ld   sp,(sp_bu)         ;Restore Stack pointer.
;
            call ckrdy              ;Clear display.
            ld   a,01
            out  (0),a
            ld   hl,msg9            ;Display RESTART message.
            ld   c,0
            call display
            LD   B,010              ;Delay for message.
X3:         LD   C,0FFH
X2:         LD   A,0FFH
X1:         DEC  A
            JR   NZ,X1
            DEC  C
            JR   NZ,X2
            DEC  B
            JR   NZ,X3
            ld   a,(erase_val)      ;Erase power down flags.
            inc  a
            ld   (erase_val),a
            ld   (bkup_key1),a
            ld   (bkup_key2),a
            jp   A99
;
;     ONE HOUR INTERRUPT
;
B99:        in   a,(PORT1a)
```

```
                ld      b,a
                bit     5,b                     ;Is interrupt 1 hour?
                jr      z,B17                   ;No.
                ld      a,1
                ld      (one_hour_flag),a
;
;       ONE MINUTE INTERRUPT
;
B17:            bit     4,b                     ;Is interrupt 1 min?
                jr      z,B01                   ;No.
                ld      a,1
                ld      (one_min_flag),a
;
;       ONE SECOND INTERRUPT
;
B01:            bit     3,b                     ;Is interrupt 1 sec?
                jp      z,B00                   ;No.
                ld      a,(one_sec_flag)
                inc     a
                ld      (one_sec_flag),a
B02:            ld      a,(tx1_enable_f)        ;Is flag set?
                or      a
                jr      z,B03                   ;No.
                ld      a,01                    ;Turn on tx1 enable.
                out0    (STAT1+IOPAGE),a
                ld      a,0
                ld      (tx1_enable_f),a
;
;       Protocol handling
;
B03:            ld      a,(rx_to30)             ;Increase 30 sec timeout.
                inc     a
                ld      (rx_to30),a
                cp      31                      ;Is it >30?
                jr      c,B04                   ;No.
                xor     a                       ;Clear timeout.
                ld      (rx_to30),a
                ld      (init_f),a              ;Init flag=0.
                ld      a,13                    ;Begin modem off sequence.
                ld      (Modem_off_count),a
;
;       Air pump
;
B04:            ld      a,(pump_flag)           ;Pump running?
                or      a
                jr      z,B05                   ;No.
                ld      a,(pump_time_sec)       ;Increase pump time.
                inc     a
                ld      (pump_time_sec),a
B05:            in      a,(PORT6c)              ;Read pressure switch.
                bit     1,a                     ;On?
                jr      z,B06                   ;No.
                ld      a,(DMAF)                ;DMA on?
                or      a
                jr      nz,B07                  ;Yes.
                in      a,(PORT5b)
```

```
                set     3,a                     ;Turn on pump.
                out     (PORT5b),a
                ld      (pump_flag),a           ;Set pump running flag.
                jr      B07
B06:            in      a,(PORT5b)
                res     3,a                     ;Turn off pump.
                out     (PORT5b),a
                xor     a                       ;Turn off flag.
                ld      (pump_flag),a
;
;       Modem control
;
B07:            in      a,(PORT6a)              ;Interrogator connected?
                ld      d,a
                bit     2,d
                jr      nz,B08                  ;No.
                ld      a,CNTLA0VAL1            ;Switch RTS to interrogator.
                out0    (CNTLA0+IOPAGE),a
                ld      a,(fst_int_f)           ;Is this first time seeing
                or      a                       ; interrogator?
                jr      nz,B09                  ;No.
                xor     a                       ;Zero init flag.
                ld      (init_f),a
                inc     a                       ;Set first interrogate flag.
                ld      (fst_int_f),a
                ld      a,STAT0VAL0             ;Disable Tx, enable Rx int.
                jr      B18
B08:            ld      a,(proto_enable)        ;Protocol enabled:
                or      a
                jp      z,B15                   ;No.
                xor     a                       ;Clear first interr flag.
                ld      (fst_int_f),a
                bit     4,d                     ;Modem connected?
                jr      nz,B09                  ;Yes.
                ld      a,STAT0VAL1             ;Disable Rx, Tx interrupts.
B18:            out0    (STAT0+IOPAGE),a
B09:            ld      a,(Modem_off_count)     ;Modem off count>=15?
                ld      e,a
                cp      15
                jr      nc,B10                  ;Yes.
                cp      14                      ;>=14?
                jr      nc,B11                  ;Yes.
                cp      13                      ;>=13?
                jr      nc,B12                  ;Yes.
                bit     3,d                     ;Carrier detect?
                jr      z,B13                   ;No.
                bit     6,d                     ;Energy detect?
                jr      nz,B14                  ;Yes.
B13:            ld      a,e                     ;Increment modem off count.
                inc     a
                ld      (Modem_off_count),a
                jr      B15
B10:            in      a,(PORT5c)              ;Power down modem.
                res     2,a
                out     (PORT5c),a
                xor     a                       ;Reset modem, on and off
```

```
              ld    (Modem_on_count),a    ; counts.
              ld    (Modem_off_count),a
              bit   2,d                   ;Interrogator connected?
              jr    z,B15                 ;Yes.
              xor   a                     ;Zero init flag.
              ld    (init_f),a
              jr    B15
B11:          bit   2,d                   ;Interrogator connected?
              jr    z,B13                 ;Yes.
              ld    a,STAT0VAL1           ;Disable Tx, Rx interrupts.
              out0  (STAT0+IOPAGE),a
              jr    B13
B12:          in    a,(PORT5c)            ;Turn off auto handshake.
              res   3,a
              out   (PORT5c),a
              jr    B13
B14:          ld    a,e                   ;Modem off count = 12?
              cp    12
              jr    z,B15                 ;Yes.
              ld    a,(init_f)            ;Does init flag = 0?
              or    a
              ld    a,9                   ;If not, set for 4 sec
              jr    nz,B16                ; without carrier.
              xor   a                     ;Else set for 12 sec.
B16:          ld    (Modem_off_count),a
B15:          ld    a,(a_d_to)            ;Increment A/D timeout.
              inc   a
              ld    (a_d_to),a
;
;       TEN MILLISECOND INTERRUPT
;
B00:          bit   1,b                   ;Is interrupt 10 mS?
              jp    z,A99                 ;No.
;
;       Scan keyboard
;
              in    a,(PORT5a)            ;Select all rows.
              or    3Fh
              out   (PORT5a),a
              in    a,(PORT6b)            ;Read columns.
              and   0Fh                   ;Any switches pushed?
              jr    nz,A00                ;Yes.
              in    a,(PORT5a)
              and   0C0h
              out   (PORT5a),a
              ld    hl,sw_value           ;Set up loop.
              ld    a,0
              ld    c,24
A01:          or    (hl)                  ;OR in value.
              inc   hl
              dec   c                     ;Done?
              jr    nz,A01                ;No.
              or    a                     ;Any non-zero values?
              jr    z,A98                 ;No.
              ld    hl,sw_value           ;Set up loop.
              ld    c,24
```

```
A02:    ld    a,(hl)              ;Read switch value.
        cp    5                   ;Does it equal 5?
        jr    z,A03               ;Yes.
        ld    (hl),0              ;Load with zero.
A03:    inc   hl
        dec   c                   ;Done?
        jr    nz,A02              ;No.
        jr    A98
A00:    ld    d,6                 ;Set up loop counter
        ld    e,1                 ; and row mask.
        ld    hl,sw_value
A04:    in    a,(PORT5a)
        and   0C0h
        or    e
        out   (PORT5a),a          ;Output row select.
        in    a,(PORT6b)          ;Read columns.
        push  de
        ld    d,4                 ;Set up column loop.
        ld    e,1
        ld    b,a
A05:    ld    a,b
        and   e                   ;Is a key pushed?
        ld    a,(hl)
        jr    z,A06               ;No.
        cp    5                   ;Is the switch value < 5?
        jr    nc,A07              ;No.
        inc   a                   ;Increase value.
        ld    (hl),a
        cp    5                   ;Just turning 5?
        jr    nz,A07              ;No.
        ld    a,6                 ;Turn on buzzer for new key.
        ld    (buzz_time),a
        ld    (key_pushed),a
        jr    A07
A06:    cp    5                   ;Is the switch value = 5?
        jr    z,A07               ;Yes.
        ld    (hl),0              ;Zero value.
A07:    inc   hl
        sla   e
        dec   d                   ;Done with all columns in row?
        jr    nz,A05              ;No.
        pop   de
        sla   e
        dec   d                   ;Done with all rows?
        jr    nz,A04              ;No.
;
;       Control buzzer
;
A98:    ld    a,(buzz_time)
        or    a                   ;Is buzz time zero?
        jr    nz,A08              ;No.
        ld    a,08h               ;Turn off buzzer.
        out   (PORT5d),a
        ld    a,(beep_number)     ;Is beep number zero?
        or    a
        jr    z,A97               ;Yes.
```

```
          ld    a,(buzz_off_time)   ;Decrease off time.
          dec   a
          ld    (buzz_off_time),a   ;Is it zero?
          jr    nz,A97              ;No.
          ld    a,(beep_number)     ;Decrease beep number.
          dec   a
          ld    (beep_number),a
          ld    a,10                ;Set another buzz time.
          ld    (buzz_time),a
          jr    A97
A08:      dec   a
          ld    (buzz_time),a
          ld    a,09h
          out   (PORT5d),a
          ld    a,20                ;Set off time.
          ld    (buzz_off_time),a
;
;    Various timers
;
A97:      ld    a,(cal_delay)
          or    a
          jr    z,L2
          dec   a
          ld    (cal_delay),a
L2:       ld    a,(sb_pulse_time)   ;Is time zero?
          or    a
          jr    nz,A09              ;No.
          in    a,(PORT5b)          ;Turn off super bubble.
          res   2,a
          out   (PORT5b),a
          jr    A10
A09:      dec   a                   ;Decrease time.
          ld    (sb_pulse_time),a
          in    a,(PORT5b)          ;Turn on super bubble.
          set   2,a
          out   (PORT5b),a
A10:      ld    a,(menu_flash_time)
          inc   a
          ld    (menu_flash_time),a
;
;    Samper event mark/bottle number
;
          in    a,(PORT6a)          ;Read port.
          ld    b,a
          bit   0,a                 ;Event mark on?
          ld    a,(event_mark)
          jr    z,C01               ;Yes
          ld    a,(event_mark2)     ;Is em2>2?
          cp    2
          jr    c,C08               ;No.
          ld    a,0                 ;Clear em2.
          ld    (event_mark2),a
C08:      ld    a,(event_mark3)     ;Is em3>2?
          cp    2
          jr    c,C09               ;No.
          ld    a,0                 ;Clear em3.
```

```
               ld    (event_mark3),a
C09:           ld    a,(event_mark)
               cp    0FEh                  ;Event mark count >= FE?
               jr    c,C99                 ;No.
               ld    a,0
               ld    (event_mark),a        ;Clear event mark count
               ld    (bottle_num_timer),a  ;and bottle # timer.
               jr    C99
C01:           inc   a
               cp    2                     ;Event mark count >=2?
               jr    nc,C02                ;Yes.
               ld    (event_mark),a        ;Save event mark count.
               jr    C99
C02:           cp    3                     ;Event mark count >=3?
               jr    c,C03                 ;No.
               ld    a,(event_mark2)       ;Is em2 0?
               or    a
               jr    nz,C07                ;No.
               ld    a,1                   ;Set em2=1.
               ld    (event_mark2),a
C07:           ld    a,(event_mark3)       ;Is em3 0?
               or    a
               jr    nz,C10                ;No.
               ld    a,1                   ;Set em3=1.
               ld    (event_mark3),a
C10:           ld    a,(bottle_num_timer)  ;Bottle # timer =0?
               or    a
               jr    z,C99                 ;Yes.
               jr    C04
C03:           ld    (event_mark),a        ;Save event mark count.
               ld    a,0
               ld    (bottle_count),a      ;Clear bottle count.
               ld    a,13                  ;Start bottle# timer.
               ld    (bottle_num_timer),a
               in    a,(PORT2a)            ;Load time of event.
               in    a,(PORT2b)
               ld    (event_hour),a
               in    a,(PORT2c)
               ld    (event_min),a
C04:           bit   1,b                   ;Is bottle # input high?
               jr    z,C05                 ;Yes.
               ld    a,0                   ;Zero pulse count.
               ld    (bottle_pulse_count),a
               jr    C99
C05:           ld    a,(bottle_pulse_count) ;Is bottle pulse count >=1?
               cp    1
               jr    nc,C06                ;Yes.
               inc   a                     ;Increase bottle pulse count.
               ld    (bottle_pulse_count),a
               jr    C99
C06:           cp    2                     ;Is bottle pulse count >=2?
               jr    nc,C99                ;Yes.
               inc   a                     ;Increase bottle pulse count.
               ld    (bottle_pulse_count),a
               ld    a,(bottle_count)      ;Increase bottle count.
               inc   a
               ld    (bottle_count),a
```

;
;       Protocol
;
```
C99:    ld    a,(init_f)           ;Is init flag zero?
        or    a
        jr    nz,E20               ;No.
        ld    a,(rx_to3)           ;Increase 3 sec timeout.
        inc   a
        ld    (rx_to3),a
        cp    0FEH                 ;Is it > 2.5 seconds?
        jr    c,E20                ;No.
        xor   a                    ;Clear timeout
        ld    (rx_to3),a
        ld    (sevF_count),a       ; and 7F count.
        ld    a,02H                ;Change baud to 4800.
        out0  (CNTLB0+IOPAGE),a
        ld    (baud),a
E20:    ld    a,(init_f)           ;Is init flag = 2?
        cp    2
        jr    nz,E90               ;No.
        ld    a,(rx_to2)           ;Increase 2 sec timeout.
        inc   a
        ld    (rx_to2),a
        cp    201                  ;Is it > 2 seconds?
        jr    c,E90                ;No.
        ld    hl,rx_data0          ;Move receive pointer to
        ld    (rx_ptr),hl          ; beginning of buffer.
        xor   a                    ;Clear rx count
        ld    (rx_count),a
        ld    (rx_to2),a           ; and timeout.
        inc   a                    ;Set char timeout error.
        ld    (char_to_error),a
        ld    (init_f),a           ;Set init flag =1.
;
E90:    ld    bc,(blocktimer)      ;Increment if not zero.
        ld    a,b
        or    c
        jr    z,E21
        dec   bc
        ld    (blocktimer),bc
;
;       Plotter jammed
;
E21:    ld    a,(DMAF)             ;DMA flag on?
        or    a
        jr    z,E22                ;No.
        ld    a,(prtr_run_time)    ;Has plotter been on 250 ms?
        cp    25
        jr    nc,E23               ;Yes.
        inc   a                    ;Increase time count.
        ld    (prtr_run_time),a
        jr    E22
E23:    in0   a,(BCR1L + IOPAGE)   ;Read DMA length.
        cp    170                  ;Is length < 170?
        jr    nc,E24               ;No.
        xor   a                    ;Clear jammed flag.
        ld    (plotter_jammed_flag),a
        jr    E22
```

```
E24:        ld      a,0FFh                  ;Set jammed flag
            ld      (plotter_jammed_flag),a
            ld      (print_done),a          ; and print done.
            xor     a                       ;Disable DMA1.
            ld      (DSTAT+IOPAGE),a
            ld      (DMAF),a                ;Clear DMA flag.
            in      a,(PORT5b)              ;Turn off 5V and motor.
            and     9Fh
            out     (PORT5b),a
;
;   Modem control
;
E22:        ld      a,(Modem_on_count)
            ld      b,a
            cp      110                     ;Modem on count>=110?
            jr      nc,E25                  ;Yes.
            cp      100                     ;Modem on count>=100?
            jr      c,E26                   ;No.
            in      a,(PORT5c)              ;Turn on autohandshake.
            set     3,a
            out     (PORT5c),a
            ld      a,b
            cp      105                     ;Modem on count >=105?
            jr      c,E27                   ;No.
            ld      a,CNTLA0VAL0            ;Set RTS for modem.
            out0    (CNTLA0+IOPAGE),a
            ld      a,STAT0VAL0             ;Enable Rx, disable Tx int.
            out0    (STAT0+IOPAGE),a
            jr      E27
E26:        cp      1                       ;Modem on count >=1?
            jr      nc,E28                  ;Yes.
            in      a,(PORT6a)              ;Ring detect?
            bit     5,a
            jr      z,E27                   ;Yes.
E29:        xor     a                       ;Reset Modem on count.
            ld      (Modem_on_count),a
            jr      E25
E28:        in      a,(PORT6a)              ;Modem connected?
            bit     4,a
            jr      z,E29                   ;No.
            bit     2,a                     ;Interrogator connected?
            jr      z,E29                   ;Yes.
            in      a,(PORT5c)              ;Power up modem.
            set     2,a
            out     (PORT5c),a
E27:        ld      a,b                     ;Increment modem on count.
            inc     a
            ld      (Modem_on_count),a
            xor     a                       ;Zero modem off count
            ld      (Modem_off_count),a
            ld      (rx_to30),a             ; and intermessage timeout.
            ld      (ck_sum_error),a        ;Clear errors.
            ld      (char_to_error),a
            ld      (pkt_flag_error),a
;
E25:        ld      a,(clock_adj_control)
            cp      2                       ;Adjusting clock?
```

```
              ld    a,RTCMRV1
              jr    z,E30              ;Yes.
              ld    a,RTCMRVAL
E30:          out   (PORT1a),a
;
              ld    a,(timrflash)
              or    a                  ;Delay time zero?
              jr    z,E31              ;Yes.
              dec   a
              ld    (timrflash),a
E31:
;
A99:          pop   iy
              pop   ix
              pop   hl
              pop   de
              pop   bc
              pop   af
              ei
              ret DMA1:         push  af
              ld    a,DSTATVAL
              out   (DSTAT+IOPAGE),a
              in    a,(PORT5b)         ;Turn on paper advance output.
              set   7,a
              out   (PORT5b),a
              res   7,a                ;Turn paper advance off.
              out   (PORT5b),a
              ld    a,03               ;Enable Int0 and Int1.
              out0  (ITC+IOPAGE),a
              pop   af
              ei
              ret INT0:         push  af
              in    a,(PORT5b)         ;Turn off 5V and motor.
              and   9Fh
              out   (PORT5b),a
              ld    a,02               ;Disable Int0.
              out0  (ITC+IOPAGE),a
              ld    a,0FFh
              ld    (print_done),a
              LD    A,0
              LD    (DMAF),A
              pop   af
              ei
              ret NMI:          push  af
              xor   a                  ;Turn off outputs.
              out   (PORT5b),a
              pop   af
              retn
```

```
SERIAL0: push af
         push bc
         push de
         push hl
         in0   a,(CNTLA0+IOPAGE)      ;Clear error flags.
         res   3,a
         out0  (CNTLA0+IOPAGE),a
         in0   a,(STAT0+IOPAGE)
         bit   7,a                    ;Receive interrupt?
         jr    nz,E00                 ;Yes
         bit   1,a                    ;Transmit interrupt?
         jr    nz,E01                 ;Yes
         jp    E99
;
E00:     ld    a,(Xcount)
         inc   a
         ld    (Xcount),a
         in0   a,(RDR0+IOPAGE)        ;Read character.
         ld    b,a
         ld    a,(proto_enable)       ;Protocol enabled?
         or    a
         jp    z,E17                  ;No.
         ld    a,(init_f)             ;Does init flag = 0?
         or    a
         jp    nz,E02                 ;No.
         xor   a                      ;Clear 3 sec time out
         ld    (rx_to3),a
         ld    a,b
         cp    7FH                    ;Does character = 7F?
         jr    nz,E03                 ;No.
         xor   a                      ;Clear bad char count.
         ld    (bad_char_count),a
         ld    a,(sevF_count)         ;Increase 7F count.
         inc   a
         ld    (sevF_count),a
         cp    04                     ;Is 7F count > 3?
         jr    nc,E04                 ;Yes.
         ld    a,01                   ;Send a 01.
         jr    E16
E04:     ld    a,02                   ;Send a 02.
         ld    (conversation),a
E16:     ld    (tx_data),a
         ld    a,01
         ld    (tx_count),a
         ld    hl,tx_data
         ld    (tx_ptr),hl
         ld    a,09H                  ;Turn on Tx interrupt.
         out0  (STAT0+IOPAGE),a
         jp    E99
E01:     ld    hl,(tx_ptr)
         ld    a,(hl)                 ;Send next byte.
         out0  (TDR0+IOPAGE),a
         inc   hl                     ;Move pointer.
         ld    (tx_ptr),hl
         ld    a,(tx_count)           ;Decrease transmit count.
         dec   a
         ld    (tx_count),a
```

```
            jp    nz,E99
            ld    a,08H              ;Turn off Tx interrupt.
            out0  (STAT0+IOPAGE),a
            jp    E99
E03:        ld    a,(sevF_count)
            cp    4                  ;Is 7F count >3?
            jr    nc,E05             ;Yes.
            ld    a,(bad_char_count) ;Increase bad char count.
            inc   a
            ld    (bad_char_count),a
            cp    3                  ;Is count > 3?
            jr    c,E06              ;No.
            xor   a                  ;Clear bad char count.
            ld    (bad_char_count),a
            in0   a,(CNTLB0+IOPAGE)  ;Change baud.
            inc   a
            cp    5
            jr    nz,E07
            ld    a,6
            jr    E08
E07:        cp    7
            jr    c,E08
            ld    a,2
E08:        out0  (CNTLB0+IOPAGE),a
            ld    (baud),a
E06:        xor   a                  ;Clear 7F count.
            ld    (sevF_count),a
            jp    E99
E05:        ld    a,b
            cp    0AAH               ;Does char = AA?
            jr    z,E09              ;Yes.
            ld    a,(AA_flag)        ;Is AA flag set?
            or    a
            jr    z,E10              ;No.
            ld    a,b
            cp    55h                ;Does char = 55?
            jr    nz,E10             ;No.
            ld    a,2                ;Set init flag =2.
            ld    (init_f),a
            xor   a                  ;Clear AA flag.
            ld    (AA_flag),a
E11:        xor   a                  ;Clear pkt flag count.
            ld    (pkt_flag_count),a
            jp    E99
E10:        xor   a                  ;Clear AA flag.
E09:        ld    (AA_flag),a
            ld    a,(pkt_flag_count) ;Increase pkt flag count.
            inc   a
            ld    (pkt_flag_count),a
            cp    32                 ;Is count >= 32?
            jp    c,E99              ;No.
            ld    (pkt_flag_error),a ;Set error flag.
            jr    E11
;
E02:        xor   a                  ;Clear interchar timeout.
            ld    (rx_to2),a
            ld    a,(init_f)         ;Does init flag=1?
            cp    1
```

```
        jr    z,E05              ;Yes.
E17:    ld    hl,(rx_ptr)
        ld    (hl),b             ;Place data in buffer.
        inc   hl                 ;Move pointer.
        ld    (rx_ptr),hl
        ld    a,(rx_count)       ;Increase Rx count.
        inc   a
        ld    (rx_count),a
        cp    28                 ;Does count=28?
        jr    c,E99              ;No.
        ld    bc,4               ;Transfer first 4 bytes.
        ld    de,result
        ld    hl,rx_data0
        ldir
        xor   a                  ;Clear incoming carry.
        ld    (result+4),a
        ld    hl,rx_data0+4
        ld    c,5
E12:    call  lng_adc            ;Form crc.
        inc   hl
        dec   c
        jr    nz,E12
        ld    c,4                ;Check crc.
        ld    de,result
E13:    ld    a,(de)
        cp    (hl)
        jr    nz,E14             ;Not equal.
        inc   hl
        inc   de
        dec   c
        jr    nz,E13
        xor   a                  ;Clear 30 second timeout.
        ld    (rx_to30),a
        ld    hl,rx_data1
        ld    (hl),a
        inc   hl
        ld    (hl),a
        inc   hl
        ld    a,0AAh
        ld    (hl),a
        inc   hl
        ld    a,55h
        ld    (hl),a
        ld    bc,28              ;Transfer data to buffer 2.
        ld    hl,rx_data0
        ld    de,rx_data1+4
        ldir
        ld    a,01               ;Set valid data flag.
        ld    (commandrdy),a
        ld    (init_f),a         ;Set init flag to 1.
E15:    ld    hl,rx_data0        ;Move pointer to beginning
        ld    (rx_ptr),hl        ; of buffer.
        xor   a                  ;Zero receive count.
        ld    (rx_count),a
        jr    E99
E14:    ld    a,01               ;Set checksum error flag.
        ld    (ck_sum_error),a
        jr    E15
```

```
;
E99:        pop     hl
            pop     de
            pop     bc
            pop     af
            ei
            ret SERIAL1:    push    af
            push    hl
            in0     a,(STAT1+IOPAGE)
            bit     1,a                     ;Tx?
            jr      nz,D00                  ;Yes.
            in0     a,(TSR1+IOPAGE)         ;Read Rx.
            ld      a,30h                   ;Clear errors.
            out0    (CNTLA1+IOPAGE),a
            jr      D02
D00:        ld      hl,(str2312_ptr)        ;Get data pointer.
            ld      a,(hl)                  ;Get data byte.
            or      a                       ;Is it 0?
            jr      nz,D01                  ;No.
            ld      a,0                     ;Turn off Tx interrupt.
            out0    (STAT1+IOPAGE),a
            jr      D02
D01:        out0    (TDR1+IOPAGE),a         ;Send byte.
            inc     hl
            ld      (str2312_ptr),hl
D02:        pop     hl
            pop     af
            ei
            ret lng_adc:    xor     a                       ;Clear carry.
            ld      a,(result+4)            ;Incoming carry?
            or      a
            jr      z,E50                   ;No.
            scf                             ;Set carry.
E50:        ld      a,(result)              ;Add first bytes.
            adc     a,(hl)
            ld      (result),a
            inc     hl
            ld      a,(result+1)            ;Add second bytes.
            adc     a,(hl)
            ld      (result+1),a
            inc     hl
            ld      a,(result+2)            ;Add third bytes.
            adc     a,(hl)
            ld      (result+2),a
            inc     hl
            ld      a,(result+3)            ;Add fourth bytes.
            adc     a,(hl)
            ld      (result+3),a
            ld      a,0                     ;Clear outgoing carry.
```

```
            jr    nc,E51              ;Carry from last add?
            ld    a,1                 ;Set outgoing carry.
E51:        ld    (result+4),a
            ret display:
            ld    a,c
            cp    40                  ;First or second line?
            jp    c,$+5               ;Branch if first line.
            add   a,24                ;Point to second line.
            or    80h                 ;Set DD address command.
            ld    c,a
            call  ckrdy
            ld    a,c
            out   (0),a               ;Write command.
10:         call  ckrdy               ;Wait until display not busy.
            ld    a,(hl)
            cp    0                   ;End of string character?
            jp    z,11                ;Yes.
            out   (1),a               ;Write character.
            inc   hl
            jp    10
11:
            ret
;
;
;
ram_cs:     ld    iy,0000
            ex    (sp),iy             ;Save return address.
            ld    bc,4000H            ;Set up counter,
            ld    hl,0000             ; sum,
            ld    ix,8000H            ; and pointer.
F00:        ld    e,(ix+00)           ;Load next operand.
            inc   ix
            ld    d,(ix+00)
            inc   ix
            add   hl,de               ;Add to sum.
            dec   bc                  ;Done?
            ld    a,b
            or    c
            jr    nz,F00              ;No.
            ex    de,hl               ;Save sum in DE'
            exx
            ex    (sp),iy             ;Replace return address.
            ret
;
ckrom:      push  ix
            ld    a,88h               ;Eliminate bank area.
            out0  (CBAR+IOPAGE),a
            ld    a,00                ;Make physical = logical
            out0  (CBR+IOPAGE),a      ; for all 64K addresses.
            ld    bc,8000h            ;Set up counter,
            ld    hl,0000             ; and sum,
            ld    ix,0000             ; and pointer.
F07:        ld    e,(ix+00)           ;Load next operand.
            inc   ix
            ld    d,(ix+00)
```

```
            inc   ix
            add   hl,de              ;Add to sum.
            dec   bc                 ;Done?
            ld    a,b
            or    c
            jr    nz,F07             ;No.
            ld    a,08h              ;Set up for 3rd 32K page.
            out0  (CBR+IOPAGE),a
            ld    bc,4000h
            ld    ix,8000h
F23:        ld    e,(ix+00)          ;Load next operand.
            inc   ix
            ld    d,(ix+00)
            inc   ix
            add   hl,de              ;Add to sum.
            dec   bc                 ;Done?
            ld    a,b
            or    c
            jr    nz,F23             ;No.
;
            ld    a,CBARVAL          ;Restore bank area.
            out0  (CBAR+IOPAGE),a
            ld    a,CBRVAL           ;Restore paging.
            out0  (CBR+IOPAGE),a
            pop   ix
            ret

END

;     JULY 31, 1990     LF3 VAU16
      NAME    lf3(16)
      RSEG    BSEG0(0)
      RSEG    FLIST(0)
      PUBLIC  CalcCheckSum(158,253)
      PUBLIC  check_ram
      PUBLIC  check_rom
      EXTERN  ckrdy
      EXTERN  ckrom
      PUBLIC  clear_display
      PUBLIC  cursor_control
      EXTERN  display
      EXTERN  DMAF
      PUBLIC  enable_tx
      EXTERN  F24
      PUBLIC  fillmem
      EXTERN  flow_table
      EXTERN  gage_block_act
      EXTERN  gate_move_flag
      PUBLIC  inbit
      PUBLIC  inbyte
      PUBLIC  inword
      EXTERN  lng_adc
      PUBLIC  load_timer
      PUBLIC  movmem
```

```
        EXTERN    msg2
        EXTERN    msg5
        PUBLIC    outbit
        EXTERN    prtr_run_time
        PUBLIC    putchr
        EXTERN    result
        EXTERN    s
        PUBLIC    sdisplay
        PUBLIC    sdisplay1
        PUBLIC    starprint
        EXTERN    timelms
        PUBLIC    toutbit
        EXTERN    ?ENT10_L11
        EXTERN    ?ENT11_L11
        EXTERN    ?SLEAVE_L11
        EXTERN    ?SCALL_IY_L10
        EXTERN    ?SRET_L10
        EXTERN    ?CL64180B_2_22_L07
port5c: EQU   52h
        RSEG  BSEG0
;
;   Read in the state of the designated bit on the
;   designated port.
;
;   char inbit(int port,char bit)
;
?0007:
    CALL  ?ENT10_L11
    DEFB  4

LD    B,(IX-2)           ;Get number of bit position.
    inc   b
    ld    a,0
    scf
LA1: rla                     ;Rotate mask into correct position.
    dec   b
    jr    nz,LA1
    POP   BC                 ;Read data byte.
    PUSH  BC
    in    d,(c)
    and   d                  ;Mask off correct bit.
    jr    z,LA2
    ld    C,1
    jr    LA3
LA2: ld   C,0
LA3:
?0000:
    JP    ?SLEAVE_L11
;
;
;
;
;
;
;
;
;
;
```

```
;
;       Read in a byte of data from input port 'port'.
;
;       char inbyte(int port)
;
?0008:
        CALL ?ENT11_L11
        DEFB 2
        DEFW -1
        LD   C,(IX-2)
        LD   B,(IX-1)
        in   a,(c)
        ld   C,A              ;RETURN VALUE IN C
?0001:
        JP   ?SLEAVE_L11
;
;
;
;
;
;
;
;
;
;
;       Read in a two byte integer from 'port' and
;       'port+1'.
;
;       int inword(int port)
;
?0009:
        CALL ?ENT11_L11
        DEFB 2
        DEFW -2
        POP  AF
        POP  BC
        PUSH BC
        PUSH AF
        in   a,(c)
        ld   D,A
        inc  bc
        in   a,(c)
        ld   B,a
        LD   C,D
?0002:
        JP   ?SLEAVE_L11
;
;
;
;
;
;
;
;
;
;
;
;       Output a 1 or 0 indicated by 'state' in designated
```

```
;   bit position and designated output port.
;
;   void outbit(int port,char bit,char state)
;
?0010:
    CALL ?ENT10_L11
    DEFB 6
    POP  BC
    PUSH BC
    in   d,(c)
    LD   E,(IX-4)            ;Form mask for correct bit.
    inc  e
    ld   a,0
    scf
LC1: rla
    dec  e
    jr   nz,LC1
    ld   e,a
    LD   A,(IX-2)            ;Is state to be one?
    or   a
    ld   a,e
    jr   nz,LC2              ;Yes.
    cpl
    and  d                   ;Make bit a zero.
    jr   LC3
LC2: or   d                   ;Make bit a one.
LC3: out  (c),a
?0003:
    JP   ?SLEAVE_L11
;
;
;
;
;
;
;
;
;
;
;
;
;   Display an ascii character string starting at
;   'position' on display.
;
;   void sdisplay(int position,char *strg)
;
?0011:
    CALL ?ENT10_L11
    DEFB 4
    POP  BC                  ;Recover 'position'
    POP  HL                  ; and text pointer.
    PUSH HL
    PUSH BC
    call display

?0004:
    JP   ?SLEAVE_L11
;
```

```
;
;
;
;
;`
;
;
;
;
;
;   void starprint(int print_flag,char *strg)
;
?0012:
    CALL  ?ENT10_L11
    DEFB  4
    in    a,(51h)              ;Turn on +5 to printer and
    or    60h                  ; printer motor.
    out   (51h),a
    ld    a,2                  ;Load source physical address.
    out0  (2ah+80h),a
    POP   BC
    POP   HL
    PUSH  HL
    PUSH  BC
    ld    de,8000h
    and   a
    sbc   hl,de
    out0  (28h+80h),1
    out0  (29h+80h),h
    LD    A,C                  ;Is print flag on?
    OR    A
    JR    Z,LE00               ;No.
    ld    a,70h                ;Load destination I/O address.
    ld    b,0
    JR    LE01
LE00:
    LD    A,80H                ;Load dummy dest address.
    ld    b,a
LE01:
    out0  (2bh+80h),a
    out0  (2ch+80h),b
    xor   a
    ld    (prtr_run_time),a    ;Zero printer run time.
    out0  (2fh+80h),a          ;Load length count.
    ld    a,250
    out0  (2eh+80h),a
    ld    a,08h                ;DCNTL:  no mem or I/O wait states,
    out0  (32h+80h),a          ; edge trig DMA1 req, mem->I/O.
    ld    a,98h                ;DSTAT:  DMA1 enabled, DMA1 end
    out0  (30h+80h),a          ; interrupt enabled.
    LD    A,0FFH
    LD    (DMAF),A
?0005:
    JP    ?SLEAVE_L11
;
;
;
;
;
;
```

```
;
;
;
;
;
;
;
;   Output a positive pulse of duration 'time'
;   milliseconds on the designated bit of the designated port.
;
;   void toutbit(int port,char bit,int time)
;
?0013:
    CALL  ?ENT10_L11
    DEFB  6
    LD    C,1
    LD    E,(IX-4)
    POP   HL
    PUSH  HL
    LD    IY,outbit
    CALL  ?SCALL_IY_L10
    ld    a,(ix-2)              ;Load delay time.
    ld    b,(ix-1)
    ld    (timelms),a
LD0: ld   a,(timelms)           ;Delay expired?
    or    a
    jr    nz,LD0                ;No.
    ld    a,b                   ;Is high byte zero?
    or    a
    jr    z,LD1                 ;Yes.
    dec   b                     ;Decrement it.
    ld    a,0ffh                ;Delay another 256 ms.
    ld    (timelms),a
    jr    LD0
LD1:
    LD    C,0
    LD    E,(IX-4)
    POP   HL
    PUSH  HL
    LD    IY,outbit
    CALL  ?SCALL_IY_L10
?0006:
    JP    ?SLEAVE_L11
;
;
;
;
;
;
;   void cursor_control( char position, char state)
;
?0014:
    CALL  ?ENT10_L11
    DEFB  4
    POP   BC                    ;Recover 'position'.
    PUSH  BC
    ld    a,C
    cp    40                    ;First or second line?
    jp    c,$+5                 ;Branch if first line.
    add   a,24                  ;Point to second line.
    or    80h                   ;Set DD address command.
```

```
        ld    c,a
        call  ckrdy
        ld    a,c
        out   (0),a              ;Write command.
;
        LD    A,(IX-2)           ;Recover 'state'.
        OR    A
        LD    B,0DH              ;Display on, cursor off, blink on.
        JP    NZ,?0015           ;Jump if on.
        LD    B,0CH              ;Display on, cursor off, blink off.
?0015:
        CALL  ckrdy
        LD    A,B
        OUT   (0),A
;
        JP    ?SLEAVE_L11
;
;
;
;
;       void clear_display()
;
?0016:
        call  ckrdy
        ld    a,01h
        out(0),a
        jp    ?SRET_L10
;
;
;
;
;
;       void sdisplayl(char *strg)
;
?0017:
        CALL  ?ENT10_L11
        DEFB  2
        POP   HL
        PUSH  HL
?0018:
        call  ckrdy
        ld    a,(hl)
        cp    0                  ;End of string character?
        jp    z,?0019            ;Yes.
        out   (1),a              ;Write character.
        inc   hl
        jp    ?0018
?0019:
        JP    ?SLEAVE_L11
;
;
;
;
;       void load_timer(int t_value)
;
;
?0020:
        CALL  ?ENT10_L11
```

```
        DEFB 2
        POP  BC
        PUSH BC
        ld   a,b
        out0 (95h),a
        ld   a,c
        out0 (94h),a
        ld   a,33h
        out0 (90h),a
        in   a,(port5c)
        res  1,a
        out  (port5c),a
?0021:
        JP   ?SLEAVE_L11
;
;
;       Enable the serial0 transmitter.
;
;       void enable_tx()
;
;
?0022:
        ld   a,09H
        out0 (84H),a
        jp   ?SRET_L10
;
;
;
;
;
;       unsigned long CalcCheckSum(char *dpacket)
;
;
?0023:
        CALL ?ENT10_L11
        DEFB 2
        ld   bc,4               ;Transfer  first 4 bytes.
        ld   de,result
        pop  hl
        push hl
        add  hl,bc
        ldir
        xor  a                  ;Clear incoming carry.
        ld   (result+4),a
        ld   bc,8               ;Set pointer to byte 5.
        pop  hl
        push hl
        add  hl,bc
        ld   c,32
?0024:
        call lng_adc            ;Form crc.
        inc  hl
        dec  c
        jr   nz,?0024
        ld   hl,result          ;Return checksum.
        ld   e,(hl)
        inc  hl
        ld   d,(hl)
```

```
        inc   hl
        ld    c,(hl)
        inc   hl
        ld    b,(hl)
        JP    ?SLEAVE_L11
;
;
;
;
;
;
;
;       char *movmem(src,dst,numb)
;       char *src;
;       char *dst;
;       int numb;
;
?0025:
        CALL  ?ENT10_L11
        DEFB  6
        pop   hl              ;src
        pop   de              ;dst
        push  de
        push  hl
        ld    c,(ix-2)
        ld    b,(ix-1)
        ldir
        pop   af
        pop   de
        push  de
        push  af
        JP    ?SLEAVE_L11
;
;
;
;
;       void fillmem(dst,numb,byte)
;       char *dst;
;       int numb;
;       char byte;
;
?0026:
        CALL  ?ENT10_L11
        DEFB  6
        pop   hl              ;dst
        pop   bc              ;numb
        push  bc
        push  hl
        ld    d,(ix-2)        ;byte
?0027:
        ld    (hl),d
        inc   hl
        dec   bc
        ld    a,b
        or    c
        jr    nz,?0027
        JP    ?SLEAVE_L11
```

```
;
;
;
;
;     void putchr(char)
;Load passed character in the next position on the display.
;
?0028:
      call  ?ENT10_L11
      DEFB  2
      pop   bc
      push  bc
      call  ckrdy
      ld    a,c
      out   (1),a
      jp    ?SLEAVE_L11
;
;
;
;
;     int check_rom()
;
?0029:
      di
      call  ckrom
      ld    b,h
      ld    c,l
      ei
      jp    ?SRET_L10
;
;
;
;
;
;     void check_ram()
;
?0030:
      di
      ld    hl,8000h      ;Fill RAM with AA.
      ld    bc,8000h
?0031:
      ld    (hl),0AAh
      inc   hl
      dec   bc
      ld    a,b
      or    c
      jr    nz,?0031
;
      ld    hl,8000h      ;Check all bytes.
      ld    bc,8000h
?0032:
      ld    a,(hl)
      cp    0AAh
      jp    nz,bad_ram
```

```
        inc   hl
        dec   bc
        ld    a,b
        or    c
        jr    nz,?0032
;
;
        ld    hl,8000h        ;Fill RAM with FF.
        ld    bc,8000h
?0033:
        ld    (hl),0FFh
        inc   hl
        dec   bc
        ld    a,b
        or    c
        jr    nz,?0033
;
        ld    hl,8000h
        ld    bc,8000h
?0034:
        ld    a,(hl)
        cp    0FFh
        jp    nz,bad_ram
        inc   hl
        dec   bc
        ld    a,b
        or    c
        jr    nz,?0034
;
;
        ld    hl,8000h        ;Fill RAM with 55.
        ld    bc,8000h
?0035:
        ld    (hl),055h
        inc   hl
        dec   bc
        ld    a,b
        or    c
        jr    nz,?0035
;
        ld    hl,8000h
        ld    bc,8000h
?0036:
        ld    a,(hl)
        cp    055h
        jp    nz,bad_ram
        inc   hl
        dec   bc
        ld    a,b
        or    c
        jr    nz,?0036
;
;
        ld    hl,8000h        ;Fill RAM with 00.
        ld    bc,8000h
?0037:
        ld    (hl),00h
        inc   hl
```

```
        dec  bc
        ld   a,b
        or   c
        jr   nz,?0037
;
        ld   hl,8000h
        ld   bc,8000h
?0038:
        ld   a,(hl)
        cp   00h
        jp   nz,bad_ram
        inc  hl
        dec  bc
        ld   a,b
        or   c
        jr   nz,?0038
;
;
good_ram:
        ld   hl,msg5
?0039:
        in   a,(2)              ;busy?
        bit  7,a
        jr   nz,?0039           ;yes.
        ld   a,0c0H
        out  (0),a              ;Write command.
?0040:
        in   a,(2)              ;busy?
        bit  7,a
        jr   nz,?0040           ;yes.
        ld   a,(hl)
        cp   0                  ;End of string character?
        jp   z,F24              ;Yes.
        out  (1),a              ;Write character.
        inc  hl
        jr   ?0040
;
bad_ram:
        ld   hl,msg2
        jr   ?0039
        jp   ?SRET_L10
;
;
;
;
        RSEG FLIST
inbit:
        DEFD ?0007
inbyte:
        DEFD ?0008
inword:
        DEFD ?0009
outbit:
        DEFD ?0010
sdisplay:
        DEFD ?0011
starprint:
        DEFD ?0012
```

```
toutbit:
    DEFD ?0013
cursor_control:
    DEFD ?0014
clear_display:
    DEFD ?0016
sdisplay1:
    DEFD ?0017
load_timer:
    DEFD ?0020
enable_tx:
    DEFD ?0022
CalcCheckSum:
    DEFD ?0023
movmem:
    DEFD ?0025
fillmem:
    DEFD ?0026
putchr:
    DEFD ?0028
check_rom:
    DEFD ?0029
check_ram:
    DEFD ?0030
    END
^Z
```

What is claimed is:

1. A method of measuring flow rates of liquid in a flow path comprising:
   changing the shape of the flow path with a barrier by inserting a multiple position gate into the flow path of a liquid;
   determining the position of the barrier having an upstream side and a downstream side;
   determining a characteristic of the flow path;
   determining the resultant flow rate;
   closing the gate to back up flow and then opening the gate after elapsed time or head increase to flush accumulated solids downstream.

2. A method of measuring flow rates of liquid in a flow path comprising:
   changing the shape of the flow path with a barrier;
   determining the position of a barrier having an upstream side and a downstream side;
   determining a characteristic of the flow path;
   determining the resultant flow rate;
   wherein the shape of the flow path is changed by inserting a multiple position gate into the flow path of a liquid; and
   opening the gate to flush accumulated solids downstream;
   the step of opening the gate includes the step of sensing solids near the gate.

3. A method of measuring flow rates of liquid in a flow path comprising:
   changing the shape of the flow path with a barrier having an upstream side and a downstream side by inserting a multiple position gate into the flow path of a liquid;
   determining the position of the barrier;
   determining a characteristic of the flow path;
   determining the resultant flow rate; and
   moving the gate from an open position above the liquid to a position in the liquid only upon sensing liquid above a predetermined height.

4. Apparatus for measuring flow rates of a liquid in a flow path comprising:
   barrier means for changing the shape of a flow path;
   said barrier means being positionable in any of a multiple of positions within the flow path;
   means for detecting the position of the barrier means and transmitting an electrical signal related thereto;
   means for measuring the depth of the flow stream; and
   means for periodically positioning said barrier means to block flow wherein a substantial head of liquid is developed and then changing the position of said barrier means to flush accumulated solids downstream.

5. Apparatus in accordance with claim 4 in which said means for periodically positioning said barrier means to block flow includes means for sensing solids and means for causing a flush cycle in which said barrier means backs up liquid to a substantial head and releases it.

6. Apparatus in accordance with claim 4 in which said means for periodically positioning said barrier means to block includes means for releasing the fluid a predetermined period of time after the barrier means is positioned to block flow.

7. Apparatus for measuring flow rates in a flow path comprising:
   a multiple position gate adapted to be positioned in the flow path for changing the shape of the flow path;
   means for periodically blocking the flow path to develop a head of pressure and releasing the flow path;
   means for measuring the head of liquid flowing along the flow path during the time the liquid is released by the multiple position gate; and
   means for determining the rate of flow of fluid from said measuring means.

* * * * *